(12) United States Patent
King-Underwood et al.

(10) Patent No.: US 9,771,354 B2
(45) Date of Patent: *Sep. 26, 2017

(54) PYRAZOLE P38 MAP KINASE INHIBITORS

(71) Applicant: Respivert Limited, Buckinghamshire (GB)

(72) Inventors: John King-Underwood, Pendock (GB); George Hardy, Robertsbridge (GB); Peter John Murray, Cheltenham (GB); Jonathan Gareth Williams, Nottingham (GB); Stuart Thomas Onions, Nottingham (GB)

(73) Assignee: Respivert Ltd., Buckinghamshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/997,820

(22) Filed: Jan. 18, 2016

(65) Prior Publication Data

US 2016/0130256 A1 May 12, 2016

Related U.S. Application Data

(63) Continuation of application No. 13/638,640, filed as application No. PCT/GB2011/050668 on Apr. 1, 2011, now abandoned.

(30) Foreign Application Priority Data

Apr. 1, 2010 (GB) .................................. 1005589.5

(51) Int. Cl.
| | | |
|---|---|---|
| C07D 403/12 | (2006.01) | |
| C07D 401/14 | (2006.01) | |
| C07D 401/12 | (2006.01) | |

(52) U.S. Cl.
CPC ......... *C07D 403/12* (2013.01); *C07D 401/12* (2013.01); *C07D 401/14* (2013.01)

(58) Field of Classification Search
None
See application file for complete search history.

(56) References Cited

U.S. PATENT DOCUMENTS

2006/0035922 A1 2/2006 Mathias et al.
2008/0300281 A1 12/2008 Dumas et al.

FOREIGN PATENT DOCUMENTS

| WO | WO 00/43384 | 7/2000 |
|---|---|---|
| WO | WO 2005/110994 A2 | 11/2005 |
| WO | WO 2006/072589 A2 | 8/2006 |
| WO | WO 2006/105844 A1 | 10/2006 |
| WO | WO 2007/017083 A1 | 2/2007 |
| WO | WO 2007/064872 A2 | 6/2007 |
| WO | WO 2007/089512 A1 | 8/2007 |
| WO | WO 2007/098448 A1 | 8/2007 |
| WO | WO 2010/038085 A2 | 4/2010 |
| WO | WO 2010/038086 A2 | 4/2010 |
| WO | WO 2010/067130 A1 | 6/2010 |
| WO | WO 2010/067131 A1 | 6/2010 |
| WO | WO 2010/112936 A1 | 10/2010 |
| WO | WO 2011/124923 A2 | 10/2011 |
| WO | WO 2011/124930 A1 | 10/2011 |

OTHER PUBLICATIONS

Shmueli, O. et al., "GeneNote: whole genome expression profiles in normal human tissues", *Comptes Rendus Biologies*, 2003, 326 (10-11): 1067-1072/Genecard.
Smith, S. et al., "Inhibitory effect of p38 mitogen-activated protein kinase inhibitors on cytokine release from human macrophages", *J. Br. J. Pharmacol.*, 2006, 149:393-404.
Hale, K. K. et al., "Differential Expression and Activation of p38 Mitogen-Activated Protein Kinase α, β, γ and δ in Inflammatory Cell Lineages", *J. Immunol.*, 1999, 162(7):4246-52.
Wang, X. S. et al., "Molecular Cloning and Characterization of a Novel p38 Mitogen-activated Protein Kinase", *J. Biol. Chem.*, 1997, 272(38):23668-23674.
Court, N. W. et al., "Cardiac Expression and Subcellular Localization of the p38 Mitogen-activated Protein Kinase Member, Stress-activated Protein Kinase-3 (SAPK3)", *J. Mol. Cell. Cardiol.*, 2002, 34(4):413-26.
Mertens, S. et al., "SAP kinase-3, a new member of the family of mammalian stress-activated protein kinases", *FEBS Lett.*, 1996, 383(3):273-6.
Kuma, Y. "BIRB796 inhibits all p38 MAPK isoforms in vitro and in vivo", *J. Biol. Chem.*, 2005, 280:19472-19479.
Underwood D.C. et al., "SB239063, a p38 MAPK inhibitor, reduces neutrophilia, inflammatory cytokines, MMP-9, and fibrosis in lung", *Am. J. Physiol. Lung Cell. Mol. Physiol.*, 2000, 279:895-902.
Nath, P. et al., "Importance of p38 mitogen-activated protein kinase pathway in allergic airway remodeling and bronchial hyper-responsiveness", *Eur. J. Pharmacol.*, 2006, 544:160-167.
Irusen, E. et al., "p38 Mitogen-activated protein kinase-induced glucocorticoid receptor phosphorylation reduces its activity: Role in steroid-insensitive asthma", *J. Allergy Clin. Immunol.*, 2002, 109:649-657.

(Continued)

*Primary Examiner* — Kamal Saeed
(74) *Attorney, Agent, or Firm* — Ada O. Wong

(57) ABSTRACT

There are provided inter alia compounds of formula (I)

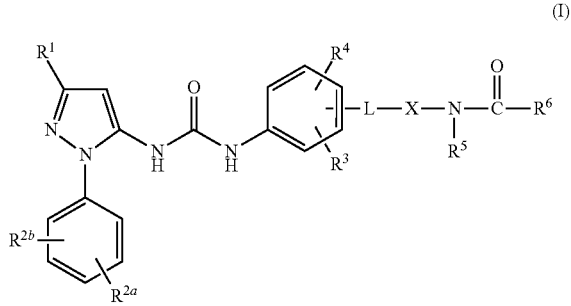

wherein $R^1$, $R^{2a}$, $R^{2b}$, $R^3$, $R^4$, L, X, $R^5$ and $R^6$ are as defined in the description for use in the treatment of inflammatory diseases.

31 Claims, 1 Drawing Sheet

(56) References Cited

OTHER PUBLICATIONS

Medicherla S. et al., "p38α-Selective Mitogen-Activated Protein Kinase Inhibitor SD-282 Reduces Inflammation in a Subchronic Model of Tobacco Smoke-Induced Airway Inflammation", *J. Pharm. Exp. Ther.*, 2008, 324:921-929.
Lee et al.., "MAP Kinase p38 Inhibitors: Clinical Results and an Intimate Look at Their Interactions with p38α Protein", *Current Med. Chem.*, 2005, 12,:2979-2994.
Mercado et al., "Formoterol restores costicosteroid sensitivity in severe asthma via p38 MAPK γ inhibition", American Thoracic Society Abstract, 2007.
Regan, J. et al.; Structure-Activity Relationships of the p38α MAP Kinase Inhibitor 1-(5-tert-Butyl-2-p-tolyl-2H-pyrazol-3-2H-pryazol-3-yl)-3-(4-(2-morpholin-4-yl-ethoxy)naphthalene-1-7-yl)urea (BIRB 795) *Journal of Medicinal Chemistry.*, 2003, 46, 4676-4686.
Silverman, R. B. The Organic Chemistry of Drug Design and Drug Action, Academic Press, pp. 19-23, 1992.

Figure 1: The effect of intranasal administration of Compound Example 9, in mice exposed to cigarette smoke, on neutrophil accumulation in BALF.
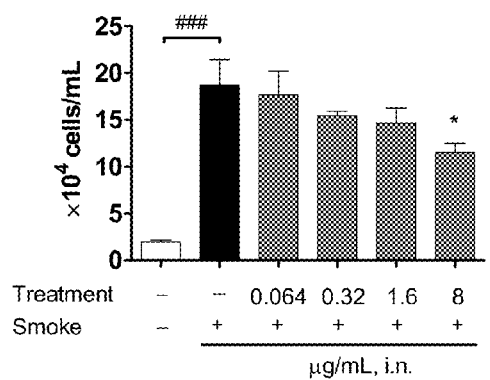
Figure 2: The effect of intranasal administration of Compound Example 9 in mice exposed to cigarette smoke, on MOMA2$^+$ macrophage accumulation in BALF.
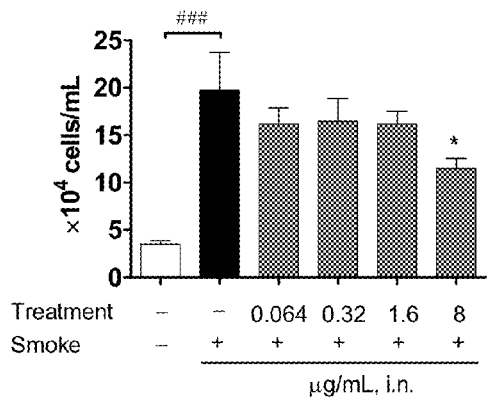

PYRAZOLE P38 MAP KINASE INHIBITORS

This application is a Continuation application of U.S. Ser. No. 13/638,640, filed Oct. 1, 2012 which is a National Stage application under 35 U.S.C. 371 of PCT International Application No. PCT/GB2011/050668, filed Apr. 1, 2011, which claims priority from Great Britain patent application number GB 1005589.5, filed Apr. 1, 2010, the contents of which are hereby incorporated by reference in their entirety.

FIELD OF THE INVENTION

The invention relates to compounds which are inhibitors of p38 mitogen-activated protein kinase enzymes (referred to herein as p38 MAP kinase inhibitors), for example the alpha and gamma kinase sub-types thereof, and their use in therapy, including in pharmaceutical combinations, especially in the treatment of inflammatory diseases, including inflammatory diseases of the lung, such as COPD.

BACKGROUND OF THE INVENTION

Four p38 MAPK isoforms (alpha, beta, gamma and delta respectively) have been identified, each displaying a tissue-specific expression pattern. The p38 MAPK alpha and beta isoforms are ubiquitously expressed throughout the body and are found in many different cell types. The p38 MAPK alpha and beta isoforms are inhibited by certain known small molecule p38 MAPK inhibitors. Earlier generations of compounds were highly toxic due to the ubiquitous expression pattern of these isoforms and off-target effects of the compounds. More recent inhibitors are improved to be highly selective for p38 MAPK alpha and beta isoforms and have a wider safety margin.

Less is known about the p38 MAPK gamma and delta isoforms. These isoforms are expressed in specific tissues/cells (unlike the p38 alpha and p38 beta isoforms). The p38 MAPK-delta isoform is expressed more in the pancreas, testes, lung, small intestine and kidney. It is also abundant in macrophages and detectable in neutrophils, CD4+ T cells and endothelial cells (Shmueli, O. et al., *Comptes Rendus Biologies* 326(10-11):1067-1072, (2003)/Genecard; Smith, S. J. *Br. J. Pharmacol.*, 2006, 149:393-404; Hale, K. K., *J. Immunol.*, 1999, 162(7):4246-52; Wang, X. S. et al., *J. Biol. Chem.*, 1997, 272(38):23668-23674.) Very little is known about the expression of p38 MAPK gamma although it is expressed more highly in brain, skeletal muscle and heart, as well as in lymphocytes and macrophages. (Shmueli, O. et al., *Comptes Rendus Biologies*, 2003, 326(10-11):1067-1072, (2003)/Genecard; Hale, K. K., *J. Immunol.*, 1999, 162(7):4246-52: Court, N. W. et al., *J. Mol. Cell. Cardiol.*, 2002, 34(4):413-26; Mertens, S. et al., *FEBS Lett.*, 1996, 383(3):273-6.)

Selective small molecule inhibitors of p38 MAPK-gamma and p38 MAPK-delta are not currently available, although one existing compound, BIRB 796, is known to have pan-isoform inhibitory activity. The p38 MAPK gamma and delta isoform inhibition is observed at higher concentrations of the compound than those required to inhibit p38 MAPK alpha and p38 beta (Kuma, Y. *J. Biol. Chem.*, 2005, 280:19472-19479). BIRB 796 also impaired the phosphorylation of p38 MAPKs or JNKs by the upstream kinase MKK6 or MKK4. Kuma discussed the possibility that the conformational change caused by the binding of the inhibitor to the MAPK protein may affect the structure of both its phosphorylation site and the docking site for the upstream activator, therefore impairing the phosphorylation of p38 MAPKs or JNKs.

p38 MAP kinase is believed to play a pivotal role in many of the signalling pathways that are involved in initiating and maintaining chronic, persistent inflammation in human disease, for example, in severe asthma and COPD. There is now abundant literature which demonstrates that p38 MAP kinase is activated by a range of pro-inflammatory cytokines and that its activation results in the recruitment and release of further pro-inflammatory cytokines. Indeed, data from some clinical studies demonstrate beneficial changes in disease activity in patients during treatment with p38 MAP kinase inhibitors. For instance Smith, S. J. *Br. J. Pharmacol.*, 2006, 149:393-404 describes the inhibitory effect of p38 MAP kinase inhibitors on TNFα (but not IL-8) release from human PBMCs. Use of inhibitors of p38 MAP kinase in the treatment of chronic obstructive pulmonary disease (COPD) is proposed. Small molecule inhibitors targeted to p38 MAPKα/β have proved to be effective in reducing various parameters of inflammation in cells and tissues obtained from patients with COPD, who are generally corticosteroid insensitive, (Smith, S. J. *Br. J. Pharmacol.*, 2006, 149:393-404) and in vivo animal models (Underwood, D. C. et al. *Am. J. Physiol.*, 2000, 279:L895-902; Nath, P. et al., *Eur. J. Pharmacol.*, 2006, 544:160-167). Irusen and colleagues also suggested the possibility of involvement of p38 MAPKα/β on corticosteroid insensitivity via reduction of binding affinity of glucocorticoid receptor (GR) in nuclei (Irusen, E. et al., *J. Allergy Clin. Immunol.*, 2002, 109:649-657). Clinical experience with a range of p38 MAP kinase inhibitors, including AMG548, BIRB 796, VX702, SCIO469 and SCIO323 has been described (Lee M. R. and Dominguez, C. *Current Med. Chem.*, 2005, 12:2979-2994).

COPD is a condition in which the underlying inflammation is reported to be substantially resistant to the anti-inflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. The recent publication of Mercado et al. (2007; *American Thoracic Society Abstract A56*) demonstrates that silencing p38 gamma has the potential to restore sensitivity to corticosteroids. Thus there may be a "two pronged" benefit to the use of a p38 MAP kinase inhibitor for the treatment of COPD and severe asthma.

However, the major obstacle hindering the utility of p38 MAP kinase inhibitors in the treatment of human chronic inflammatory diseases has been the toxicity observed in patients. This has been sufficiently severe to result in the withdrawal from clinical development of many of the compounds progressed, including all those specifically mentioned above.

There remains a need to identify and develop new compounds therapeutically useful as p38 MAP kinase inhibitors which have improved therapeutic potential, in particular which are more efficacious, longer acting and/or less toxic at the relevant therapeutic dose. An objective of the present invention is to provide compounds which inhibit p38 MAP kinase, for example with certain sub-type specificity, which show good anti-inflammatory potential, in particular suitable for use in therapy.

SUMMARY OF THE INVENTION

According to the invention, there is provided a compound of formula (I)

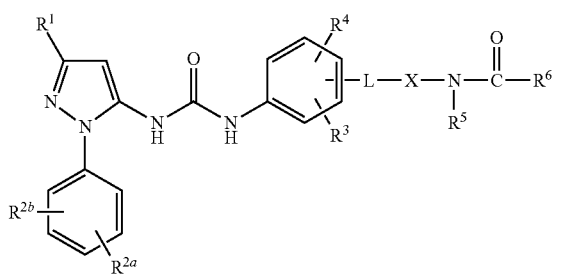

wherein:

R[1] is H,
phenyl, or
a saturated or unsaturated branched or unbranched $C_{1-10}$ alkylene acyclic or alicyclic chain wherein one or more carbons in the chain (for example 1 to 3, such as 1, 2 or 3 carbons) are optionally replaced by a heteroatom(s) independently selected from O, N and $S(O)_n$ and the chain is optionally substituted by:
one oxo group and/or
one or more halogen atoms (for example 1 to 6);

R[2a] is H, halo, saturated or unsaturated branched or unbranched $C_{1-8}$ alkylene chain, wherein one or more carbons (for example 1 to 3, such as 1, 2 or 3 carbons) are optionally replaced by a heteroatom(s) independently selected from O, N and/or $S(O)_m$ and the chain is optionally substituted by one or more halogen atoms (for example 1 to 6);

R[2b] is H, halo, $C_{1-6}$ alkoxy or $C_{1-6}$ alkyl optionally substituted by OH;

R[3] is halo, haloalkyl, $S(O)_p C_{1-6}$ alkyl or cyano;

R[4] is H, halo, haloalkyl, or cyano; or

R[3] and R[4] taken together with the carbons atoms to which they are attached form:
a 5 to 6 membered saturated or partially unsaturated carbocyclic ring, or
a 5 to 6 membered saturated or partially unsaturated or unsaturated heterocyclic ring containing 1 or more (such as 1 or 2) heteroatoms independently selected from N, O and/or S;

L is saturated or unsaturated branched or unbranched $C_{1-6}$ alkylene chain (such as a $C_{1-3}$ alkylene), wherein one or more carbons (for example 1 to 3, such as 1, 2 or 3 carbons) are optionally replaced by a heteroatom selected from —O— and/or S, and the chain is optionally substituted by one or two oxo groups (for example 1 or 2);

X is pyridine or pyrimidine optionally substituted by $C_{1-3}$ alkyl, or $C_{1-3}$ haloalkyl;

R[5] H or $C_{1-4}$ alkyl;

R[6] is selected from:
a) a saturated or unsaturated, branched or unbranched $C_{1-10}$ alkyl chain, wherein optionally at least one carbon (for example 1, 2 or 3 carbons, suitably 1 or 2, in particular 1 carbon) is replaced by a heteroatom independently selected from O, N, $S(O)_p$, wherein said chain is optionally, substituted by one or more groups (for example 1, 2 or 3 groups) independently selected from oxo, halogen, a $C_{6-10}$ aryl group, a 5 or 6 membered heteroaryl group, a 5 or 6 membered heterocyclyl group or a $C_{3-8}$ cycloalkyl group,
each aryl, heteroaryl, heterocyclyl or cycloalkyl group bearing 0 to 3 substituents selected from halogen, hydroxyl, $C_{1-6}$ alkyl, $C_{1-6}$ alkoxy, $C_{1-6}$ haloalkyl, amino, $C_{1-4}$ mono or $C_{2-8}$ di-alkyl amino, $C_{1-4}$ mono or $C_{2-8}$ di-acyl amino, $S(O)_q C_{1-6}$ alkyl, $C_{0-6}$ alkylC(O) $C_{1-6}$ alkyl or $C_{0-6}$ alkylC(O)N$C_{0-6}$ alkyl $C_{0-6}$ alkyl, $C_{0-6}$ alkylC(O)$C_{1-6}$ heteroalkyl,
with the proviso that the atom linked directly to the carbonyl in —NR[5]C(O)— is not an oxygen or a sulfur atom; and b) a $C_{0-8}$ alkyl-heterocycle wherein the heterocyclyl group has 5 or 6 members and comprises at least one heteroatom (for example 1, 2 or 3, suitably 1 or 2, in particular 1 heteroatom) selected from O, N, and S, and said heterocycle is optionally substituted by one, two or three groups independently selected from halogen, hydroxyl, $C_{1-6}$ alkyl, $C_{1-6}$ alkoxy, $C_{1-6}$ haloalkyl, amino, $C_{1-4}$ mono and $C_{2-8}$ di-alkyl amino, $C_{1-4}$ mono or $C_{2-8}$ di-acyl amino, $S(O)_q C_{1-6}$ alkyl, $C_{0-6}$ alkylC(O)$C_{1-6}$ alkyl, $C_{0-6}$ alkylC(O) N$C_{0-6}$ alkyl $C_{0-6}$ alkyl or $C_{0-6}$ alkylC(O)$C_{0-6}$ heteroalkyl;

n is 0, 1 or 2;
m is 0, 1 or 2;
p is 0, 1 or 2;
q is 0, 1 or 2; or
a pharmaceutically acceptable salt thereof, including all stereoisomers, tautomers and isotopic derivatives thereof.

The relative positions of the substituents R[3], R[4] and L in the aromatic nucleus of compounds of formula (I) are not fixed. For example, the substituent R[3] may be in any one of the positions within the ring, namely position 2, 3, 4, 5 or 6. If present, R[4] may be in any position other those occupied by the "aniline nitrogen" and by substituent R[3]. Finally the group L may be attached to the aromatic system in any position that remains unoccupied by the "anilino nitrogen" and, if present, the substituents R[3] and R[4].

BRIEF DESCRIPTION OF THE FIGURES

FIG. 1 shows the effect of intranasal administration of compound Example 9 on neutrophil accumulation in BALF in mice previously exposed to cigarette smoke.

FIG. 2 shows the effect of intranasal administration of compound Example 9 on activated macrophage accumulation in BALF in mice previously exposed to cigarette smoke.

DETAILED DESCRIPTION OF THE INVENTION

Alkyl as used herein refers to straight chain or branched chain alkyl, such as, without limitation, methyl, ethyl, n-propyl, iso-propyl, butyl, n-butyl and tert-butyl. In one embodiment alkyl refers to straight chain alkyl. Alkylene is to be interpreted in a similar manner to alkyl.

An acyclic chain refers to a chain without ring atoms. An alicyclic chain refers to an aliphatic chain with ring atoms.

Alkoxy as used herein refers to straight or branched chain alkoxy, for example methoxy, ethoxy, propoxy, butoxy. Alkoxy as employed herein also extends to embodiments in which the oxygen atom is located within the alkyl chain, for example —$C_{1-3}$ alkylO$C_{1-3}$ alkyl, such as —$CH_2CH_2OCH_3$ or —$CH_2OCH_3$. Thus in one embodiment the alkoxy is linked through carbon to the remainder of the molecule. In one embodiment the alkoxy is linked through oxygen to the remainder of the molecule, for example —$OC_{1-6}$ alkyl. In one embodiment the disclosure relates to a straight chain alkoxy.

Heteroalkyl as employed herein is intended to refer to a branched or straight chain alkyl wherein one or more, such as 1, 2 or 3 carbons are replaced by a heteroatom, selected from N, O or S(O)$_r$, wherein r represents 0, 1 or 2. The heteroatom may replace a primary, secondary or tertiary carbon, that is, for example, SH, OH or NH$_2$ for CH$_3$, or NH or O or SO$_2$ for —CH$_2$— or N for a —CH— or a branched tertiary carbon, as technically appropriate.

Haloalkyl as employed herein refers to alkyl groups having 1 to 6 halogen atoms, for example 1 to 5 halogens, including perhaloalkyl, in particular perchloroalkyl or perfluoroalkyl, more specifically —CCl$_3$, —CF$_2$CF$_3$ or CF$_3$.

$C_{1-4}$ mono and $C_{2-8}$ di-acyl amino are intended to refer to —NHC(O)C$_{1-4}$ alkyl and to —N(C=OC$_{1-4}$ alkyl)(C=OC$_{1-4}$ alkyl) respectively.

$C_{1-4}$ mono and $C_{2-8}$ di-alkyl amino are intended to refer to —NHC$_{1-4}$ alkyl and to —N(C$_{1-4}$ alkyl)(C$_{1-4}$ alkyl) respectively.

Aryl as used herein refers to, for example $C_{6-14}$ mono or polycyclic systems having from 1 to 3 rings wherein at least one ring is aromatic including phenyl, naphthyl, anthracenyl, 1,2,3,4-tetrahydronaphthyl and the like, such as phenyl and naphthyl.

Heteroaryl is a 6 to 10 membered aromatic monocylic ring or bicyclic ring system wherein at least one ring is an aromatic nucleus comprising one or more, for example 1, 2, 3 or 4 heteroatoms independently selected from O, N and S. Examples of heteroaryls include: pyrrole, oxazole, thiazole, isothiazole, imidazole, pyrazole, isoxazole, pyridine, pyridazine, pyrimidine, pyrazine, benzothiophene, benzofuran, or 1, 2, 3 and 1, 2, 4 triazole.

Heterocyclyl as employed herein refers to a 5 to 6 membered saturated or partially unsaturated non-aromatic ring comprising one or more, for example 1, 2, 3 or 4 heteroatoms independently selected from O, N and S optionally one or two carbons in the ring may bear an oxo substituent. The definition of $C_{5-6}$ heterocycle as employed herein refers to a 5 to 6 membered saturated or partially unsaturated non-aromatic carbocyclic ring comprising one or more, for example 1, 2, 3 or 4 heteroatoms independently selected from O, N and S, wherein each heteroatom replaces a carbon atom and optionally one or two carbons may bear an oxo substitutent. Clearly any valancies of a heteroatom not employed in forming or retaining the ring structure may be filled by hydrogen or a substituent, as appropriate. Thus substituents on heterocycles may be on carbon or on a heteroatom, such as nitrogen as appropriate. Examples of heterocycles and $C_{5-6}$ heterocycles include pyrroline, pyrrolidine, tetrahydrofuran, tetrahydrothiophene, pyrazoline, imidazoline, pyrazolidine, imidazolidine, oxoimidazolidine, dioxolane, thiazolidine, isoxazolidine, pyran, dihydropyran, piperidine, piperazine, morpholine, dioxane, thiomorpholine and oxathiane.

Halogen includes fluoro, chloro, bromo or iodo, in particular fluoro, chloro or bromo, especially fluoro or chloro.

Oxo as used herein refers to C=O and will usually be represented as C(O).

S(O)$_q$C$_{1-6}$ alkyl may, for example, include —SO$_2$Me.

$C_{3-8}$ cycloalkyl as employed herein is intended to refer to a saturated or partially unsaturated non-aromatic ring containing 3 to 8 carbon atoms, where the ring contains less than 8 carbons the ring may optionally bear one or more alkyl groups such that the number of carbon atoms in the ring plus the number of carbons in the alkyl substituents is not more than eight in total or 10 in the case of $C_{3-10}$ cycloalkyls.

$C_{1-10}$ alkyl includes $C_2$, $C_3$, $C_4$, $C_5$, $C_6$, $C_7$, $C_8$ or $C_9$ as well as $C_1$ and $C_{10}$ $C_{0-8}$ alkyl includes $C_1$, $C_2$, $C_3$, $C_4$, $C_5$, $C_6$, or $C_7$ as well as $C_0$ and $C_8$.

In relation to a saturated or unsaturated, branched or unbranched $C_{1-10}$ alkyl chain (or similar language used herein), wherein at least one carbon (for example 1, 2 or 3 carbons, suitably 1 or 2, in particular 1) is replaced by a heteroatom selected from O, N, S(O)$_p$, wherein said chain is optionally, substituted by one or more groups independently selected from oxo, halogen, an aryl group, a heteroaryl group or a heterocyclyl group, it will be clear to persons skilled in the art that the heteroatom may replace a primary, secondary or tertiary carbon, that is CH$_3$, —CH$_2$— or a —CH—, a tertiary carbon group or —CH=, as technically appropriate.

Saturated or unsaturated, branched or unbranched $C_{1-10}$ alkyl alicyclic chain is intended to refer to $C_{3-10}$ cycloalkyl.

In one embodiment $R^1$ is —C$_{1-6}$ alkyl optionally substituted by OH, $C_{3-10}$ cycloalkyl, $C_{3-10}$ heterocycloalkyl, $C_{1-6}$ haloalkyl, $C_{1-6}$ alkylOC(O)CH$_3$.

In one embodiment of the disclosure there is provided compounds of formula (I), wherein $R^1$ is methyl, ethyl, propyl, iso-propyl, butyl or tert-butyl, in particular tert-butyl.

In one embodiment $R^1$ is —C(CH$_3$)$_2$CH$_2$OH.

In one embodiment $R^1$ is cyclopropyl, or 1-methylcyclopropyl, cyclopentyl, cyclohexyl, or 1-methylcyclohexyl, or adamantyl.

In one embodiment $R^1$ is tetrahydropyranyl or 4-methyltetrahydro-2H-pyran-4-yl.

In one embodiment $R^1$ is —CF$_3$, —CF$_2$CF$_3$ or —CCl$_3$.

In one embodiment $R^1$ is phenyl.

In one embodiment $R^{2a}$ is in the 2, 3, or 4 position (i.e. ortho, meta or para position), in particular the para (4) position.

In one embodiment $R^{2a}$ is methyl, ethyl, n-propyl, iso-propyl, n-butyl or tert-butyl, in particular methyl, for example in position 3 or 4.

In one embodiment $R^{2a}$ is —OH, for example in position 3 or 4.

In one embodiment $R^{2a}$ is halo, such as chloro, for example in position 3 or 4.

In one embodiment $R^{2a}$ is —C$_{1-6}$ alkyl substituted by a hydroxyl group such as —CH$_2$OH, for example in position 3 or 4.

In one embodiment $R^{2a}$ is —C$_{1-6}$ alkoxy, such as —OCH$_3$, for example in position 3 or 4.

In one embodiment $R^{2a}$ is —SC$_{1-6}$ alkyl, such as —SCH$_3$, for example in position 3 or 4.

In one embodiment $R^{2a}$ is —SO$_2$C$_{1-6}$ alkyl, such as —SO$_2$CH$_3$ for example in the 3 or 4 position.

In one embodiment $R^{2a}$ is —OCF$_3$, for example located in position 3 or 4.

In one embodiment $R^{2a}$ is —NR'R" wherein R" is H, —C$_{1-3}$ alkyl or —SO$_2$C$_{1-3}$alkyl, and R" is H or —C$_{1-3}$ alkyl, for example located in position 3 or 4. In one embodiment $R^{2a}$ is —NH$_2$, for example in position 3 or 4.

In one embodiment $R^{2a}$ is —NHSO$_2$CH$_3$, for example in position 3 or 4.

In one embodiment $R^{2b}$ is H.

In one embodiment $R^{2b}$ is halo, such as chloro, for example in position 3.

In one embodiment $R^{2a}$ is chloro and $R^{2b}$ is chloro, for example 3,4-dichloro.

In one embodiment $R^{2a}$ chloro is and $R^{2b}$ is —OCH$_3$, for example in positions 3,4 respectively.

In one embodiment $R^{2a}$ is —OCH$_3$ and $R^{2b}$ is —OCH$_3$, for example in position 3,4.

In one embodiment $R^{2a}$ chloro is and $R^{2b}$ is —OH, for example in position 3,4 respectively.

In one embodiment $R^3$ is in position 2, relative to the anilino nitrogen atom.

In one embodiment $R^4$ is in position 3 or position 5, in particular position 3.

In one embodiment L is in position 4.

In one embodiment $R^3$ is fluoro, chloro, —$SO_2CH_3$, or —$CF_3$.

In one $R^4$ is H, chloro or cyano.

In one embodiment $R^3$ and $R^4$ respectively represent chloro and cyano or both represent chloro, for example in positions 2 and 3 respectively.

In one embodiment $R^3$ and $R^4$ together with the phenyl to which they are attached represents indazolyl or 5,6,7,8-tetrahydronaphthalenyl.

The combined definition of $R^3$ and $R^4$ for compounds of formula (I) does not extend to aromatic carbcyclic groups such as naphthylene.

In one embodiment L represents O, $CH_2$, C=O or $S(O)_t$ where t is 0, 1 or 2, in particular 0 or 2.

In one embodiment L represents —$OCH_2$— or —$OCH_2CH_2$—.

In one embodiment when L represents —$OCH_2$— or —$OCH_2CH_2$—, $R^3$ and $R^4$ taken together with the carbons atoms to which they are attached does not represent quinoline.

In one embodiment X is pyridine.

In one embodiment $R^5$ is H.

In one embodiment 1, 2, 3 or 4 carbon atoms are replaced in the alkyl chain of $R^6$ by heteroatoms independently selected from O, N, S(O)p.

In one embodiment the heteroatom(s) replacing carbon(s) in the alkyl chain fragment of $R^6$ are selected from N and O.

In one embodiment the fragment $R^6$ is a saturated or unsaturated, branched or unbranched $C_{1-10}$ alkyl chain wherein at least one carbon (for example 1, 2, 3 or 4 carbons, in particular 1 or 2 carbons) is replaced by a heteroatom selected from O, N, $S(O)_p$, wherein said chain is optionally substituted by one or more groups selected from oxo, halogen, an aryl group, a heteroaryl group, a heterocyclyl group, or a $C_{3-8}$ cycloalkyl each aryl, heteroaryl, heterocyclyl or cycloalkyl group as per defined above for compounds of formula (I).

In one embodiment $R^6$ is a saturated or unsaturated, branched or unbranched $C_{1-8}$ alkyl chain or a $C_{1-6}$ alkyl chain, wherein at least one carbon is replaced by a heteroatom selected from —O, —N, $S(O)_p$. Alternatively, in this embodiment the alkyl chain may be a $C_{2-8}$ alkyl or a $C_{3-6}$ alkyl group, such as a $C_4$ alkyl or a $C_5$ alkyl group.

In one embodiment a nitrogen atom in the alkyl chain is directly bonded to the carbonyl of the fragment —$NR^5C(O)$ and additionally may be, for example, a terminal amino group. Thus in one embodiment $R^6$ represents $N(C_{1-4}$ alkyl$)C_{1-4}$ alkyl, $NHC_{1-9}$ alkyl, such as $NHC_{1-5}$ alkyl or $NH_2$, in particular —$NH_2$.

In one embodiment $R^6$ represents —$NHC_{1-6}$ alkyl such as —$NHCH_3$ or —$NHCH_2CH_3$ or —$NHCH(CH_3)_2$.

In one embodiment the $C_{1-10}$ alkyl chain of $R^6$ is substituted by at least or only one oxo group, for example substitution on the chain consists of a single oxo group.

In one embodiment the $C_{1-10}$ alkyl chain of $R^6$ is substituted by at least or only 1, 2, 3, 4, 5 or 6 halogen atoms.

In one embodiment $R^6$ is $C_{1-4}$alkyl-V—$R^7$, such as $C_{1-3}$alkyl-V—$R^7$ wherein:

V is a heteroatom selected from $NR^V$, O or $S(O)_p$;
$R^V$ represents H or $C_{1-3}$ alkyl;
$R^7$ is H or —$C_{1-3}$ alkyl, and p is as defined above, with the proviso that the total alkyl chain length is not more than 10 carbon atoms, including replacement heteroatoms and that the resulting radical $R^6$ is a stable group, for example —$CH_2SCH_3$, —$CH_2SO_2CH_3$, —$CH_2NHCH_3$, —$CH_2N(CH_3)_2$—$C(CH_3)_2NHCH_3$, —$CH(CH_3)N(CH_3)_2$, —$(CH_2)_3CH_2NHCH_3$, —$(CH_2)_3N(CH_3)_2$, —$CH_2OH$, —$CH_2OCH_3$, —$CH(CH_3)OCH_3$, or —$(CH_2)_2OCH_3$.

In one embodiment $R^6$ is $C_{1-3}$ alkyl-V—($C_{2-3}$ alkyl-Z—$R^8)_k$ wherein:

V is a heteroatom selected from N, NH, O or $S(O)_p$, such as N or NH
(V is N in the case where k=2, or will be selected from NH, O or $S(O)_p$, in the case where k is 1, in particular NH);
Z is independently selected from NH, O or $S(O)_p$;
$R^8$ is H or —$C_{1-3}$alkyl;
k is an integer 1 or 2 (such as 1); and
p is as defined above, with the proviso that the total alkyl chain length is not more than 10 carbon atoms, including replacement heteroatoms and that the resulting radical $R^6$ is a stable group. Suitably $R^6$ is $C_{1-3}$ alkyl-V—$C_{2-3}$ alkyl-$OCH_3$ such as $C_{1-3}$ alkyl-V—$(CH_2)_2OCH_3$, in particular —$CH_2O(CH_2)_2OCH_3$ and $CH_2S(CH_2)_2OCH_3$, or —$CH_2NH(CH_2)_2OCH_3$, $C_{1-3}$ alkyl-V—($C_{2-3}$ alkyl-$OCH_3)_k$ wherein k represents 2, such as —$CH_2N[(CH_2)_2OCH_3]_2$.

In one embodiment $R^6$ is $C_{1-3}$ alkyl-V—$C_{2-3}$ alkyl-Z—$C_{2-3}$ alkyl-Y—$R^9$, wherein V, Z and Y are independently a heteroatom selected from NH, O or S(O)p,
$R^9$ is H or methyl, and
p is as defined above, with the proviso that the total alkyl chain length is not more than 10 carbon atoms, including replacement heteroatoms and that the resulting radical Q is a stable group. Suitably Q is a radical such as —$CH_2V(CH_2)_2O(CH_2)_2OCH_3$, for example, —$CH_2O(CH_2)_2O(CH_2)_2OCH_3$, or —$CH_2NH(CH_2)_2O(CH_2)_2OCH_3$, or —$CH_2S(CH_2)_2O(CH_2)_2OCH_3$.

In one embodiment $R^6$ represents —$NR^{10}R^{11}$, and thus —$NR^5C(O)R^6$ comprises of a urea, where $R^{10}$ and $R^{11}$ independently represent hydrogen or a $C_{1-9}$ saturated or unsaturated, branched or unbranched alkyl chain, wherein one or more carbons, such as 1, 2 or 3 are optionally replaced by a heteroatom selected from O, N or $S(O)_p$. Said chain is optionally substituted by one or more groups independently selected from oxo, halogen, an aryl group, a heteroaryl group, a heterocyclyl or $C_{3-8}$ cycloalkyl group (such as oxo, halogen, an aryl group, a heteroaryl group or a heterocyclyl group), each aryl, heteroaryl or heterocyclyl group bearing 0 to 3 substituents independently selected from the relevant substituents listed above for compounds of formula (I), for example halogen, $C_{1-6}$ alkyl, $C_{1-6}$ alkoxy, $C_{1-6}$ haloalkyl, amino, $C_{1-4}$ mono or $C_{2-8}$ di-alkyl amino and $C_{1-4}$ mono or $C_{2-8}$ di-acyl amino with the proviso that the total alkyl chain length is not more than 10 carbon atoms, including replacement heteroatoms and that the resulting radical $R^6$ is a stable group.

In this urea embodiment in one sub-embodiment $R^{10}$ represents hydrogen.

Examples of ureas include those in which $R^{10}$ and $R^{11}$ are both hydrogen and thus $R^6$ is —$NH_2$, or where $R^6$ is —$NHCH_3$ or —$N(CH_3)_2$ thereby providing, for example, a fragment —$NR^5C(O)NH_2$ or —$NR^3C(O)NHCH_3$ or —$NR^3C(O)N(CH_3)_2$.

Examples of ureas containing a heteroatom in the alkyl chain include those in which $R^6$ is —$NH(CH_2)_2OCH_3$ or —$N[(CH_2)_2OCH_3]_2$. In one embodiment $R^6$ represents —$NHC_{2-6}$alkylO$C_{1-3}$alkyl, such as —$NHCH_2CH_2OCH_3$.

Examples of ureas containing an oxo substituent include those in which $R^6$ is —NHCH$_2$C(O)NH—C$_{2-3}$ alkyl-X$^1$—C$_{1-3}$ alkyl, wherein X$^1$ is a heteroatom selected from N, O or S(O)$_p$ and p is defined as above. Examples of the latter include those wherein $R^6$ is —NHCH$_2$C(O)NHCH$_2$CH$_2$OCH$_3$. Thus in one embodiment of the disclosure $R^6$ represents the radical —NHC$_{1-4}$ alkylC(O)NHC$_2$alkylOCH$_3$ such as —NHCH$_2$C(O)NHCH$_2$CH$_2$OCH$_3$.

In one embodiment $R^6$ represents —NHC$_{1-4}$ alkylC(O)R$^{12}$ wherein R$^{12}$ is selected from OH or —NR$^{13}$R$^{14}$ where R$^{13}$ is hydrogen or C$_{1-3}$ alkyl and R$^{14}$ is hydrogen or C$_{1-3}$ alkyl, for example —NHC$_{1-4}$ alkylC(O)R$^{12}$ is —NHCH$_2$C(O)OH, —NHCH$_2$C(O)NH$_2$ or —NHCH$_2$C(O)NHCH$_3$.

In one embodiment $R^6$ represents —NHC$_{1-4}$ alkylC(O)OC$_{1-3}$ alkyl, such as, for example, —NHCH$_2$C(O)OCH$_2$CH$_3$.

In a further sub-embodiment of ureido derivatives $R^6$ represents —N(R$^{15}$)C$_{2-3}$ alkyl-V—(C$_{2-3}$ alkyl-Z—R$^{16}$)$_k$ wherein:

V represents N, NH, O, S(O)p;
Z represents NH, O, S(O)p;
k is an integer 1 or 2;
p is an integer 0, 1 or 2
R$^{15}$ represents H or C$_{1-3}$ alkyl; and
R$^{16}$ is H or C$_{1-3}$ alkyl such as C$_{1-3}$ alkyl;

with the proviso that the total alkyl chain length is not more than 10 carbon atoms, including replacement heteroatoms and that the resulting radical $R^6$ is a stable group.

In one embodiment $R^6$ is a saturated or unsaturated, branched or unbranched C$_{1-10}$ alkyl chain, wherein at least one carbon is replaced by a heteroatom selected from O, N, and S(O)$_p$, wherein said chain is substituted by an aryl group bearing 0 to 3 substituents, for example 1, 2 or 3, such as 1 or 2 substituents independently selected from the relevant substituents listed above for compounds of formula (I), for example from halogen, C$_{1-6}$ alkyl, C$_{1-6}$ alkoxy, C$_{1-6}$ haloalkyl, amino and C$_{1-4}$ mono or C$_{2-8}$ di-alkyl amino and C$_{1-4}$ mono or C$_{2-8}$ di-acyl amino, such as a saturated or unsaturated, branched or unbranched C$_{1-10}$ alkyl chain, wherein at least one carbon is replaced by a heteroatom selected from O, N, and S(O)$_p$, wherein said chain is substituted by an aryl group bearing 0 to 3 substituents, for example 1, 2 or 3, such as 1 or 2 substituents independently selected from halogen, C$_{1-6}$ alkyl, C$_{1-6}$ alkoxy, C$_{1-6}$ haloalkyl, amino and C$_{1-4}$ mono or di-alkyl amino. In one embodiment the said aryl group is phenyl, for example substituted phenyl or unsubstituted phenyl.

In one embodiment $R^6$ represents —NHC$_{0-6}$ alkylphenyl, such as —NHphenyl or —NHbenzyl.

Examples of the fragment —NR$^5$C(O)R$^6$ wherein R$^6$ comprises substituted benzyl include: —NR$^5$C(O)CH$_2$NHCH$_2$C$_6$H$_4$(OCH$_3$) such as —NHC(O)CH$_2$NHCH$_2$C$_6$H$_4$(OCH$_3$), for example where the methoxy substituent is in the ortho, meta or para position, such as the para position.

In one embodiment $R^6$ is a saturated or unsaturated, branched or unbranched C$_{1-10}$ alkyl chain, wherein at least one carbon is replaced by a heteroatom selected from O, N, and S(O)$_p$, wherein said chain is substituted by a heteroaryl group bearing 0 to 3 substituents (for example 1, 2 or 3, such as 1 or 2 substituents) independently selected from the relevant substituents listed above for compounds of formula (I), for example halogen, C$_{1-6}$ alkyl, C$_{1-6}$ alkoxy, C$_{1-6}$ alkyl amino, C$_{1-4}$ mono or C$_{2-8}$ di-alkyl amino and C$_{1-4}$ mono or C$_{2-8}$ di-acyl amino, such as a saturated or unsaturated, branched or unbranched C$_{1-10}$ alkyl chain, wherein at least one carbon is replaced by a heteroatom selected from O, N, and S(O)p, wherein said chain is substituted by a heteroaryl group bearing 0 to 3 substituents for example 1, 2 or 3, such as 1 or 2 substituents selected from halogen, C$_{1-6}$ alkyl, C$_{1-6}$ alkoxy, C$_{1-6}$ alkyl amino, C$_{1-4}$ mono or di-alkyl amino. In one embodiment the said heteroaryl group is selected from, thiophene, oxazole, thiazole, isothiazole, imidazole, pyrazole, isoxazole, isothiazole, oxadiazole, 1,2,3 or 1,2,4 triazole, pyridine, pyridazine, pyrimidine, pyrazine and, in particular pyridine and pyrimidine, especially pyridine.

In one embodiment $R^6$ represents —NHC$_{1-6}$ alkylheteroaryl, for example —NH(CH$_2$)$_3$imidazolyl or —NHCH$_2$isoxazole wherein the isoxazole is optionally substituted, such as —NHCH$_2$isoxazole(CH$_3$).

In one embodiment $R^6$ represents —NHC$_{1-4}$ alkylC(O)NHC$_{1-3}$alkylheteroaryl, for example a nitrogen containing heteroaryl group or a nitrogen and oxygen containing heteroaryl, more specifically —NHCH$_2$C(O)NHCH$_2$CH$_2$pyridinyl, in particular where pyridinyl is linked through carbon, for example pyridin-4-yl or —NHCH$_2$C(O)NHCH$_2$CH$_2$CH$_2$imidazolyl, in particular where imidazolyl is linked through nitrogen.

In one embodiment $R^6$ is a saturated or unsaturated, branched or unbranched C$_{1-10}$ alkyl chain, wherein at least one carbon is replaced by a heteroatom selected from O, N and S(O)p wherein said chain is substituted by a heterocyclyl group bearing 0 to 3 substituents (for example 1, 2 or 3, such as 1 or 2 substituents) independently selected from the relevant substituents listed above for compounds of formula (I), for example halogen, C$_{1-6}$ alkyl, C$_{1-6}$ alkoxy, C$_{1-6}$ haloalkyl amino, C$_{1-4}$ mono or C$_{2-8}$ di-alkyl amino and C$_{1-4}$ mono or C$_{2-8}$ di-acyl amino, such as a saturated or unsaturated, branched or unbranched C$_{1-10}$ alkyl chain, wherein at least one carbon is replaced by a heteroatom selected from O, N and S(O)$_P$ wherein said chain is substituted by a heterocyclyl group bearing 0 to 3 substituents, for example 1, 2 or 3, such as 1 or 2 substituents selected from halogen, C$_{1-6}$ alkyl, C$_{1-6}$ alkoxy, C$_{1-6}$ haloalkyl amino, C$_{1-4}$ mono or C$_{2-8}$ di-alkyl amino.

In one embodiment a heterocyclyl of $R^6$ is selected, from a 5 or 6 membered saturated or partially unsaturated ring system comprising one or more (for example 1, 2 or 3 in particular 1 or 2) heteroatoms independently selected from O, N and S, for example pyrrolidine, tetrahydrofuran, tetrahydrothiophene, piperidine, piperazine, morpholine, 1,4-dioxane, pyrrolidine and oxoimidazolidine such as pyrrolidine, tetrahydrofuran, tetrahydrothiophene, piperidine, piperazine, morpholine, and 1,4-dioxane, in particular piperidine, piperazine, and morpholine.

In one embodiment a heterocyclic group may be linked to the alkyl chain of $R^6$ or to the carbonyl of —NR$^5$C(O)— through carbon or nitrogen, in particular a nitrogen atom.

In one embodiment $R^6$ is —C$_{0-3}$ alkylheterocycle (for example —C$_{0-1}$ alkylheterocycle) said heterocyclyl group comprising at least one heteroatom (for example 1, 2 or 3, in particular 1 or 2, heteroatoms) selected from O, N and S, and is optionally substituted by one or two or three groups independently selected from the relevant substituents listed above for compounds of formula (I), for example halogen, C$_{1-6}$ alkyl, C$_{1-6}$ alkoxy, C$_{1-6}$ haloalkyl, amino, C$_{1-4}$ mono and di-alkyl amino and C$_{1-4}$ mono or C$_{2-8}$ di-acyl amino.

In one embodiment $R^6$ is —C$_0$ alkylheterocycle, for example a tetrahydropyranyl or a pyrrolidinyl or a morpholinyl or a piperazinyl or an oxoimidazolinyl group, such as 2-oxoimidazolidinyl group.

In one embodiment in which $R^6$ is —C$_0$ alkylheterocycle, the heterocycle is linked through carbon, and is, for example, a C-linked tetrahydropyran or a C-linked piperidine or a C-linked morpholine or a C-linked piperazine.

In one embodiment in which $R^6$ is —$C_0$alkylheterocycle, the heterocyclic group containing one or more N atoms is linked through N. This embodiment provides for ureas in which one of the urea nitrogens is embedded within a heterocyclic ring. Examples of this embodiment include, but are not limited to, an N-linked morpholine or an N-linked piperidine or an N-linked piperazine, said N-linked piperizinyl group optionally bearing an additional C- or N-substituent (such as an N-methyl group or N—$CH_2CH_2OCH_3$ group. In one embodiment $R^6$ is a heterocyclyl linked through nitrogen such as piperidinyl, in particular 4-hydroxypiperidinyl or piperazinyl, such as 4-methyl pierazinyl. Thus in one embodiment $R^6$ represents a heterocyclyl group, for example a nitrogen containing heterocyclyl group, in particular linked through N, such as morpholinyl or piperazinyl optionally substituted by methyl, especially 4-methyl, or piperidinyl.

In one embodiment $R^6$ represents tetrahydrofuranyl, morpholinyl, piperidinyl such as piperidinyl bearing one hyroxyl substituent, piperazinyl such as piperazinyl bearing one methyl substituent or pyrrolidinyl such a pyrrolidinyl bearing one di-methyl amino substituent. The ring may be linked through the heteroatom, such as nitrogen. Alternatively, the ring may be linked through carbon. The substituent may, for example be para relative to the atom through which the ring is linked to the remainder of the molecule.

In one embodiment $R^6$ is a —$C_1$ alkylheterocycle, for example tetrahydropyranylmethyl or a C- or N-linked piperazinylmethyl optionally bearing a substituent (for example a $C_{1-6}$ alkyl substitutent such as methyl or a $C_{1-6}$ alkoxy substituent such as —$CH_2CH_2OCH_3$). Additional examples include a C- or N-linked pyrrolidinylmethyl, or a C- or N-linked oxoimidazolinyl methyl (such as 2-oxoimidazolidinylmethyl, said heterocycle optionally bearing a substitutent (such as N-methyl or N—$SO_2CH_3$).

In one embodiment $R^6$ represents —NHheterocyclyl (wherein the heterocyclyl bears 0 to 3 substituents selected from the relevant list of substituents listed above for compounds of formula (I), for example halogen, hydroxy, $C_{1-6}$ alkyl, $C_{1-6}$ alkoxy, $C_{1-6}$ haloalkyl, amino, $C_{1-4}$ mono or di-alkyl amino, —S(O)q$C_{1-6}$ alkyl, $C_{1-4}$ mono or $C_{2-8}$ di-acyl amino, $C_{0-6}$ alkylC(O)$C_{1-6}$ alkyl or $C_{0-6}$ alkylC(O)$C_{1-6}$ heteroalkyl), such as where the ring is linked through carbon, for example 2-piperidinyl or 3-piperidinyl or 4-piperidinyl, in particular 1-acetylpiperidin-4-yl, 1-methylpiperidin-4-yl, 1-(methylsulfonyl)piperidin-4-yl or 1-(2-(2-methoxyethoxy)acetyl)piperidin-4-yl.

In one embodiment $R^6$ represents —NH$C_{1-6}$ alkylheterocyclyl for example a nitrogen containing heterocyclyl group, in particular one linked through nitrogen, such as —NHCH$_2$CH$_2$morpholine, —NH(CH$_2$)$_3$morpholine or —NH(CH$_2$)$_4$morpholine.

In one embodiment $R^6$ represents —NH$C_{1-6}$ alkylC(O) heterocyclyl (wherein the heterocyclyl bears 0 to 3 substituents selected from the relevant list of substituents listed above for compounds of formula (I), for example halogen, hydroxy, $C_{1-6}$ alkyl, $C_{1-6}$ alkoxy, $C_{1-6}$ haloalkyl, amino, $C_{1-4}$ mono or di-alkyl amino, $C_{1-4}$ mono or $C_{2-8}$ di-acyl amino, $C_{0-6}$ alkylC(O)$C_{1-6}$ alkyl or $C_{0-6}$ alkylC(O)$C_{1-6}$ heteroalkyl) for example a nitrogen containing heterocyclyl group, in particular one linked through nitrogen, such as —NHCH$_2$C(O)-1-pyrrolindinyl, —NHCH$_2$C(O)-1-piperidinyl, —NHCH$_2$C(O)-4-morpholinyl or —NHCH$_2$C(O)piperazinyl such as —NHCH$_2$C(O)-4-methyl-1-piperazinyl.

In one embodiment $R^6$ represents —NH$C_{1-4}$ alkylC(O) NH$C_{1-3}$alkylheterocyclyl for example a nitrogen containing heterocyclyl group or a nitrogen and/or oxygen containing heterocyclyl, such as —NHCH$_2$C(O)NHCH$_2$CH$_2$morpholinyl, in particular where morpholinyl is linked through nitrogen.

In one embodiment $R^6$ represents —N($C_{1-3}$ alkyl)$C_{1-6}$ alkylheterocyclyl, for example a nitrogen containing heterocyclyl group, in particular linked through nitrogen, such as —N(CH$_3$)CH$_2$CH$_2$morpholine, —N(CH$_3$)(CH$_2$)$_3$morpholine or —N(CH$_3$)(CH$_2$)$_4$morpholine.

In one embodiment $R^6$ is —$C_{1-3}$alkyl-G-$C_{1-3}$alkylheterocycle wherein G is a heteroatom selected from NH, O or S(O)$_p$ said heterocyclyl group comprising at least one heteroatom (for example 1, 2 or 3, in particular 1 or 2, heteroatoms) selected from O, N, and S, and is optionally substituted by one or two or three groups independently selected from relevant substituents listed above for compounds of formula (I), for example halogen, $C_{1-6}$ alkyl, $C_{1-6}$ alkoxy, $C_{1-6}$ haloalkyl, amino, $C_{1-4}$ mono and di-alkyl amino and $C_{1-4}$ mono or di-acyl amino such as one or two or three groups halogen, $C_{1-6}$ alkyl, $C_{1-6}$ alkoxy, $C_{1-6}$ haloalkyl, amino, $C_{1-4}$ mono and di-alkyl amino. Suitably $R^6$ is —CH$_2$G(CH$_2$)$_2$heterocycle for example —CH$_2$G(CH$_2$)$_2$tetrahydropyranyl; or —CH$_2$G(CH$_2$)$_2$morpholinyl in which the heterocyclyl is linked through nitrogen or carbon; or CH$_2$G(CH$_2$)$_2$piperazinyl in which the heterocyclyl is linked through nitrogen or carbon and optionally bearing a further C- or N-substituent (for example a $C_{1-6}$ alkyl substitutent such as methyl or a $C_{1-6}$ alkoxy substituent such as —CH$_2$CH$_2$OCH$_3$); or —CH$_2$G(CH$_2$)$_2$pyrrolidinyl, in which the heterocyclyl is linked through nitogen or carbon, for example linked through nitrogen; or —CH$_2$G(CH$_2$)$_2$oxoimidazolinyl (such as 2-oxoimidazolidinyl) for example linked through N and optionally bearing an additional C- or N-substitutent (such as N-methyl or N—SO$_2$CH$_3$), and in which G is O or NH.

In one embodiment G is O.

In one embodiment G is NH.

In one embodiment $R^6$ is a saturated or unsaturated $C_{1-10}$ alkyl chain wherein at least one carbon (for example 1, 2 or 3 carbons) is replaced by a heteroatom selected from O, N, S(O)p wherein said chain is substituted by a $C_{3-8}$ carbocyclyl group and said alkyl chain is optionally substituted by one or more (for example 1 or 2) groups selected from oxo and halogen. In one embodiment said $C_{3-8}$ carbocyclyl group bears one or more groups (for example 1, 2 or 3 groups) independently selected from halogen, hydroxyl, $C_{1-6}$ alkyl, $C_{1-6}$ alkoxy, $C_{1-6}$ haloalkyl, amino, $C_{1-4}$ mono or di-alkyl amino, $C_{1-4}$ mono or di-acyl amino, S(O)q$C_{1-6}$ alkyl, $C_{0-6}$ alkylC(O)$C_{1-6}$ alkyl or $C_{0-6}$ alkylC(O)$C_{1-6}$ heteroalkyl.

In one embodiment $R^6$ represents —NH$C_{3-6}$ cycloalkyl, such as —NHcyclopropyl, —NHcyclopentyl or —NHcyclohexyl.

In one embodiment the aryl, heteroaryl or heterocyclyl group bears at least one —S(O)q$C_{1-6}$ alkyl substitutent and optionally bears one or two further relevant substituents independently selected from the list of substituents defined above for compounds of formula (I).

In one embodiment the $C_{5-6}$ heterocycle bears at least one —S(O)q$C_{1-6}$ alkyl substitutent and optionally bears one or two further substituents independently selected from the relevant list of substituents defined above for compounds of formula (I).

In one embodiment the aryl, heteroaryl or heterocyclyl group bears at least one hydroxyl substituent and optionally bears one or two further substituents independently selected from the relevant list of substituents defined above for compounds of formula (I).

In one embodiment the $C_{5-6}$ heterocycle bears at least one hydroxyl substituent and optionally bears one or two further substituents independently selected from the relevant list of substituents defined above for compounds of formula (I).

In one embodiment the aryl, heteroaryl or heterocyclyl group bears at least one $C_{1-4}$ mono and/or di-acyl amino substituent and optionally bears one or two further substituents independently selected from the relevant list defined above for compounds of formula (I).

In one embodiment the $C_{5-6}$ heterocycle bears at least one $C_{1-4}$ mono and/or di-acyl amino substituent and optionally bears one or two further substituents independently selected from the relevant list defined above for compounds of formula (I).

In one embodiment the aryl, heteroaryl or heterocyclyl group bears at least one $C_{0-6}$ alkylC(O)$C_{1-6}$ heteroalkyl substituent and optionally bears one or two further substituents independently selected from the relevant list defined above for compounds of formula (I).

In one embodiment the $C_{5-6}$ heterocycle bears at least one $C_{0-6}$ alkylC(O)$C_{1-6}$ heteroalkyl substituent and optionally bears one or two further substituents independently selected from the relevant list defined above for compounds of formula (I).

In one embodiment the aryl, heteroaryl or heterocyclyl group bears at least one $C_{0-6}$ alkylC(O)$C_{1-6}$ alkyl substituent and optionally bears one or two further substituents independently selected from the relevant list defined above for compounds of formula (I).

In one embodiment the $C_{5-6}$ heterocycle bears at least one $C_{0-6}$ alkylC(O)$C_{1-6}$ alkyl substituent and optionally bears one or two further substituents independently selected from the relevant substituents defined above for compounds of formula (I).

In one embodiment the alkyl chain fragment of $R^6$ does not bear any optional substituents.

In one embodiment the alkyl chain of $R^6$ is saturated.

In one embodiment the alkyl chain of $R^6$ is unbranched.

In one embodiment the alkyl chain fragment of $R^6$ bears 1, 2, or 3, for example 1 or 2, in particular 1 optional substituent.

It will be clear to persons skilled in the art that the heteroatom may replace a primary, secondary or tertiary carbon, that is a $CH_3$, $-CH_2-$ or a $-CH-$, group, as technically appropriate.

In one embodiment p is 0 or 2.

In one embodiment p is 1.

In one embodiment compounds of the disclosure include those in which the fragment $R^6$ is:
- $-CH_2OH$;
- $-CH_2OC_{1-6}$ alkyl, in particular $-CH_2OCH_3$;
- $-CH_2CH_2OCH_3$;
- $-CH_2O(CH_2)_2OCH_3$;
- $-CH(CH_3)OCH_3$;
- $-CH_2NHCH_3$ or $-CH_2N(CH_3)_2$;
- $-CH_2NHCH_2CH_2OCH_3$ or $-CH_2NHC(O)CH_2OCH_3$;
- $-CH_2SCH_3$, $-CH_2S(O)_2CH_3$ or $-CH_2NHC(O)CH_2S(O)_2CH_3$; or
- $-CH_2NHC(O)CH_2$.

In one embodiment compounds of the disclosure include those in which $R^6$ in formula (I) is represented by:
- $-CH_2OH$, in particular $-CH_2OH$;
- $-CH_2OC_{1-6}$ alkyl, in particular $-CH_2OCH_3$, especially $-CH_2OCH_3$;
- $-CH_2O(CH_2)_2OCH_3$, in particular $-CH_2O(CH_2)_2OCH_3$;
- $-CH(CH_3)OCH_3$ in particular $-CH(CH_3)OCH_3$;
- $-CH(CH_3)NHC_{1-3}$ alkyl in particular $-CH(CH_3)NHCH_3$;
- $-CH(CH_3)N(C_{1-3}$ alkyl)$_2$ in particular $-CH(CH_3)N(CH_3)_2$;
- $-C(CH_3)_2NHCH_3$ in particular $-C(CH_3)_2NHCH_3$;
- $-(CH_2)_2OC_{1-6}$ alkyl, such as $-(CH_2)_2OCH_3$, in particular $-(CH_2)_2OCH_3$;
- $-(CH_2)_3NHC_{1-3}$ alkyl in particular $-(CH_2)_3NHCH_3$;
- $-(CH_2)_3N(C_{1-3}$ alkyl)$_2$ in particular $-(CH_2)_3N(CH_3)_2$;
- $-CH_2NHC_{1-3}$ alkyl in particular $-CH_2NHCH_3$;
- $-CH_2NH(CH_2)_2OCH_3$;
- $-CH_2SCH_3$;
- $-CH_2S(CH_2)_2OCH_3$;
- $-CH_2S(CH_2)_2O(CH_2)_2OCH_3$;
- $-CH_2SOCH_3$;
- $-CH_2S(O)_2CH_3$;
- $-CH_2N[(CH_2)_2OCH_3]_2$;
- $-NH_2$;
- $-NHC_{1-9}$ alkyl, such as $-NHC_{1-7}$ alkyl, in particular $-NHCH_3$
- $-N(C_{1-4}$ alkyl)$C_{1-5}$ alkyl in particular $-N(CH_3)_2$; or
- $-NHCH_2CONH(CH_2)_2OCH_3$.

In one embodiment compounds of the disclosure include compounds of formula (I) in which $C_{0-8}$alkylheterocyclyl of $R^6$ is represented by:
- -tetrahydropyranyl, such as -tetrahydro-2H-pyran-4-yl;
- -morpholinyl such as -4-morpholinyl or $-NHC(O)(3$-morpholinyl);
- -pyrrolidinyl, such as -pyrrolidin-1-yl;
- -piperazinyl, such as -piperazin-1-yl;
- -methylpiperazinyl, such as -4-methylpiperazin-1-yl;
- -[(methoxyethyl)piperazinyl], such as -[4-(2-methoxyethyl)piperazin-1-yl];
- -oxoimidazolidinyl such as -2-oxoimidazolidinyl, in particular -2-oxoimidazolidin-1-yl;
- $-CH_2$-tetrahydropyranyl, such as $-CH_2$-tetrahydro-2H-pyran-4-yl;
- $-CH_2$-morpholinyl, such as $-CH_2$-4-morpholinyl;
- $-CH_2$-pyrrolidinyl, such as $-CH_2$-pyrrolidin-1-yl;
- $-CH_2$-piperazinyl, such as $-CH_2$-piperazin-1-yl;
- $-CH_2$-(methylpiperazinyl), such as $-CH_2$-(4-methylpiperazin-1-yl);
- $-CH_2$-[(methoxyethyl)piperazinyl], such as $-CH_2$-[4-(2-methoxyethy)piperazin-1-yl];
- $-CH_2SCH_2CH_2$-morpholinyl, such as, for example, $-CH_2SCH_2CH_2$-4-morpholinyl, or $-CH_2SCH_2CH_2$-3-morpholinyl; and
- $-CH_2SO_2CH_2CH_2$-morpholinyl, such as for example $-CH_2SO_2CH_2CH_2$-4-morpholinyl, or $-CH_2SO_2CH_2CH_2$-3-morpholinyl.

In one embodiment of the fragment $R^6$, the saturated or unsaturated, branched or unbranched $C_{1-10}$ alkyl chain, wherein at least one carbon is replaced by a heteroatom selected from $-O$, $-N$, $S(O)p$ is a linker selected from: $-CH_2OCH_2-$, $-CH_2NHCH_2-$, $-CH_2NH-$ and $-CH_2OCH_2CH_2-$. These fragments may optionally terminate in an aryl group, a heteroaryl group a heterocyclyl group or $C_{3-8}$ cycloalkyl group, such as an aryl group, a heteroaryl group a heterocyclyl group as defined for fragment $R^6$ above.

In one embodiment the disclosure relates to compounds of formula (IA):

(IA)

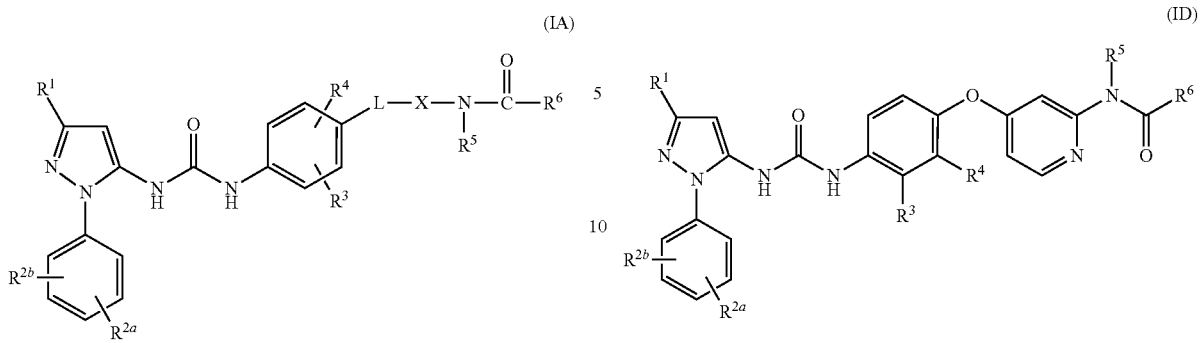

wherein $R^1$, $R^{2a}$, $R^{2b}$, $R^3$, $R^4$, $R^5$, L, X, and $R^6$ are defined above for compounds of formula (I).

In one embodiment the disclosure relates to compounds of formula (IB):

(IB)

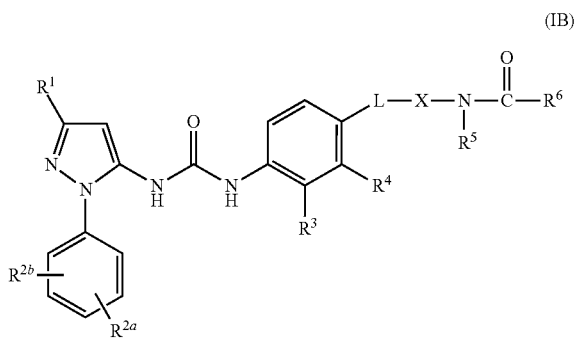

wherein $R^1$, $R^{2a}$, $R^{2b}$, $R^3$, $R^4$, $R^5$, L, X, and $R^6$ are defined above for compounds of formula (I).

In one embodiment the disclosure relates to compounds of formula (IC):

(IC)

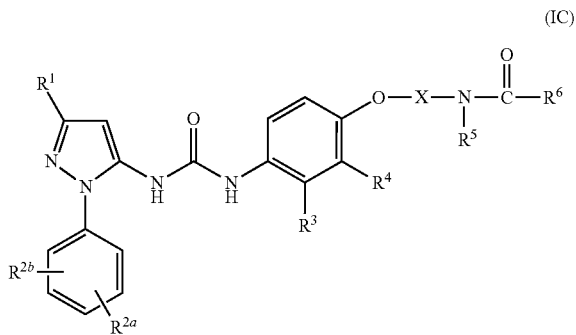

wherein $R^1$, $R^{2a}$, $R^{2b}$, $R^3$, $R^4$, $R^5$, X, and $R^6$ are defined above for compounds of formula (I).

In one embodiment the disclosure relates to compounds of formula (ID):

(ID)

wherein $R^1$, $R^{2a}$, $R^{2b}$, $R^3$, $R^4$, $R^5$ and $R^6$ are defined above for compounds of formula (I).

In one embodiment the compound is:
N-(4-(4-(3-(3-tert-Butyl-1-p-tolyl-1H-pyrazol-5-yl)ureido)-3-fluorophenoxy)pyridin-2-yl)-2-methoxyacetamide;
N-(4-(4-(3-(3-tert-Butyl-1-p-tolyl-1H-pyrazol-5-yl)ureido)-3-(methylsulfonyl)phenoxy)pyridin-2-yl)-2-methoxyacetamide;
N-(4-(4-(3-(3-tert-Butyl-1-p-tolyl-1H-pyrazol-5-yl)ureido)-3-(trifluoromethyl)phenoxy)pyridin-2-yl)-2-methoxyacetamide;
N-(4-(4-(3-(3-tert-Butyl-1-p-tolyl-1H-pyrazol-5-yl)ureido)-3-chloro-2-cyanophenoxy)pyridin-2-yl)-2-methoxyacetamide;
N-(4-(4-(3-(3-tert-Butyl-1-p-tolyl-1H-pyrazol-5-yl)ureido)-5,6,7,8-tetrahydronaphthalen-1-yloxy)pyridin-2-yl)-2-methoxyacetamide;
N-(4-(5-(3-(3-tert-Butyl-1-p-tolyl-1H-pyrazol-5-yl)ureido)quinolin-8-yloxy)pyridin-2-yl)-2-methoxyacetamide;
N-(4-(7-(3-(3-tert-Butyl-1-p-tolyl-1H-pyrazol-5-yl)ureido)-1H-indazol-4-yloxy)pyridin-2-yl)-2-methoxyacetamide;
N-Methyl-N'-4-(4-(3-(3-tert-Butyl-1-p-anisyl-1H-pyrazol-5-yl)ureido)-2,3-dichlorophen-1-yloxy)pyridin-2-ylurea;
N-(4-(4-(3-(3-tert-Butyl-1-(4-(methylthio)phenyl)-1H-pyrazol-5-yl)ureido)-2,3-dichlorophenoxy)pyridin-2-yl)pyrrolidine-1-carboxamide;
(R)—N-(4-(4-(3-(3-tert-Butyl-1-(4-hydroxyphenyl)-1H-pyrazol-5-yl)ureido)-2,3-dichlorophenoxy)pyridin-2-yl)-3-(dimethylamino)pyrrolidine-1-carboxamide;
N-(4-((4-(3-(3-tert-Butyl-1-p-tolyl-1H-pyrazol-5-yl)ureido)-2,3-dichlorophenoxy)methyl)pyridin-2-yl)-2-methoxyacetamide;
N-(4-((4-(3-(3-tert-Butyl-1-(4-methoxyphenyl)-1H-pyrazol-5-yl)ureido)-2,3-dichlorophenoxy)methyl)pyridin-2-yl)-2-methoxyacetamide;
N-(4-((5-(3-(3-tert-Butyl-1-p-tolyl-1H-pyrazol-5-yl)ureido)quinolin-8-yloxy)methyl)pyridin-2-yl)-2-methoxyacetamide;
N-(4-((5-(3-(3-tert-Butyl-1-(4-methoxyphenyl)-1H-pyrazol-5-yl)ureido)quinolin-8-yloxy)methyl)pyridin-2-yl)-2-methoxyacetamide;
1-(3-tert-Butyl-1-(4-methoxyphenyl)-1H-pyrazol-5-yl)-3-(2,3-dichloro-4-((2-(3-methylureido)pyridin-4-yl)methoxy)phenyl)urea;
N-(4-((4-(3-(3-tert-Butyl-1-(p-tolyl)-1H-pyrazol-5-yl)ureido)-2,3-dichlorophenoxy)methyl)pyridin-2-yl)pyrrolidine-1-carboxamide;
N-(4-((4-(3-(3-tert-Butyl-1-(4-methoxyphenyl)-1H-pyrazol-5-yl)ureido)-2,3-dichlorophenoxy)methyl)pyridin-2-yl)pyrrolidine-1-carboxamide;
1-(3-tert-Butyl-1-(p-tolyl)-1H-pyrazol-5-yl)-3-(8-((2-(3-methylureido)pyridin-4-yl)methoxy)quinolin-5-yl)urea;

3-(4-(4-(3-(3-tert-Butyl-1-(4-methoxyphenyl)-1H-pyrazol-5-yl)ureido)-2,3-dichlorophenoxy)pyridin-2-yl)-1,1-dimethylurea;

N-(4-(4-(3-(3-tert-Butyl-1-(4-methoxyphenyl)-1H-pyrazol-5-yl)ureido)-2,3-dichlorophenoxy)pyridin-2-yl)-2-methoxyacetamide;

N-(4-(4-(3-(3-tert-Butyl-1-(4-hydroxyphenyl)-1H-pyrazol-5-yl)ureido)-2,3-dichlorophenoxy)pyridin-2-yl)-2-methoxyacetamide;

1-(3-tert-Butyl-1-(4-hydroxyphenyl)-1H-pyrazol-5-yl)-3-(2,3-dichloro-4-((2-(3-methylureido)pyridin-4-yl)oxy)phenyl)urea;

(R)—N-(4-(4-(3-(3-tert-Butyl-1-(4-hydroxyphenyl)-1H-pyrazol-5-yl)ureido)-2,3-dichlorophenoxy)pyridin-2-yl)-3-(dimethylamino)pyrrolidine-1-carboxamide;

(S)—N-(4-(4-(3-(3-tert-Butyl-1-(4-hydroxyphenyl)-1H-pyrazol-5-yl)ureido)-2,3-dichlorophenoxy)pyridin-2-yl)-3-(dimethylamino)pyrrolidine-1-carboxamide;

N-(4-(4-(3-(3-tert-Butyl-1-(4-methoxyphenyl)-1H-pyrazol-5-yl)ureido)-2,3-dichlorophenoxy)pyridin-2-yl)pyrrolidine-1-carboxamide;

N-(4-(4-(3-(3-tert-Butyl-1-(4-hydroxyphenyl)-1H-pyrazol-5-yl)ureido)-2,3-dichlorophenoxy)pyridin-2-yl)pyrrolidine-1-carboxamide;

(R)—N-(4-(4-(3-(3-tert-Butyl-1-(4-methoxyphenyl)-1H-pyrazol-5-yl)ureido)-2,3-dichlorophenoxy)pyridin-2-yl)-3-(dimethylamino)pyrrolidine-1-carboxamide;

N-(4-(4-(3-(3-tert-Butyl-1-(4-methoxyphenyl)-1H-pyrazol-5-yl)ureido)-2,3-dichlorophenoxy)pyridin-2-yl)-3-hydroxypyrrolidine-1-carboxamide;

N-(4-(4-(3-(3-tert-Butyl-1-(4-methoxyphenyl)-1H-pyrazol-5-yl)ureido)-2,3-dichlorophenoxy)pyridin-2-yl)isoindoline-2-carboxamide;

N-(4-(4-(3-(3-tert-Butyl-1-(p-tolyl)-1H-pyrazol-5-yl)ureido)-2-chlorophenoxy)pyridin-2-yl)-2-methoxyacetamide;

3-(4-(4-(3-(3-tert-Butyl-1-(p-tolyl)-1H-pyrazol-5-yl)ureido)-2,3-dichlorophenoxy)pyridin-2-yl)-1,1-dimethylurea;

N-(4-(4-(3-(3-tert-Butyl-1-(p-tolyl)-1H-pyrazol-5-yl)ureido)-2-(trifluoromethyl)phenoxy)pyridin-2-yl)-2-methoxyacetamide;

N-(4-(4-(3-(3-tert-Butyl-1-(p-tolyl)-1H-pyrazol-5-yl)ureido)-2-(methylsulfonyl)phenoxy)pyridin-2-yl)-2-methoxyacetamide;

1-(3-tert-Butyl-1-(p-tolyl)-1H-pyrazol-5-yl)-3-(2,3-dichloro-4-((2-(3-methylureido)pyridin-4-yl)oxy)phenyl)urea;

N-(4-(4-(3-(3-tert-Butyl-1-(p-tolyl)-1H-pyrazol-5-yl)ureido)-2,3-dichlorophenoxy)pyridin-2-yl)pyrrolidine-1-carboxamide;

N-(4-(6-(3-(3-tert-Butyl-1-(p-tolyl)-1H-pyrazol-5-yl)ureido)-2,3-difluorophenoxy)pyridin-2-yl)-2-methoxyacetamide;

N-(4-(4-(3-(3-tert-Butyl-1-(p-tolyl)-1H-pyrazol-5-yl)ureido)-3-chloro-2-(trifluoromethyl)phenoxy)pyridin-2-yl)-2-methoxyacetamide;

N-(4-(4-(3-(3-tert-Butyl-1-(p-tolyl)-1H-pyrazol-5-yl)ureido)-5-chloro-2-fluorophenoxy)pyridin-2-yl)-2-methoxyacetamide;

N-(4-(4-(3-(3-tert-Butyl-1-(p-tolyl)-1H-pyrazol-5-yl)ureido)-3-chloro-2-fluorophenoxy)pyridin-2-yl)-2-methoxyacetamide;

N-(4-(3-Bromo-4-(3-(3-tert-butyl-1-(p-tolyl)-1H-pyrazol-5-yl)ureido)phenoxy)pyridin-2-yl)-2-methoxyacetamide;

N-(4-(2-Bromo-4-(3-(3-tert-butyl-1-(p-tolyl)-1H-pyrazol-5-yl)ureido)phenoxy)pyridin-2-yl)-2-methoxyacetamide;

N-(4-(4-(3-(3-tert-Butyl-1-(p-tolyl)-1H-pyrazol-5-yl)ureido)-3-chlorophenoxy)pyridin-2-yl)-2-methoxyacetamide;

N-(4-((8-(3-(3-tert-Butyl-1-(p-tolyl)-1H-pyrazol-5-yl)ureido)quinolin-5-yl)oxy)pyridin-2-yl)-2-methoxyacetamide;

N-(4-(4-(3-(3-tert-Butyl-1-(p-tolyl)-1H-pyrazol-5-yl)ureido)-2,3-dichlorophenoxy)pyridin-2-yl)-2-methoxyacetamide;

N-(4-(4-(3-(3-tert-Butyl-1-(p-tolyl)-1H-pyrazol-5-yl)ureido)-2,5-dichlorophenoxy)pyridin-2-yl)-2-methoxyacetamide;

N-(4-(2,3-Dichloro-4-(3-(3-(1-methylcyclohexyl)-1-(p-tolyl)-1H-pyrazol-5-yl)ureido)phenoxy)pyridin-2-yl)pyrrolidine-1-carboxamide;

1-(2,3-Dichloro-4-((2-(3-methylureido)pyridin-4-yl)oxy)phenyl)-3-(3-(1-methylcyclohexyl)-1-(p-tolyl)-1H-pyrazol-5-yl)urea or a pharmaceutically acceptable salt thereof, including all stereoisomers, tautomers and isotopic derivatives thereof.

In one embodiment the compound is:

N-(4-(4-(3-(3-tert-Butyl-1-p-tolyl-1H-pyrazol-5-yl)ureido)-3-fluorophenoxy)pyridin-2-yl)-2-methoxyacetamide;

N-(4-(4-(3-(3-tert-Butyl-1-p-tolyl-1H-pyrazol-5-yl)ureido)-3-(methylsulfonyl)phenoxy)pyridin-2-yl)-2-methoxyacetamide;

N-(4-(4-(3-(3-tert-Butyl-1-p-tolyl-1H-pyrazol-5-yl)ureido)-3-(trifluoromethyl)phenoxy)pyridin-2-yl)-2-methoxyacetamide;

N-(4-(4-(3-(3-tert-Butyl-1-p-tolyl-1H-pyrazol-5-yl)ureido)-3-chloro-2-cyanophenoxy)pyridin-2-yl)-2-methoxyacetamide;

N-(4-(4-(3-(3-tert-Butyl-1-p-tolyl-1H-pyrazol-5-yl)ureido)-5,6,7,8-tetrahydronaphthalen-1-yloxy)pyridin-2-yl)-2-methoxyacetamide;

N-(4-(5-(3-(3-tert-Butyl-1-p-tolyl-1H-pyrazol-5-yl)ureido)quinolin-8-yloxy)pyridin-2-yl)-2-methoxyacetamide;

N-(4-(7-(3-(3-tert-Butyl-1-p-tolyl-1H-pyrazol-5-yl)ureido)-1H-indazol-4-yloxy)pyridin-2-yl)-2-methoxyacetamide;

N-(4-(4-(3-(3-tert-Butyl-1-(4-(hydroxymethyl)phenyl)-1H-pyrazol-5-yl)ureido)-2,3-dichlorophenoxy)pyridin-2-yl)-2-(methylamino)acetamide;

N-Methyl-N'-4-(4-(3-(3-tert-butyl-1-p-anisyl-1H-pyrazol-5-yl)ureido)-2,3-dichlorophen-1-yloxy)pyridin-2-ylurea;

N-(4-(4-(3-(3-tert-Butyl-1-(4-(methylthio)phenyl)-1H-pyrazol-5-yl)ureido)-2,3-dichlorophenoxy)pyridin-2-yl)pyrrolidine-1-carboxamide;

(R)—N-(4-(4-(3-(3-tert-Butyl-1-(4-hydroxyphenyl)-1H-pyrazol-5-yl)ureido)-2,3-dichlorophenoxy)pyridin-2-yl)-3-(dimethylamino)pyrrolidine-1-carboxamide;

1-(4-(4-(3-(3-tert-Butyl-1-(4-methoxyphenyl)-1H-pyrazol-5-yl)ureido)-2,3-dichlorophenoxy)pyridin-2-yl)-3-ethylurea;

1-(3-tert-Butyl-1-(4-methoxyphenyl)-1H-pyrazol-5-yl)-3-(2,3-dichloro-4-((2-(3-(2-(dimethylamino)ethyl)ureido)pyridin-4-yl)oxy)phenyl)urea;

N-(4-((4-(3-(3-tert-Butyl-1-p-tolyl-1H-pyrazol-5-yl)ureido)-2,3-dichlorophenoxy)methyl)pyridin-2-yl)-2-methoxyacetamide;

N-(4-((4-(3-(3-tert-Butyl-1-(4-methoxyphenyl)-1H-pyrazol-5-yl)ureido)-2,3-dichlorophenoxy)methyl)pyridin-2-yl)-2-methoxyacetamide;

N-(4-((5-(3-(3-tert-Butyl-1-p-tolyl-1H-pyrazol-5-yl)ureido)quinolin-8-yloxy)methyl)pyridin-2-yl)-2-methoxyacetamide;

N-(4-((5-(3-(3-tert-Butyl-1-(4-methoxyphenyl)-1H-pyrazol-5-yl)ureido)quinolin-8-yloxy)methyl)pyridin-2-yl)-2-methoxyacetamide;

1-(3-tert-Butyl-1-(4-methoxyphenyl)-1H-pyrazol-5-yl)-3-(2,3-dichloro-4-((2-(3-methylureido)pyridin-4-yl)methoxy)phenyl)urea;

N-(4-((4-(3-(3-tert-Butyl-1-(p-tolyl)-1H-pyrazol-5-yl)ureido)-2,3-dichlorophenoxy)methyl)pyridin-2-yl)pyrrolidine-1-carboxamide;

N-(4-((4-(3-(3-tert-Butyl-1-(4-methoxyphenyl)-1H-pyrazol-5-yl)ureido)-2,3-dichlorophenoxy)methyl)pyridin-2-yl)pyrrolidine-1-carboxamide;

1-(3-tert-Butyl-1-p-tolyl-1H-pyrazol-5-yl)-3-(8-((2-(3-methylureido)pyridin-4-yl)methoxy)quinolin-5-yl)urea;

N-(6-(4-(3-(3-tert-Butyl-1-(4-hydroxymethyl)phenyl)-1H-pyrazol-5-yl)ureido)-2,3-dichlorophenoxy)pyrimidin-4-yl)-4-(dimethylamino)butanamide;

N-(4-(4-(3-(3-tert-Butyl-1-(4-methoxyphenyl)-1H-pyrazol-5-yl)ureido)-2,3-dichlorophenoxy)pyrimidin-2-yl)-2-methoxyacetamide;

1-(3-tert-Butyl-1-p-tolyl-1H-pyrazol-5-yl)-3-(2,3-dichloro-4-(6-(3-(2-(dimethylamino)ethyl)ureido)pyrimidin-4-yloxy)phenyl)urea;

1-(4-(4-(3-(3-tert-Butyl-1-(4-(hydroxymethyl)phenyl)-1H-pyrazol-5-yl)ureido)-2,3-dichlorophenoxy)pyrimidin-2-yl)-3-methylurea;

N-(4-((4-(3-(3-tert-Butyl-1-(4-methoxyphenyl)-1H-pyrazol-5-yl)ureido)-2,3-dichlorophenylthio)methyl)pyridin-2-yl)-2-methoxyacetamide;

N-(4-(4-(3-(3-tert-Butyl-1-p-tolyl-1H-pyrazol-5-yl)ureido)-3-chlorophenoxy)pyridin-2-yl)-2-methoxyacetamide;

N-(4-(4-(3-(3-tert-Butyl-1-p-tolyl-1H-pyrazol-5-yl)ureido)-2-cyanophenoxy)pyridin-2-yl)-2-methoxyacetamide;

N-(4-(4-(3-(3-tert-Butyl-1-p-tolyl-1H-pyrazol-5-yl)ureido)-2-chlorophenoxy)pyridin-2-yl)-2-methoxyacetamide;

N-(4-(4-(3-(3-tert-Butyl-1-p-tolyl-1H-pyrazol-5-yl)ureido)-2-trifluoromethylphenoxy)pyridin-2-yl)-2-methoxyacetamide;

N-(4-(4-(3-(3-tert-Butyl-1-p-tolyl-1H-pyrazol-5-yl)ureido)-2-methylsulfonylphenoxy)pyridin-2-yl)-2-methoxyacetamide;

N-(4-(3-bromo-4-(3-(3-tert-Butyl-1-p-tolyl-1H-pyrazol-5-yl)ureido)phenoxy)pyridin-2-yl)-2-methoxyacetamide;

N-(4-(2-bromo-4-(3-(3-tert-Butyl-1-p-tolyl-1H-pyrazol-5-yl)ureido)phenoxy)pyridin-2-yl)-2-methoxyacetamide;

N-(4-(4-(3-(3-tert-Butyl-1-p-tolyl-1H-pyrazol-5-yl)ureido)-2,3-difluorophenoxy)pyridin-2-yl)-2-methoxyacetamide;

N-(4-(4-(3-(3-tert-Butyl-1-p-tolyl-1H-pyrazol-5-yl)ureido)-3-chloro-2-fluorophenoxy)pyridin-2-yl)-2-methoxyacetamide;

N-(4-(4-(3-(3-tert-Butyl-1-p-tolyl-1H-pyrazol-5-yl)ureido)-2,3-dichlorophenoxy)pyridin-2-yl)-2-methoxyacetamide;

N-(4-(4-(3-(3-tert-Butyl-1-p-tolyl-1H-pyrazol-5-yl)ureido)-3-chloro-2-trifluoromethylphenoxy)pyridin-2-yl)-2-methoxyacetamide;

N-(4-(4-(3-(3-tert-Butyl-1-p-tolyl-1H-pyrazol-5-yl)ureido)-5-chloro-2-fluorophenoxy)pyridin-2-yl)-2-methoxyacetamide;

N-(4-(4-(3-(3-tert-Butyl-1-p-tolyl-1H-pyrazol-5-yl)ureido)-2,5-dichlorophenoxy)pyridin-2-yl)-2-methoxyacetamide;

N-(4-(8-(3-(3-tert-Butyl-1-p-tolyl-1H-pyrazol-5-yl)ureido)quinolin-5-yloxy)pyridin-2-yl)-2-methoxyacetamide;

N-(4-(4-(3-(3-tert-Butyl-1-(4-hydroxyphenyl)-1H-pyrazol-5-yl)ureido)-2,3-dichlorophenoxy)pyridin-2-yl)-2-methoxyacetamide;

N-(4-(4-(3-(3-tert-Butyl-1-(4-methoxyphenyl)-1H-pyrazol-5-yl)ureido)-2,3-dichlorophenoxy)pyridin-2-yl)-2-(methylamino)acetamide;

N-(4-(4-(3-(3-tert-Butyl-1-(4-methoxyphenyl)-1H-pyrazol-5-yl)ureido)-2,3-dichlorophenoxy)pyridin-2-yl)-2-(dimethylamino)acetamide;

N-(4-(4-(3-(3-tert-Butyl-1-(4-methoxyphenyl)-1H-pyrazol-5-yl)ureido)-2,3-dichlorophenoxy)pyridin-2-yl)-2-methoxyacetamide;

N-(4-(4-(3-(3-tert-Butyl-1-(4-methoxyphenyl)-1H-pyrazol-5-yl)ureido)-2,3-dichlorophenoxy)pyridin-2-yl)-2-morpholinoacetamide;

N-(4-(4-(3-(3-tert-Butyl-1-(4-hydroxymethylphenyl)-1H-pyrazol-5-yl)ureido)-2,3-dichlorophenoxy)pyridin-2-yl)-2-(dimethylamino)acetamide;

N-(4-(4-(3-(3-tert-Butyl-1-(4-hydroxymethylphenyl)-1H-pyrazol-5-yl)ureido)-2,3-dichlorophenoxy)pyridin-2-yl)-4-(dimethylamino)butanamide;

N-(4-(4-(3-(3-tert-Butyl-1-(4-hydroxymethylphenyl)-1H-pyrazol-5-yl)ureido)-2,3-dichlorophenoxy)pyridin-2-yl)-2-morpholinoacetamide;

N-(4-(4-(3-(3-tert-Butyl-1-(4-hydroxymethylphenyl)-1H-pyrazol-5-yl)ureido)-2,3-dichlorophenoxy)pyridin-2-yl)-2-methoxyacetamide;

1-(3-tert-Butyl-1-p-tolyl-1H-pyrazol-5-yl)-3-(2,3-dichloro-4-(2-(3-methylureido)pyridin-4-yloxy)phenyl)urea;

1-(3-tert-Butyl-1-(4-hydroxphenyl)-1H-pyrazol-5-yl)-3-(2,3-dichloro-4-(2-(3-methylureido)pyridin-4-yloxy)phenyl)urea;

1-(3-tert-Butyl-1-(4-hydroxymethylphenyl)-1H-pyrazol-5-yl)-3-(2,3-dichloro-4-(2-(3-methylureido)pyridin-4-yloxy)phenyl)urea;

1-(3-tert-Butyl-1-(4-hydroxymethyl-3-methoxyphenyl)-1H-pyrazol-5-yl)-3-(2,3-dichloro-4-(2-(3-methylureido)pyridin-4-yloxy)phenyl)urea;

1-(3-tert-Butyl-1-(3-chloro-4-hydroxymethylphenyl)-1H-pyrazol-5-yl)-3-(2,3-dichloro-4-(2-(3-methylureido)pyridin-4-yloxy)phenyl)urea;

1-(4-(4-(3-(3-tert-Butyl-1-(4-hydroxymethylphenyl)-1H-pyrazol-5-yl)ureido)-2,3-dichlorophenoxy)pyridin-2-yl)-3-cyclopropylurea;

1-(3-tert-Butyl-1-p-tolyl-1H-pyrazol-5-yl)-3-(5-(2-(3-methylureido)pyridin-4-yloxy)quinolin-8-yl)urea;

1-(3-tert-Butyl-1-(4-methoxyphenyl)-1H-pyrazol-5-yl)-3-(5-(2-(3-methylureido)pyridin-4-yloxy)quinolin-8-yl)urea;

1-(3-tert-Butyl-1-(4-methoxyphenyl)-1H-pyrazol-5-yl)-3-(8-(2-(3-methylureido)pyridin-4-yloxy)quinolin-5-yl)urea;

Methyl 4-(3-tert-butyl-5-(3-(2,3-dichloro-4-(2-(3-methylureido)pyridin-4-yloxy)phenyl)ureido)-1H-pyrazol-1-yl)benzoate;

4-(3-tert-Butyl-5-(3-(2,3-dichloro-4-(2-(3-methylureido)pyridin-4-yloxy)phenyl)ureido)-1H-pyrazol-1-yl)benzoic acid;

1-(4-(8-(3-(3-tert-Butyl-1-(4-hydroxymethylphenyl)-1H-pyrazol-5-yl)ureido)quinolin-5-yloxy)pyridin-2-yl)-3-methylurea;

1-(4-(5-(3-3-tert-Butyl-1-(4-hydroxymethylphenyl)-1H-pyrazol-5-yl)ureido)quinolin-8-yloxy)pyridin-2-yl)-3-methylurea;

3-(4-(4-(3-(3-tert-Butyl)-1-p-tolyl-1H-pyrazol-5-yl)ureido)-2,3-dichlorophenoxy)pyridin-2-yl)-1,1-dimethylurea;

3-(4-(4-(3-(3-tert-Butyl-1-(4-methoxyphenyl)-1H-pyrazol-5-yl)ureido)-2,3-dichlorophenoxy)pyridin-2-yl)-1,1-dimethylurea;

1-(4-(4-(3-(3-tert-Butyl-1-(4-methoxyphenyl)-1H-pyrazol-5-yl)ureido)-2,3-dichlorophenoxy)pyridin-2-yl)-3-cyclopropylurea;
1-(4-(4-(3-(3-tert-Butyl-1-(4-methoxyphenyl)-1H-pyrazol-5-yl)ureido)-2,3-dichlorophenoxy)pyridin-2-yl)-3-(2-hydroxyethyl)urea;
1-(4-(4-(3-(3-tert-Butyl-1-(4-methoxyphenyl)-1H-pyrazol-5-yl)ureido)-2,3-dichlorophenoxy)pyridin-2-yl)-3-(2-methoxyethyl)urea;
1-(4-(4-(3-(3-tert-Butyl-1-(4-methoxyphenyl)-1H-pyrazol-5-yl)ureido)-2,3-dichlorophenoxy)pyridin-2-yl)-3-(2-morpholinoethyl)urea;
1-(3-(1H-Imidazol-1-yl)propyl)-3-(4-(4-(3-(3-tert-butyl-1-(4-methoxyphenyl)-1H-pyrazol-5-yl)ureido)-2,3-dichlorophenoxy)pyridin-2-yl)urea;
1-(3-tert-Butyl-1-(4-hydroxymethylphenyl)-1H-pyrazol-5-yl)-3-(2,3-dichloro-4-(2-(3-(2-(dimethylamino)ethyl)ureido)pyridin-4-yloxy)phenyl)urea;
1-(4-(4-(3-(3-tert-Butyl-1-(4-hydroxymethylphenyl)-1H-pyrazol-5-yl)ureido)-2,3-dichlorophenoxy)pyridin-2-yl)-3-(2-morpholinoethyl)urea;
N-(4-(4-(3-(3-tert-Butyl-1-p-tolyl-1H-pyrazol-5-yl)ureido)-2,3-dichlorophenoxy)pyridin-2-yl)pyrrolidine-1-carboxamide;
1-(3-(1-Methylcyclohexyl)-1-p-tolyl-1H-pyrazol-5-yl)-3-(2,3-dichloro-4-(2-(3-methylureido)pyridin-4-yloxy)phenyl)urea;
N-(4-(2,3-Dichloro-4-(3-(3-(1-methylcyclohexyl)-1-p-tolyl-1H-pyrazol-5-yl)ureido)phenoxy)pyridin-2-yl)pyrrolidine-1-carboxamide;
N-(4-(4-(3-(3-tert-Butyl-1-(4-hydroxyphenyl)-1H-pyrazol-5-yl)ureido)-2,3-dichlorophenoxy)pyridin-2-yl)pyrrolidine-1-carboxamide;
N-(4-(4-(3-(3-(tert-Butyl)-1-(4-methoxyphenyl)-1H-pyrazol-5-yl)ureido)-2,3-dichlorophenoxy)pyridin-2-yl)pyrrolidine-1-carboxamide;
N-(4-(4-(3-(3-tert-Butyl-1-(4-hydroxymethylphenyl)-1H-pyrazol-5-yl)ureido)-2,3-dichlorophenoxy)pyridin-2-yl)pyrrolidine-1-carboxamide;
1-(3-tert-Butyl-1-(4-methoxyphenyl)-1H-pyrazol-5-yl)-3-(2-chloro-3-cyano-4-(2-(3-cyclopropylureido)pyridin-4-yloxy)phenyl)urea;
N-(4-(4-(3-(3-tert-Butyl-1-(4-methoxyphenyl)-1H-pyrazol-5-yl)ureido)-3-chloro-2-cyanophenoxy)pyridin-2-yl)pyrrolidine-1-carboxamide;
(S)—N-(4-(4-(3-(3-tert-Butyl-1-(4-hydroxyphenyl)-1H-pyrazol-5-yl)ureido)-2,3-dichlorophenoxy)pyridin-2-yl)-3-(dimethylamino)pyrrolidine-1-carboxamide;
(R)—N-(4-(4-(3-(3-tert-Butyl-1-(4-methoxyphenyl)-1H-pyrazol-5-yl)ureido)-2,3-dichlorophenoxy)pyridin-2-yl)-3-(dimethylamino)pyrrolidine-1-carboxamide;
(S)—N-(4-(4-(3-(3-tert-Butyl-1-(4-methoxyphenyl)-1H-pyrazol-5-yl)ureido)-2,3-dichlorophenoxy)pyridin-2-yl)-3-(dimethylamino)pyrrolidine-1-carboxamide;
(S)—N-(4-(4-(3-(3-tert-Butyl-1-(4-hydroxymethylphenyl)-1H-pyrazol-5-yl)ureido)-2,3-dichlorophenoxy)pyridin-2-yl)-3-(dimethylamino)pyrrolidine-1-carboxamide;
(S)—N-(4-(4-(3-(3-tert-Butyl-1-(4-hydroxymethyl-3-methoxyphenyl)-1H-pyrazol-5-yl)ureido)-2,3-dichlorophenoxy)pyridin-2-yl)-3-(dimethylamino)pyrrolidine-1-carboxamide;
N-(4-(4-(3-(3-tert-Butyl-1-(4-methoxyphenyl)-1H-pyrazol-5-yl)ureido)-2,3-dichlorophenoxy)pyridin-2-yl)-3-hydroxypyrrolidine-1-carboxamide;
N-(4-(4-(3-(3-tert-Butyl-1-(4-methoxyphenyl)-1H-pyrazol-5-yl)ureido)-2,3-dichlorophenoxy)pyridin-2-yl)-2,2-dimethylpyrrolidine-1-carboxamide;
N-(4-(4-(3-(3-tert-Butyl-1-(4-methoxyphenyl)-1H-pyrazol-5-yl)ureido)-2,3-dichlorophenoxy)pyridin-2-yl)-4-(dimethylamino)piperidine-1-carboxamide;
N-(4-(6-(3-(3-tert-Butyl-1-p-tolyl-1H-pyrazol-5-yl)ureido)-2,3-difluorophenoxy)pyridin-2-yl)-2-methoxyacetamide;
N-(6-(4-(3-(3-tert-Butyl-1-p-tolyl-1H-pyrazol-5-yl)ureido)-2,3-dichlorophenoxy)pyrimidin-4-yl)-2-methoxyacetamide;
N-(4-(4-(3-(3-tert-Butyl-1-p-tolyl-1H-pyrazol-5-yl)ureido)-2,3-dichlorophenoxy)pyrimidin-2-yl)-2-methoxyacetamide;
N-(6-(4-(3-(3-tert-Butyl-1-(4-methoxyphenyl)-1H-pyrazol-5-yl)ureido)-2,3-dichlorophenoxy)pyrimidin-4-yl)-2-methoxyacetamide;
N-(6-(4-(3-(3-tert-Butyl-1-(3-hydroxymethylphenyl)-1H-pyrazol-5-yl)ureido)-2,3-dichlorophenoxy)pyrimidin-4-yl)-2-methoxyacetamide;
N-(6-(4-(3-(3-tert-Butyl-1-(4-hydroxymethylphenyl)-1H-pyrazol-5-yl)ureido)-2,3-dichlorophenoxy)pyrimidin-4-yl)-2-methoxyacetamide;
N-(4-(4-(3-(3-tert-Butyl-1-(4-hydroxymethylphenyl)-1H-pyrazol-5-yl)ureido)-2,3-dichlorophenoxy)pyrimidin-2-yl)-2-methoxyacetamide;
1-(3-tert-Butyl-1-p-tolyl-1H-pyrazol-5-yl)-3-(2,3-dichloro-4-(6-(3-methylureido)pyrimidin-4-yloxy)phenyl)urea;
1-(3-tert-Butyl-1-p-tolyl-1H-pyrazol-5-yl)-3-(2,3-dichloro-4-(2-(3-methylureido)pyrimidin-4-yloxy)phenyl)urea;
1-(3-tert-Butyl-1-(4-methoxyphenyl)-1H-pyrazol-5-yl)-3-(2,3-dichloro-4-(6-(3-methylureido)pyrimidin-4-yloxy)phenyl)urea;
1-(3-tert-Butyl-1-(4-methoxyphenyl)-1H-pyrazol-5-yl)-3-(2,3-dichloro-4-(2-(3-methylureido)pyrimidin-4-yloxy)phenyl)urea;
1-(3-tert-Butyl-1-(4-hydroxymethylphenyl)-1H-pyrazol-5-yl)-3-(2,3-dichloro-4-(6-(3-methylureido)pyrimidin-4-yloxy)phenyl)urea;
1-(3-tert-Butyl)-1-(4-methoxyphenyl)-1H-pyrazol-5-yl)-3-(2,3-dichloro-4-(6-(3-(2-(dimethylamino)ethyl)ureido)pyrimidin-4-yloxy)phenyl)urea;
1-(3-tert-Butyl-1-(4-hydroxymethylphenyl)-1H-pyrazol-5-yl)-3-(2,3-dichloro-4-(6-(3-(2-(dimethylamino)ethyl)ureido)pyrimidin-4-yloxy)phenyl)urea;
1-(4-((4-(3-(3-tert-Butyl-1-p-tolyl-1H-pyrazol-5-yl)ureido)-2,3-dichlorophenoxy)methyl)pyridin-2-yl)-3-methylurea or a pharmaceutically acceptable salt thereof, including all stereoisomers, tautomers and isotopic derivatives thereof.

The pharmaceutically acceptable salts as mentioned hereinabove are meant to include therapeutically active non-toxic acid addition salt forms that the compounds of formula (I) is/are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Examples of salts of compound (I) include all pharmaceutically acceptable salts, such as, without limitation, acid addition salts of mineral acids such as HCl and HBr salts and addition salts of organic acids such as a methansulfonic acid salt.

The disclosure herein extends to solvates of compounds of formula (I). Examples of solvates include hydrates.

The compounds of the disclosure include those where the atom specified is a naturally occurring or non-naturally occurring isotope. In one embodiment the isotope is a stable isotope. Thus the compounds of the disclosure include, for example deuterium containing compounds and the like.

The compounds described herein may include one or more stereogenic centres, and the disclosure extends to include racemates, and to both enantiomers (for example each substantially free of the other enantiomer) and all stereoisomers, such as diastereomers resulting therefrom. In one embodiment one enantiomeric form is present in a purified form that is substantially free of the corresponding enantiomeric form.

The disclosure also extends to all polymorphic forms of the compounds herein defined.

Compounds of formula (I) can be prepared by a process comprising reacting a compound of formula (II):

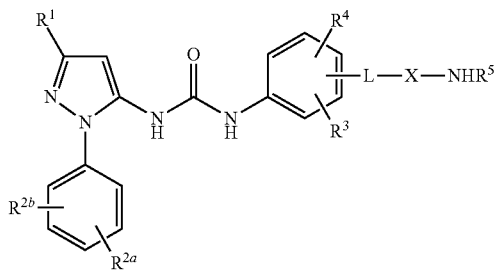
(II)

wherein L X, $R^1$, $R^{2a}$, $R^{2b}$, $R^3$ $R^4$ and $R^5$ are as defined above for compounds of formula (I) with a compound of formula (IIIa):

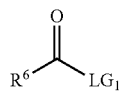
(IIIa)

where $R^6$ is as defined above for compounds of formula (I) and $LG_1$ is a leaving group for example halogen, such as chloro.

When $NR^5C(O)R^6$ is $NR^5C(O)NHR^*$, wherein R* is the remainder of the fragment $R^6$, compounds of formula (I) can be prepared by reacting compounds of formula (II) with a compound of formula (IIIb):

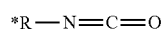
*R—N=C=O  (IIIb)

The reaction is suitably carried out in the presence of an organic base such as DIPEA or triethylamine and in an aprotic solvent or solvent mixture such as a mixture of DCM and DMF.

Alternatively compounds of formula (I), in which $NR^5C(O)R^6$ is $NR^5C(O)NHR^*$, may be prepared by process in which a compound of formula (II) is reacted with a compound of formula (IVa):

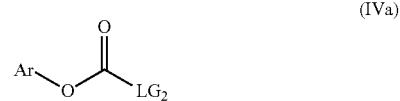
(IVa)

wherein $LG_2$ is a leaving group such as chloro and ArO a is leaving group, such as phenoxide, to provide a compound of formula (IIa)

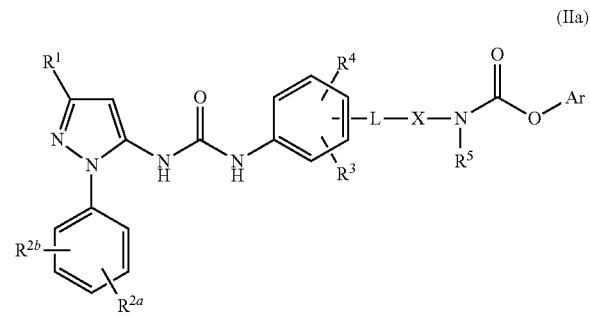
(IIa)

followed by reaction with an amine $R^*NH_2$, to provide the compound of formula (I)

Alternatively compounds of formula (I) can be prepared by reacting a compound of formula (V):

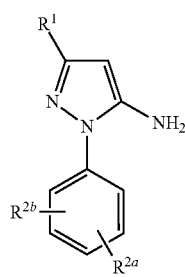
(V)

where $R^1$, $R^{2a}$ and $R^{2b}$ are as defined above for compounds of formula (I), with a compound of formula (IVb):

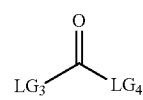
(IVb)

wherein $LG_3$ and $LG_4$ each independently represent leaving groups, to generate a compound of formula (VIa), for example when $LG_3$ and $LG_4$ both represent imidazolyl; or a compound of formula (VIb), for example when the groups $LG_3$ and $LG_4$ represent halogen, such chloro or trihalomethoxy such as trichloromethoxy)

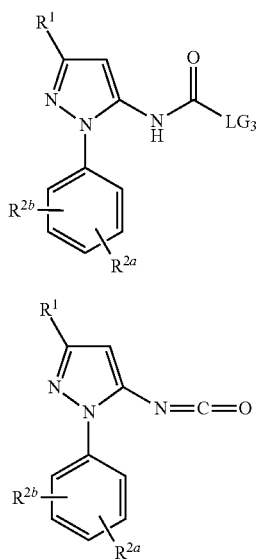

followed by reaction with a compound of formula (VII):

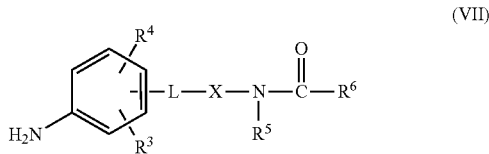

wherein $R^3$, $R^4$, L, X, $R^5$ and $R^6$ are as defined above for compounds of formula (I).

The reaction is suitably carried out in an aprotic solvent such as dichloromethane in the presence of a sterically hindered base, for example DIPEA.

It will be understood by persons skilled in the art that compounds represented by formulae (VIa) and (VIb) are generally reactive intermediates, and may be formed in situ and reacted directly, without isolation, with a compound of formula (VII) to provide a compound of formula (I). Furthermore it will be understood by those skilled in the art that the use of appropriate protective groups may be required during the processes described above, for any of the groups $R^1$, $R^{2a}$ $R^{2b}$ and $R^6$ that comprise of chemically sensitive functional groups, for example that contain a OH group or an $NH_2$ function Compounds of formula (II) can be prepared by reacting a compound of formula (VIII) wherein $R^3$, $R^4$, $R^5$, L and X are as defined above for compounds of formula (I)

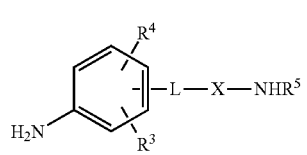

with a compound of formula (VIa) or a compound of formula (VIb), generated as described above from a compound of formula (V), in an aprotic solvent such as dichloromethane and a suitable base, for example DIPEA and, employing appropriate protective groups for chemically sensitive functionality.

Compounds of formula (VII) may be prepared by reacting a compound of formula (IX):

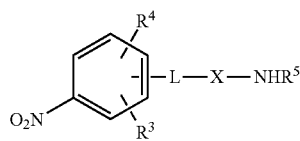

wherein $R^3$, $R^4$, $R^5$, L and X are as defined above for compounds of formula (I), with a compound of formula (IIIa) or (IIIb). The reaction is suitably carried out in the presence of an organic base such as DIPEA or triethylamine in an aprotic solvent or solvent mixture, such as. DCM and DMF. Alternatively the compounds of formula (IX) may be reacted with a compound of formula (IVa) followed by reaction with an amine of formula $R^*NH_2$.

From the intermediates so generated compounds of formula (VII) are then revealed by reduction of the nitro arene to the corresponding amine, for example by hydrogenation in the presence of a suitable catalyst, such as palladium on carbon. In certain cases it may be advantageous to conduct the reduction step chemically, for example under dissolving metal conditions, such as with iron in glacial acetic acid.

Compounds of formula (V) can be derived from the condensation of a phenylhydrazine of formula (X):

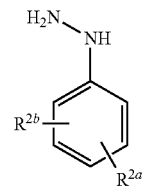

wherein $R^{2a}$, and $R^{2b}$ as are defined above for compounds of formula (I), with a compound of formula (XI):

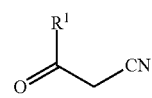

wherein $R^1$ is as defined above for compounds of formula (I).

The reaction may be effected in an alcoholic solvent such as ethanol and in the presence of a mineral acid, such as HCl followed by treatment with a base, such as lithium hydroxide, in a solvent such as THF, to liberate the product as a free base.

Compounds of formula (I) wherein any of the substituents $R^1$, or $R^{2a}$ or $R^{2b}$ contains a sensitive functional group may be prepared from a compound of formula (V), by the processes described above, in which the said functionality is suitably protected during the synthetic transformations, followed by an appropriate deprotection step. For example, a compound of formula (V) in which $R^1$, or $R^{2a}$ or $R^{2b}$ comprises a hydroxyalkyl, may be converted into a compound of formula (I) by the methods described above, by protecting the hydroxyl functionality, for example as a silyl ether. The hydroxyl group can be revealed at the end of the synthetic sequence by cleavage of the protective group: for example a silyl protective group may be removed with, tetrabutylammonium fluoride.

Compounds of formula (V) wherein any of the substituents $R^1$, or $R^{2a}$ or $R^{2b}$ consists of a hydroxyalkyl such as, for example, —(CH$_2$)$_n$CH$_2$OH may be prepared by the reduction of compounds of formula (V) in which one or more of the substituents $R^1$, or $R^{2a}$ or $R^{2b}$ comprises of the corresponding acid such as, for example —(CH$_2$)$_x$CO$_2$H, wherein x is as appropriate for compounds of formula (I), employing a reagent such as borane in a suitable solvent, for example THF. The hydroxyl may then be optionally protected, for example as a silyl ether, and this intermediate converted into a compound of formula (I) in which $R^1$, or $R^{2a}$ or $R^{2b}$ is a protected hydroxyalkyl group, by one of the methods described above.

Compounds of formula (VIII) may be prepared by the reduction of a compound of formula (IX) to the corresponding amine, for example using hydrogenation in the presence of a suitable catalyst such as palladium on carbon.

Certain compounds of formula (IX) wherein the group L comprises of a fragment represented by —O(CH$_2$)$_{1-5}$— may be obtained by the reaction of a compound of formula (XIIa), wherein X and $R^5$ are as defined for compounds of formula (I)

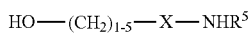
(XIIa)

and a compound of formula (XIII):

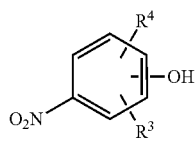
(XIII)

wherein $R^3$ and $R^4$ are as defined above for compounds of formula (I), for example under Mitsunobu coupling conditions, typically in the presence of a triarylphosphine such as triphenylphosphine and a dialkyl azodicarboxylate such as diisopropylazodicarboxylate. The reaction is suitably carried out in a polar aprotic solvent such as THF.

Alternatively, certain compounds of formula (IX) wherein the group L comprises of a fragment represented by —O(CH$_2$)$_{1-5}$— may be obtained by a nucleophilic aromatic substitution (S$_N$Ar) reaction of a compound of formula (XIIa) with a compound of (XIV)

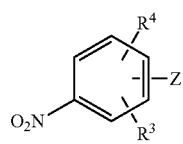
(XIV)

wherein $R^3$ and $R^4$ are as defined above for compounds of formula (I) and Z is a halogen atom, most preferably fluorine. The reaction is conveniently conducted in the presence of a strong base such as sodium hydride and in an aprotic solvent such as THF.

Certain compounds of formula (IX) wherein the group L is O, that is an oxa linker, may be obtained by the reaction of a compound of formula (XIIb), wherein X and $R^5$ are as defined for compounds of formula (I)

(XIIb)

and a compound of formula (XIV). The reaction may be conducted in the presence of an organic base such DBU in a polar aprotic solvent such as acetonitrile.

Certain compounds of formula (IX) wherein the group L is O, that is an oxa linker, may be obtained by the reaction of a compound of formula (XIIc), wherein X and $R^5$ are as defined for compounds of formula (I) and Y is a halogen atom preferably chlorine

(XIIc)

and a compound of formula (XIII). The reaction may be effected in a polar aprotic solvent, such as NMP, in the presence of a strong mineral acid, such conc. hydrochloric acid and at an elevated temperature for example at 170° C. or 190° C.

Certain compounds of formula (VII) wherein the group L is O, that is an oxa linker, may be obtained via the reaction of a compound of formula (XIId),

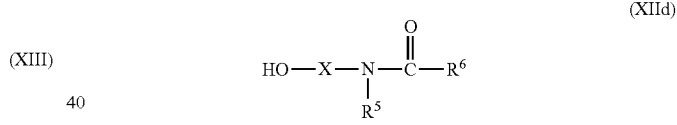
(XIId)

wherein X, $R^5$ and $R^6$ are as defined for compounds of formula (I) with a compound of formula (XIV) providing compounds of formula (XV).

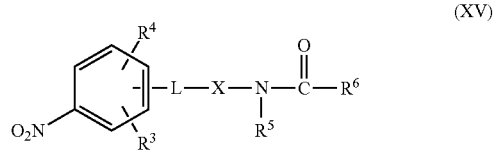
(XV)

In those cases where the compound of formula (XIV) is a highly activated electrophile ($R^3$ and/or $R^4$ are electron withdrawing substituents) the reaction may be conveniently carried out in a polar aprotic solvent, such as acetonitrile and in the presence of an organic base, for example DBU and at RT. In those instances where the compound of formula (XIV) is a less reactive electrophile ($R^3$ and/or $R^4$ are electron donating substituents) the reaction can be effected in a polar aprotic solvent such as DMSO, employing a base such as K$_2$CO$_3$ and at elevated temperatures such or 90° C. to 100° C.

Compounds of formula (VII) are revealed from compounds of formula (XV) by the reduction of the nitroarene to the corresponding amine. This transformation may be conducted by catalytic hydrogenation in a suitable solvent mixture such as a mixture of DCM, MeOH and acetic acid, over an appropriate metal catalyst, for example platinum supported on graphite, at RT. Alternatively it may be advantageous to conduct the reduction step by chemical means, for example using a metal such as iron powder, in an acid, such as glacial acetic acid at an elevated temperature, such as 60° C.

Certain compounds of formula (II) wherein X, $R^1$, $R^{2a}$, $R^{2b}$, $R^3$ $R^4$ and $R^5$ are as defined above for compounds of formula (I) and the group L is $CH_2$, that is a methylene linker; or is C(O), that is a keto group; or is S, that is a thio ether linker; may be prepared from a compound of formula (VIII) wherein $R^3$, $R^4$, $R^5$ and X are as defined above and L is either is $CH_2$, or is C(O) or is S; by reaction with a compound of formula (VIa) or a compound of formula (VIb) as described above.

A compound of formula (VIII) wherein $R^3$, $R^4$, $R^5$ and X are as defined above and L is either $CH_2$, or is C(O) may be obtained by the deprotection of the corresponding protected derivatives (VIIIa) or (VIIIb), respectively, wherein $P^1$ and $P^2$ represent suitable amine protective groups. For example, where $P^1$ and $P^2$ both represent Boc protective groups the desired compounds of formula (VIII) are revealed from compounds (VIIIa) or (VIIIb) by treatment with acid such as TFA, in an inert solvent such as DCM, conveniently at 0° C. to RT.

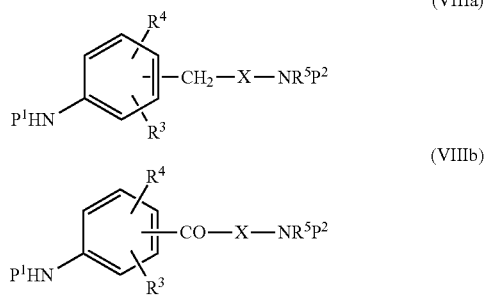

A compound of formula (VIIIa) may be obtained from a carbinol compound of formula (XVI) by a reductive process for the removal of the hydroxyl group. For example the compound of formula (XVI) can be converted into a sulfonate ester by treatment with a sulfonyl chloride, for example into the mesylate (XVIa) by treatment with methanesulfonyl chloride, in an aprotic solvent such as DCM at 0° C. to RT in the presence of a base such as triethylamine.

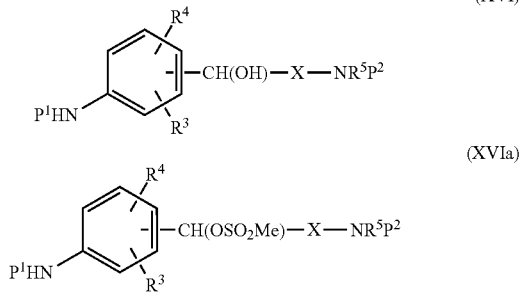

The compound of formula (XVIa) may then be transformed into the compound of formula (VIIIa) by reaction with a reducing agent, such as sodium borohydride, in a polar protic solvent such as methanol, typically at 0° C. to RT.

A compound of formula (VIIIb) may also be obtained from the carbinol compound of formula (XVI) by an oxidative process to convert the secondary alcohol into a keto group. For example the compound of formula (XVI) may be converted into the compound of formula (VIIIb) by treatment with an oxidising agent such as manganese dioxide in a suitable solvent such as DCM, at an appropriate temperature such as 0° C. to RT.

Compounds of formula (XVI) may be prepared by the treatment of an aromatic bromide of formula (XVII), wherein $R^3$, $R^4$, and $P^1$ are as defined above, with an alkyllithium, for example n-butyllithium, in an inert, aprotic solvent such at THF, at suitable temperature, for example at −78° C., if necessary with adjustment of the temperature to, for example, 0, followed by reaction with a carboxaldehyde of formula (XVIII), wherein X, $R^5$, and $P^2$ are as defined above:

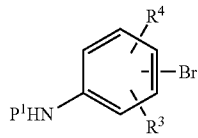

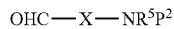

Compounds of formula (VIII) wherein $R^3$, $R^4$, $R^5$ and X are as defined above and L is S, that is L is a thioether linker, may be prepared from a compound of formula (VIIIc) wherein the group Ar is a electron rich aromatic nucleus, thereby making the radical —$CH_2Ar$ susceptible to cleavage by acidolysis. A suitable aromatic group for this purpose is, for example 2,4-dimethoxybenzene or the like. The desired compound of formula (VIII), as defined above, may be obtained from the compound of formula (VIIIc) by acid mediated cleavage, for example with hydrochloric acid in an alcoholic solvent such methanol, at an elevated temperature such as at reflux:

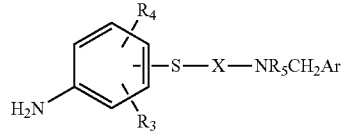

Compounds of formula (VIIIc) are obtainable from the reaction of a compound of formula (XIX) wherein $R^3$, $R^4$, and X are as defined above and Y is a halogen atom, preferably chlorine, with a compound of (XX), wherein $R^5$ and Ar are as defined above. The reaction may be carried out by heating the compound of formula (XX) as a solution in the neat amine of formula (XX) at a suitable temperature, such as 120° C.:

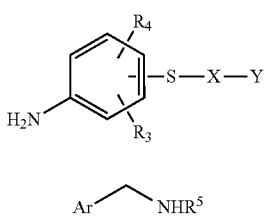

(XIX)

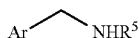

(XX)

Compounds of formula (XIX) may be prepared by reduction of compounds of formula (XXI), for example by catalytic reduction using hydrogen and a suitable metal catalyst. The reduction step is conveniently carried out in a mixture of solvents such as EtOAc, MeOH and AcOH, over platinum on carbon, at an elevated temperature such as 50° C.:

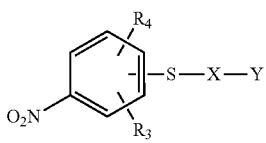

(XXI)

Compounds of formula (XXI) may be prepared by the reaction of compounds of formula (XIV), as defined above, with a compound of formula (XXII) wherein X is as defined above, Z is a halogen atom, preferably fluorine and Y is a halogen atom, preferably chlorine together with a suitable sulfur nucleophile. For example the reaction can be carried using sodium hydrogensulfide as the sulfur source in a polar aprotic solvent such as DMF and in the presence of a organic base, for example DIPEA, at ambient temperature:

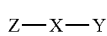

(XXII)

Certain compounds of formula (I) wherein, $R^1$, $R^{2a}$, $R^{2b}$, $R^3$, $R^4$ and X are as previously defined, $R^5$ is H and L is $SO_2$, that is L is a sulfonyl linker, may be prepared from a compound of formula (IIc) by one or more of the processes described above.

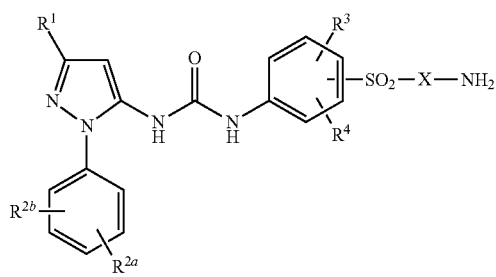

(IIc)

Compounds of formula (IIc) can be derived from a compound of formula (XXIII),

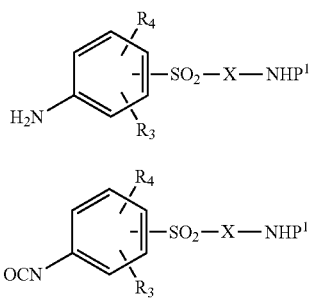

(XXIII)

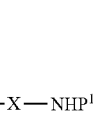

(XXIIIa)

wherein $R^3$ $R^4$ X and $P^1$ are as previously defined, by conversion, in situ, into an isocyanate of formula (XXIIIa) followed by, without isolation, reaction with a compound of formula (V). The transformation may be effected by exposing the compound of formula (XXIII) to a compound of formula (IVb); wherein, for example, the group $LG_3$ is halogen such as chlorine and the group $LG_4$ is trihalomethoxy such as trichloromethoxy, such that the compound of formula (IVb) is diphosgene, and subsequently of admixing the compound of formula (V). The reaction is conveniently conducted in an inert aprotic solvent such as DCM and may be cooled, for example to 0° C. The desired compounds of formula (IIc) are then revealed from the products so obtained by a deprotection step. For example, where $P^1$ represents a Boc group the compounds of formula (IIc) are obtained following removal of the protective group with an acid such as TFA, in an inert solvent such as DCM, conveniently at 0° C. to RT.

Compounds of formula (XXIII) may be obtained by the reduction of compounds of formula (XXIV).

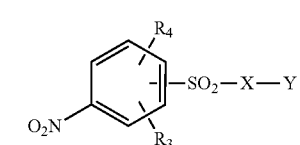

(XXIV)

The reduction may be carried out, for example, by hydrogenation over a suitable catalyst, such as palladium on carbon, in an appropriate solvent system such as a mixture of EtOAc, MeOH and AcOH, and if necessary with warming, for example at 30° C.

Compounds of formula (XXIV) are accessible from compounds of formula (XXIa)

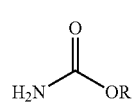

(XXIa)

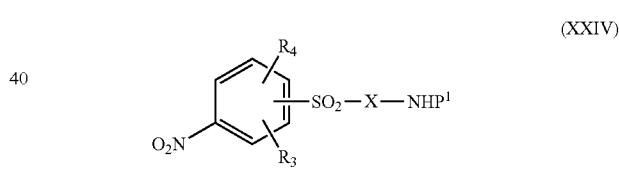

(XXV)

wherein, $R^3$, $R^4$ and X are as previously defined above and Y is a halogen atom, preferably chlorine, by an amidation reaction employing a compound of formula (XXV). A suitable compound of formula (XXV) for this transformation is that in which R represents tert-butyl such that the said compound (XXV) is H₂NBoc. Suitable conditions for this conversion are, for example, the reaction of a compound of formula (XXIa) with a compound of formula (XXV) in the presence of a catalytic system, such as that generated from Pd₂(dba)₃ in the presence of the phosphine ligand such as XantPhos. The reaction is conveniently conducted in a polar aprotic solvent such as THF and in the presence of a base, for example, an inorganic base such as cesium carbonate.

Compounds of formula (XXIa) wherein $R^3$ and $R^4$ are as previously defined and X is pyridine may be derived from a compound of formula (XXVI) where $R^3$ and $R^4$ are defined above for compounds of formula (I):

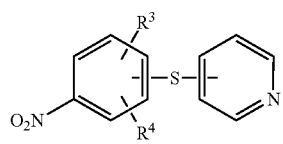
(XXVI)

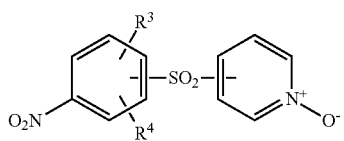
(XXVII)

by oxidation to a compound of formula (XXVII) followed by treatment with a chlorinating agent. A suitable chlorinating reagent for the conversion of a compound of formula (XXVI) into a compound of formula (XXVII) is, for example, m-CPBA. The reaction may be effected in a halogenated solvent such as DCM and typically below RT, for example at 0° C. The subsequent chlorination step may be carried out using a reagent such a phosphorus oxychloride at an elevated temperature, for example at 100° C.

Compounds of formula (XXVI) may be obtained from the reaction of a compound of formula (XIV) as defined previously, with a compound of formula (XXVIII):

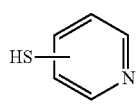
(XXVIII)

The reaction is conveniently conducted in a polar aprotic solvent such as DMF and typically in the presence of a base, for example an inorganic base such as potassium carbonate, and if necessary with cooling, for example, to 0° C.

Certain compounds of formula (I) in which $R^3$ and $R^4$, together with the carbons atoms to which they are attached, form a 5 to 6 membered saturated or partially unsaturated carbocyclic ring, or a 5 to 6 membered saturated or partially unsaturated heterocyclic ring may be prepared from a compound of formula (XXIX)

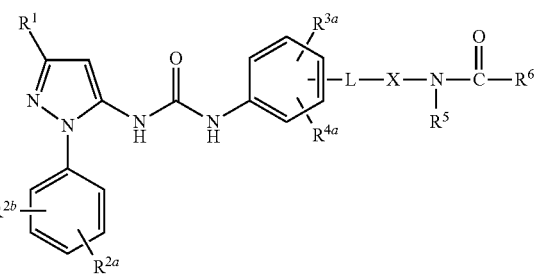
(XXIX)

in which $R^1$, $R^{2a}$, $R^{2b}$, L, X, $R^5$ and $R^6$ are as defined above for compounds of formula (I) and $R^{3a}$ and $R^{4a}$, together with the carbons atoms to which they are attached, form a 5 to 6 membered aromatic ring, or a 5 to 6 membered heteroaromatic ring, by a process involving the partial saturation of the said ring. The reduction may be effected by catalytic hydrogenation under forcing conditions, for example in a mixture of MeOH and acetic acid, over a catalyst, for example palladium on charcoal and at an elevated temperature, such as 80° C.

Compounds of formulae (IIIa), (IIIb) (IVa), (IVb) (V), (X), (XI), (XIIa), (XIIb), (XIIc), (XIII) (XIV), (XVII), (XVIII), (XX), (XXII), (XXV), (XXVIII) and certain other compounds illustrated in the schemes are either commercially available, or were obtained using the cited procedures, or can be readily prepared by conventional methods by those skilled in the art. See for example Regan, J. et al.; *J. Med. Chem.*, 2003, 46:4676-4686, WO 00/043384, WO 2007/087448 and WO 2007/089512.

Protecting groups may be required to protect chemically sensitive groups during one or more of the reactions described above, to ensure that the process is efficient. Thus if desired or necessary, intermediate compounds may be protected by the use of conventional protecting groups. Protecting groups and means for their removal are described in "Protective Groups in Organic Synthesis", by Theodora W. Greene and Peter G. M. Wuts, published by John Wiley & Sons Inc; 4ᵗʰ Rev Ed., 2006, ISBN-10: 0471697540.

Novel intermediates are claimed as an aspect of the invention.

In one aspect the compounds are useful in treatment, for example COPD and/or asthma.

The p38MAPK inhibitory compounds developed to date have typically been intended for oral administration. This method of dosing involves optimization to achieve an adequate duration of action by selecting compounds that have an appropriate pharmacokinetic profile. This strategy ensures that a therapeutically effective drug concentration is established and maintained after and between doses to provide the desired clinical benefit. The inevitable consequence of this regimen is that all body tissues, especially liver and gut, are likely to be exposed chronically to therapeutically active concentrations of the drug, whether or not they are adversely affected in the diseased state.

An alternative strategy is to design treatment approaches in which the drug is dosed directly to the inflamed organ (topical therapy). While this approach is not suitable for treating all chronic inflammatory diseases, it has been extensively exploited in lung diseases (asthma, COPD), skin diseases (atopic dermatitis and psoriasis), nasal diseases (allergic rhinitis) and gastrointestinal diseases (ulcerative colitis).

In topical therapy, efficacy can be achieved either by ensuring that the drug has a sustained duration of action and is retained in the relevant organ to minimize the risk of systemic toxicity; or by producing a formulation which generates a "reservoir" of the active drug which is available to sustain the drug's desired effects. The first approach is exemplified by the anticholinergic drug tiotropium (Spiriva). This compound is administered topically to the lung as a treatment for COPD, and has an exceptionally high affinity for its target receptor resulting in a very slow off rate and a consequent sustained duration of action.

There is provided according to one aspect of the present disclosure use of a formulation of a compound of formula (I) as a p38 MAP kinase inhibitor, for example administered topically to the lung.

In one aspect of the disclosure the compounds herein are particularly suitable for topical delivery, such as topical delivery to the lungs, in particular for the treatment of COPD.

Thus is one aspect there is provided use of compounds of formula (I) for the treatment of COPD and/or asthma, in particular COPD or severe asthma, by inhalation i.e. topical administration to the lung. Advantageously, administration to the lung allows the beneficial effects of the compounds to be realised whilst minimising the side-effects for patients.

In one aspect the compounds have a longer durations of action than BIRB 796.

In one embodiment the compounds are suitable for sensitizing patients to treatment with a corticosteroid.

The compounds herein may also be useful for the treatment of rheumatoid arthritis.

Further, the present invention provides a pharmaceutical composition comprising a compound according to the disclosure optionally in combination with one or more pharmaceutically acceptable diluents or carriers.

Diluents and carriers may include those suitable for parenteral, oral, topical, mucosal and rectal administration.

As mentioned above, such compositions may be prepared e.g. for parenteral, subcutaneous, intramuscular, intravenous, intra-articular or peri-articular administration, particularly in the form of liquid solutions or suspensions; for oral administration, particularly in the form of tablets or capsules; for topical e.g. pulmonary or intranasal administration, particularly in the form of powders, nasal drops or aerosols and transdermal administration; for mucosal administration e.g. to buccal, sublingual or vaginal mucosa, and for rectal administration e.g. in the form of a suppository.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

Compositions suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitably the compound of formula (I) is administered topically to the lung. Hence we provide according to the invention a pharmaceutical composition comprising a compound of the disclosure optionally in combination with one or more topically acceptable diluents or carriers. Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser. Topical administration to the lung may also be achieved by use of a dry-powder formulation. A dry powder formulation will contain the compound of the disclosure in finely divided form, typically with a mass mean diameter (MMAD) of 1-10 µm. The formulation will typically contain a topically acceptable diluent such as lactose, usually of large particle size e.g. a mass mean diameter (MMAD) of 100 µm or more. Examples of dry powder delivery systems include SPINHALER, DISKHALER, TURBOHALER, DISKUS and CLICKHALER.

Compounds according to the disclosure are intended to have therapeutic activity. In a further aspect, the present invention provides a compound of the disclosure for use as a medicament.

Compounds according to the disclosure may also be useful in the treatment of respiratory disorders including COPD (including chronic bronchitis and emphysema), asthma, paediatric asthma, cystic fibrosis, sarcoidosis, idiopathic pulmonary fibrosis, allergic rhinitis, rhinitis, sinusitis, especially asthma, chronic bronchitis and COPD.

Compounds of the disclosure may also re-sensitise the patient's condition to treatment with a corticosteroid, when the patient's condition has become refractory to the same.

Compounds of the disclosure may also prevent a patient's condition from becoming refractory to treatment with a corticosteroid.

Compounds according to the disclosure are also expected to be useful in the treatment of certain conditions which may be treated by topical or local therapy including allergic conjunctivitis, conjunctivitis, allergic dermatitis, contact dermatitis, psoriasis, ulcerative colitis, inflamed joints secondary to rheumatoid arthritis or osteoarthritis.

Compounds of the disclosure are also expected to be useful in the treatment of certain other conditions including rheumatoid arthritis, pancreatitis, cachexia, inhibition of the growth and metastasis of tumours including non-small cell lung carcinoma, breast carcinoma, gastric carcinoma, colorectal carcinomas and malignant melanoma.

Compounds of the disclosure are believed to be useful as anti-viral agents, for example in the treatment of conditions including influenza. In particular the compounds of the present disclosure may be suitable for the use in the treatment or prevention of said viral infection and in particular may be capable of reducing viral load and/or ameliorating symptoms after infection.

Thus, in a further aspect, the present invention provides a compound as described herein for use in the treatment of the above mentioned conditions.

In a further aspect, the present invention provides use of a compound as described herein for the manufacture of a medicament for the treatment of the above mentioned conditions.

In a further aspect, the present invention provides a method of treatment of the above mentioned conditions which comprises administering to a subject an effective amount of a compound of the disclosure or a pharmaceutical composition thereof.

The word "treatment" is intended to embrace prophylaxis as well as therapeutic treatment.

A compound of the disclosure may also be administered in combination with one or more other active ingredients e.g. active ingredients suitable for treating the above mentioned conditions. For example possible combinations for treatment of respiratory disorders include combinations with steroids (e.g. budesonide, beclomethasone dipropionate, fluticasone propionate, mometasone furoate, fluticasone furoate), beta agonists (e.g. terbutaline, salbutamol, salmeterol, formoterol) and/or xanthines (e.g. theophylline).

EXPERIMENTAL SECTION

Abbreviations used herein are as defined below (Table 1). Any abbreviations not defined are intended to convey their generally accepted meaning.

TABLE 1

| Abbreviations | |
|---|---|
| AcOH | glacial acetic acid |
| aq | Aqueous |

TABLE 1-continued

| Abbreviations | |
|---|---|
| Ac | Acetyl |
| ATP | adenosine-5'-triphosphate |
| BALF | bronchoalveolae lavage fluid |
| 9-BBN | 9-borabicyclo[3.3.1]nonane |
| Boc | tert-butoxycarbonyl |
| br | Broad |
| BSA | bovine serum albumin |
| CatCart ® | catalytic cartridge |
| CBz | Benzyloxycarbonyl |
| CDI | 1,1-carbonyl-diimidazole |
| COPD | chronic obstructive pulmonary disease |
| d | Doublet |
| DCM | Dichloromethane |
| DIAD | Diisopropylazadicarboxylate |
| DIBAL-H | diisobutylaluminium hydride |
| DIPEA | N,N-diisopropylethylamine |
| DMF | N,N-dimethylformamide |
| DMSO | dimethyl sulfoxide |
| EDC•HCl | 1-ethyl-3-(3-dimethylaminopropyl)-carbodiimide•hydrochloride |
| (ES$^+$) | electrospray ionization, positive mode |
| Et | Ethyl |
| EtOAc | ethyl acetate |
| Ex. No. | Example Number |
| FCS | foetal calf serum |
| HATU | O-(7-azabenzotriazole-1-yl)-N,N,N',N'-tetramethyluronium hexafluorophosphate |
| HOBt | 1-hydroxybenzotriazole |
| hr | hour(s) |
| HRP | horseradish peroxidise |
| JNK | c-Jun N-terminal kinase |
| KHMDS | potassium hexamethyldisilazane |
| (M + H)$^+$ | protonated molecule |
| MAPK | mitogen protein activated protein kinase |
| Me | Methyl |
| MeCN | Acetonitrile |
| MeOH | Methanol |
| MHz | Megahertz |
| min | minute(s) |
| MOM-Br | bromomethyl methyl ether |
| MTT | 3-(4,5-Dimethylthiazol-2-yl)-2,5-diphenyltetrazolium bromide |
| m/z: | mass-to-charge ratio |
| NMM | N-methylmorpholine (4-methylmorpholine) |
| NMP | 1-methylpyrrolidin-2-one (N-methyl-2-pyrrolidone) |
| NMR | nuclear magnetic resonance (spectroscopy) |
| Oxone ® | potassium peroxymonosulfate |
| Ph | Phenyl |
| PBS | phosphate buffered saline |
| Pd$_2$(dba)$_3$ | tris(dibenzylideneacetone)dipalladium(0) |
| PPh$_3$ | Triphenylphosphine |
| PyBOP ® | (benzotriazol-1-yloxy)tripyrrolidinophosphonium hexafluorophosphate |
| q | Quartet |
| RT | room temperature |
| RP HPLC | reverse phase high performance liquid chromatography |
| s | Singlet |
| SCX | solid supported cation exchange (resin) |
| SDS | sodium dodecyl sulphate |
| S$_N$Ar | nucleophilic aromatic substitution |
| t | Triplet |
| TBAF | tetrabutylammonium fluoride |
| TBDMS-Cl | tert-butyldimethylchlorosilane |
| TFA | trifluoroacetic acid |
| THF | Tetrahydrofuran |
| TMB | 3,3',5,5'-tetramethylbenzidine |
| TNFα | tumor necrosis factor alpha |
| TMS-Cl | trimethylsilyl chloride [chlorotrimethylsilane] |
| XantPhos | 4,5-bis(diphenylphosphino)-9,9-dimethylxanthene |

General Procedures

All starting materials and solvents were either obtained from commercial sources or prepared according to the literature citation. Unless otherwise stated all reactions were stirred. Organic solutions were routinely dried over anhydrous magnesium sulfate. Hydrogenations were preformed on a Thales H-cube flow reactor under the conditions stated.

Column chromatography was performed on pre-packed silica (230-400 mesh, 40-63 μM) to cartridges using the amount indicated. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% $NH_3$ in MeOH.

Preparative Reverse Phase High Performance Liquid Chromatography:

Agilent Scalar column C18, 5 μm (21.2×50 mm), flow rate 28 mL·min$^{-1}$ eluting with a $H_2O$-MeCN gradient containing 0.1% v/v formic acid over 10 min using UV detection at 215 and 254 nm. Gradient information: 0.0-0.5 min; 95% $H_2O$-5% MeCN; 0.5-7.0 min; ramped from 95% $H_2O$-5% MeCN to 5% $H_2O$-95% MeCN; 7.0-7.9 min; held at 5% $H_2O$-95% MeCN; 7.9-8.0 min; returned to 95% $H_2O$-5% MeCN; 8.0-10.0 min; held at 95% $H_2O$-5% MeCN.

Analytical Methods

Reverse Phase High Performance Liquid Chromatography:

Method 1: Agilent Scalar column C18, 5 μm (4.6×50 mm) or Waters XBridge C18, 5 μm (4.6×50 mm) flow rate 2.5 mL min$^{-1}$ eluting with a $H_2O$-MeCN gradient containing either 0.1% v/v formic acid (Method 1 acidic) or $NH_3$ (Method 1 basic) over 7 min employing UV detection at 215 and 254 nm. Gradient information: 0.0-0.1 min, 95% $H_2O$-5% MeCN; 0.1-5.0 min, ramped from 95% $H_2O$-5% MeCN to 5% $H_2O$-95% MeCN; 5.0-5.5 min, held at 5% $H_2O$-95% MeCN; 5.5-5.6 min, held at 5% $H_2O$-95% MeCN, flow rate increased to 3.5 mL min$^{-1}$; 5.6-6.6 min, held at 5% $H_2O$-95% MeCN, flow rate 3.5 mL min$^{-1}$; 6.6-6.75 min, returned to 95% $H_2O$-5% MeCN, flow rate 3.5 mL min$^{-1}$; 6.75-6.9 min, held at 95% $H_2O$-5% MeCN, flow rate 3.5 mL min$^{-1}$; 6.9-7.0 min, held at 95% $H_2O$-5% MeCN, flow rate reduced to 2.5 mL min$^{-1}$.

Method 2: Agilent Extend C18 column, 1.8 μm (4.6×30 mm) at 40° C.; flow rate 2.5-4.5 mL min$^{-1}$ eluting with a $H_2O$-MeCN gradient containing 0.1% v/v formic acid over 4 min employing UV detection at 254 nm. Gradient information: 0-3.00 min, ramped from 95% $H_2O$-5% MeCN to 5% $H_2O$-95% MeCN; 3.00-3.01 min, held at 5% $H_2O$-95% MeCN, flow rate increased to 4.5 mL min$^{-1}$; 3.01-3.50 min, held at 5% $H_2O$-95% MeCN; 3.50-3.60 min, returned to 95% $H_2O$-5% MeCN, flow rate reduced to 3.50 mL min$^{-1}$; 3.60-3.90 min, held at 95% $H_2O$-5% MeCN; 3.90-4.00 min, held at 95% $H_2O$-5% MeCN, flow rate reduced to 2.5 mL min$^{-1}$.

$^1$H NMR Spectroscopy:

$^1$H NMR spectra were acquired on a Bruker Avance III spectrometer at 400 MHz, using residual undeuterated solvent as reference General Synthetic Processes for the Ether Linked Pyridine Genus Analogues of the Ether Linked Pyriridines Incorporating a Terminal Amide The genus of compound examples that possess a terminal N-acyl aminopyridine (Pyridine Amides) were prepared by the reaction of a compound represented by Intermediate A with a compound represented by Intermediate B, under appropriate coupling conditions.

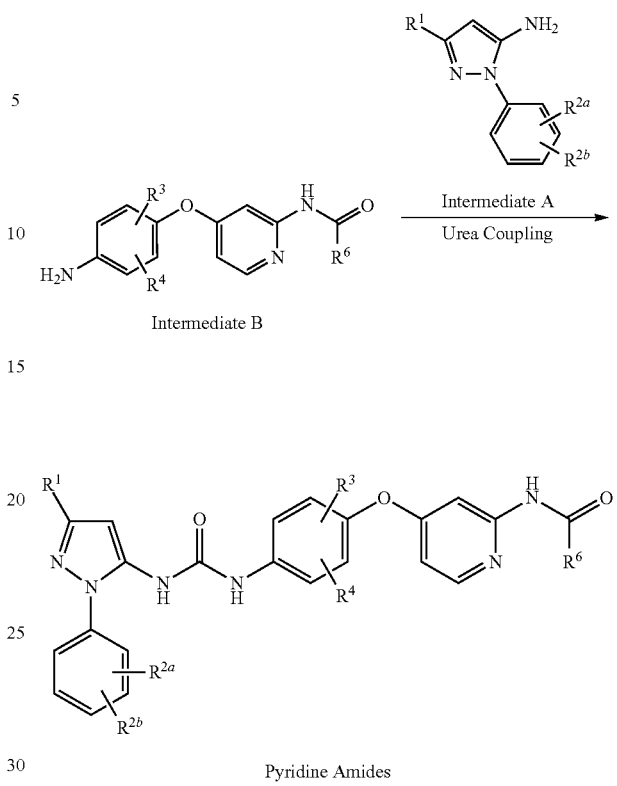

Pyridine Amides

Suitable conditions under which this transformation can be effected include the conversion of an Intermediate A into the corresponding N-acyl imidazolide with, for example, carbonyl diimidazole. The resulting N-acyl imidazole is typically generated in situ and reacted directly with an Intermediate B, (most often at a supra-stoichiometric ratio) without isolation or purification, to provide amide examples of the ether genus.

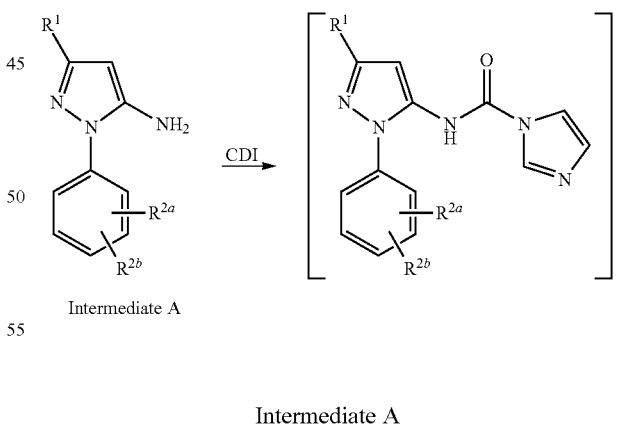

Intermediate A

The individual, 5-aminopyrazole examples of Intermediate A are either known compounds, and were prepared by the cited literature methods, or were obtained by the procedures disclosed herein. The general synthetic process used to generate the compounds disclosed herein involves the condensation of a substituted acetonitrile with a phenyl hydrazine.

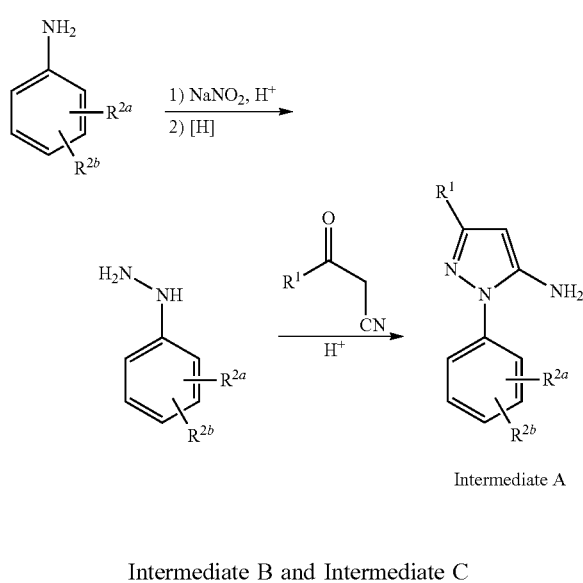

Intermediate A

Intermediate B and Intermediate C

Compounds represented by Intermediate B were derived from an $S_NAr$ reaction between an N-acyl aminopyridinol and a suitably substituted nitrofluorobenzene, followed by reduction to the corresponding aniline derivative. Alternatively, the $S_NAr$ coupling step was conducted using an aminopyridinol (Y=OH) to generate compounds represented by Intermediate C, followed by N-acylation of the aminopyridine ether to provide compounds represented by Intermediate B. An electrophilic process was also used to prepare compounds represented by Intermediate C, whereby a halopyridine (Y=Cl) was reacted with a nitrophenol (Z=OH) under acidic conditions. A sub genus of compounds represented by Intermediate B, comprising of glycinamide derivatives, was obtained by reacting compounds represented by Intermediate C with chloroacetyl chloride followed by treatment with an appropriate amine.

aromatic or heteroaromatic nucleus. Compounds represented by Intermediate D were obtained by processes analogous to those discussed above, that proceed through Intermediate B and Intermediate A.

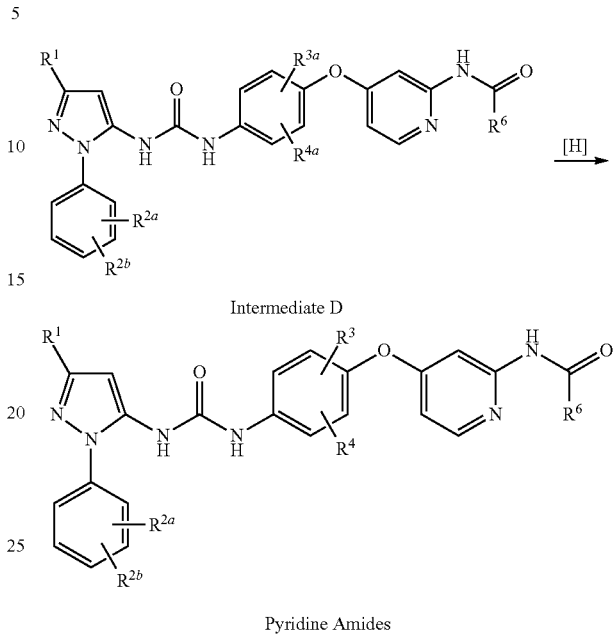

Intermediate D

Pyridine Amides

Analogues of the Ether Linked Pyridines Incorporating a Terminal Urea

Further compound examples of the disclosure incorporate a terminal ureidopyridine (Pyridine Ureas). Compounds of this genus revealed herein were obtained from a compound represented by Intermediate E by reaction with an Intermediate A under appropriate coupling conditions, as disclosed above. Alternatively examples of this compound class were generated by the reaction of the corresponding aminopyridine, represented by Intermediate F, with an isocyanate, or

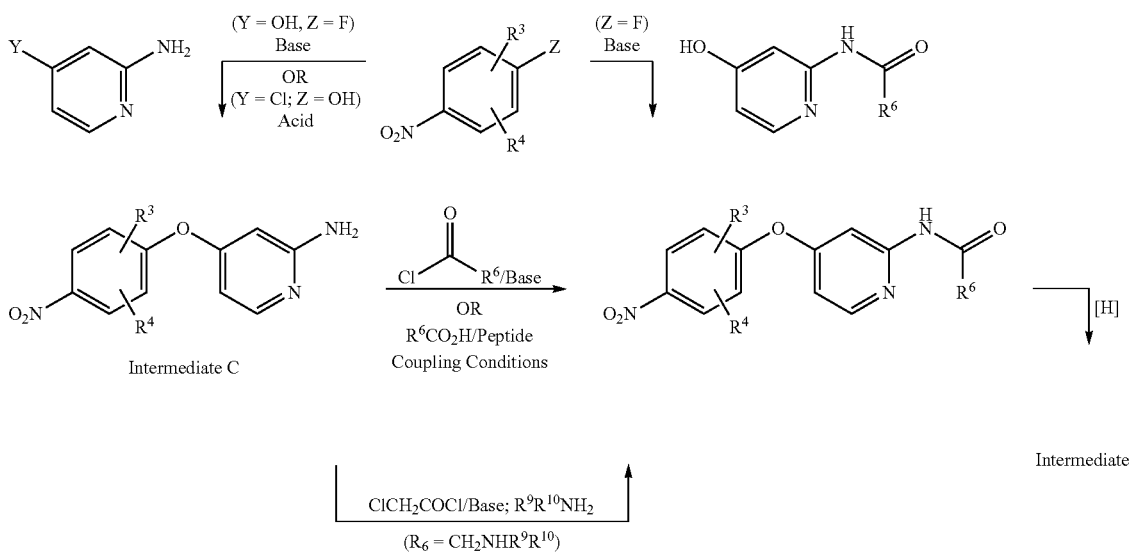

Intermediate B

Further compounds of the disclosure were obtained by the partial reduction of a compound represented by Intermediate D in which the groups $R^{3a}$ and $R^{4a}$ taken together form an by prior activation with an suitable aryl haloformate (such as phenyl carbonochloridate) and subsequent treatment with an amine.

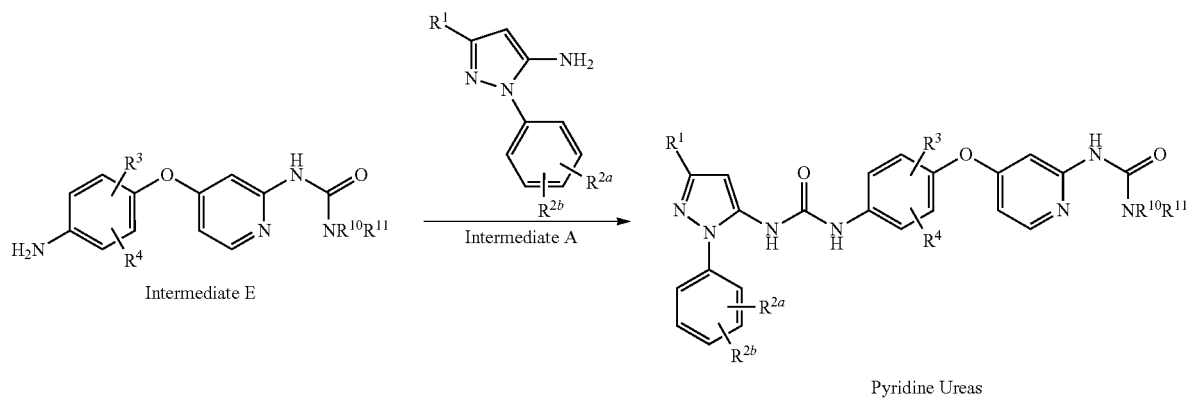

Pyridine Ureas

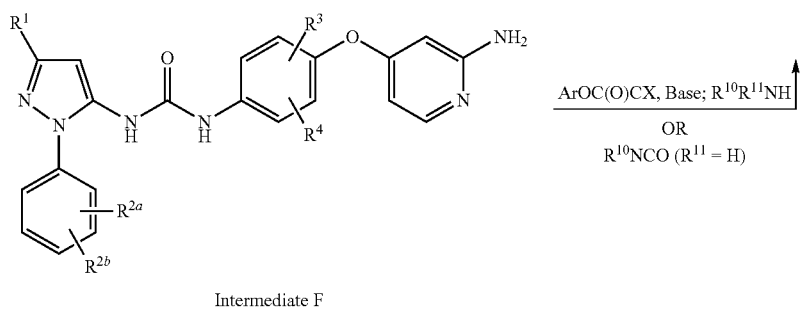

Intermediate F

Intermediate E

Compounds represented by Intermediate E were generated from compounds represented by Intermediate C, by the conversion of the aminopyridine motif into the desired ureido derivative, by one of the methods described below, followed by reduction of the nitroarene to the corresponding naphthylamine.

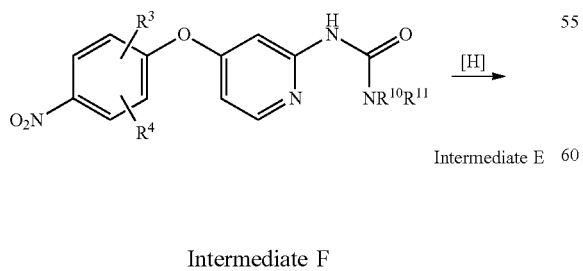

Intermediate F

Compounds represented by Intermediate F were generated from compounds represented by Intermediate C, by reduction of the nitroarene to the corresponding arylamine followed by chemoselective acylation with Intermediate A under suitable coupling conditions, such as one of the methods described below.

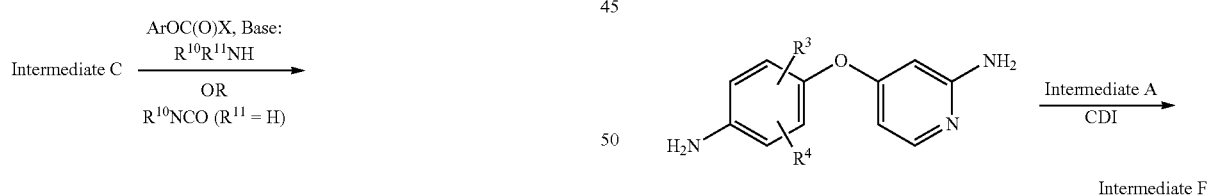

Intermediate F

General Synthetic Processes for the Methylether Linked Pyridine Genus

Analogues of the Methylether Linked Pyridines Incorporating a Terminal Amide

The genus of compound examples that possess a terminal N-acylaminoheteroaryl (Compounds of Formula (I) for which —NR$^5$(C=O)Q represents an amide) were prepared by a process represented by the reaction of an Intermediate A with an Intermediate G, under appropriate coupling conditions as discussed above.

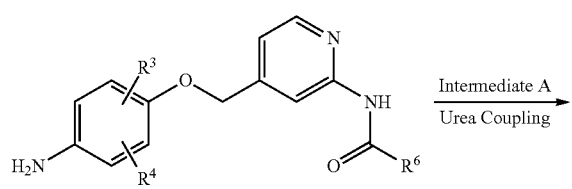

Intermediate G

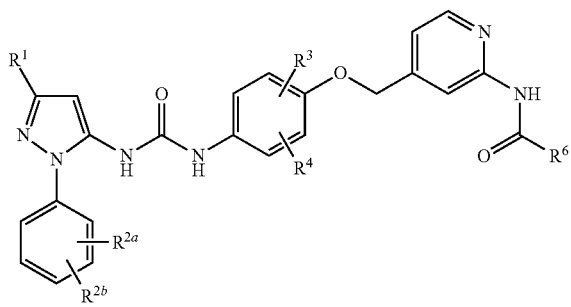

Amide Examples

Intermediate G

Compounds represented by Intermediate G were derived by the N-acylation of compounds represented by Intermediate H followed by reduction of the nitroarene, by a suitable process, such as catalytic hydrogenation or a dissolving metal reduction.

Intermediate H

Compounds represented by Intermediate H were derived from a nucleophilic aromatic substitution reaction ($S_NAr$ reaction) between an (aminoheteroaryl)methanol such as (2-aminopyridin-4-yl)methanol and a suitably substituted nitrobenzene, such as a substituted fluoronitobenzene (X=F), under basic conditions. Alternatively compounds represented by Intermediate H were obtained from the reaction of an (aminoheteroaryl)methanol, such as (2-aminopyridin-4-yl)methanol with a nitrophenol under Mitsunobu coupling conditions, typically in the presence of a triarylphosphine and a dialkyl azodicarboxylate.

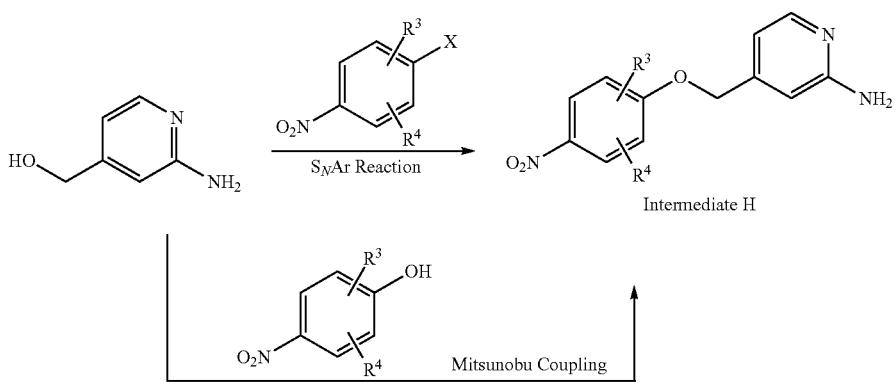

Analogues of the Methylether Linked Pyridines Incorporating a Terminal Urea

The genus of compound examples that possess a terminal ureidoheteroaryl (compounds of the genus for which —NR$^5$ (C=O)Q represents a urea) were prepared by a process represented by the reaction of an Intermediate A with an Intermediate J, under appropriate coupling conditions, as discussed above.

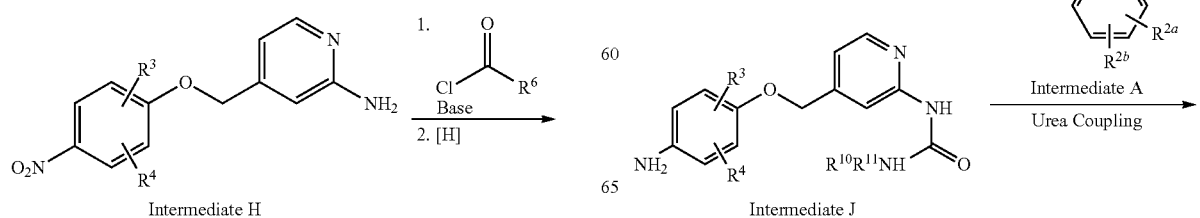

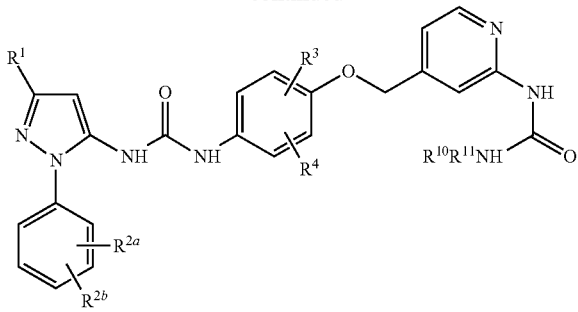

Urea Examples

Intermediate J

Compounds represented by Intermediate J were also generated from compounds represented by Intermediate H, employing a three step process. Conversion of the terminal aminoheteroaryl into a reactive carbamate, such as a phenyl carbamate, followed by treatment with an amine and subsequent reduction of the nitroarene provided the desired ureido derivatives represented by Intermediate H. In some instances it was advantageous to invert the order in which the second and third steps of the process were conducted

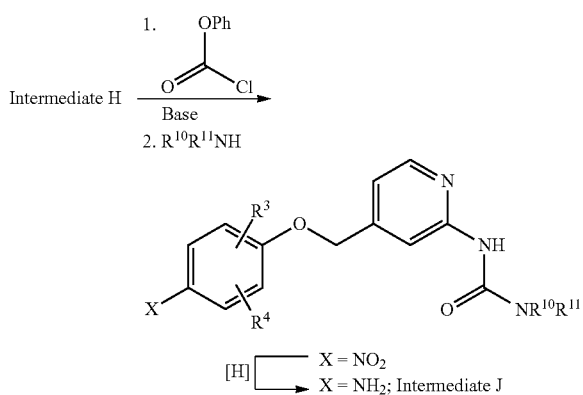

General Synthetic Processes for the Ether Linked Pyrimidine Genera

Analogues of the Ether Linked Pyrimidines Incorporating a Terminal Amide

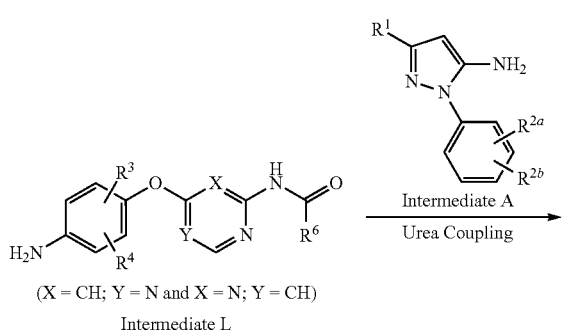

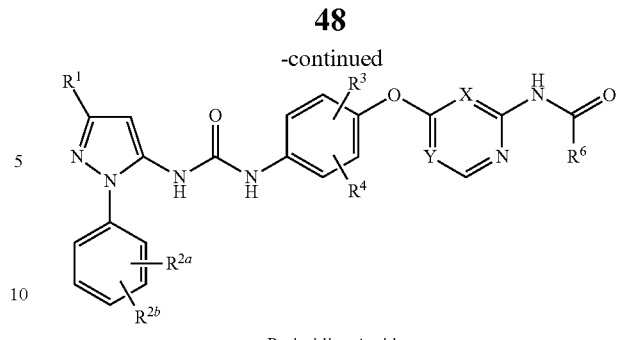

Pyrimidine Amides

The genera of compound examples that possess a terminal N-acyl aminopyrimidine (Pyrimidine Amides) were prepared by the reaction of a compound represented by Intermediate A with a compound represented by Intermediate L, employing appropriate coupling conditions, such as those described above, for the Pyridine Amides.

Intermediate K and Intermediate L

Compounds represented by Intermediate K were derived from the N-acylation and subsequent reduction of compounds represented by Intermediate J. These aryloxypyrimidine intermediates were obtained from an $S_NAr$ reaction between an aminopyrimidinol and a suitably substituted nitrobenzene.

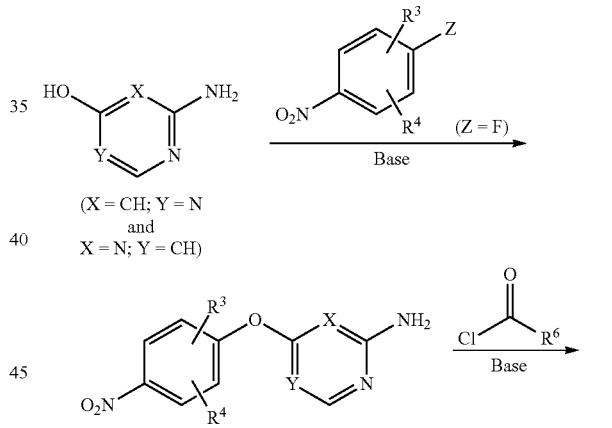

Analogues of the Ether Linked Pyrimidines Incorporating a Terminal Urea

The class of compound examples incorporating a ureido pyrimidine (Pyrimidine Ureas) were obtained from a coupling reaction of compounds represented by Intermediate M with compounds represented by Intermediate A, using the methodologies used to prepare other examples of the disclosure, such as the Pyridine Amides, described above.

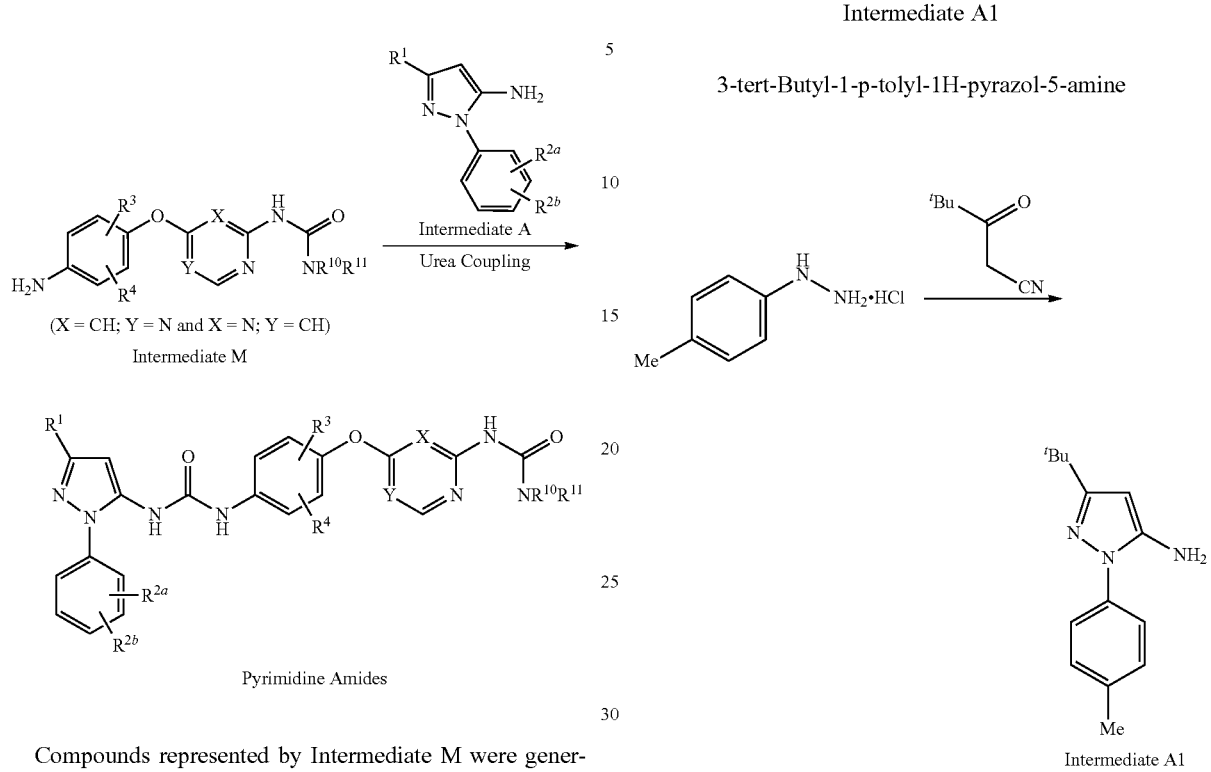

Compounds represented by Intermediate M were generated from compounds represented by Intermediate K, by conversion of the aminopyrimdine into a bis-aryloxycarbonyl derivative, followed by chemoselective reduction of the nitroarene, and subsequent treatment of the product with the desired amine, R⁵R⁶NH. In some instances it was advantageous to invert the order in which the second and third steps of the process were conducted

Compound Examples

Intermediate A1

3-tert-Butyl-1-p-tolyl-1H-pyrazol-5-amine

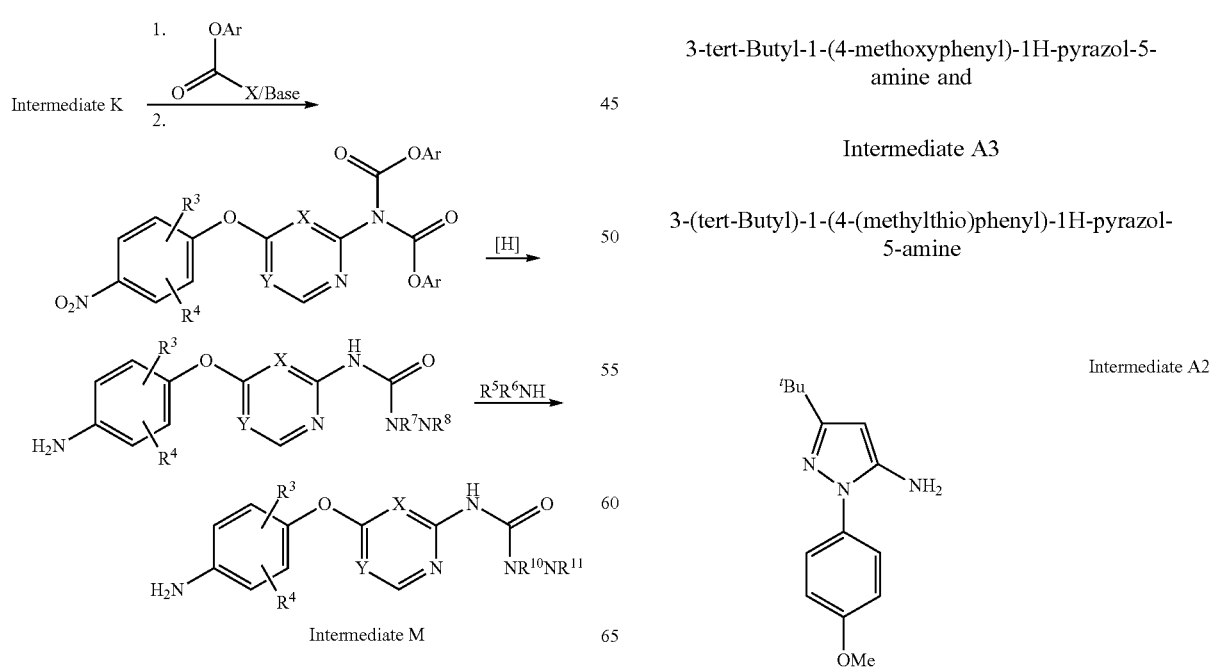

The aminopyrazole Intermediate A1 was prepared by the condensation of p-tolylhydrazine hydrochloride and 4,4-dimethyl-3-oxopentanenitrile according to the published procedure: Cirillo, P. F. et al., WO 2000/43384, 27 Jul. 2000.

Intermediate A2

3-tert-Butyl-1-(4-methoxyphenyl)-1H-pyrazol-5-amine and

Intermediate A3

3-(tert-Butyl)-1-(4-(methylthio)phenyl)-1H-pyrazol-5-amine

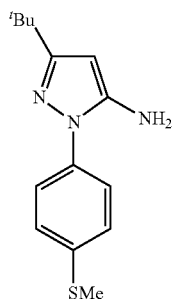

Intermediate A3

The anisoyl and methylthio analogues Intermediate A2 and Intermediate A3, were prepared in an analogous manner to Intermediate A1 according to the published procedures: Mathias, J. P. et al., US 2006/0035922, 10 Aug. 2005.

Intermediate A4

3-tert-Butyl-1-(4-(tert-butyldimethylsilyloxy)phenyl)-1H-pyrazol-5-amine

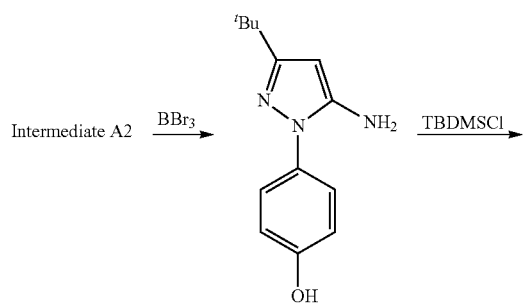

Intermediate A4

The silyl ether protected phenol, Intermediate 4, was prepared in a two step process from Intermediate A2. Lewis acid promoted demethylation of Intermediate A2 to the corresponding phenol was accomplished according to the published procedure: Dumas, J. et al., WO 2005/110994 24 Nov. 2005. The resulting phenol was protected with TBDMSCl according to the published procedure: Mathias, J. P. et al., US 2006/0035922, 10 Aug. 2005.

Intermediate A5

3-tert-Butyl-1-(4-((tert-butyldimethylsilyloxy)methyl)phenyl)-1H-pyrazol-5-amine

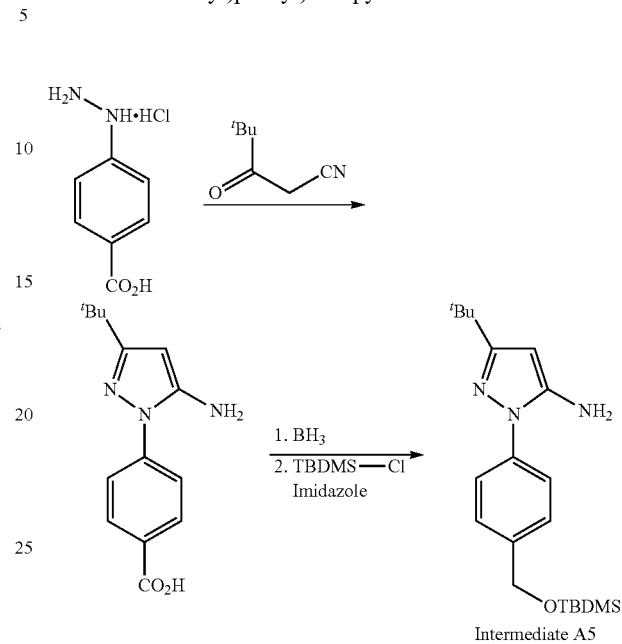

Intermediate A5

The silyl ether protected benzyl alcohol, Intermediate A5 was prepared via a three step process as previously described: Ito, K. et al., WO 2010/067131, 17 Jun. 2010.

Intermediate A6

3-tert-Butyl-1-(4-(tert-butyldimethylsilyloxymethyl)-3-methoxyphenyl)-1H-pyrazol-5-amine

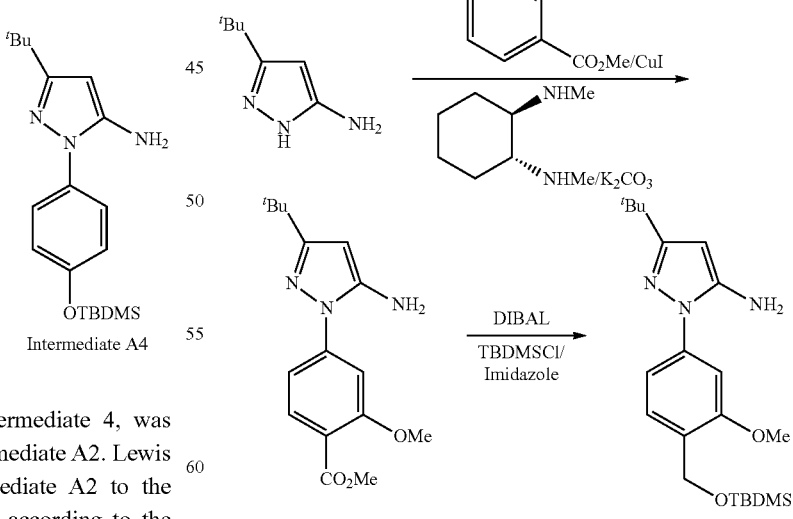

Intermediate A6

To a solution of methyl-4-iodo-2-methoxybenzoate (10.0 g, 34.2 mmol) in toluene (90 mL) was added 3-tert-butyl-1H-pyrazol-5-amine (5.24 g, 37.7 mmol) followed by (1R, 2R)—N¹,N²-dimethylcyclohexane-1,2-diamine (870 mg, 1.08 mL, 6.85 mmol) and potassium carbonate (14.9 g, 108 mmol). The mixture was purged with $N_2$, copper(I) iodide (326 mg, 1.71 mmol) was added and the reaction mixture was heated at reflux under $N_2$ for 18 hr. The mixture was cooled to RT and was partitioned between EtOAc (100 mL) and water (3×150 mL). The organic layer was separated and washed with aq. citric acid solution (1% w/v, 150 mL) followed by water (150 mL), and was then dried and evaporated in vacuo. The residue was purified by flash column chromatography ($SiO_2$, 330 g, EtOAc in isohexane, 0-100%, gradient elution) to afford methyl 4-(5-amino-3-tert-butyl-1H-pyrazol-1-yl)-2-methoxybenzoate as a buff coloured solid (3.62 g, 35%); $R^t$ 1.93 min (Method 2); m/z 304 $(M+H)^+$ $(ES^+)$.

The amino ester prepared above was combined with material obtained from a separate experiment to provide a single batch of the compound (7.83 g, 25.8 mmol) that was taken up into THF (80 mL) and cooled to 0° C. To this solution was added a solution of DIBAL (1 M in toluene, 77 mL, 77 mmol), dropwise, and the reaction mixture warmed to RT for 3 hr and then re-cooled to 0° C. and treated with saturated aq. sodium potassium tartrate (100 mL). The resulting precipitate was removed by filtration and the organic and aq components of the biphasic filtrate were separated. Organic phase was retained and the aq layer was extracted with EtOAc (3×200 mL). The combined organic extracts were dried and evaporated in vacuo and the residue was purified flash column chromatography ($SiO_2$, 120 g, EtOAC in isohexane, 0-100%, gradient elution) to afford (4-(5-amino-3-(tert-butyl)-1H-pyrazol-1-yl)-2-methoxyphenyl)methanol as a buff coloured solid (6.02 g, 80% yield); $R^t$ 1.22 min (Method 2); m/z 276 $(M+H)^+$ $(ES^+)$.

To a solution of the amino alcohol obtained above (6.00 g, 21.8 mmol) in THF (60 mL) under $N_2$ was added imidazole (1.71 g, 25.1 mmol) and TBDMSCI (3.61 g, 24.0 mmol) and the mixture maintained at RT for 72 hr. Additional portions of TBDMSCI (900 mg, 6.00 mmol) and imidazole (427 mg, 29.0 mmol) were added and after a further 24 hr the reaction mixture was evaporated in vacuo. The residue was taken up into EtOAc (50 mL) and was washed with saturated aq. $NaHCO_3$ (3×50 mL). The EtOAc layer was separated, dried and evaporated in vacuo and the residue was co-evaporated with MeOH (3×30 mL) to afford the title compound, Intermediate A6, as a cream coloured solid (8.60 g, 99%); $R^t$ 2.86 min (Method 2); m/z 390 $(M+H)^+$ $(ES^+)$.

Intermediate A7

3-(1-Methylcyclohexyl)-1-(p-tolyl)-1H-pyrazol-5-amine

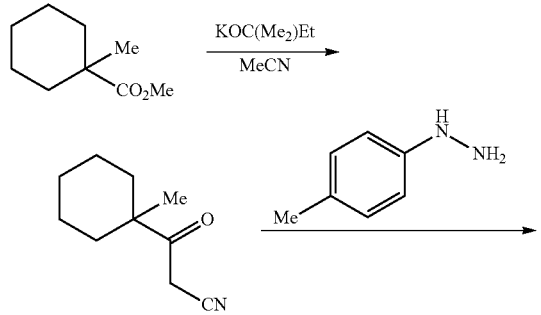

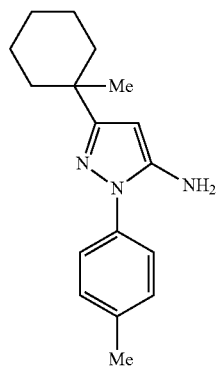

Intermediate A7

To a solution of acetonitrile (500 μL, 10.0 mmol) in THF (30 mL) at RT was added a solution of potassium 2-methylbutan-2-olate (1.7 M in THF, 16.9 mL, 28.7 mmol), followed by methyl 1-methylcyclohexanecarboxylate (2.24 g, 14.4 mmol) and the reaction mixture maintained at RT for 17 hr. The mixture was concentrated to ~20 mL in vacuo, diluted with EtOH (20 mL) and p-tolylhydrazine hydrochloride (1.52 g, 9.57 mmol) was added. The resulting mixture was acidified to pH1 by the addition of concentrated aq HCl and was then heated to 70° C. for 5 hr. The reaction mixture was cooled to RT for 16 hr and was concentrated to ~20 mL in vacuo, diluted with water (30 mL) and basified to pH12 by the addition of aq NaOH (2M). The solution was extracted with EtOAc (2×20 mL) and the combined organic extracts were washed with brine (30 mL), dried and evaporated in vacuo. The residue was purified by flash column chromatography ($SiO_2$, EtOAc in isohexane, 0-20%, gradient elution) to afford the title compound, Intermediate A7, as a yellow oil, (approximately 50% pure, containing 3-(1-methylcyclohexyl)-3-oxopropanenitrile) (1.3 g, 25%); $R^t$ 1.97 min (Method 2); m/z 270 $(M+H)^+$ $(ES^+)$. The material was used in subsequent reactions without further purification.

Intermediate B1

N-(4-(4-Amino-3-fluorophenoxy)pyridin-2-yl)-2-methoxyacetamide

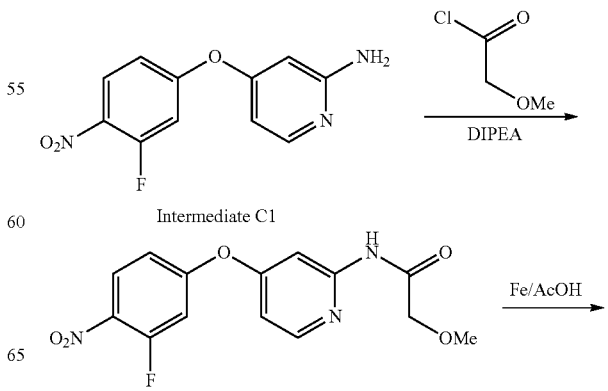

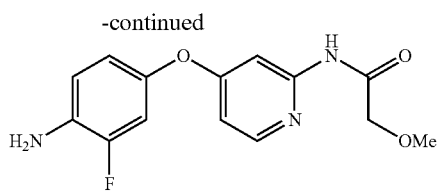

Intermediate B1

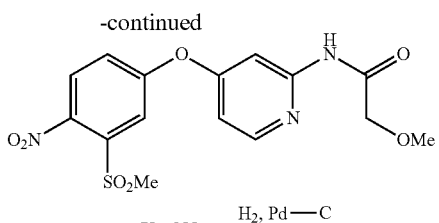

Intermediate B2

To a solution of Intermediate C1 (260 mg, 0.73 mmol) in dry DCM (4.0 mL) at 0° C. under $N_2$ was added DIPEA (340 µL, 2.1 mmol) followed by 2-methoxyacetyl chloride (140 µL, 1.57 mmol). The reaction mixture was warmed to RT for 3 hr and was then quenched by the addition of a solution of 1% $NH_3$ in MeOH (1.0 mL). After 10 min the mixture was evaporated in vacuo and the residue was purified by flash column chromatography ($SiO_2$, 12 g, EtOAc in isohexane, 0-100%, gradient elution) to afford N-(4-(3-fluoro-4-nitrophenoxy)pyridin-2-yl)-2-methoxyacetamide as a white solid (30 mg, ~90% purity, 11%): $R^t$ 1.94 min (Method 2); m/z 322 $(M+H)^+$ $(ES^+)$. This material was used directly in the next step.

To a solution of N-(4-(3-fluoro-4-nitrophenoxy)pyridin-2-yl)-2-methoxyacetamide (30 mg, 90% pure, 0.084 mmol) in AcOH (1.0 mL) was added iron powder (31 mg, 0.560 mmol) and the reaction mixture was heated at 60° C. for 2 hr and was then cooled to RT. A saturated aq. solution of $NaHCO_3$ (6.0 mL) was added slowly, and the mixture was extracted with EtOAc (2×30 mL). The combined organic extracts were washed with saturated aq. $NaHCO_3$ (15 mL), water (15 mL), and brine (15 mL), then dried and evaporated in vacuo to afford the title compound, Intermediate B1, as a dark yellow oil (26 mg, ~80% purity, 85%): $R^t$ 1.36 min (Method 2); m/z 292 $(M+H)^+$ $(ES^+)$. This material was used in the next step without further purification Intermediate B2

N-(4-(4-Amino-3-(methylsulfonyl)phenoxy)pyridin-2-yl)-2-methoxyacetamide

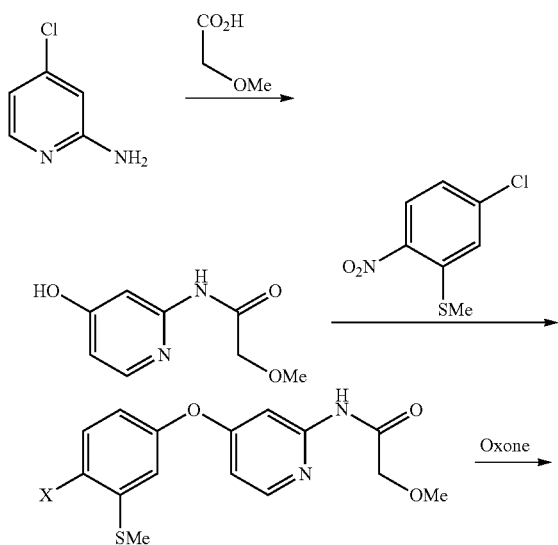

A mixture of 2-methoxyacetic acid (123 mL, 1.60 mol) and 4-chloropyridin-2-amine (51.5 g, 401 mmol) was heated at 165° C. for 5 hr. After cooling to RT the mixture was diluted with EtOAc (500 mL), and stirred at 70° C. for 1 hr. The mixture was re-cooled to RT, and the solid was collected by filtration and washed with EtOAc (2×150 mL). The yellow solid was suspended in water (150 mL) and treated with sodium hydroxide (6 M, 53.4 mL, 320 mmol). After stirring at RT for 1 hr, the golden solid was collected by filtration, washed with ice cold water (2×30 mL) and diethyl ether (300 mL) and was dried under vacuum overnight to furnish N-(4-hydroxypyridin-2-yl)-2-methoxyacetamide, as a pale yellow solid (43 g, 57%): m/z 182 $(M+H)^+$ $(ES^+)$.

To a suspension of potassium carbonate (865 mg, 6.26 mmol) in dry DMSO (8.0 mL) was added (5-chloro-2-nitrophenyl)(methyl)sulfane (910 mg, 4.47 mmol), and N-(4-hydroxypyridin-2-yl)-2-methoxyacetamide (977 mg, 5.36 mmol) to give a dark orange reaction mixture which was heated to 80° C. for 16 hr and then at 100° C. for 20 hr. The resulting mixture was cooled to RT and was partitioned between water (100 mL) and EtOAc (100 mL). The aq layer was extracted with EtOAc (70 mL) and the combined organic extracts were washed with water (4×50 mL) and with brine (50 mL) and then dried and evaporated in vacuo. The residue was triturated with EtOAc/isohexane (1:1 v/v, 15 mL) to afford 2-methoxy-N-(4-(3-(methylthio)-4-nitrophenoxy)pyridin-2-yl)acetamide as an orange solid (1.25 g, 79%); $R^t$ 4.37 min (Method 1 basic); m/z 350 $(M+H)^+$ $(ES^+)$.

To a solution of 2-methoxy-N-(4-(3-(methylthio)-4-nitrophenoxy)pyridin-2-yl)acetamide (400 mg, 1.1 mmol) in DCM (5 mL) was added Oxone® (1.76 g, 2.86 mmol) followed by water (0.5 mL) and MeOH (2.0 mL) and the reaction mixture was maintained at RT for 20 hr. The mixture was diluted with DCM (60 mL) and was washed with water (20 mL), then dried and evaporated in vacuo to afford 2-methoxy-N-(4-(3-(methylsulfonyl)-4-nitrophenoxy)pyridin-2-yl)acetamide, as a yellow oil (380 mg, ~90% purity, 78%): $R^t$ 1.72 min (Method 2); m/z 382 $(M+H)^+$ $(ES^+)$. This material was used in the next step without further purification.

A solution of 2-methoxy-N-(4-(3-(methylsulfonyl)-4-nitrophenoxy)pyridin-2-yl)acetamide (180 mg, 0.425 mmol) in a mixture of MeOH, DCM and AcOH (25:10:0.1 v/v/v, 35 mL) was subjected to hydrogenation by passage through a Thales H-cube (1.0 mL min$^{-1}$, 40° C., 30 mm 10% Pd/C Cat-Cart, full hydrogen mode, two passages). The reaction mixture was evaporated in vacuo and the residue was co-evaporated with toluene (3.0 mL) to afford the title compound, Intermediate B2, as a colourless oil (138 mg, ~80% purity, 74.0%); $R^t$ 1.40 min (Method 2); m/z 352 $(M+H)^+$ $(ES^+)$. This product was used as obtained without further purification.

Intermediate B3

N-(4-(4-Amino-3-(trifluoromethyl)phenoxy)pyridin-2-yl)-2-methoxyacetamide

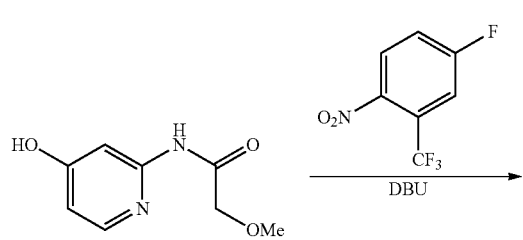

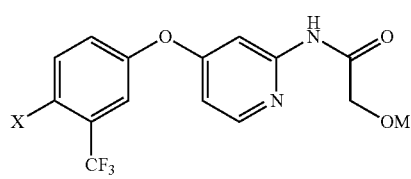

Intermediate B3

To a suspension of N-(4-hydroxypyridin-2-yl)-2-methoxyacetamide (479 mg, 2.63 mmol) in MeCN (5.0 mL) at RT was added DBU (0.430 μL, 2.87 mmol) and after 20 min, 4-fluoro-1-nitro-2-(trifluoromethyl)benzene (330 μL, 2.39 mmol) was added drop-wise over 10 min. The reaction mixture was maintained at RT for 16 hr and was then partitioned between water (10 mL) and EtOAc (50 mL). The aq layer was extracted with EtOAc (50 mL) and the combined organic extracts were washed with saturated aq $NaHCO_3$ (20 mL), water (20 mL) and brine (20 mL) and then dried. Evaporation of the volatiles in vacuo afforded 2-methoxy-N-(4-(4-nitro-3-(trifluoromethyl)phenoxy)pyridin-2-yl)acetamide as a bright yellow oil (920 mg, 98%); $R^t$ 4.47 min (Method 1 basic); m/z 372 (M+H)$^+$ (ES$^+$).

A solution of 2-methoxy-N-(4-(4-nitro-3-(trifluoromethyl)phenoxy)pyridin-2-yl)acetamide (300 mg, 0.81 mmol) in MeOH (35 mL) and AcOH (0.5 mL) was subjected to hydrogenation by passage through a Thales H-cube (1.0 mL 40° C., 30 mm 10% Pt/C Cat-Cart, full hydrogen mode, two passages). The reaction mixture was evaporated in vacuo and the residue was purified by flash column chromatography (SiO$_2$, 40 g, 0-20% [1% NH$_3$ in MeOH] in DCM, 0-20%, gradient elution) to afford the title compound, Intermediate B3, as an orange oil (210 mg, ~75% purity 57%); $R^t$ 4.24 min (Method 1 basic); m/z 342 (M+H)$^+$ (ES$^+$). This material was used in subsequent reactions without further purification.

Intermediate B4

N-(4-(4-Amino-3-chloro-2-cyanophenoxy)pyridin-2-yl)-2-methoxyacetamide

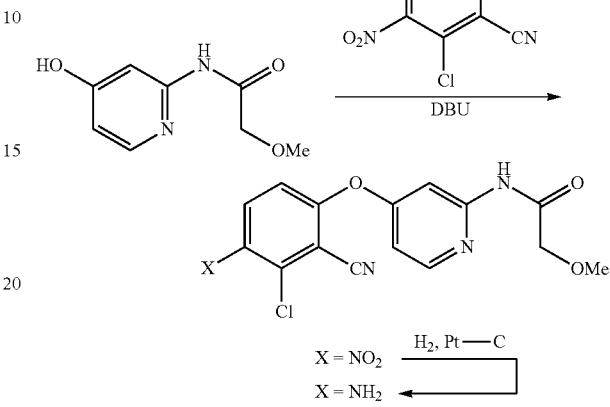

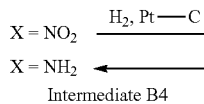

Intermediate B4

To a suspension of N-(4-hydroxypyridin-2-yl)-2-methoxyacetamide (300 mg, 2.63 mmol) in MeCN (4.0 mL) at RT was added DBU (270 μL, 1.81 mmol). After 15 min the resulting mixture was added dropwise over 30 min to a solution of 2-chloro-6-fluoro-3-nitrobenzonitrile (462 mg, 2.31 mmol) in dry MeCN (5.0 mL) at 0° C. The reaction mixture was warmed to RT and after 16 hr water (10 mL) was added. The mixture was maintained at RT for a further 30 min and the solid which separated was isolated by filtration to afford N-(4-(3-chloro-2-cyano-4-nitrophenoxy)pyridin-2-yl)-2-methoxyacetamide as a bright yellow solid (0.311 g, 52%); $R^t$ 4.09 min (Method 1 basic); m/z 363 (M+H)$^+$ (ES$^+$).

A solution of N-(4-(3-chloro-2-cyano-4-nitrophenoxy)pyridin-2-yl)-2-methoxyacetamide (100 mg, 0.28 mmol) in a mixture of MeOH and DCM (10:1 v/v, 22 mL) containing AcOH (4 drops) was subjected to hydrogenation by passage through a Thales H-cube (1.0 mL min$^{-1}$, 50° C., 55 mm 10% Pt/C Cat-Cart, full hydrogen mode). The reaction mixture was evaporated in vacuo to afford the title compound, Intermediate B4, (87 mg, ~90% purity, 85%); $R^t$ 1.68 min (Method 2); m/z 333 (M+H)$^+$ (ES$^+$). This impure material was used without further purification in subsequent synthetic transformations.

Intermediate B5

N-(4-(5-Aminoquinolin-8-yloxy)pyridin-2-yl)-2-methoxyacetamide

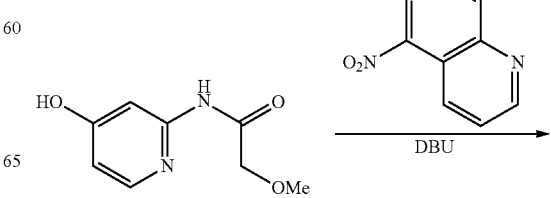

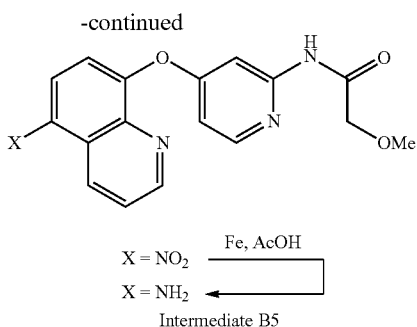

X = NO₂  Fe, AcOH
X = NH₂ ← Intermediate B5

To a suspension of N-(4-hydroxypyridin-2-yl)-2-methoxyacetamide (417 mg, 2.29 mmol) in MeCN (5.0 mL) was added DBU (0.380 µL, 2.50 mmol) and the reaction mixture kept at RT for 1 hr. A suspension of 8-fluoro-5-nitroquinoline (400 m g, 2.08 mmol) in MeCN (5.0 mL) was added and the reaction mixture was maintained at RT for 16 hr, during which time it became dark red in colour. Water (10 mL) was added and the reaction mixture was stirred vigorously for a further 30 min and was then partitioned between EtOAc (100 mL) and water (40 mL). The organic layer was separated and was extracted with water (3×40 mL) and brine (30 mL), then dried and evaporated in vacuo to afford 2-methoxy-N-(4-(5-nitroquinolin-8-yloxy)pyridin-2-yl)acetamide as a dark yellow oil (638 mg, 82%); $R^t$ 1.79 min (Method 2); m/z 355 $(M+H)^+$ $(ES^+)$.

A mixture of 2-methoxy-N-(4-(5-nitroquinolin-8-yloxy)pyridin-2-yl)acetamide (200 mg, 0.564 mmol) and iron powder (189 mg, 3.39 mmol) in AcOH (4.0 mL) was heated to 50° C. for 2 hr. The reaction mixture was cooled to RT and was added cautiously to a stirred solution of saturated aq NaHCO₃ and the mixture extracted with EtOAc (100 mL). The organic phase was separated and was washed with saturated aq NaHCO₃ (20 mL), water (20 mL) and brine (20 mL) and was then dried and evaporated in vacuo to afford the title compound, Intermediate B5, as a yellow solid (182 mg, 94%); $R^t$ 0.99 min (Method 2); m/z 325 $(M+H)^+$ $(ES^+)$.

Intermediate B6

N-(4-(7-Amino-1H-indazol-4-yloxy)pyridin-2-yl)-2-methoxyacetamide

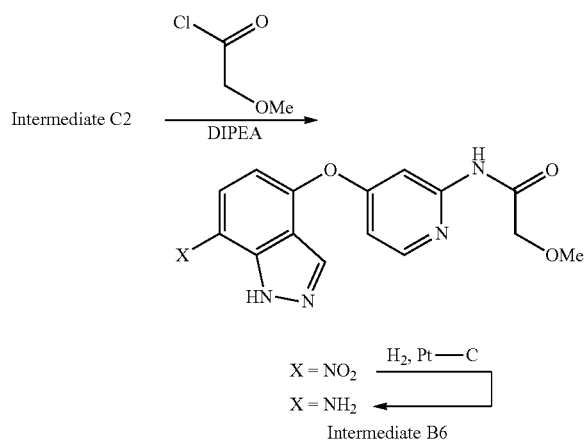

X = NO₂  H₂, Pt—C
X = NH₂ ← Intermediate B6

To a suspension of Intermediate C2 (60 mg, 0.22 mmol) in DCM (2.0 mL) containing DIPEA (77 µL, 0.44 mmol) at 0° C. was added 2-methoxyacetyl chloride (24 µL, 0.27 mmol) in two portions. The mixture was maintained at 0° C. for 10 min and was then warmed to RT. After 1 hr an additional portion of 2-methoxyacetyl chloride (12 µL, 0.13 mmol) was added and the mixture was kept at RT for 20 min. The reaction was quenched by the addition of a solution of NH₃ in MeOH (7M, 2.0 mL) and after 5 min the mixture was evaporated in vacuo. The residue was purified by flash column chromatography (SiO₂, 12 g, EtOAc in isohexane, 0-100%, gradient elution) to afford 2-methoxy-N-(4-(7-nitro-1H-indazol-4-yloxy)pyridin-2-yl)acetamide as a pale yellow solid (24 mg, 30%); $R^t$ 1.60 min (Method 2); m/z 344 $(M+H)^+$ $(ES^+)$ A solution of 2-methoxy-N-(4-(7-nitro-1H-indazol-4-yloxy)pyridin-2-yl)acetamide (20 mg, 0.06 mmol) in a mixture of THF and DMF (5:2, v/v, 7.0 mL) was subjected to hydrogenation by passage through a Thales H-cube (0.8 mL min⁻¹, 50° C., 30 mm 10% Pt/C Cat-Cart, full hydrogen mode). The reaction mixture was evaporated in vacuo to afford the title compound, Intermediate B6 as a brown oil (19 mg, 99%); $R^t$ 1.20 min (Method 2); m/z 314 $(M+H)^+$ $(ES^+)$. This material was used in the subsequent step without further purification.

Intermediate B7

N-(4-(4-Amino-2,3-dichlorophenoxy)pyridin-2-yl)pyrrolidine-1-carboxamide

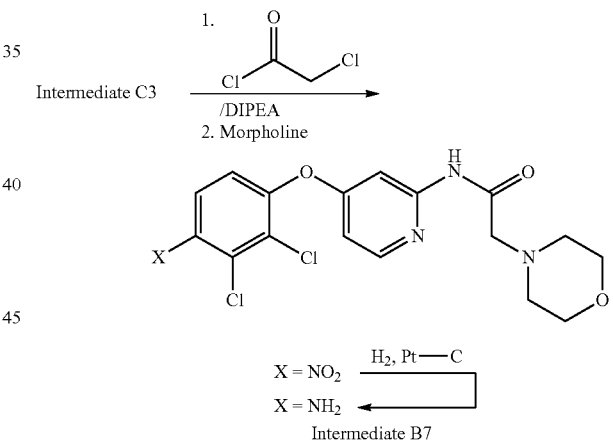

X = NO₂  H₂, Pt—C
X = NH₂ ← Intermediate B7

To a solution of Intermediate C3 (6.00 g, 20.0 mmol) and DIPEA (8.0 mL, 46 mmol) in THF (35 mL) under N₂ at 0° C. was added 2-chloroacetyl chloride (1.8 mL, 23 mmol) and the reaction mixture maintained at 0° C. for 30 min and then warmed to RT for 2 hr. The mixture was re-cooled to 0° C., treat with a second aliquot of 2-chloroacetyl chloride (1.8 mL, 23 mmol) and was then warmed to RT for a further 1.5 hr. The resulting mixture was diluted with saturated aq NaHCO₃ (50 mL) and extracted with DCM (3×50 mL) and the combined organic extracts dried and evaporated in vacuo. The residue was taken up into THF (10.0 mL) containing DIPEA (7.6 mL, 44 mmol) and was cooled to 0° C. under N₂ and treated with morpholine (5.8 mL, 66 mmol). The reaction mixture was warmed to RT for 16 hr and was then diluted with saturated aq NaHCO₃ (75 mL) and extracted with DCM (3×50 mL). The combined organic extracts were dried and evaporated in vacuo and the residue was purified by flash column chromatography (SiO$_2$, 120 g, [5% MeOH in EtOAc] in isohexane, 0-100%, gradient elution) to afford N-(4-(2,3-dichloro-4-nitrophenoxy)pyridin-2-yl)-2-morpholino acetamide as a brown oil (6.53 g, 92% pure by HPLC, 70%); R$^t$ 1.58 min (Method 2); m/z 427 (M+H)$^+$ (ES$^+$). This material was used directly in the next step without further purification.

A mixture of the nitroarene obtained above (6.53 g, 92% pure, 14.1 mmol) and iron powder (4.7 g, 84 mmol) in AcOH (50 mL) was heated to 50° C. for 1.5 hr and then cooled to RT and filtered through a pad of celite. The pad was washed with EtOAc (2×50 mL) and then with THF (2×50 mL) and the combined filtrate and washings were evaporated in vacuo. After co-evaporation of the residue with toluene it was partitioned between EtOAc/THF (3:1 v/v, 120 mL) and saturated aq NaHCO$_3$ (120 mL). The aq layer was separated and was extracted with EtOAc/THF (3:1 v/v, 2×100 mL) and the combined organic layers were dried and evaporated in vacuo to afford the title compound, Intermediate B7, as a brown solid (3.88 g, 65%); R$^t$ 1.32 min (Method 2); m/z 397 (M+H)$^+$ (ES$^+$).

Intermediate B8 tert-Butyl (2-((4-(4-amino-2,3-dichlorophenoxy)pyridin-2-yl)amino)-2-oxoethyl)(methyl)carbamate

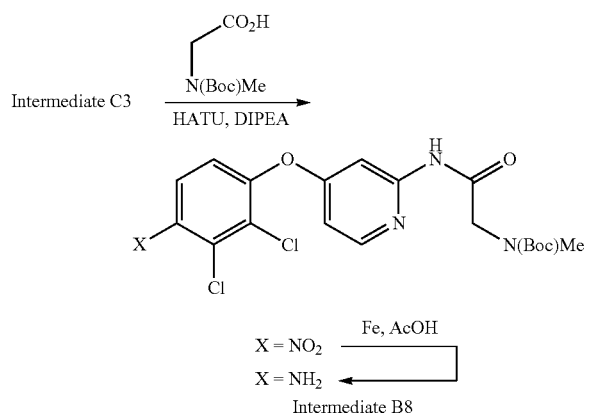

To a solution of Intermediate C3 (3.50 g, 11.7 mmol) and 2-((tert-butoxycarbonyl)(methyl)amino)acetic acid (2.76, 14.6 mmol) in dry DMF (40.0 mL) at 0° C. under N$_2$ was added DIPEA (3.6 mL, 20 mmol) followed by HATU (5.54 g, 14.6 mmol) and the reaction mixture warmed to RT for 18 hr and then partitioned between EtOAc (150 mL) and saturated aq. NaHCO$_3$ (150 mL). The aq layer was separated and extracted with EtOAc (2×100 mL) and the combined organic extracts were dried and evaporated in vacuo. The residue was purified by flash column chromatography (SiO$_2$, 80 g, EtOAc in isohexane, 20-80%, gradient elution) to afford tert-butyl (2-((4-(2,3-dichloro-4-nitrophenoxy)pyridin-2-yl)amino)-2-oxoethyl)(methyl)carbamate as an orange oil (5.20 g, 95%): R$^t$ 2.54 min (Method 2); m/z 471 (M+H)$^+$ (ES$^+$).

To a solution of the nitroarene product, obtained above, (5.19 g, 11.0 mmol) in AcOH (60.0 mL) was added iron powder (3.69 g, 66.1 mmol) and the mixture heated at 50° C. for 1 hr and then cooled to RT and filtered through a pad of celite. The pad was washed sequentially with EtOAc and with THF and the combined filtrate and washings were evaporated in vacuo. The residue was co-evaporated with toluene and then partitioned between saturated aq. NaHCO$_3$ (200 mL) and EtOAc/THF (3:1 v/v, 200 mL). The aq layer was separated and was extracted with EtOAc/THF (3:1 v/v, 2×150 mL) and the combined organic extracts were dried and evaporated in vacuo to afford the title compound, Intermediate B8, as a brown solid (3.95 g, 80%): R$^t$ 2.18 min (Method 2); m/z 441 (M+H)$^+$ (ES$^+$).

Intermediate C1

4-(3-Fluoro-4-nitrophenoxy)pyridin-2-amine

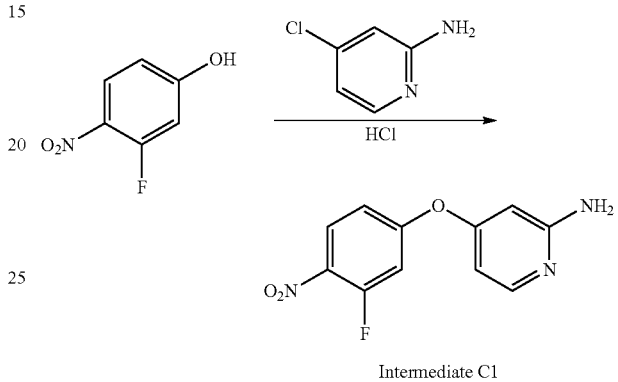

Intermediate C1

To a solution of 3-fluoro-4-nitrophenol (1.16 g, 7.38 mmol) in dry NMP (1.5 mL) was added 4-chloropyridin-2-amine (633 mg, 4.92 mmol) and conc. hydrochloric acid (approx. 11 M, 45 µL, ~0.5 mmol). The reaction mixture was placed in a preheated heating block and maintained at 160° C. for 2 hr, then at 170° C. for 2 hr and finally at 190° C. for 6 hr. The reaction mixture was cooled to RT and was subjected to SCX capture and release. The crude product so obtained was purified by flash column chromatography (SiO$_2$, 40 g, MeOH in DCM, 0-2%, gradient elution) to afford the title compound, Intermediate C1, as a white solid (0.26 g, ~70% purity, 15%); R$^t$ 1.10 min (Method 2); m/z 250 (M+H)$^+$ (ES$^+$). This material was contaminated with 4-chloropyridin-2-amine and was used without further purification.

Intermediate C2

4-(7-Nitro-1H-indazol-4-yloxy)pyridin-2-amine

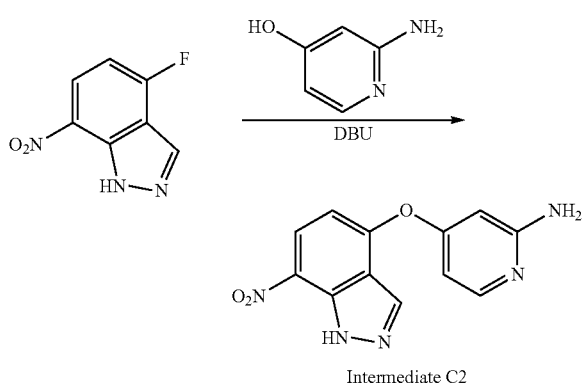

Intermediate C2

To a suspension of 2-aminopyridin-4-ol (228 mg, 2.07 mmol) in MeCN (1.5 mL) was added DBU (310 μL, 2.07 mmol) and the mixture maintained at RT until all the solids were completely dissolved, when 4-fluoro-7-nitro-1H-indazole (250 mg, 1.380 mmol) was added in a single portion. The reaction mixture was kept at RT for 1 hr and was then partitioned between EtOAc (20 mL) and a mixture of brine (10 mL) and water (20 mL). The aq layer was extracted with EtOAc (2×10 mL) and the combined organic extracts were washed with brine (50 mL), dried and evaporated in vacuo. The residue was purified by flash column chromatography ($SiO_2$, 12 g, EtOAc in DCM, 0-100%, then MeOH in EtOAc, 0-2%, gradient elution) to afford the title compound, Intermediate C2, as a yellow solid (65 mg, 16%); $R^t$ 1.10 min (Method 2); m/z 272 (M+H)$^+$ (ES$^+$).

Intermediate C3

4-(2,3-Dichloro-4-nitrophenoxy)pyridin-2-amine

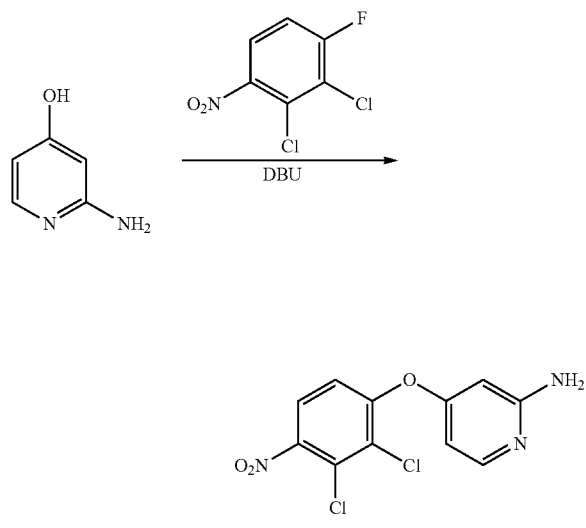

Intermediate C3

To a suspension of 2-aminopyridin-4-ol (750 mg, 6.81 mmol) in MeCN (10.0 mL) was added DBU (1.34 mL, 8.91 mmol) and the mixture maintained at RT for 30 min until a solution was obtained. A solution of 2,3-dichloro-1-fluoro-4-nitrobenzene (1.10 g, 5.24 mmol) in MeCN (5.0 mL) was added and the reaction mixture kept at RT for 16 hr. The resulting mixture was concentrated in vacuo to ca 5 mL. and was then partitioned between water (40 mL) and EtOAc (30 mL). The aq layer was extracted with EtOAc (30 mL) and the combined organic extracts were washed with brine (30 mL), dried and then evaporated in vacuo. The residue was triturated with $Et_2O$ (20 mL) to afford the title compound, Intermediate C3, as a yellow solid (1.30 g, 79%); $R^t$ 1.63 min (Method 2); m/z 300/302 (M+H)$^+$, (ES$^+$)

Intermediate D1

N-(4-(4-(3-(3-tert-Butyl-1-p-tolyl-1H-pyrazol-5-yl)ureido)naphthalen-1-yloxy)pyridin-2-yl)-2-methoxyacetamide

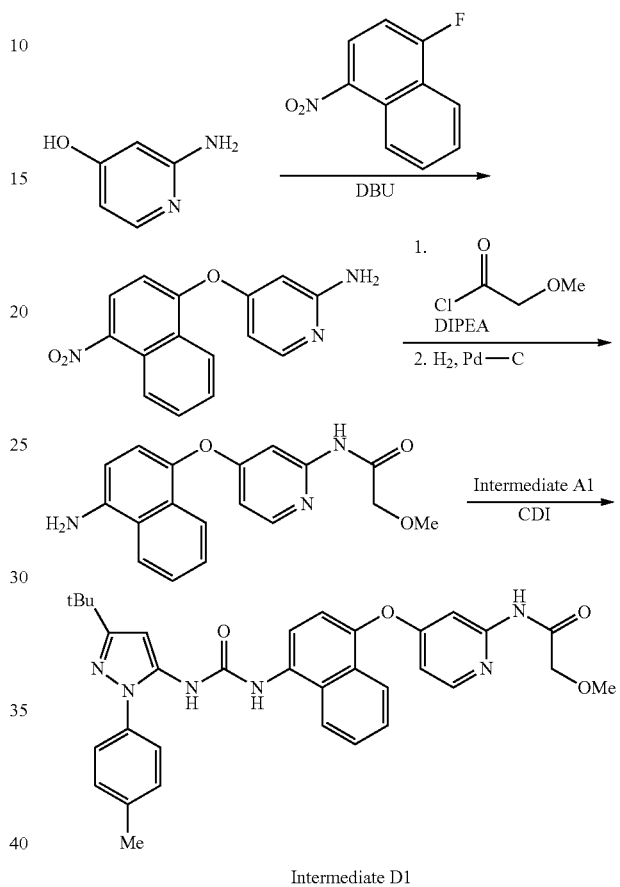

Intermediate D1

To a stirred suspension of 2-aminopyridin-4-ol (53.9 g, 489 mmol) in MeCN (500 mL) was added DBU (102 mL, 678 mmol) dropwise over 30 min. The resulting solution was maintained at RT for 30 min and was then treated dropwise with a solution of 1-fluoro-4-nitronaphthalene (72.0 g, 377 mmol) in acetonitrile (400 mL) over 50 min. After stirring overnight at RT the reaction was heated at 50° C. for 2 hr. The reaction was removed from the heat, and with stirring, was diluted with water (600 mL) portionwise to minimise the risk of rapid crystallization. The mixture was allowed to cool to RT over 2 hr and was then cooled further to 0° C. The yellow precipitate so produced was collected by filtration and washed sequentially with a mixture of water and acetonitrile (1:1, 2×100 mL) and then with water (500 mL) to give 4-(4-nitronaphthalen-1-yloxy)pyridin-2-amine, as a yellow solid (76.0 g, 70%): m/z 283 (M+H)$^+$ (ES$^+$).

To a stirred suspension of 4-(4-nitronaphthalen-1-yloxy)pyridin-2-amine (71.8 g, 255 mmol) in dry DCM (1.1 L) and DIPEA (84.0 mL, 511 mmol), at 0° C. (ice bath) was added dropwise 2-methoxyacetyl chloride (35.0 mL, 383 mmol) over 20 min. The resulting red solution was stirred at RT for 1 hr and was then treated with a solution of $NH_3$ in MeOH (7 M, 100 mL). A precipitate formed immediately and the reaction mixture was stirred for a further 15 min and the volatiles were evaporated in vacuo. The solid residue was triturated with water (900 mL), collected by filtration and washed with water (2×250 mL) to give 2-methoxy-N-(4-(4-nitronaphthalen-1-yloxy)pyridin-2-yl)acetamide, as a yellow solid (89.1 g, 96%): m/z 354 (M+H)$^+$ (ES$^+$).

To a solution of 2-methoxy-N-(4-(4-nitronaphthalen-1-yloxy)pyridin-2-yl)acetamide (50.0 g, 142 mmol) in DMF (500 mL) under nitrogen was added palladium on carbon (10% w/w, 5.0 g, 14.1 mmol). The mixture was purged with hydrogen and maintained under a slight positive hydrogen atmosphere for 48 hr. The catalyst was removed by filtration through celite and the pad washed with DMF (2×100 mL) and then DCM (100 mL). The solvents were removed in vacuo to afford a dark brown residue which was treated with water (150 mL) and the mixture evaporated. Toluene (100 mL) was added and evaporated to remove residual water. After drying overnight under vacuum, the material was triturated from diethyl ether (250 mL) to afford N-(4-(4-aminonaphthalen-1-yloxy)pyridin-2-yl)-2-methoxyacetamide, as a green solid (43.3 g, 85%): m/z 324 (M+H)$^+$ (ES$^+$).

To a suspension of CDI (32.5 g, 200 mmol) in dry DCM (300 mL) was added Intermediate A1 (46.0 g, 200 mmol) portionwise over 1 hr and the mixture was stirred at RT for 2 hr, over which time a yellow solution was formed. An aliquot of this solution (220 mL, 147 mmol), was added dropwise over 20 min to a solution of N-(4-(4-aminonaphthalen-1-yloxy)pyridin-2-yl)-2-methoxyacetamide (40.0 g, 111 mmol) in DCM (600 mL) The reaction mixture was stirred at RT for 18 hr and ethanol (50.0 mL) was added. After a further 1.5 hr the solvent was removed in vacuo to yield a purple oil which was taken up into EtOAc (1.0 L) and was washed sequentially with sat. NaHCO$_3$ solution (2×250 mL), water (2×250 mL) and brine (2×200 mL) and was then dried. The solvent was removed in vacuo to yield a dark red viscous oil (75 g) which was purified through a silica plug (SiO$_2$, 500 g, EtOAc in isohexane, 20-100%, gradient elution) to provide a brown solid (64.5 g). This material was combined with a second identically prepared batch (129 g in total) and re-crystallised (isohexane/EtOAc, 2:5, 4.0 L) to afford the title compound, Intermediate D1, as a pale brown solid (101 g, 78%); m/z 579 (M+H)$^+$ (ES$^+$).

Intermediate E1

1-(4-(4-Amino-2,3-dichlorophenoxy)pyridin-2-yl)-3-methylurea

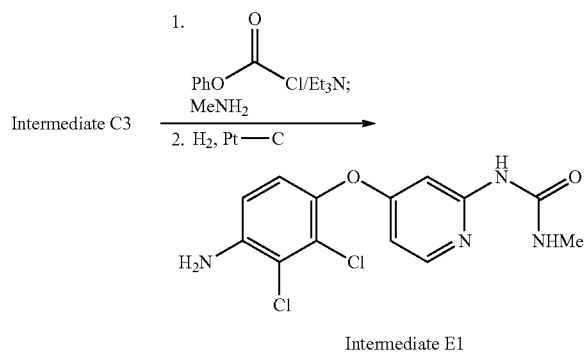

To a solution of triethylamine (543 µL, 3.90 mmol) and phenyl carbonochloridate (409 µL, 3.25 mmol) in DCM (8.0 mL) was added, portion-wise, Intermediate C3, (390 mg, 1.30 mmol) and the reaction mixture maintained at RT for 16 hr. A solution of methanamine (2M in THF, 325 µL, 6.50 mmol) was added and after a further 24 hr at RT the reaction mixture was quenched by the addition of methanolic NH$_3$ (1% solution, 5.0 mL) and was evaporated in vacuo. The residue was triturated with saturated NaHCO$_3$ (20 mL) then washed with water and dried in vacuo to afford 1-(4-(2,3-dichloro-4-nitrophenoxy)pyridin-2-yl)-3-methylurea as a yellow solid (290 mg, 60%); R$^t$ 4.72 min (Method 1 basic); m/z 357/359 (M+H)$^+$, (ES$^+$)

A solution of 1-(4-(2,3-dichloro-4-nitrophenoxy)pyridin-2-yl)-3-methylurea (290 mg, 0.812 mmol) in a mixture of methanol (35 mL), DCM (20 mL), THF (20 mL) and AcOH (1.0 mL) was subjected to hydrogenation by passage through a Thales H-cube (1.0 mL min$^{-1}$, 40° C., 55 mm, 10% Pt/C Cat-Cart, full hydrogen mode) and was then evaporated in vacuo. The residue was subjected to SCX capture and release to afford the title compound, Intermediate E1, as a brown solid which was used without further purification (147 mg, 80% pure, 44%); R$^t$ 1.48 min (Method 2); m/z 327/329 (M+H)$^+$ (ES$^+$).

Intermediate E2

N-(4-(4-Amino-2,3-dichlorophenoxy)pyridin-2-yl)pyrrolidine-1-carboxamide

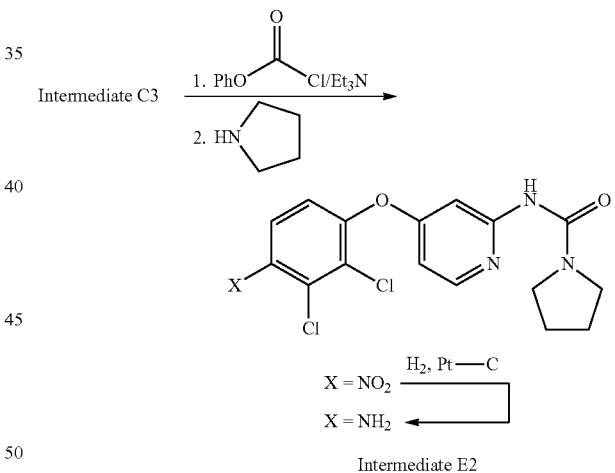

To a solution of phenyl carbonochloridate (2.1 mL, 16.7 mmol) and triethylamine (2.8 mL, 20.0 mmol) in DCM (40 mL) at 0° C. was added Intermediate C3 (2.0 g, 6.7 mmol) as a solid in five equal portions. The reaction mixture was warmed to RT and after 16 hr pyrrolidine (2.8 mL, 33.3 mmol) was added dropwise. The reaction mixture was maintained at RT for 2 hr and was then quenched by the addition of 1% solution of NH$_3$ in MeOH (30 mL) and after a further 30 min was evaporated in vacuo. The residue was partitioned between saturated aq NaHCO$_3$ (50 mL) and EtOAc (50 mL). The organic phase was separated and was washed with brine (50 mL), and then dried and evaporated in vacuo. The residue was triturated with EtOAc (30 mL) to afford the desired product as a yellow solid. The supernatant was evaporated in vacuo and the residue was purified by flash column chromatography (SiO$_2$, EtOAc in isohexane, 50-100%, gradient elution) to furnish a second batch of product, which was combined with the first to afford N-(4-(2,3-dichloro-4-nitrophenoxy)pyridin-2-yl)pyrrolidine-1-carboxamide as a yellow solid (2.22 g, 82%); R$^t$ 1.89 min (Method 2); m/z 397/399 (M+H)$^+$ (ES)$^+$.

A solution of N-(4-(2,3-dichloro-4-nitrophenoxy)pyridin-2-yl)pyrrolidine-1-carboxamide (2.20 g, 5.54 mmol) in a mixture of MeOH (100 ml), DCM (25 ml) and AcOH (2.0 mL) was subjected to hydrogenation by passage through a Thales H-cube (1.0 mL min$^{-1}$, 40° C., 55 mm 10% Pt/C Cat-Cart, full hydrogen mode). The reaction mixture was evaporated in vacuo and the residue was partitioned between saturated aq NaHCO$_3$ (75 mL) and EtOAc (100 mL). The organic phase was separated and was washed with brine (50 mL) and then dried and evaporated in vacuo. The residue was triturated with methanol (20 mL) and the supernatant was decanted and evaporated in vacuo to afford the title compound, Intermediate E2, as a brown solid (1.66 g, 75% pure (LCMS), 61%); R$^t$ 4.40 min (Method 1, basic); m/z 397/399 (M+H)$^+$ (ES)$^+$. This material was used as obtained, without further purification.

Intermediate E3

(R)—N-(4-(4-Amino-2,3-dichlorophenoxy)pyridin-2-yl)-3-(dimethylamino)pyrrolidine-1-carboxamide

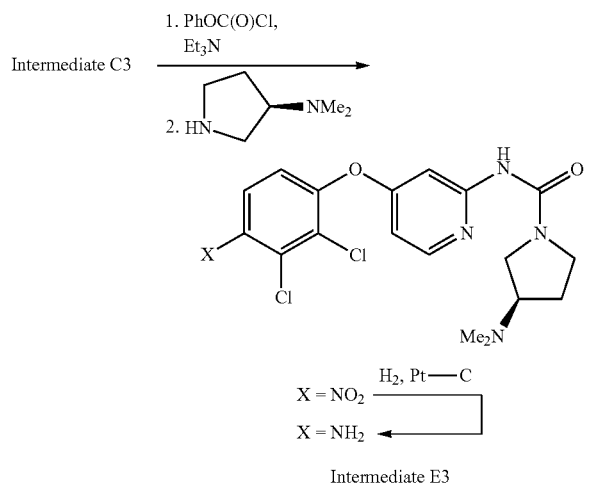

Intermediate E3

To a solution of triethylamine (700 µL, 5.00 mmol) in dry DCM (10.0 mL) at 0° C. was added phenyl carbonochloridate (520 µL, 4.17 mmol) and after an interval of 10 min Intermediate C3 (500 mg, 1.7 mmol) was added and the mixture allowed to warm to RT. After 1.5 hr the reaction mixture was re-cooled to 0° C. and a solution of (R)—N,N-dimethylpyrrolidin-3-amine (500 µL, 3.93 mmol) in DCM (1.0 mL) was added and the mixture warmed to RT for 4 hr. An additional aliquot of (R)—N,N-dimethylpyrrolidin-3-amine (250 µL, 1.97 mmol) was added and after a further 16 hr the reaction mixture was quenched by the addition of NH$_3$ in MeOH (1% solution, 6.0 mL) and evaporated in vacuo. The residue was partitioned between EtOAc (20 mL) and saturated aq NaHCO$_3$ (20 mL) and the organic layer was separated, washed with brine (5.0 mL) and then dried and evaporated in vacuo. The residue was purified by flash column chromatography (SiO$_2$, 80 g, MeOH in DCM, 0-20%, gradient elution) to afford (R)—N-(4-(2,3-dichloro-4-nitrophenoxy)pyridin-2-yl)-3-(dimethylamino)pyrrolidine-1-carboxamide as a yellow solid (510 mg, 68%); R$^t$ 1.39 min (method 2); m/z 440/442 (M+H)$^+$, (ES$^+$).

A solution of the nitroarene, obtained above, (120 mg, 290 mmol) in a mixture of MeOH (18 mL), DCM (9.0 mL) and AcOH (2.0 mL) was subjected to hydrogenation by passage through a Thales H-cube (1.0 mL min$^{-1}$, 40° C., 30 mm 10% Pt/C Cat-Cart, full hydrogen mode). The reaction mixture was evaporated in vacuo and the residue was co-evaporated with toluene (10 mL) and then partitioned between EtOAc (20 mL) and saturated aq NaHCO$_3$ (20 mL). The aq layer was extracted with EtOAc (2×20 mL) and the combined organic extracts were washed with brine (15 mL), dried and evaporated in vacuo. The residue was purified by flash column chromatography (SiO$_2$, 40 g, [5% NH$_3$ in MeOH] in DCM, 0-100%, gradient elution) to afford the title compound, Intermediate E3, as a pink amorphous solid (170 mg, 35%); R$^t$ 1.10 min (method 2); m/z 410/412 (M+H)$^+$, (ES$^+$).

Intermediate E4

1-(4-(4-Amino-2,3-dichlorophenoxy)pyridin-2-yl)-3-(2-morpholinoethyl)urea

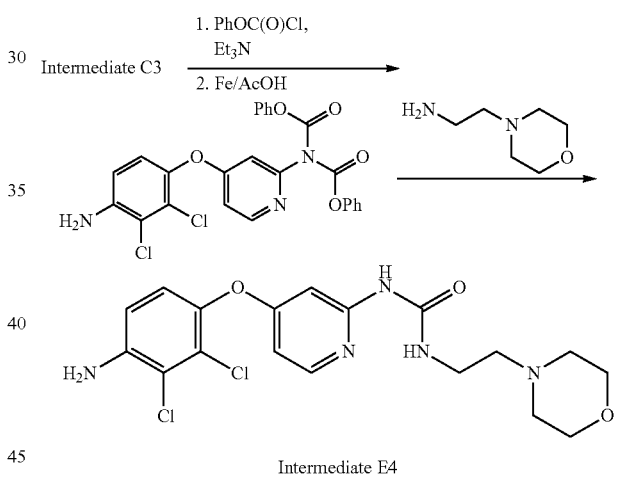

Intermediate E4

To a solution of Intermediate C3 (10.0 g, 33 mmol) and triethylamine (14.0 mL, 100 mmol) in DCM (150 mL) at 0° C. under N$_2$ was added phenyl carbonochloridate (20.0 mL, 160 mmol) and the reaction mixture warmed to RT for 2 hr. The resulting mixture was washed with water (150 mL) and the organic layer was separated, dried and evaporated in vacuo. The residue was co-evaporated with toluene (100 mL) and was then triturated with isohexane (150 mL), resulting in the formation of a brown solid that was isolated by filtration and dried in vacuo. The solid was taken up in AcOH (200 mL), iron powder (14.8 g, 264 mmol) was added and the mixture was heated to 60° C. for 1.5 hr and was then cooled to RT and filtered through a celite pad. The pad was washed with EtOAc (100 mL) and then DCM (100 mL) and the filtrate and washings were combined, evaporated in vacuo and then co-evaporated with toluene (300 mL). The residue was dissolved in EtOAc (200 mL) and was washed with saturated aq. K$_2$CO$_3$ (50 mL). The aq layer was separated and was extracted with EtOAc (2×100 mL) and DCM (100 mL) and the combined organic extracts were dried and evaporated in vacuo to afford N,N-diphenoxycarbonyl-4-(4-amino-2,3-dichlorophenoxy)pyridin-2-amine as a brown/yellow solid (20.8 g, 70% pure by HPLC, 77%); $R^t$ 3.85 min (Method 2); m/z 510/512 $(M+H)^+$ $(ES^+)$. This material was used directly in the next step (below).

To a solution of the bis-phenoxycarbonyl amine obtained above (10.0 g, 70% pure, 14 mmol) in dry THF (100 mL), under $N_2$ at 0° C. was added 2-morpholinoethanamine (10.3 mL, 78 mmol) and the reaction mixture warmed to RT for 22 hr. The resulting mixture was evaporated in vacuo and the residue was purified twice by flash column chromatography ($SiO_2$, 80 g, EtOAc in isohexane, 0-100%, MeOH in EtOAc, 0-15%, gradient elution, then $SiO_2$, 80 g, [10% MeOH in EtOAc] in isohexane, 0-100%, gradient elution) to afford the title compound, Intermediate E4, as a white solid (3.05 g, 47%, 35% from Intermediate C3); $R^t$ 1.11 min (Method 2); m/z 426/428 $(M+H)^+$ $(ES^+)$.

Intermediate E5

1-(4-(4-Amino-2,3-dichlorophenoxy)pyridin-2-yl)-3-cyclopropylurea

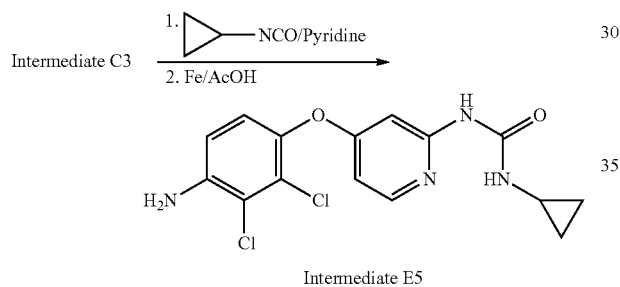

Intermediate E5

To a stirred solution of Intermediate C3 (150 mg, 0.50 mmol) in dry pyridine (6.0 mL) at 0° C. under $N_2$ was added isocyanatocyclopropane (170 mg, 2.0 mmol) and the reaction mixture warmed to RT for 72 hr. The reaction was quenched by addition of $NH_3$ in MeOH (1% w/v, 4.0 mL) and was then evaporated in vacuo. The residue was purified by flash column chromatography ($SiO_2$, 12 g, [5% MeOH in EtOAc] in isohexane, 0-75%, gradient elution) to afford 1-cyclopropyl-3-(4-(2,3-dichloro-4-nitrophenoxy)pyridin-2-yl)urea as a pale yellow powder (176 mg, 91%); $R^t$ 2.19 min (Method 2); m/z 383/385 $(M+H)^+$, $(ES^+)$ A mixture of 1-cyclopropyl-3-(4-(2,3-dichloro-4-nitrophenoxy)pyridin-2-yl)urea (170 mg, 0.444 mmol) and iron powder (149 mg, 2.66 mmol) in AcOH (5.0 mL) was heated to 60° C. for 1.5 hr. The reaction mixture was cooled to RT and was added cautiously to a stirred solution of saturated aq $NaHCO_3$ (100 mL) and the mixture was extracted with EtOAc/THF (3:1 v/v, 100 mL, 2×75 mL). The combined organic extracts were dried and evaporated in vacuo to afford the title compound, Intermediate E5, as a brown solid (158 mg, 99%); $R^t$ 0.1.69 min (Method 2); m/z 353/355 $(M+H)^+$ $(ES^+)$.

Intermediate F1

1-(4-((2-Aminopyridin-4-yl)oxy)-2,3-dichlorophenyl)-3-(3-tert-butyl-1-(4-methoxyphenyl)-1H-pyrazol-5-yl)urea

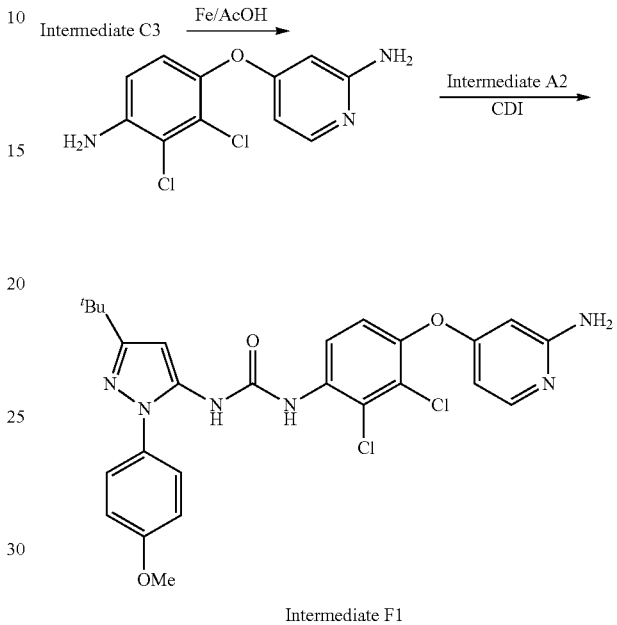

Intermediate F1

To a solution of Intermediate C3 (3.18 g, 10.60 mmol) in AcOH (30 mL) was added iron powder (3.55 g, 63.6 mmol) and the mixture heated at 60° C. for 1 hr, then cooled to RT and poured slowly on to solid $K_2CO_3$ (40 g). The resulting mixture was diluted with water (100 mL) and extracted with EtOAc (2×75 mL). The combined organic extracts were washed sequentially with saturated aq. $NaHCO_3$ (100 mL), water and brine and then dried, and evaporated in vacuo to afford 4-(4-amino-2,3-dichlorophenoxy)pyridin-2-amine as a yellow oil (2.86 g, 95%); $R^t$ 3.92 min (Method 1 basic); m/z 271 $(M+H)^+$ $(ES^+)$.

To a suspension of CDI (2.92 g, 18.0 mmol) in DCM (15.0 mL) was added Intermediate A2 portionwise over 40 min and the reaction mixture maintained at RT for 1 hr. This solution was added, in aliquots over 6 hr, to a solution of 4-(4-amino-2,3-dichlorophenoxy)pyridin-2-amine (2.86 g, 10.6 mmol) in DCM (75 mL), after which MeOH (20 mL) was added and the resulting mixture evaporated in vacuo. The residue was partitioned between EtOAc (150 mL) and saturated aq. $NaHCO_3$ (150 mL). The organic layer was separated and washed with water (75 mL) and brine (75 mL) and then dried and evaporated in vacuo. The residue was purified by flash column chromatography ($SiO_2$, 120 g, MeOH in DCM, 2-4%, gradient elution) to afford Intermediate F1 as a white solid (1.80 g, 30%); $R^t$ 1.85 min (Method 2); m/z 541 $(M+H)^+$ $(ES^+)$.

Intermediate G1

N-(4-((2,3-Dichloro-4-aminophenoxy)methyl)pyridin-2-yl)-2-methoxyacetamide

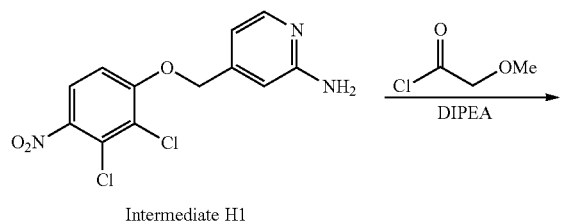

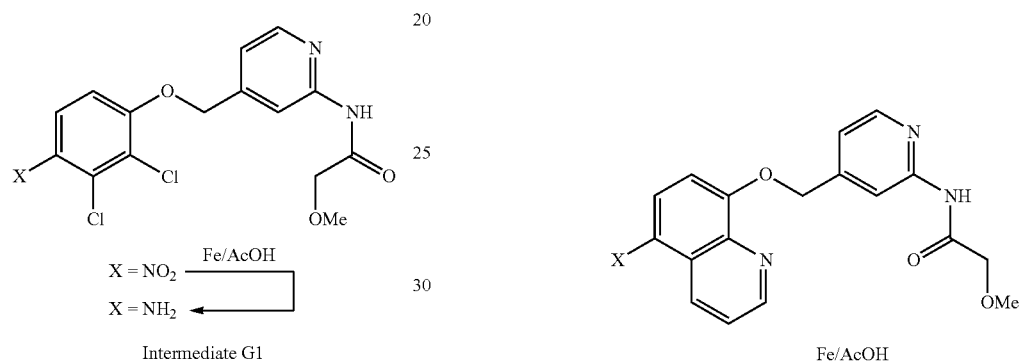

To a solution of Intermediate H1 (750 mg, 2.39 mmol) and DIPEA (1.7 mL, 9.5 mmol) in dry THF (25 mL) at 0° C. under $N_2$ was added 2-methoxyacetyl chloride (660 µL, 7.16 mmol) and the mixture warmed to RT. After 2 hr the reaction was quenched by the addition of a solution $NH_3$ in MeOH (1%, 10 mL) and after 1 hr the mixture was evaporated in vacuo. The residue was purified by flash column chromatography ($SiO_2$, 40 g, MeOH in DCM, 0-5%, gradient elution) to afford N-(4-((2,3-dichloro-4-nitrophenoxy)methyl)pyridin-2-yl)-2-methoxyacetamide as an orange solid (500 mg, 52%); $R^t$ 4.80 min (Method 1 basic); m/z 384/386 $(M+H)^+$ $(ES^+)$.

A mixture of N-(4-((2,3-dichloro-4-nitrophenoxy)methyl)pyridin-2-yl)-2-methoxyacetamide (490 mg, 1.27 mmol) and iron powder (425 mg, 7.61 mmol) in AcOH (10.0 mL) was heated at 60° C. for 45 min and was then cooled to RT and filtered through celite. The filter pad was washed with EtOAc and THF and the combined filtrate and washings were evaporated in vacuo. The residue was co-evaporated with toluene in vacuo and was then partitioned between EtOAc/THF (3:1 v/v, 80 mL) and saturated aq. $NaHCO_3$. The aq. layer was extracted with EtOAc/THF (3:1 v/v, 2×60 mL) and the combined organic extracts were dried and evaporated in vacuo to furnish the title compound, Intermediate G1, as a brown solid (433 mg, 91%); $R^t$ 4.20 min (Method 1 basic); m/z 354/356 $(M+H)^+$ $(ES^+)$.

Intermediate G2

N-(4-((5-Aminoquinolin-8-yloxy)methyl)pyridin-2-yl)-2-methoxyacetamide

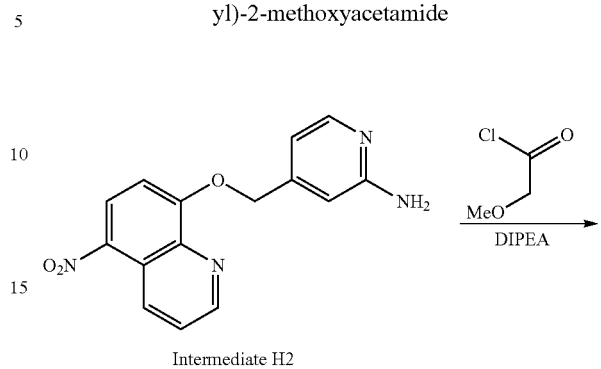

To a solution of Intermediate H2 (500 mg, 1.69 mmol) and DIPEA (590 µL, 3.40 mmol) in dry THF (15.0 mL) at 0° C. under $N_2$ was added 2-methoxyacetyl chloride (230 µL, 2.53 mmol) and the mixture then warmed to RT for 30 min. The reaction was quenched by the addition of solution of $NH_3$ in methanol (1 M, 5.0 mL, 5.0 mmol) and after for 30 min at RT the mixture was evaporated in vacuo. The residue was triturated with water (50 mL, 2×25 mL), then dissolved in DCM (50 mL), dried and evaporated in vacuo to afford 2-methoxy-N-(4-((5-nitroquinolin-8-yloxy)methyl)pyridin-2-yl)acetamide as a yellow solid (576 mg, 93%); $R^t$ 1.73 min (Method 2); m/z 369 $(M+H)^+$ $(ES^+)$.

A mixture of 2-methoxy-N-(4-((5-nitroquinolin-8-yloxy)methyl)pyridin-2-yl)acetamide (546 mg, 1.48 mmol) and iron powder (579 mg, 10.4 mmol) in AcOH (10.0 mL) was heated at 60° C. for 1 hr then cooled to RT and filtered through celite. The filter pad was washed with EtOAc (100 mL) and the combined filtrate and washings were evaporated in vacuo. The residue was partitioned between EtOAc (100 mL) and saturated aq. $NaHCO_3$ (100 mL). The organic layer was dried and evaporated in vacuo to afford the title compound, Intermediate G2, as a yellow solid (463 mg, 92%); $R^t$ 0.94 min (Method 2); m/z 339 $(M+H)^+$ $(ES^+)$.

Intermediate H1

4-((2,3-Dichloro-4-nitrophenoxy)methyl)pyridin-2-amine

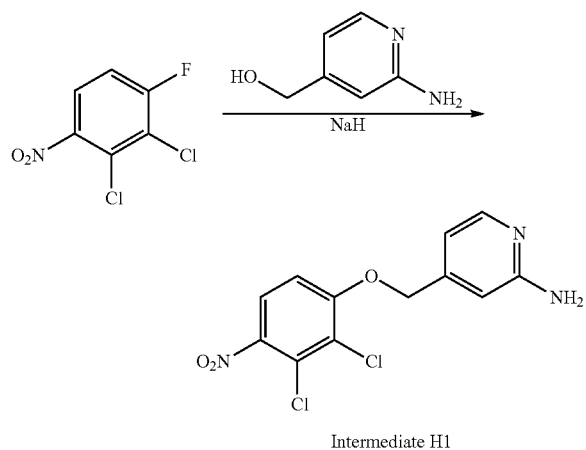

Intermediate H1

A suspension of NaH (60% w/w in mineral oil, 387 mg, 9.67 mmol) was added to a solution of (2-aminopyridin-4-yl)methanol (1.00 g, 8.06 mmol) in dry THF (20 mL) at 0° C. under $N_2$. After 30 min a solution of 2,3-dichloro-1-fluoro-4-nitrobenzene (1.86 g, 8.86 mmol) in dry THF (10.0 mL) was added slowly and the reaction mixture was warmed to RT. After 2 hr the reaction was quenched by the slow addition of MeOH (5.0 mL) after which the reaction mixture was evaporated in vacuo. The residue was triturated with MeOH, and the resulting solid was isolated by filtration, washed with MeOH and dried in vacuo to afford the title compound, Intermediate H1, as an orange solid (1.067 g, 41%); $R^r$ 4.62 min (Method 1 basic); m/z 314/316 (M+H)$^+$ (ES$^+$).

Intermediate H2

4-((5-Nitroquinolin-8-yloxy)methyl)pyridin-2-amine

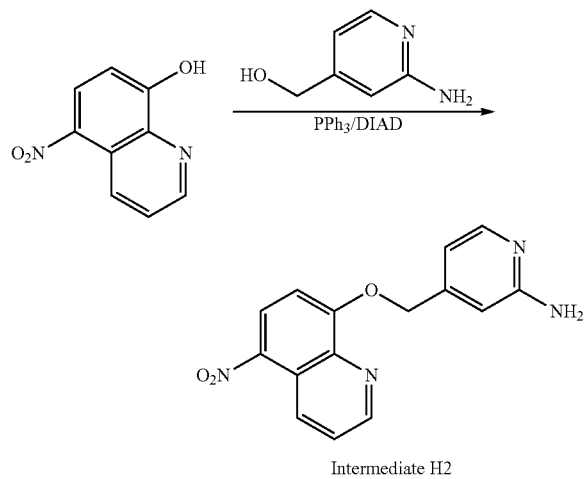

Intermediate H2

To a suspension of 5-nitroquinolin-8-ol (2.30 g, 12.2 mmol), triphenylphosphine (4.10 g, 15.8 mmol) and (2-aminopyridin-4-yl)methanol (1.66 g, 13.4 mmol) in THF (50 mL) under $N_2$ at −70° C. was added DIAD (3.31 mL, 17.0 mmol) and the reaction mixture then warmed to RT for 16 hr. The mixture was evaporated in vacuo and the residue was triturated with MeOH (50 mL), and the solid collected by filtration and washed with MeOH (2×50 mL) and Et$_2$O (2×50 mL). The Mitsunobu coupling reaction was then repeated using the following amended protocol: To a suspension of 5-nitroquinolin-8-ol (1.50 g, 7.90 mmol), triphenylphosphine (3.10 g, 11.8 mmol) and (2-aminopyridin-4-yl)methanol (1.18 g, 9.47 mmol) in THF (25 mL) at RT under $N_2$ was added DIAD (2.15 mL, 11.0 mmol), dropwise over 10 min. After 1 hr the reaction mixture was combined with the previously isolated solid and the mixture was purified directly (without further work-up) by flash column chromatography (SiO$_2$, 120 g, MeOH in DCM, 1-10%, gradient elution) to afford the title compound, Intermediate H2, as a yellow solid (1.5 g, 25%); $R^r$ 3.73 min (Method 1 basic); m/z 297 (M+H)$^+$ (ES$^+$).

Intermediate J1

N-1-(4-((4-Amino-2,3-dichlorophenoxy)methyl)pyridin-2-yl)-3-methylurea

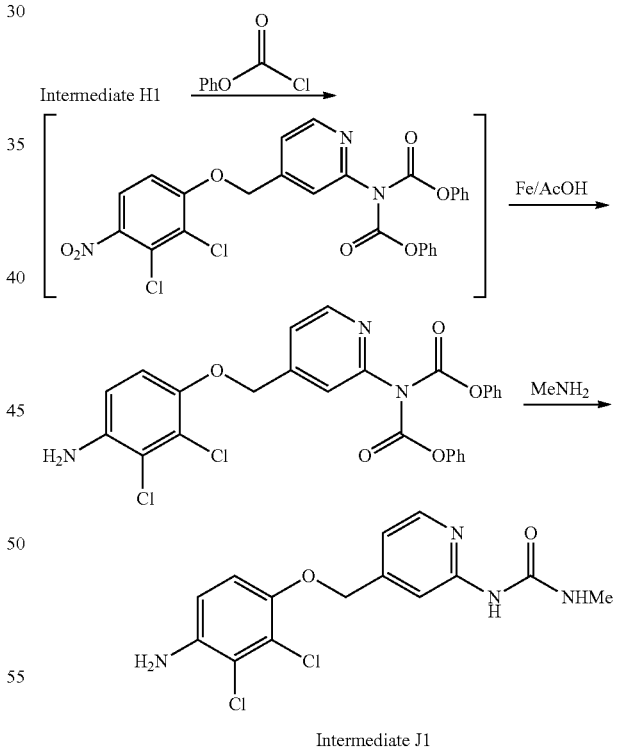

Intermediate J1

To a solution of Intermediate H1 (750 mg, 2.4 mmol) and triethylamine (1.2 mL, 8.4 mmol) in dry DCM (35 mL) at 0° C. under $N_2$ was added phenyl chloroformate (900 μL, 7.16 mmol) and the reaction mixture warmed to RT for 2 hr. The mixture was partitioned between DCM (25 mL) and water (50 mL) and the aq. layer was separated and extracted with DCM (40 mL). The combined organic extracts were dried and evaporated in vacuo to afford 2-(N,N-(diphenoxycarbonyl)amino)-4-((2,3-dichloro-4-nitrophenoxy)methyl)pyridine as a brown oil (1.60 g, 120% recovery); $R^t$ 5.20 min (method 1 basic); m/z 554/556 (M+H)$^+$ (ES$^+$). This material was used directly in the next step without additional purification.

A mixture of 2-(N,N-(diphenoxycarbonyl)amino)-4-((2,3-dichloro-4-nitrophenoxy)methyl)pyridine (1.60 g, crude product from previous step) and iron powder (800 mg, 14.3 mmol) in AcOH (18 mL) was heated at 60° C. for 1.75 hr and was then cooled to RT and filtered through celite. The filter pad was washed with EtOAc and THF and the combined filtrate and washings were evaporated in vacuo. The residue was co-evaporated with toluene in vacuo and was then partitioned between EtOAc/THF (4:1 v/v, 100 mL) and saturated aq. NaHCO$_3$ (100 mL). The aq. layer was separated and extracted with EtOAc/THF (4:1 v/v, 75 mL) and the combined organic extracts were washed with brine (75 mL), dried and evaporated in vacuo. The residue was taken up into THF (20 mL) and was cooled to 0° C. and then treated with a solution of MeNH$_2$ in THF (2 M, 12.0 mL, 24 mmol). The resulting mixture was maintained at 0° C. for 30 min and then warmed to RT for 1.5 hr. The mixture was evaporated in vacuo and the residue was purified by flash column chromatography (SiO$_2$, 40 g, [5% MeOH in EtOAc] in isohexane, 0-75%, gradient elution) to afford the title compound, Intermediate J1, as a beige solid (348 mg, ~90% purity, 38% from Intermediate H1); $R^t$ 4.28 min (Method 1 basic); m/z 341/343 (M+H)$^+$ (ES$^+$).

Intermediate J2

N-(4-((4-Amino-2,3-dichlorophenoxy)methyl)pyridin-2-yl)pyrrolidine-1-carboxamide

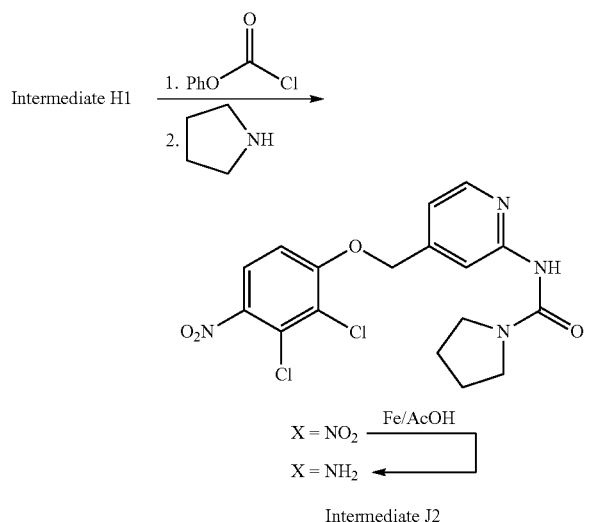

To a solution of Intermediate H1 (1.00 g, 3.2 mmol) in dry DCM (40 mL) at 0° C. under N$_2$ was added phenyl carbonochloridate (1.2 mL, 9.6 mmol) and triethylamine (1.8 mL, 12.7 mmol) and the reaction mixture warmed to RT for 2.25 h. The mixture was re-cooled to 0° C. and pyrrolidine (1.1 mL, 12.7 mmol) was added and the reaction mixture then warmed to RT for 21 hr. An additional aliquot of pyrrolidine (0.53 mL, 6.4 mmol) was added and after 4 hr the mixture was partitioned between DCM (40 mL) and saturated aq. NaHCO$_3$ (70 mL). The aq. layer was extracted with DCM (70 mL) and the combined organic layers were separated and dried and then evaporated in vacuo. The residue was purified by flash column chromatography (SiO$_2$, 80 g, MeOH in DCM, 0-4%, gradient elution) to afford N-(4-((2,3-dichloro-4-nitrophenoxy)methyl)pyridin-2-yl)pyrrolidine-1-carboxamide as a yellow solid (930 mg, ~90% purity, 64%); $R^t$ 4.93 min (method 1 basic); m/z 411/413 (M+H)$^+$ (ES$^+$). This material was used directly without further purification.

A mixture of iron powder (428 mg, 7.6 mmol) and N-(4-((2,3-dichloro-4-nitrophenoxy)methyl)pyridin-2-yl)pyrrolidine-1-carboxamide (450 mg, ~90% purity, 1.00 mmol) in AcOH (10 mL) was heated at 60° C. for 1.5 hr and was then cooled to RT and filtered through celite. The filter pad was washed with EtOAc and THF and the combined filtrate and washings were evaporated in vacuo. The residue was co-evaporated with toluene in vacuo and was then partitioned between EtOAc/THF (4:1 v/v, 100 mL) and saturated aq. NaHCO$_3$ (75 mL). The aq. layer was extracted with EtOAc/THF (4:1 v/v, 60 mL) and the combined organic extracts were dried and evaporated in vacuo to furnish the title compound, Intermediate J2, as a grey solid (325 mg, ~85% purity, 73%); $R^t$ 4.35 min (Method 1 basic); m/z 381/383 (M+H)$^+$ (ES$^+$).

Intermediate J3

1-(4-((5-Aminoquinolin-8-yloxy)methyl)pyridin-2-yl)-3-methylurea

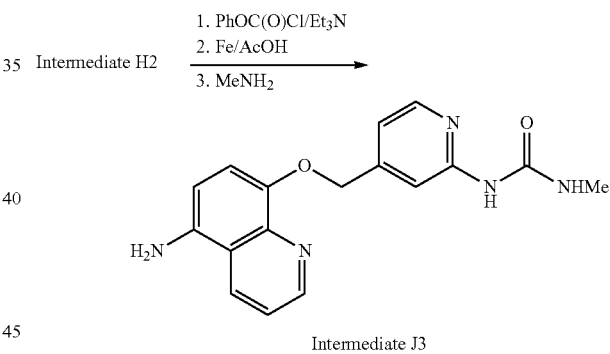

To a suspension of Intermediate H2 (500 mg, 1.69 mmol) in dry DCM (15 mL) containing triethylamine (706 µL, 5.06 mmol) at 0° C. was added phenyl carbonochloridate (446 µL, 3.54 mmol) and the mixture maintained at 0° C. for 30 min. The reaction mixture was treated with a solution of MeNH$_2$ in MeOH (2M, 4.2 mL, 8.4 mmol) and kept at 0° C. for 2 hr during which time a precipitate formed. The precipitate was collected by filtration and washed with water (50 mL) and Et$_2$O (2×50 mL) and was then taken up into AcOH (10.0 mL). Iron powder (684 mg, 12.3 mmol) was added and the mixture was heated at 60° C. for 1 hr and was then filtered through celite. The celite pad was washed with EtOAc (100 mL) and the filtrate and washings were combined and evaporated in vacuo. The residue was taken up into EtOAc (100 mL) and was washed with saturated aq. NaHCO$_3$ (100 mL), then dried and evaporated in vacuo. The residue was taken up in a solution of MeNH$_2$ in THF (2 M, 20 mL, 40 mmol) and the mixture was set aside at RT for 16 hr and then evaporated in vacuo. The residue was purified by flash column chromatography (SiO$_2$, 80 g, MeOH in DCM, 0-10%, gradient elution) to afford the title compound, Intermediate J3, as an orange solid (276 mg, 49%); R$^t$ 0.69 min (Method 2); m/z 324 (M+H)$^+$ (ES$^+$).

Intermediate J4

N-(4-((5-Aminoquinolin-8-yloxy)methyl)pyridin-2-yl)pyrrolidine-1-carboxamide

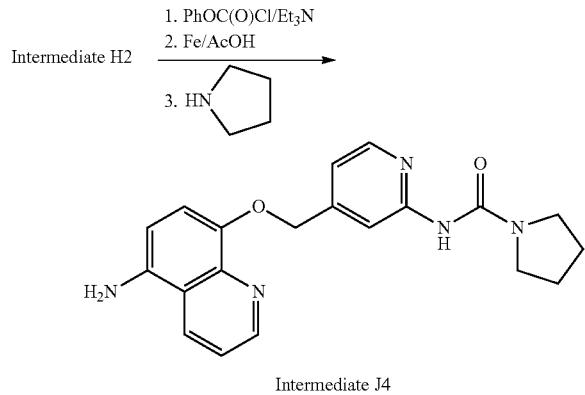

Intermediate J4

To a suspension of Intermediate H2 (469 mg, 1.58 mmol) in dry DCM (15 mL) containing triethylamine (660 μL, 4.75 mmol) at 0° C. was added phenyl carbonochloridate (420 μL, 3.32 mmol) and the mixture maintained at 0° C. for 1 hr. The reaction was quenched by the addition of water (10 mL) and the organic layer was separated and evaporated in vacuo. The residue was taken up into AcOH (10 mL), iron powder (619 mg, 11.1 mmol) was added and the mixture was heated at 60° C. for 1 hr and then filtered through celite. The celite pad was washed with EtOAc (100 mL) and the filtrate and washings were combined and evaporated in vacuo. The residue was taken up in EtOAc (100 mL) and was washed with saturated aq. NaHCO$_3$ (100 mL) then dried and evaporated in vacuo. To a solution of the residue in anhydrous THF (15 mL) was added pyrrolidine (1.30 mL, 15.8 mmol) and the mixture kept at RT for 64 hr and then evaporated in vacuo. The residue was purified by flash column chromatography (SiO$_2$, 80 g, MeOH in DCM, 0-10%, gradient elution) to afford the title compound, Intermediate J4, as an orange solid (399 mg, 69% yield); R$^t$ 0.79 min (Method 2); m/z 364 (M+H)$^+$ (ES$^+$).

Intermediate K1

6-(2,3-Dichloro-4-nitrophenoxy)pyrimidin-4-amine

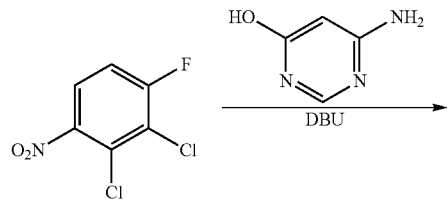

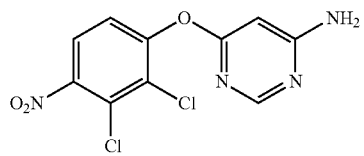

Intermediate K1

To a solution of 6-aminopyrimidin-4(3H)-one (1.00 g, 9.00 mmol) and DBU (1.5 mL, 10 mmol) in dry DMSO (10.0 mL) was added a solution of 2,3-dichloro-1-fluoro-4-nitrobenzene (1.99 g, 9.45 mmol) in dry DMSO (5.0 mL) over 2 min. The reaction mixture was maintained at RT for 1.5 hr and was then diluted with MeOH (20 mL). After 16 hr the resulting mixture was acidified with TFA (2.0 mL) and was then subjected to SCX capture and release. The crude product so obtained was purified by flash column chromatography (SiO$_2$, 40 g, EtOAc in isohexane, 40-100%, gradient elution) to afford the title compound, Intermediate K1, as a pale yellow powder (630 mg, 23%); R$^t$ 4.17 min (Method 1 basic); m/z 301/303 (M+H)$^+$ (ES$^+$).

Intermediate K2

4-(2,3-Dichloro-4-nitrophenoxy)pyrimidin-2-amine

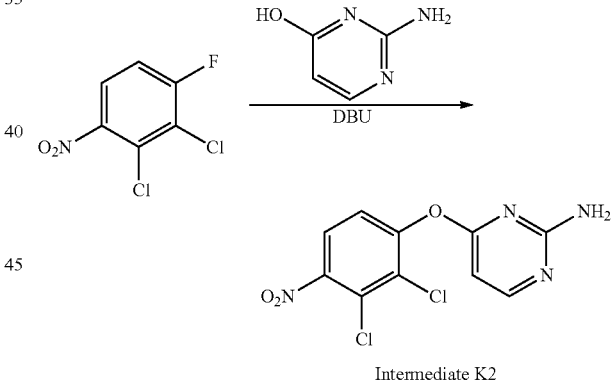

Intermediate K2

To a solution of 2-aminopyrimidin-4-ol (750 mg, 6.75 mmol) and DBU (1.3 mL, 8.4 mmol) in dry DMSO (10.0 mL) was added a solution of 2,3-dichloro-1-fluoro-4-nitrobenzene (1.49 g, 7.09 mmol) in dry DMSO (5.0 mL) over 2 min and the reaction mixture maintained at RT for 68 hr. The resulting mixture was diluted with MeOH (15 mL), acidified by the addition of TFA (3.0 mL) and was then subjected to SCX capture and release. The crude product so obtained was purified by flash column chromatography (SiO$_2$, 120 g, [5% MeOH in EtOAc] in isohexane, 0-100%, gradient elution) to afford the title compound, Intermediate K2, as a beige solid (830 mg, 41%); R$^t$ 4.40 min (Method 1 basic); m/z 301/303 (M+H)$^+$ (ES$^+$).

Intermediate L1

N-(6-(4-Amino-2,3-dichlorophenoxy)pyrimidin-4-yl)-4-(dimethylamino)butanamide

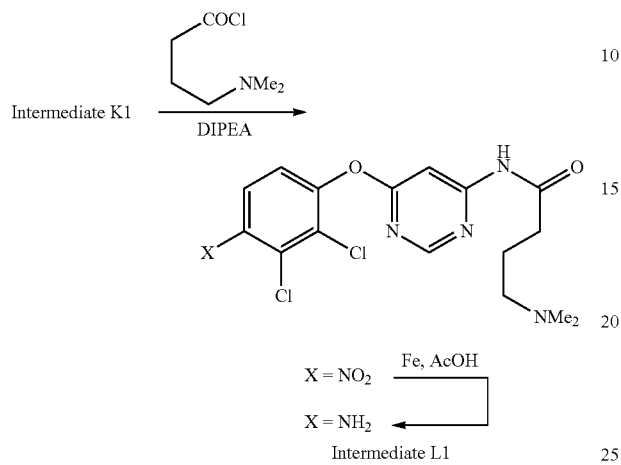

To a solution of 4-(dimethylamino)butanoic acid hydrochloride (4.35 g, 26.0 mmol) in dry DCM (30 mL) was added oxalyl chloride (2.6 ml, 31 mmol) followed by DMF (10 drops) and the reaction mixture maintained at RT for 1 hr. An aliquot of this solution (10.0 mL, 9.0 mmol) was then added to a solution of Intermediate K1 (521 mg, 1.73 mmol) and DIPEA (3.0 mL, 17 mmol) in dry THF (20 mL) under nitrogen at 0° C. After 18 hr this reaction mixture was treat with a further portion of the pre-formed acid chloride solution (2.0 mL, 2.0 mmol) and after a further 24 hr was quenched by addition of MeOH (4.0 mL). After 30 min the reaction mixture was partitioned between DCM (50 mL) and saturated aq. $NaHCO_3$ (75 mL). The aq layer was separated and extracted with DCM (2×50 mL) and the combined organic extracts were dried and evaporated in vacuo. The residue was purified by flash column chromatography ($SiO_2$, 40 g, MeOH in DCM, 0-5%, gradient elution then [1% $NH_3$ in MeOH] in DCM, 5-15%, gradient elution) to afford N-(6-(2,3-dichloro-4-nitrophenoxy)pyrimidin-4-yl)-4-(dimethylamino)butanamide as an orange solid (461 mg, 63%); Rt 1.43 min (Method 2); m/z 414/416 $(M+H)^+$ $(ES^+)$.

A suspension of the nitroarene (461 mg, 1.11 mmol) and iron powder (373 mg, 6.68 mmol) in AcOH (10.0 mL) was heated at 55° C. for 1.5 hr and was then cooled to RT and filtered through a pad of celite. The pad was washed with EtOAc and THF and the filtrate and washings were combined and evaporated in vacuo. The residue was co-evaporated with toluene and was then partitioned between a mixture of EtOAc/THF (3:1 v/v, 75 mL) and saturated aq. $NaHCO_3$ (100 mL). The aq layer was separated and extracted with EtOAc/THF (3:1 v/v, 2×75 mL) and the combined organic extracts were dried and evaporated in vacuo to afford the title compound, Intermediate L1, as a yellow solid (412 mg, 95%); Rt 1.18 min (Method 2); m/z 384/386 $(M+H)^+$ $(ES^+)$.

Intermediate L2

N-(4-(4-Amino-2,3-dichlorophenoxy)pyrimidin-2-yl)-2-methoxyacetamide

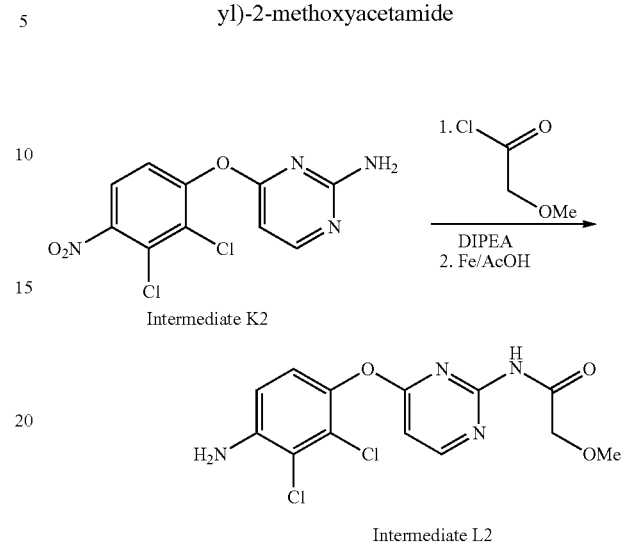

To a solution of Intermediate K2 (415 mg, 1.38 mmol) and DIPEA (600 µL, 3.5 mmol) in dry THF (15 mL) under nitrogen at 0° C. was added 2-methoxyacetyl chloride (220 µL, 2.4 mmol). The reaction mixture was warmed to RT for 2 hr and was then quenched by addition of $NH_3$ (6.0 mL of 1% solution in MeOH). After 16 hr the mixture was evaporated in vacuo and the residue was triturated with water (10 mL) to afford N-(4-(2,3-dichloro-4-nitrophenoxy)pyrimidin-2-yl)-2-methoxyacetamide as a beige powder (429 mg, 80%); $R^t$ 4.39 min (Method 1 basic); m/z 373/375 $(M+H)^+$ $(ES^+)$.

A suspension of the nitroarene, obtained above, (175 mg, 0.47 mmol) and iron powder (183 mg, 3.28 mmol) in AcOH (6.0 mL) was heated at 60° C. for 1.5 hr and was then cooled to RT and filtered through a pad of celite. The pad was washed with EtOAc and THF and the filtrate and washings were combined and evaporated in vacuo. The residue was co-evaporated with toluene and was then partitioned between EtOAc (50 mL) and saturated aq. $NaHCO_3$ (75 mL). The aq layer was extracted with EtOAc (2×50 mL) and the combined organic extracts were dried and evaporated in vacuo to afford the title compound, Intermediate L2, as a beige powder (156 mg, 97%); $R^t$ 3.86 min (Method 1 basic); m/z 343/345 $(M+H)^+$ $(ES^+)$.

Intermediate M1

1-(6-(4-Amino-2,3-dichlorophenoxy)pyrimidin-4-yl)-3-(2-(dimethylamino)ethyl)urea

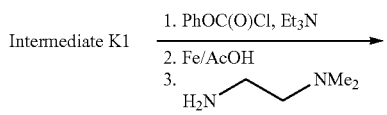

Intermediate M1

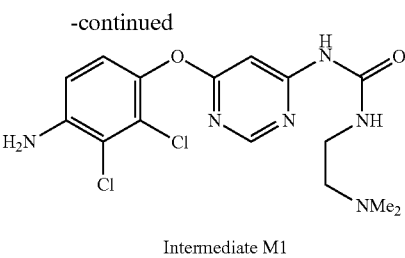

To a solution of Intermediate K1 (350 mg, 1.16 mmol) and triethylamine (800 µL, 6.0 mmol) in DCM (12.0 mL) at 0° C. under $N_2$ was added phenyl carbonochloridate (590 µL, 4.7 mmol) and the reaction mixture then warmed to RT. After 2 hr the mixture was partitioned between DCM (30 mL) and water (50 mL) and the aq layer was separated and extracted with DCM (30 mL). The combined organic extracts were dried and evaporated in vacuo to give a residue which was taken up into AcOH (8.0 mL). Iron powder (454 mg, 8.13 mmol) was added and the mixture was heated to 60° C. for 1.5 hr and then cooled to RT and filtered through a celite pad. The pad was washed with EtOAc and THF and the filtrate and washings were combined and evaporated in vacuo. The residue was co-evaporated with toluene and was then taken up in EtOAc (75 mL) and washed with saturated aq. $NaHCO_3$ (100 mL). The aq layer was separated and extracted with EtOAc (75 mL) and the combined organic extracts were washed with brine (75 mL), dried and evaporated in vacuo to afford N,N-diphenoxy carbonyl-6-(4-amino-2,3-dichlorophenoxy)pyrimidin-4-amine, which was used directly in the next step.

The material obtained above was taken up in THF (15 mL), cooled to 0° C. under $N_2$ and was then treated dropwise, over 3 min, with a solution of N,N-dimethylethylenediamine (510 µL, 4.7 mmol) in THF (2.0 mL). The reaction mixture was warmed to RT and after 5 hr was treat with additional N,N-dimethylethylenediamine (25 µL, 2.3 mmol). After a a further 15 hr at RT the reaction mixture was evaporated in vacuo and the residue was purified by flash column chromatography ($SiO_2$, 40 g, [5% MeOH in EtOAc] in isohexane, 0-80%, gradient elution, then MeOH in EtOAc, 0-15%, gradient elution) to afford the title compound, Intermediate M1, as a pale yellow oil (326 mg, 92% pure by HPLC, 67% from Intermediate K1); $R^t$ 4.12 min (Method 1 basic); m/z 385/387 $(M+H)^+$ $(ES^+)$.

Intermediate M2

1-(4-(4-Amino-2,3-dichlorophenoxy)pyrimidin-2-yl)-3-methylurea

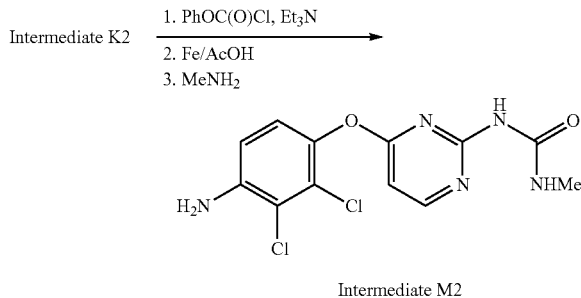

To a solution of Intermediate K2 (400 mg, 1.30 mmol) and triethylamine (0.83 mL, 6.0 mmol) in DCM (15 mL) at 0° C. under $N_2$ was added phenyl carbonochloridate (0.59 mL, 4.7 mmol). The reaction mixture was warmed to RT and after 17 hr was partitioned between DCM (30 mL) and water (20 mL). The aq layer was separated and was extracted with DCM (25 mL) and the combined organic extracts were dried and evaporated in vacuo. The residue was taken up into AcOH (10.0 mL), iron powder (520 mg, 9.30 mmol) was added and the mixture was heated to 60° C. for 1.5 hr and was then cooled to RT and filtered through a celite pad. The pad was washed with EtOAc and THF and the combined filtrate and washings were evaporated in vacuo and then co-evaporated with toluene. The residue was taken up in EtOAc (100 mL) and washed with saturated aq. $NaHCO_3$ (100 mL). The aq layer was separated and was extracted with EtOAc (75 mL). The combined organic extracts were washed with brine (75 mL) and then dried and evaporated in vacuo to afford a crude sample of N,N-diphenoxycarbonyl-4-(4-amino-2,3-dichlorophenoxy)pyrimidin-2-amine, which was immediately dissolved in THF (18 mL) and cooled to 0° C. under $N_2$. A solution of methylamine in THF (8.0 mL, 2.0 M, 16 mmol) was added and the reaction mixture was warmed to RT and after 3 days was evaporated in vacuo. The residue was purified by flash column chromatography ($SiO_2$, 40 g, [5% MeOH in EtOAc] in isohexane, 20-85%, gradient elution) to afford the title compound, Intermediate M2 as a white solid (260 mg, 92% pure by HPLC, 55% from Intermediate K2); $R^t$ 4.09 min, (Method 1 basic); m/z 328/330 $(M+H)^+$ $(ES^+)$.

Example 1

N-(4-(4-(3-(3-tert-Butyl-1-p-tolyl-1H-pyrazol-5-yl)ureido)-3-fluorophenoxy)pyridin-2-yl)-2-methoxyacetamide

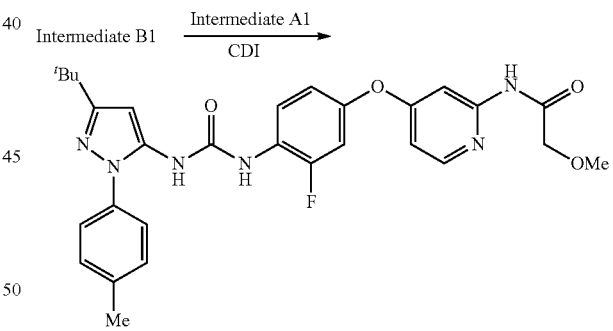

Example 1

To a solution of CDI (424 mg, 2.62 mmol) in dry DCM (5.0 mL) under $N_2$ and was added solid 3-tert-butyl-1-p-tolyl-1H-pyrazol-5-amine (600 mg, 2.62 mmol) in four equal portions over 10 min and the resulting yellow solution maintained at RT for 16 hr. An aliquot of this solution (0.4 mL, 0.21 mmol) was added to a solution of Intermediate B1, (26 mg, 80% pure, 0.071 mmol) in dry DCM (0.5 mL) and the reaction mixture kept at RT for 16 hr and then quenched by the addition of MeOH (1.0 mL). After 5 min the mixture was evaporated in vacuo and the residue was purified by flash column chromatography ($SiO_2$, 4 g, EtOAc in isohexane, 0-50% gradient elution) to afford impure product as a colourless oil. This material was dissolved in EtOAc (1.0 mL) and precipitated by the addition of isohexane (10 mL). The supernatant was decanted and the solid was purified by flash column chromatography (SiO$_2$, 4 g, MeOH in DCM, 0-2%, gradient elution). The resulting oil was dissolved in EtOAc (1.0 mL) and was precipitated by the addition of isohexane (10 mL) and collected by filtration to afford the title compound, Example 1, as a white solid (8 mg, 20%): R$^t$ 5.22 min (Method 1, basic); m/z 547 (M+H)$^+$ (ES$^+$); $^1$H NMR (400 MHz, DMSO-d$_6$) δ: 1.27 (9H, s), 2.38 (3H, s), 4.02 (2H, s), 6.39 (1H, s), 6.71 (1H, dd), 7.00 (1H, br d), 7.25 (1H, dd), 7.35 (2H, d), 7.40 (2H, d), 7.64 (1H, d), 8.19 (2H, overlapping m), 8.82 (1H, s), 9.01 (1H, s), 10.08 (1H, s). (OMe peak obscured by HOD peak).

Example 2

N-(4-(4-(3-(3-tert-Butyl-1-p-tolyl-1H-pyrazol-5-yl)ureido)-3-(methylsulfonyl)phenoxy)pyridin-2-yl)-2-methoxyacetamide

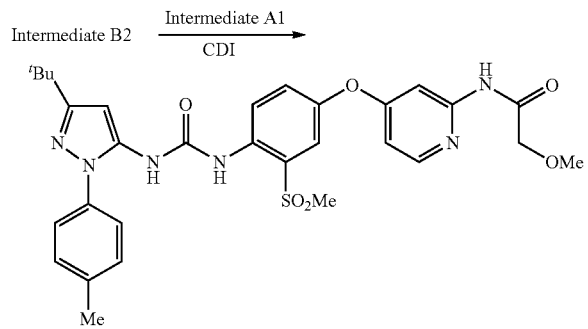

Example 2

To a solution of CDI (424 mg, 2.62 mmol) in dry DCM (5.0 mL) under N$_2$ and was added solid Intermediate A1 (600 mg, 2.62 mmol) in four equal portions over 10 min and the resulting yellow solution kept at RT for 16 hr. An aliquot (1.4 ml, 0.65 mmol) of this solution was added to a solution of Intermediate B2 (138 mg, ~80% purity, 0.314 mmol) in dry DCM (2.0 mL) and the reaction mixture was maintained at RT for 16 hr. A second aliquot of the CDI adduct (0.40 mL, 0.21 mmol) was added and the mixture was warmed to 35° C. for a further 24 hr. The reaction mixture was quenched by the addition of MeOH (1.0 mL) and after 10 min was evaporated in vacuo. The residue was purified by flash column chromatography (SiO$_2$, 12 g, EtOAc in isohexane, 0-100% gradient elution) to afford impure product as a colourless oil. This material was taken up into EtOAc (2.0 mL) and then precipitated by the addition of isohexane (10 mL). The supernatant was decanted and the solid was purified by flash column chromatography (SiO$_2$, 4 g, MeOH in DCM, 0-2%, gradient elution). The resulting oil was dissolved in EtOAc (2.0 mL) and precipitated by the addition of isohexane (10 mL) and the resulting solid was collected by filtration to afford the title compound, Example 2, as an off-white solid (31 mg, 16%): R$^t$ 4.85 min (Method 1, basic); m/z 607 (M+H)$^+$ (ES$^+$); $^1$H NMR (400 MHz, DMSO-d$_6$) δ: 1.28 (9H, s), 2.36 (3H, s), 3.26 (3H, s), 3.33 (3H, s), 4.03 (2H, s), 6.37 (1H, s), 6.76 (1H, dd), 7.32 (2H, d), 7.43 (2H, d), 7.55 (2H, overlapping d), 7.69 (1H, d), 8.07 (1H, d), 8.24 (1H, d), 8.70 (1H, s), 9.52 (1H, s), 10.15 (1H, s).

Example 3

N-(4-(4-(3-(3-tert-Butyl-1-p-tolyl-1H-pyrazol-5-yl)ureido)-3-(trifluoromethyl)phenoxy)pyridin-2-yl)-2-methoxyacetamide

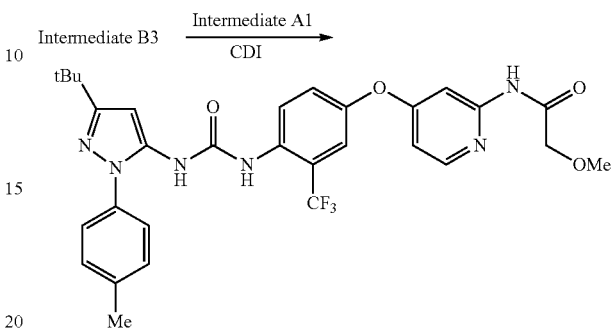

Example 3

To a solution of CDI (1.06 g, 6.54 mmol) in dry DCM (10.0 mL) under N$_2$ and was added solid Intermediate A1 (1.50 g, 6.54 mmol) in four equal portions over 10 min and the resulting yellow solution was stirred for 16 hr at RT. An aliquot of this solution (0.75 mL, 0.49 mmol) was added to a solution of Intermediate B3, (80 mg, ~75% purity, 0.18 mmol) in dry DCM (1.0 mL) and the reaction mixture was maintained at RT for 16 hr. The reaction was quenched by the addition of MeOH (1.0 mL) and after 10 min the mixture was evaporated in vacuo. The residue was purified by flash column chromatography (SiO$_2$, 12 g, EtOAc in isohexane, 0-100%, gradient elution). The crude product so obtained taken up into EtOAc and isohexane (10 mL) added. The precipitate was collected by filtration to afford the title compound, Example 3, as a pale orange solid (36 mg, 33%); R$^t$ 5.25 min (Method 1 basic); m/z 597 (M+H)$^+$ (ES$^+$); $^1$H NMR (400 MHz, DMSO-d$_6$) δ: 1.27 (9H, s), 2.38 (3H, s), 3.34 (3H, s), 4.03 (2H, s), 6.35 (1H, s), 6.74 (1H, dd), 7.34 (2H, d), 7.40 (2H, m), 7.50 (1H, dd), 7.53 (1H, d), 7.68 (1H, d), 7.88 (1H, d), 8.23 (1H, d), 8.47 (1H, s), 9.03 (1H, s), 10.14 (1H, s)

Example 4

N-(4-(4-(3-(3-tert-Butyl-1-p-tolyl-1H-pyrazol-5-yl)ureido)-3-chloro-2-cyanophenoxy)pyridin-2-yl)-2-methoxyacetamide

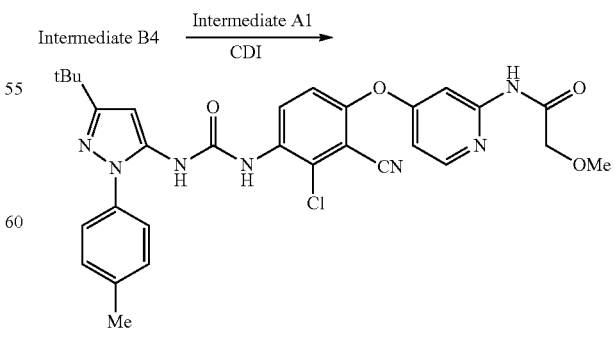

Example 4

To a solution of CDI (1.06 g, 6.54 mmol) in dry DCM (10 mL) under N₂ and was added solid Intermediate A1 (1.50 g, 6.54 mmol) in four equal portions over 10 min and the resulting yellow solution was stirred for 16 hr at RT. An aliquot of this solution (75 μL, 0.49 mmol) was added to a solution of Intermediate B4, (87 mg, ~90% purity, 0.235 mmol) in dry DCM (2.0 mL) and the reaction mixture was maintained at RT for 16 hr. An additional aliquot of the pyrazole-CDI adduct (150 μL, 0.08 mmol) was added and the mixture maintained at RT for 12 hr. The reaction was quenched by the addition of MeOH (1.0 mL) and after 10 min was evaporated in vacuo. The residue was purified by flash column chromatography (SiO₂, 12 g, EtOAc in isohexane, 0-60%, gradient elution). The crude material so obtained was taken up in EtOAc and was precipitated by addition of isohexane (10 mL). The precipitate was collected by filtration to afford the title compound, Example 4, as a white solid (84.5 mg, 60%); $R^t$ 5.18 min (Method 1 basic); m/z 589 (M+H)⁺ (ES⁺); ¹H NMR (400 MHz, DMSO-d₆) δ: 1.27 (9H, s), 2.38 (3H, s), 3.33 (3H, s), 4.05 (2H, s), 6.39 (1H, s), 6.85 (1H, dd), 7.35 (2H, d), 7.41 (3H, overlapping m), 7.73 (1H, d), 8.29 (1H, d), 8.45 (1H, d), 8.99 (1H, s), 9.21 (1H, s), 10.27 (1H, s).

Example 5

N-(4-(4-(3-(3-tert-Butyl-1-p-tolyl-1H-pyrazol-5-yl)ureido)-5,6,7,8-tetrahydronaphthalen-1-yloxy)pyridin-2-yl)-2-methoxyacetamide

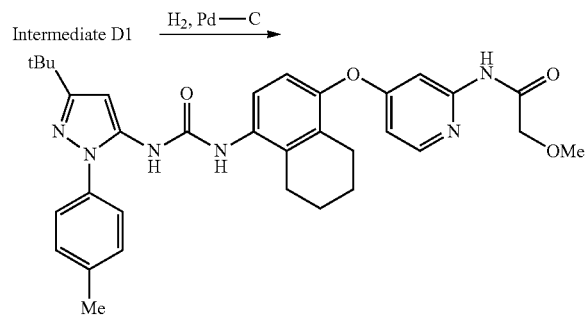

Example 5

A solution of Intermediate D1, (100 mg, 0.173 mmol) in MeOH (75 mL) and AcOH (0.15 mL) was subjected to hydrogenation by passage through a Thales H-cube (1.0 mL min⁻¹, 80° C., 55 mm 10% Pd/C Cat-Cart, full hydrogen mode). The reaction mixture was evaporated in vacuo and the residue purified by flash column chromatography (SiO₂, 4 g, EtOAc in isohexane, 40-100%, gradient elution) to afford the title compound, Example 5, as a white solid (21 mg, 20%); $R^t$ 2.62 min (Method 2); m/z 583 (M+H)⁺ (ES⁺); ¹H NMR (400 MHz, DMSO-d₆) δ: 1.27 (9H, s), 1.64 (2H, m), 1.70 (2H, m), 2.38 (3H, s), 2.46 (2H, m), 2.53 (2H, m), 3.33 (3H, s), 4.01 (2H, s), 6.35 (1H, s), 6.57 (1H, dd), 6.91 (1H, d), 7.34 (2H, d), 7.41 (2H, d), 7.57 (1H, d), 7.65 (1H, d), 8.15 (1H, d), 8.19 (1H, br s), 8.74 (1H, br s), 10.02 (1H, br s)

Example 6

N-(4-(5-(3-(3-tert-butyl-1-p-tolyl-1H-pyrazol-5-yl)ureido)quinolin-8-yloxy)pyridin-2-yl)-2-methoxyacetamide

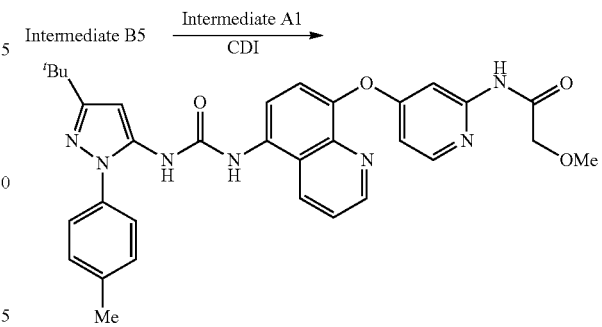

Example 6

To a solution of CDI (1.06 g, 6.54 mmol) in dry DCM (10.0 mL) under N₂ was added Intermediate A1 (1.50 g, 6.54 mmol) as a solid, in four equal portions, over 10 min and the resulting yellow solution was stirred at RT for 16 hr. An aliquot of this solution (1.0 mL, 0.65 mmol) was added to a solution of Intermediate B5, (100 mg, 0.308 mmol) in dry DCM (2.0 mL) and the reaction mixture was maintained at RT for 20 hr. The reaction was quenched by the addition of MeOH (1.0 mL) and after a further 5 min was evaporated in vacuo. The residue was purified twice by flash column chromatography (SiO₂, 12 g, EtOAc in isohexane, 0-100%, gradient elution and then SiO₂, 12 g, MeOH in DCM, 0-2%, gradient elution). The crude material so obtained was taken up in EtOAc (2.0 mL) and isohexane (10 mL) was added to give a precipitate which was collected by filtration to afford the title compound, Example 6, as an off-white solid (100 mg, 54%); $R^t$ 4.78 min (Method 1 basic); m/z 580 (M+H)⁺ (ES⁺); ¹H NMR (400 MHz, DMSO-d₆) δ: 1.28 (9H, s), 2.40 (3H, s), 3.30 (3H, s), 3.97 (2H, s), 6.42 (1H, s), 6.59 (1H, dd), 7.38 (2H, d), 7.47 (2H, d), 7.53 (1H, br s), 7.62 (2H, m), 8.02 (1H, d), 8.11 (1H, d), 8.45 (1H, d), 8.78 (1H, s), 8.84 (1H, d), 9.25 (1H, s), 9.96 (1H, s).

Example 7

N-(4-(7-(3-(3-tert-Butyl-1-p-tolyl-1H-pyrazol-5-yl)ureido)-1H-indazol-4-yloxy)pyridin-2-yl)-2-methoxyacetamide

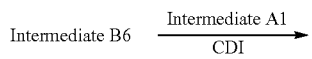

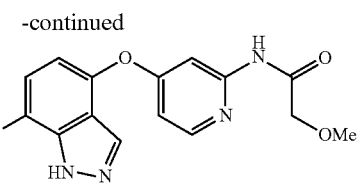

Example 7

To a solution of CDI (83 mg, 0.51 mmol) in dry DCM (2.0 mL) under N₂ was added dropwise a solution of Intermediate A1 (117 mg, 0.51 mmol) in DCM (2.0 mL) and the resulting yellow solution was stirred at RT for 16 hr. An aliquot of this solution (2.0 mL, 0.25 mmol) was added to a solution of Intermediate B6 (19 mg, 0.06 mmol) in dry DMF (1.0 mL) and the mixture was maintained at RT for 16 hr. The reaction was quenched by the addition of MeOH (2.0 mL) and after 20 min was evaporated in vacuo. The residue was subjected to SCX capture and release and the crude product so obtained was purified by flash column chromatography (SiO₂, 4.0 g, MeOH in DCM, 2-6%, gradient elution) to afford the title compound, Example 7, as a white solid (10 mg, 90% pure (NMR), 25%); $R^t$ 2.40 min (Method 2); m/z 569 (M+H)⁺ (ES⁺); ¹H NMR (400 MHz, DMSO-d₆, 100° C.) δ: 1.32 (9H, s), 2.39 (3H, s), 3.39 (3H, s), 4.00 (2H, s), 6.38 (1H, s), 6.72 (1H, dd), 6.78 (1H, d), 7.32 (2H, m), 7.45 (2H, m), 7.70 (1H, d), 7.87 (1H, br s), 8.19 (1H, d), 8.39 (1H, br s), 8.92 (1H, br s), 9.52 (1H, br s).

Example 8

N-(4-(4-(3-(3-tert-Butyl-1-(4-(hydroxymethyl)phenyl)-1H-pyrazol-5-yl)ureido)-2,3-dichlorophenoxy)pyridin-2-yl)-2-(methylamino)acetamide

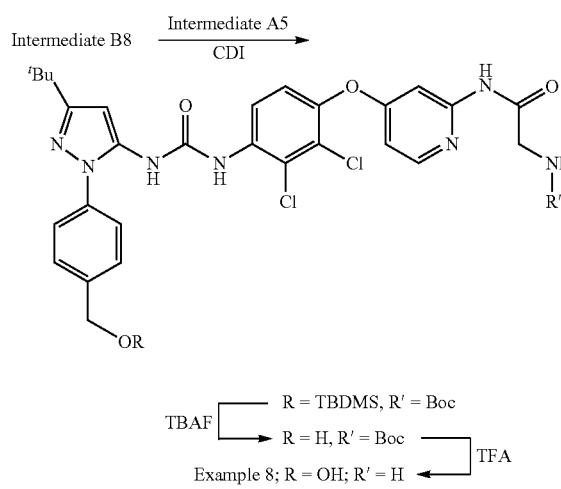

To a solution of CDI (2.30 g, 14.2 mmol) in dry DCM (30 mL) at RT was added Intermediate A5 (5.09 g, 14.2 mmol) portionwise over 25 min and the reaction mixture maintained at RT for 18 hr. An aliquot of the resulting solution (18 mL, 8.5 mmol) was added to a solution of Intermediate B8, (2.50 g, 5.7 mmol) in THF (30 mL) and the reaction mixture maintained at RT. Additional aliquots of the preformed CDI adduct (3.6 mL, 1.7 mmol) were added after 3.5 and 6 hr and after 24 hr the reaction mixture was partitioned between saturated aq. NaHCO₃ (150 mL) and DCM (100 mL). The aq layer was separated, extracted with DCM (100 mL) and the combined organic extracts were dried and evaporated in vacuo. The residue was purified by flash column chromatography (SiO₂, 120 g, [5% MeOH in EtOAc] in isohexane, 0-40%, gradient elution) to provide tert-butyl 2-(4-(4-(3-(3-tert-butyl-1-(4-((tert-butyldimethylsilyloxy)methyl)phenyl)-1H-pyrazol-5-yl)ureido)-2,3-dichlorophenoxy)pyridin-2-yl amino)-2-oxoethyl(methyl)carbamate as an off white solid (3.36 g, 71%); $R^t$ 3.31 min (Method 2); m/z 413 (M+H)²⁺/2, (ES⁺);

To a solution of the N-Boc silyl ether, obtained above, (3.35 g, 4.10 mmol) in dry THF (40 mL) was added TBAF (1 M solution in THF, 5.5 mL, 5.5 mmol) and the reaction mixture kept at RT for 5 hr and then partitioned between DCM (100 mL) and saturated aq. NaHCO₃ (100 mL). The aq layer was separated and extracted with DCM (2×75 mL) and the combined organic extracts were dried and evaporated in vacuo. The residue was taken up into DCM (40 mL) and was treated, at 0° C. under N₂, with TFA (10.0 mL). The reaction mixture was warmed to RT for 3 hr, was evaporated in vacuo and the residue purified by SCX capture and release. The crude product so obtained was triturated with ether to afford the title compound, Example 8, as a white solid (2.26 g, 89%); $R^t$ 1.56 min (Method 2); m/z 612 (M+H)⁺, (ES⁺); ¹H NMR (400 MHz, DMSO-d₆) δ: 1.28 (9H, s), 3.17 (3H, d), 3.23 (2H, s), 4.12 (1H, t), 4.58 (2H, d), 5.34 (1H, t), 6.40 (1H, s), 6.71 (1H, dd), 7.40 (1H, d), 7.48 (4H, s), 7.63 (1H, d), 8.18 (1H, d), 8.21 (1H, d), 8.89 (1H, s), 9.25 (1H, s) 10.10 (1H, br s).

Example 9

N-Methyl-N'-4-(4-(3-(3-tert-butyl-1-p-anisyl-1H-pyrazol-5-yl)ureido)-2,3-dichlorophen-1-yloxy)pyridin-2-ylurea

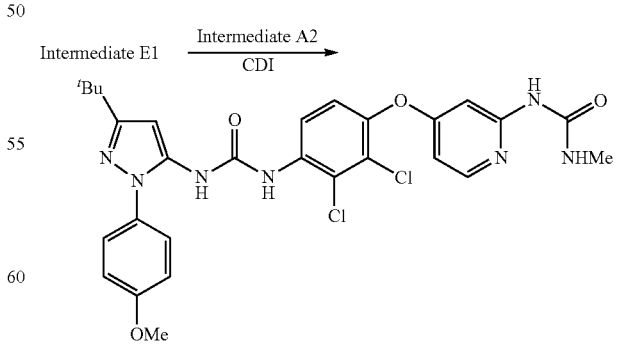

To a suspension of CDI (60.0 mg, 0.367 mmol) in DCM (1.0 mL) was added Intermediate A2 (90 mg, 0.367 mmol)

and the reaction mixture maintained at RT for 4 hr. A solution of Intermediate E1 (60 mg, 0.183 mmol) in DCM (1.5 mL) was added and the resulting mixture kept at RT for 64 hr and then diluted with DCM (10 mL). The organic solution was washed with water (10 mL) and brine (10 mL) and was dried and evaporated in vacuo. The residue was purified by flash column chromatography (SiO$_2$, EtOAc in isohexane, 20-100%, gradient elution) and then by trituration with a mixture of Et$_2$O and MeOH (1:1 v/v, 3.0 mL) to afford the title compound, Example 9, as an off-white solid (22 mg, 20%); R$^t$ 5.42 min (Method 1 basic); m/z 598/600 (M+H)$^+$, (ES$^+$); $^1$H NMR (400 MHz, DMSO-d$_6$) δ: 1.26 (9H, s), 2.67 (3H, d), 3.81 (3H, s), 6.36 (1H, s), 6.54 (1H, dd), 6.85 (1H, d), 7.09 (2H, d), 7.36 (1H, d), 7.42 (2H, d), 7.84 (1H, br s), 8.07 (1H, d), 8.16 (1H, d), 8.85 (1H, s), 9.15 (2H, s).

Example 10

N-(4-(4-(3-(3-tert-Butyl-1-(4-(methylthio)phenyl)-1H-pyrazol-5-yl)ureido)-2,3-dichlorophenoxy)pyridin-2-yl)pyrrolidine-1-carboxamide

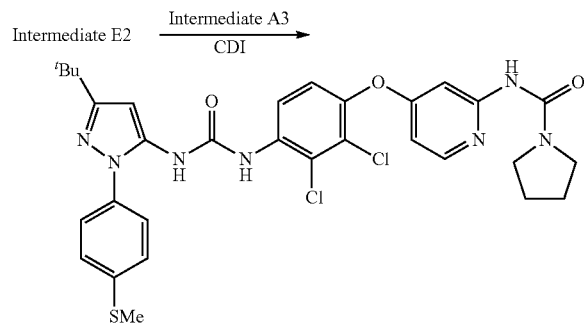

Example 10

To a solution of CDI (88 mg, 0.545 mmol) in DCM (1.0 mL) was added Intermediate A3, (142 mg, 0.545 mmol) and after 3 hr at RT the mixture was diluted with DCM (2.0 mL) and Intermediate E2 (100 mg, 75% pure, 0.20 mmol) was added. The reaction mixture was maintained at RT for 96 hr and was then partitioned between DCM (10 mL) and water (10 mL). The organic phase was separated and washed with brine (10 mL) and was then dried and evaporated in vacuo. The residue was purified by flash column chromatography (SiO$_2$, EtOAc in isohexane, 20-100%, gradient elution) and the impure product so obtained was triturated with isohexane/EtOAc (1:1, v/v, 3 mL) to afford the title compound, Example 10, as a white solid (46 mg, 33%); R$^t$ 5.65 min (Method 1, basic); m/z 656/654 (M+H)$^+$ (ES)$^+$; $^1$H NMR (400 MHz, DMSO-d$_6$) δ: 1.27 (9H, s), 2.53 (3H, s), 1.80 (4H, br m), 3.35 (4H, br m, partially obscured by HOD peak), 6.39 (1H, s), 6.55 (1H, dd), 7.36 (1H, d), 7.41-7.43 (3H, overlapping m), 7.48 (2H, m), 8.12 (1H, d), 8.17 (1H, d), 8.76 (1H, s), 8.85 (1H, br s), 9.24 (1H, br s).

Example 11

(R)—N-(4-(4-(3-(3-tert-Butyl-1-(4-hydroxyphenyl)-1H-pyrazol-5-yl)ureido)-2,3-dichlorophenoxy)pyridin-2-yl)-3-(dimethylamino)pyrrolidine-1-carboxamide

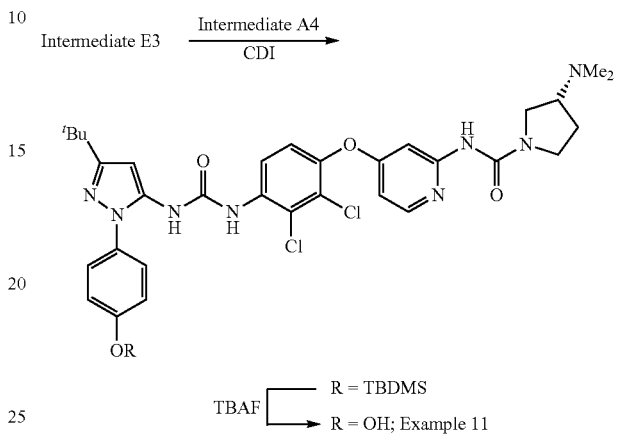

To a solution of CDI (328 mg, 2.03 mmol) in dry DCM (7.0 mL) at RT was added, Intermediate A4, (700 mg, 2.03 mmol) in solid portions over 20 min and the reaction mixture maintained at RT for 3.5 hr. To an aliquot of the resulting solution (2.7 mL, 0.78 mmol) was added a solution of Intermediate E3, (170 mg, 0.41 mmol) in dry DCM (1.7 mL) and the reaction maintained at RT for 16 hr. The reaction mixture was loaded, without prior work-up, directly onto a silica column and was purified by flash column chromatography (SiO$_2$, 12 g, [5% NH$_3$ in MeOH] in DCM, 0-100%, gradient elution) to provide (R)—N-(4-(4-(3-(3-tert-butyl-1-(4-(tert-butyldimethylsilyloxy)phenyl)-1H-pyrazol-5-yl)ureido)-2,3-dichlorophenoxy)pyridin-2-yl)-3-(dimethylamino)pyrrolidine-1-carboxamide as a beige solid (170 mg, 50%); R$^t$ 5.97 min (method 1 basic); m/z 779/781 (M+H)$^+$, (ES$^+$).

To a solution of the silyl ether, obtained above, (165 mg, 0.211 mmol) in dry THF (4.0 mL) was added TBAF (1 M solution in THF, 232 µL, 0.232 mmol) and the reaction mixture kept at RT for 10 min and then partitioned between EtOAc (10 mL) and saturated aq NaHCO$_3$ (2.0 mL). The organic layer was separated and dried and was evaporated in vacuo. The residue was purified by flash column chromatography (SiO$_2$, 12 g, NH$_3$ in MeOH (0.35 M solution), isocratic elution) to afford the title compound, Example 11, as a white amorphous solid (98 mg, 68%); R$^t$ 4.89 min (method 1 basic); m/z 667/669 (M+H)$^+$, (ES$^+$); $^1$H NMR (400 MHz, DMSO-d$_6$) δ: 1.26 (9H, s), 1.65 (1H, m), 2.01 (1H, m), 2.14 (6H, s), 2.61 (1H, m), 3.07 (1H, m), 3.28 (1H, m), 3.53 (1H, m), 3.62 (1H, m), 6.35 (1H, s), 6.58 (1H, dd), 6.89 (2H, m), 7.28 (2H, m), 7.35 (1H, d), 7.40 (1H, d), 8.11 (1H, d), 8.16 (1H, d), 8.79 (1H, s), 8.87 (1H, s), 9.11 (1H, s), 9.79 (1H, s).

Example 12

1-(4-(4-(3-(3-tert-Butyl-1-(4-methoxyphenyl)-1H-pyrazol-5-yl)ureido)-2,3-dichlorophenoxy)pyridin-2-yl)-3-ethylurea

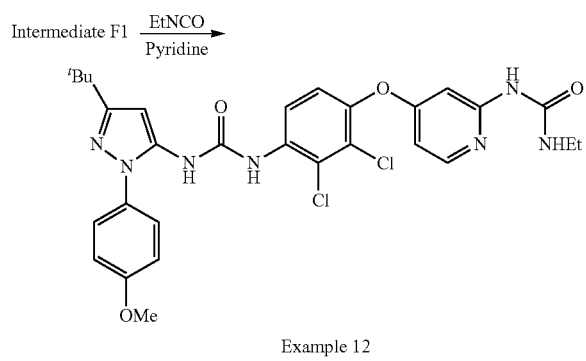

Example 12

To a stirred solution of Intermediate F1 (69 mg, 0.13 mmol) in dry pyridine (3.5 mL) at 0° C. under $N_2$ was added ethylisocyanate (81 μL, 1.0 mmol) and the reaction mixture warmed to RT. After 24 hr additional ethyl isocyanate (81 μL, 1.0 mmol) was added and the reaction mixture was warmed to 35° C. for a further 24 hr and then quenched by addition of $NH_3$ (3.0 mL of a 1% solution in MeOH). After 1 hr the reaction mixture was evaporated in vacuo and the residue was purified by flash column chromatography ($SiO_2$, 12 g, MeOH in EtOAc, 0-10%, gradient elution then $SiO_2$, 12 g, [5% MeOH in EtOAc] in isohexane, 0-50%, gradient elution) to afford the title compound, Example 12, as a white powder (26 mg, 33%); $R^t$ 2.50 min (Method 2); m/z 612/614 (M+H)$^+$, (ES$^+$); $^1$H NMR (400 MHz, DMSO-d$_6$) δ: 1.05 (3H, t), 1.27 (9H, s), 3.13 (2H, qd), 3.82 (3H, s), 6.37 (1H, s), 6.55 (1H, dd), 6.89 (1H, d), 7.10 (2H, m), 7.36 (1H, d), 7.42 (2H, m), 7.87 (1H, br s), 8.08 (1H, d), 8.17 (1H, d), 8.85 (1H, s), 9.08 (1H, s), 9.16 (1H, s).

Example 13

1-(3-tert-Butyl-1-(4-methoxyphenyl)-1H-pyrazol-5-yl)-3-(2,3-dichloro-4-((2-(3-(2-(dimethylamino)ethyl)ureido)pyridin-4-yl)oxy)phenyl)urea

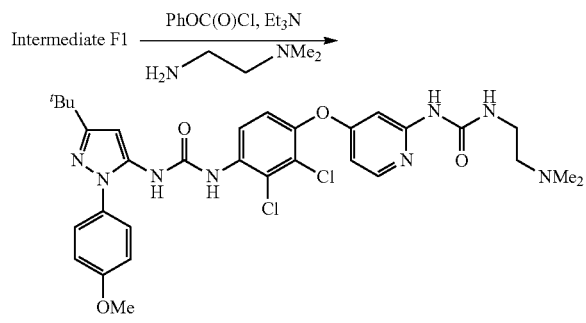

Example 13

To a solution of phenyl carbonochloridate (41 μL, 0.32 mmol) and triethylamine (54 μL, 0.39 mmol) in DCM at −10° C. under $N_2$ was added Intermediate F1 (70 mg, 0.13 mmol) and the reaction mixture warmed to RT for 4.5 hr and then treated with N,N-dimethylethylenediamine (42 μL, 0.39 mmol). The mixture was maintained at RT for 17 hr, a second portion of N,N-dimethyethylenediamine (85 μL, 0.78 mmol) was added and after 4 hr the mixture was warmed to 35° C. for 2 hr and finally cooled to RT. The reaction mixture was quenched by addition of $NH_3$ (3.0 mL of a 1% solution in MeOH) and after 45 min was evaporated in vacuo. The residue was purified by flash column chromatography ($SiO_2$, 12 g, [1% $NH_3$ in MeOH] in DCM, 0-5%, gradient elution) and the material so obtained was partitioned between DCM (15 mL) and saturated aq. $NaHCO_3$ (15 mL). The organic layer was separated and washed with saturated aq. $NaHCO_3$ (15 mL) and then dried and evaporated in vacuo to afford the title compound, Example 13, as a pale yellow powder (14 mg, 11%); $R^t$ 5.57 min (Method 1 basic); m/z 655/657 (M+H)$^+$ (ES$^+$); $^1$H NMR (400 MHz, DMSO-d$_6$) δ: 1.27 (9H, s), 2.16 (6H, s), 2.31 (2H, t), 3.16 (2H, m), 2.82 (3H, s), 6.37 (1H, s), 6.53 (1H, dd), 6.94 (1H, d), 7.09 (2H, m), 7.36 (1H, d), 7.43 (2H, d), 7.83 (1H, br s), 8.07 (1H, d), 8.16 (1H, d), 8.85 (1H, s), 9.16 (2H, br s).

Example 14

N-(4-((4-(3-(3-tert-Butyl-1-p-tolyl-1H-pyrazol-5-yl)ureido)-2,3-dichlorophenoxy)methyl)pyridin-2-yl)-2-methoxyacetamide

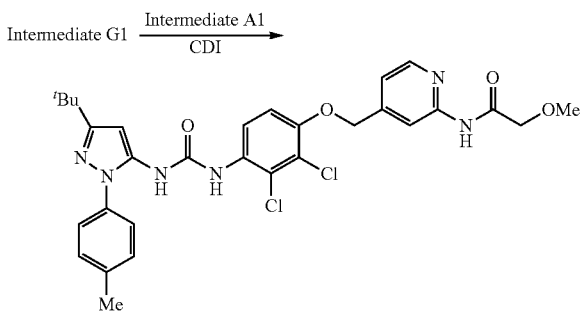

Example 14

To a stirred solution of CDI (223 mg, 1.38 mmol) in dry DCM (3.5 mL) was added Intermediate A1 (315 mg, 1.38 mmol) as a solid, portion-wise, over 12 min and the resulting solution maintained at RT for 4 hr. An aliquot of this solution (2.0 mL, 0.79 mmol) was added to a solution of Intermediate G1, (140 mg, 0.39 mmol) in dry THF (5.0 mL), and the reaction mixture was kept at RT for 17 hr and was then partitioned between saturated aq. $NaHCO_3$ (30 mL) and DCM (30 mL). The aq. layer was extracted with DCM (30 mL) and the combined organic extracts were dried and evaporated in vacuo. The residue was purified by flash column chromatography ($SiO_2$, 12 g, [5% MeOH in EtOAc] in isohexane, 0-45%, gradient elution) to afford the title compound, Example 14, as an off white solid (127 mg, 52%); $R^t$ 5.40 min (Method 1 basic); m/z 611/613 (M+H)$^+$ (ES$^+$); $^1$H NMR (400 MHz, DMSO-d$_6$) δ: 1.26 (9H, s), 2.37 (3H, s), 3.37 (3H, s), 4.07 (2H, s), 5.31 (2H, s), 6.34 (1H, s), 7.18-7.23 (2H, overlapping m), 7.31-7.34 (2H, overlapping m), 7.38-7.40 (2H, overlapping m), 7.85 (1H, d), 8.21 (1H, br s), 8.33 (1H, dd), 8.60 (1H, br s), 8.95 (1H, br s), 10.01 (1H, br s).

Example 15

N-(4-((4-(3-(3-tert-Butyl-1-(4-methoxyphenyl)-1H-pyrazol-5-yl)ureido)-2,3-dichlorophenoxy)methyl)pyridin-2-yl)-2-methoxyacetamide

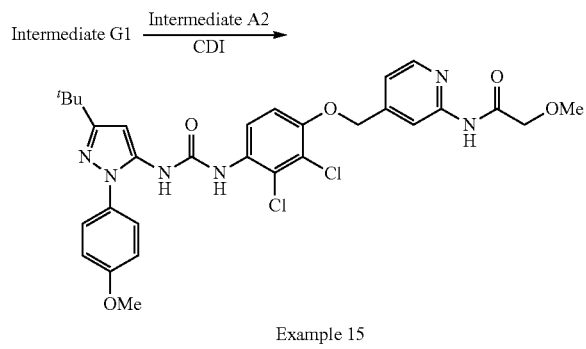

Example 15

To a stirred solution of CDI (223 mg, 1.38 mmol) in dry DCM (3.5 mL) was added Intermediate A2 (337 mg, 1.38 mmol) as a solid, portion-wise, over 15 min and the resulting solution maintained at RT for 4 hr. An aliquot of this solution (2.0 mL, 0.79 mmol) was added to a solution of Intermediate G1 (140 mg, 0.39 mmol) in dry THF (5.0 mL) and the reaction mixture was kept at RT for 17 hr. The resulting mixture was partitioned between saturated aq. NaHCO$_3$ (30 mL) and DCM (30 mL) and the aqueous layer was separated and extracted with DCM (30 mL). The combined organic extracts were dried and evaporated in vacuo and the residue was purified by flash column chromatography (SiO$_2$, 12 g, [5% MeOH in EtOAc] in isohexane, 0-50%, gradient elution then SiO$_2$, 12 g, MeOH in DCM, 0-2.5%, gradient elution) to afford the title compound, Example 15, as a white solid (78 mg, 31%); R$^t$ 5.27 min (Method 1 basic); m/z 627/629 (M+H)$^+$ (ES$^+$); $^1$H NMR (400 MHz, DMSO-d$_6$) δ: 1.26 (9H, s), 3.37 (3H, s), 3.82 (3H, s), 4.07 (2H, s), 5.32 (2H, s), 6.32 (1H, s), 7.08 (2H, m), 7.18-7.21 (2H, overlapping m), 7.41 (2H, m), 7.85 (1H, d), 8.21 (1H, br s), 8.33 (1H, dd), 8.60 (1H, br s), 8.91 (1H, br s), 10.01 (1H, br s).

Example 16

N-(4-((5-(3-(3-tert-Butyl-1-p-tolyl-1H-pyrazol-5-yl)ureido)quinolin-8-yloxy)methyl)pyridin-2-yl)-2-methoxyacetamide

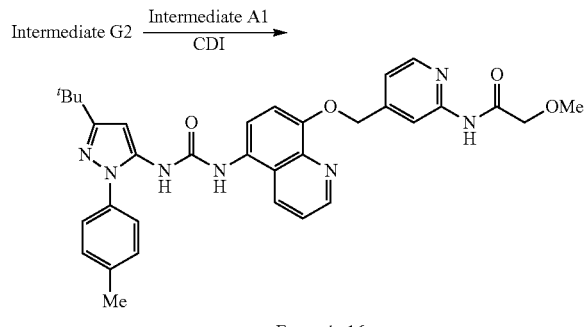

Example 16

To a suspension of CDI (973 mg, 6.00 mmol) in dry DCM (10.0 mL) under N$_2$ was added Intermediate A1 (1.38 g, 6.00 mmol) as a solid, in four equal portions, over 10 min and the resulting solution maintained at RT for 16 hr. An aliquot of this solution (473 μL, 0.284 mmol) was added to a suspension of Intermediate G2 (100 mg, 0.296 mmol) in anhydrous DCM (5.0 mL) and the reaction mixture kept at RT for 24 hr. The reaction mixture, in its entirety, was purified by flash column chromatography (SiO$_2$, 40 g, MeOH in DCM, 0-10%, gradient elution) to afford the title compound, Example 16, as a yellow solid (108 mg, 59%); R$^t$ 4.60 min (Method 1 basic); m/z 594 (M+H)$^+$ (ES$^+$); $^1$H NMR (400 MHz, DMSO-d$_6$) δ: 1.27 (9H, s), 2.39 (3H, s), 3.36 (3H, s), 4.06 (2H, s), 5.39 (2H, s), 6.35 (1H, s), 7.22 (1H, d), 7.30 (1H, dd), 7.36 (2H, m), 7.44 (2H, m), 7.60 (1H, dd), 7.64 (1H, d), 8.24 (1H, br s), 8.27 (1H, dd), 8.34 (1H, dd), 8.59 (1H, br s), 8.89 (1H, br s), 8.92 (1H, dd), 10.04 (1H, br s).

Example 17

N-(4-((5-(3-(3-tert-Butyl-1-(4-methoxyphenyl)-1H-pyrazol-5-yl)ureido)quinolin-8-yloxy)methyl)pyridin-2-yl)-2-methoxyacetamide

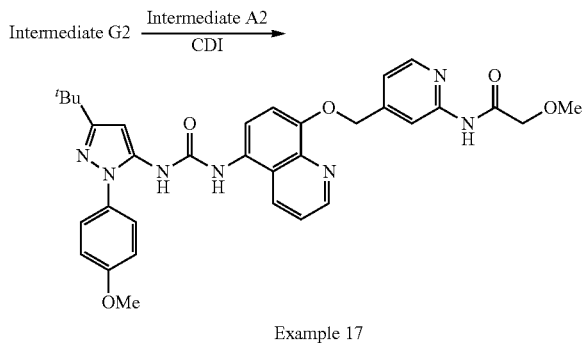

Example 17

To a suspension of CDI (973 mg, 6.00 mmol) in dry DCM (6.0 mL) under N$_2$ was added Intermediate A2 (1.47 g, 6.00 mmol) as a solid, in two equal portions, over 10 min and the resulting solution maintained at RT for 16 hr. A portion of this solution (473 μL, 0.473 mmol) was added to a suspension of Intermediate G2 (100 mg, 0.296 mmol) in dry DCM (5.0 mL) and the reaction mixture kept at RT for 24 hr. The reaction mixture was, in its entirety, (without work up) purified by flash column chromatography (SiO$_2$, 40 g, MeOH in DCM, 0-10%, gradient elution) to afford the title compound, Example 17, as a yellow solid (161 mg, 85%); R$^t$ 4.49 min (Method 1 basic); m/z 610 (M+H)$^+$ (ES$^+$); $^1$H NMR (400 MHz, DMSO-d$_6$) δ: 1.26 (9H, s), 3.36 (3H, s), 3.83 (3H, s), 4.06 (2H, s), 5.39 (2H, s), 6.33 (1H, s), 7.10 (2H, m), 7.22 (1H, d), 7.30 (1H, dd), 7.46 (2H, m), 7.60 (1H, dd), 7.65 (1H, d), 8.24 (1H, br s), 8.26 (1H, dd), 8.34 (1H, dd), 8.54 (1H, br s), 8.88 (1H, br s), 8.92 (1H, dd), 10.04 (1H, br s).

Example 18

1-(3-tert-Butyl-1-(4-methoxyphenyl)-1H-pyrazol-5-yl)-3-(2,3-dichloro-4-((2-(3-methylureido)pyridin-4-yl)methoxy)phenyl)urea

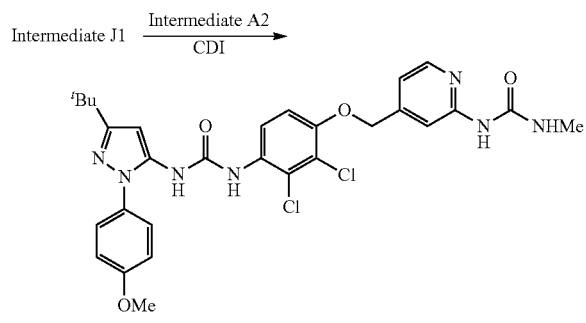

Example 18

To a suspension of CDI (973 mg, 6.00 mmol) in dry DCM (6.0 mL) under $N_2$ was added Intermediate A2 (1.47 g, 6.00 mmol) as a solid, in two equal portions, over 10 min and the resulting solution maintained at RT for 16 hr. An aliquot of this solution (440 µL, 0.44 mmol) was added dropwise to a cooled solution of Intermediate J1 (85 mg, ~90% purity, 0.23 mmol) in dry THF (5.0 mL) at 0° C. and the reaction mixture then warmed to RT for 18 hr. The resulting mixture was partitioned between DCM (30 mL) and saturated aq. $NaHCO_3$ (30 mL). The aqueous layer was separated and extracted with DCM (30 mL) and the combined organic extracts were dried and evaporated in vacuo. The residue was purified flash column chromatography ($SiO_2$, 12 g, [5% MeOH in EtOAc] in isohexane, 0-75%, gradient elution) to afford the title compound, Example 18, as a white solid (83 mg, 60%); $R^t$ 5.27 min (Method 1 basic); m/z 612/614 $(M+H)^+$ $(ES^+)$; $^1H$ NMR (400 MHz, DMSO-$d_6$) δ: 1.26 (9H, s), 2.73 (3H, d), 3.81 (3H, s), 5.23 (2H, s), 6.32 (1H, s), 6.97 (1H, br d), 7.08 (2H, m), 7.17 (1H, d), 7.39-7.42 (3H, overlapping m), 7.84 (1H, d), 8.10 (1H, br s), 8.18 (1H, d), 8.60 (1H, br s), 8.92 (1H, br s), 9.35 (1H, br s).

Example 19

N-(4-((4-(3-(3-tert-Butyl-1-(p-tolyl)-1H-pyrazol-5-yl)ureido)-2,3-dichlorophenoxy)methyl)pyridin-2-yl)pyrrolidine-1-carboxamide

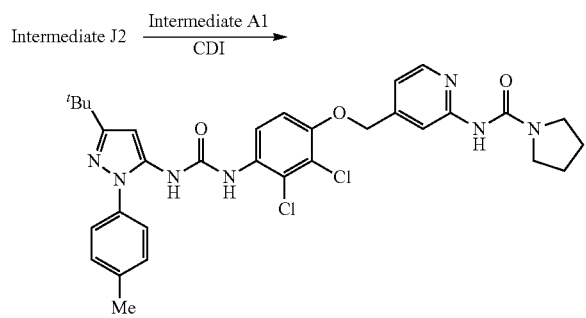

Example 19

To a suspension of CDI (973 mg, 6.00 mmol) in dry DCM (10.0 mL) under $N_2$ was added Intermediate A1 (1.376 g, 6.00 mmol) as a solid, in four equal portions, over 10 min and the resulting solution maintained at RT for 16 hr. A portion of this solution (550 µL, 0.33 mmol) was added dropwise to a cooled solution of Intermediate J2 (105 mg, ~85% purity, 0.23 mmol) in dry THF (4.0 mL) at 0° C. and the reaction mixture warmed to RT for 3.5 hr and then partitioned between DCM (30 mL) and saturated aq. $NaHCO_3$ (30 mL). The aq. layer was extracted with DCM (30 mL) and the combined organic layers were dried and evaporated in vacuo. The residue was purified flash column chromatography ($SiO_2$, 12 g, [5% MeOH in EtOAc] in isohexane, 0-75%, gradient elution) to afford the title compound, Example 19, as an off-white solid (107 mg, 70%); $R^t$ 5.45 min (Method 1 basic); m/z 637/639 $(M+H)^+$ $(ES^+)$; $^1H$ NMR (400 MHz, DMSO-$d_6$) δ: 1.26 (9H, s), 1.83 (4H, m), 2.37 (3H, s), 3.39 (4H, m), 5.25 (2H, s), 6.34 (1H, s), 7.03 (1H, d), 7.18 (1H, d), 7.32-7.40 (4H, overlapping m), 7.84 (1H, d), 8.00 (1H, s), 8.23 (1H, d), 8.60 (1H, br s), 8.69 (1H, br s), 8.96 (1H, br s).

Example 20

N-(4-((4-(3-(3-tert-Butyl-1-(4-methoxyphenyl)-1H-pyrazol-5-yl)ureido)-2,3-dichlorophenoxy)methyl)pyridin-2-yl)pyrrolidine-1-carboxamide

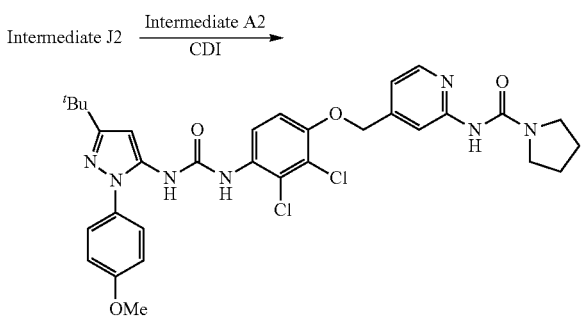

Example 20

To a suspension of CDI (973 mg, 6.00 mmol) in dry DCM (6.0 mL) under $N_2$ was added Intermediate A2 (1.47 g, 6.00 mmol) as a solid, in two equal portions, over 10 min and the resulting solution maintained at RT for 16 hr. An aliquot of this solution (0.55 mL, 0.55 mmol) was added dropwise to a cooled solution of Intermediate J2 (105 mg, ~85% purity, 0.23 mmol) in dry THF (4.0 mL) at 0° C. and the reaction mixture then warmed to RT for 4 hr. The mixture was partitioned between DCM (30 mL) and saturated aq. $NaHCO_3$ (30 mL) and the aq layer separated and extracted with DCM (30 mL) The combined organic extracts were dried and evaporated in vacuo and the residue was purified by flash column chromatography ($SiO_2$, 12 g, [5% MeOH in EtOAc] in isohexane, 0-75%, gradient elution) to afford the title compound, Example 20, as an off-white solid (111 mg, 71%); $R^t$ 5.34 min (Method 1 basic); m/z 653/655 $(M+H)^+$ $(ES^+)$; $^1H$ NMR (400 MHz, DMSO-$d_6$) δ: 1.26 (9H, s), 1.83 (4H, m), 3.39 (4H, m), 3.81 (3H, s), 5.25 (2H, s), 6.32 (1H, s), 7.03 (1H, dd), 7.08 (2H, m), 7.18 (1H, d), 7.41 (2H, m), 7.84 (1H, d), 8.00 (1H, br s), 8.23 (1H, dd), 8.60 (1H, br s), 8.69 (1H, br s), 8.92 (1H, br s).

Example 21

1-(3-tert-Butyl-1-p-tolyl-1H-pyrazol-5-yl)-3-(8-((2-(3-methylureido)pyridin-4-yl)methoxy)quinolin-5-yl)urea

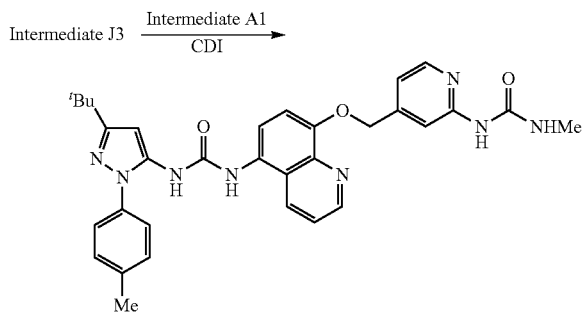

Example 21

To a suspension of CDI (973 mg, 6.00 mmol) in dry DCM (10.0 mL) under $N_2$ was added Intermediate A1 (1.38 g, 6.00 mmol) as a solid, in four equal portions, over 10 min and the resulting solution maintained at RT for 16 hr. An aliquot of this solution (247 µL, 0.148 mmol) was added to a suspension of Intermediate J3 (50 mg, 0.16 mmol) in dry DCM (5.0 mL) and the reaction mixture kept at RT for 5 hr. The resulting suspension was diluted with DCM (5.0 mL) and the solid was collected by filtration and then suspended in water (5.0 mL) and sonicated for 3 min. The solid was collected by filtration, washed with water (2×2.5 mL) and dried in vacuo at 45° C. for 16 hr to afford the title compound, Example 21, as a white solid (70 mg, 74%); $R^t$ 4.67 min (Method 1 basic); m/z 579 (M+H)$^+$ (ES$^+$); $^1$H NMR (400 MHz, DMSO-$d_6$) δ: 1.27 (9H, s), 2.39 (3H, s), 2.72 (3H, d), 5.31 (2H, s), 6.35 (1H, s), 7.08 (1H, dd), 7.20 (1H, d), 7.36 (2H, m), 7.43-7.45 (3H, overlapping m), 7.60 (1H, dd), 7.64 (1H, d), 8.14 (1H, br s), 8.19 (1H, d), 8.27 (1H, dd), 8.58 (1H, br s), 8.89 (1H, br s), 8.92 (1H, dd), 9.33 (1H, br s).

Example 22

N-(6-(4-(3-(3-tert-Butyl-1-(4-hydroxymethyl)phenyl)-1H-pyrazol-5-yl)ureido)-2,3-dichlorophenoxy)pyrimidin-4-yl)-4-(dimethylamino)butanamide

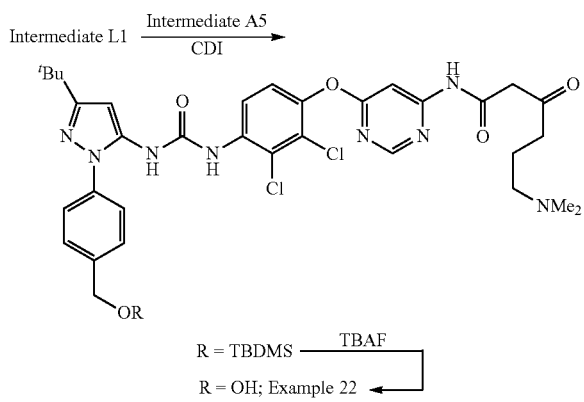

To a solution of CDI (652 mg, 4.02 mmol) in dry DCM (8.0 mL) at RT was added Intermediate A5 (1.62 g, 4.02 mmol) portionwise over 15 min and the reaction mixture maintained at RT for 4 hr. An aliquot of the resulting solution (3.5 mL, 1.8 mmol) was added to a solution of Intermediate L1, (79 mg, 0.23 mmol) in DCM/THF (3:1 v/v, 4.0 mL) and the reaction mixture was maintained at RT for 72 hr. An additional aliquot of the pre-formed CDI adduct (500 µL, 0.25 mmol) was added and after a further 2.5 hr the reaction mixture was partitioned between saturated aq. NaHCO$_3$ (60 mL) and DCM (50 mL). The aq layer was separated and extracted with DCM (50 mL) and the combined organic extracts were dried and evaporated in vacuo. The residue was purified twice by flash column chromatography (SiO$_2$, 80 g, [10% (7M NH$_3$ in MeOH) in EtOAc] in EtOAc, 0-100%, gradient elution; repeated once) to provide N-(6-(4-(3-(3-(tert-butyl)-1-(4-(((tert-butyldimethylsilyl)oxy)methyl)phenyl)-1H-pyrazol-5-yl)ureido)-2,3-dichlorophenoxy)pyrimidin-4-yl)-4-(dimethylamino)butanamide as a yellow solid (610 mg, 68%); $R^t$ 2.67 min (method 2); m/z 406 (M+H)$^{2+}$/2, (ES$^+$);

To a solution of the silyl ether, obtained above, (610 mg, 0.75 mmol) in dry THF (6.0 mL) was added TBAF (1.0 M solution in THF, 0.9 mL, 0.9 mmol) and the reaction mixture kept at RT for 18 hr and then partitioned between EtOAc (75 mL) and saturated aq NaHCO$_3$ (50 mL). The aq layer was extracted with EtOAc (75 mL) and the organic extracts were combined, washed with brine (50 mL) and then dried and evaporated in vacuo. The residue was triturated with ether and then purified by SCX capture and release to afford the title compound, Example 22, as a yellow amorphous solid (450 mg, 88%); $R^t$ 1.66 min (method 2); m/z 655 (M+H)$^+$, (ES$^+$); $^1$H NMR (400 MHz, DMSO-$d_6$) δ: 1.29 (9H, s), 1.71 (2H, tt), 2.14 (6H, s), 2.24 (2H, t), 2.45 (2H, t), 4.57 (2H, d), 5.23 (1H, m), 6.39 (1H, s), 7.36 (1H, d), 7.48 (4H, s), 7.66 (1H, d), 8.09 (1H, d), 8.47 (1H, d), 8.79 (1H, br s), 9.14 (1H, br s), 11.03 (1H, br s).

Example 23

N-(4-(4-(3-(3-tert-Butyl-1-(4-methoxyphenyl)-1H-pyrazol-5-yl)ureido)-2,3-dichlorophenoxy)pyrimidin-2-yl)-2-methoxyacetamide

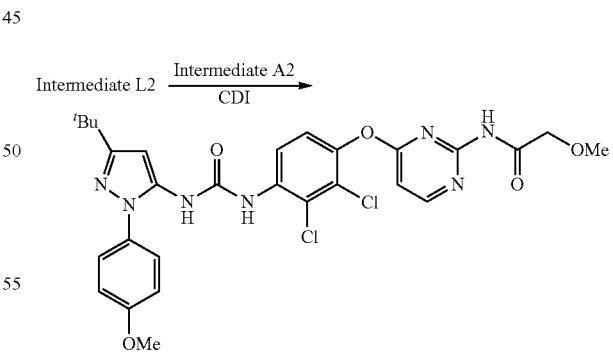

Example 23

To a solution of CDI (149 mg, 0.920 mmol) in dry DCM (2.0 mL) at RT was added Intermediate A2 (226 mg, 0.920 mmol) portionwise over 5 min and the reaction mixture maintained at RT for 20 hr. An aliquot of the resulting solution (1.0 mL, 0.50 mmol) was added to a solution of Intermediate L2 (79 mg, 0.23 mmol) in DCM/THF (3:1 v/v, 4.0 mL) and the reaction mixture was maintained at RT.

After 7.5 hr a further portion of the pre-formed CDI adduct (250 μL, 0.12 mmol) was added and after a further 24 hr the reaction mixture was partitioned between saturated aq. NaHCO₃ (20 mL) and DCM (20 mL). The aq layer was separated and extracted with DCM (20 mL) and the combined organic extracts were dried and evaporated in vacuo. The residue was purified by flash column chromatography (SiO₂, 12 g, [5% MeOH in EtOAc] in isohexane, 0-65%, gradient elution) to provide the title compound, Example 23, as a white solid (81 mg, 56%); $R^t$ 5.12 min (Method 1 basic); m/z 614/616 (M+H)⁺, (ES⁺); ¹H NMR (400 MHz, DMSO-d₆) δ: 1.27 (9H, s), 3.15 (3H, s), 3.82 (3H, s), 3.90 (2H, s), 6.37 (1H, s), 6.89 (1H, d), 7.09 (2H, m), 7.40-7.45 (3H, overlapping m), 8.15 (1H, d), 8.55 (1H, d), 8.83 (1H, s), 9.13 (1H, s), 10.42 (1H, s).

Example 24

1-(3-tert-Butyl-1-p-tolyl-1H-pyrazol-5-yl)-3-(2,3-dichloro-4-(6-(3-(2-(dimethylamino)ethyl)ureido)pyrimidin-4-yloxy)phenyl)urea

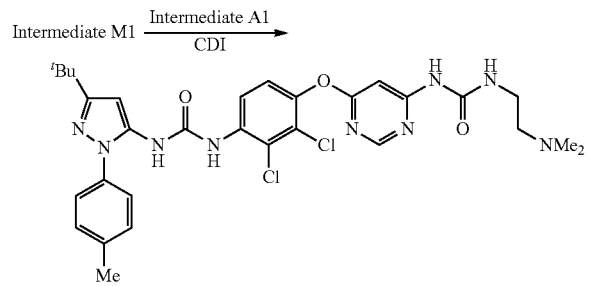

Example 24

To a solution of CDI (510 mg, 3.15 mmol) in dry DCM (6.0 mL) at RT was added Intermediate A1 (722 mg, 3.15 mmol) portionwise over 15 min and the reaction mixture maintained at RT for 20 hr. An aliquot of the resulting solution (840 μL, 0.44 mmol) was added to a solution of Intermediate M1, (81 mg, 0.21 mmol) in dry DCM (4.0 mL) and the reaction mixture was maintained at RT for 1 day and was then partitioned between saturated aq. NaHCO₃ (20 mL) and DCM (20 mL). The aq layer was separated and extracted with DCM (20 mL) and the combined organic extracts were dried and evaporated in vacuo. The residue was purified by flash column chromatography (SiO₂, 12 g, [1% NH₃ in MeOH] in DCM, 0-10%, gradient elution) to provide the title compound, Example 24, as a white solid (53 mg, 37%); $R^t$ 5.39 min (Method 1 basic); m/z 640/642 (M+H)⁺, (ES⁺); ¹H NMR (400 MHz, DMSO-d₆) δ: 1.27 (9H, s), 2.16 (6H, s), 2.33 (2H, t), 2.34 (3H, s), 3.21 (2H, td), 6.38 (1H, s), 7.23-7.28 (2H, overlapping m), 7.33-7.37 (3H, overlapping m), 7.41 (2H, m), 8.08 (1H, d), 8.35 (1H, d), 8.83 (1H, br s), 9.17 (1H, br s), 9.68 (1H, br s).

Example 25

1-(4-(4-(3-(3-tert-Butyl-1-(4-(hydroxymethyl)phenyl)-1H-pyrazol-5-yl)ureido)-2,3-dichlorophenoxy)pyrimidin-2-yl)-3-methylurea

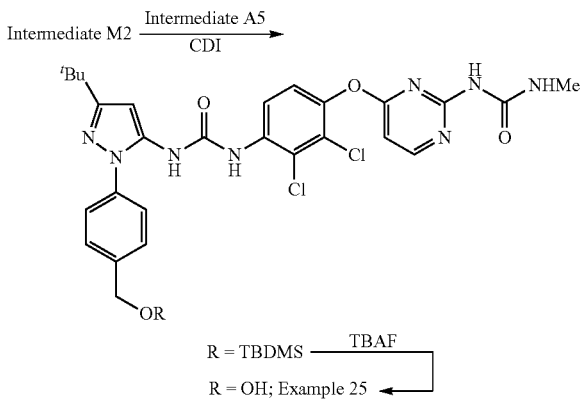

To a solution of CDI (303 mg, 1.87 mmol) in dry DCM (5.0 mL) at RT was added Intermediate A5 (750 mg, 1.87 mmol) in solid portions over 5 min and the reaction mixture maintained at RT for 20 hr. An aliquot of the resulting solution (1.0 mL, 0.37 mmol) was added to a solution of Intermediate M2, (60 mg, 0.18 mmol) in dry THF (3.0 mL) and the reaction mixture was maintained at RT for 3.5 hr A second aliquot of the pre-formed CDI adduct (300 μL, 0.11 mmol) was added and after 3 days the reaction mixture was partitioned between saturated aq. NaHCO₃ (20 mL) and DCM (20 mL). The aq layer was separated and extracted with DCM (20 mL) and the combined organic extracts were dried and evaporated in vacuo. The residue was purified by flash column chromatography (SiO₂, 12 g, [5% MeOH in EtOAc] in isohexane, 0-35%, gradient elution then SiO₂, 12 g, MeOH in DCM, 0-4%, gradient elution) to provide 1-(4-(4-(3-(3-(tert-butyl)-1-(4-(((tert-butyldimethylsilyl)oxy)methyl) phenyl)-1H-pyrazol-5-yl)ureido)-2,3-dichlorophenoxy)pyrimidin-2-yl)-3-methylurea as a white solid (91 mg, 62%); $R^t$ 6.30 min (Method 1 basic); m/z 755/757 (M+H)⁺, (ES⁺).

To a solution of the silyl ether, obtained above, (90 mg, 0.12 mmol) in dry THF (5.0 mL) was added TBAF (1.0 M solution in THF, 149 μL, 0.149 mmol) and the reaction mixture kept at RT for 7 hr and then partitioned between DCM (20 mL) and saturated aq NaHCO₃ (25 mL). The aq layer was separated and extracted with DCM (25 mL) and the combined organic extracts were washed with brine (30 mL), dried and evaporated in vacuo. The residue was purified by flash column chromatography (SiO₂, 12 g, [5% MeOH in EtOAc] in isohexane, 0-80%, gradient elution) and the impure material so obtained was triturated with ether to afford the title compound, Example 25, as a white amorphous solid (30 mg, 68%); $R^t$ 5.07 min (Method 1 basic); m/z 599/601 (M+H)⁺, (ES⁺); ¹H NMR (400 MHz, DMSO-d₆) δ: 1.28 (9H, s), 2.48 (3H, d), 4.57 (2H, d), 5.33 (1H, t), 6.40 (1H, s), 6.77 (1H, d), 7.40-7.52 (5H, overlapping m), 8.11-8.16 (2H, overlapping m), 8.48 (1H, d), 8.90 (1H, br s), 8.19 (1H, br s), 9.80 (1H, br s).

Example 26

N-(4-((4-(3-(3-tert-Butyl-1-(4-methoxyphenyl)-1H-pyrazol-5-yl)ureido)-2,3-dichlorophenylthio)methyl)pyridin-2-yl)-2-methoxyacetamide

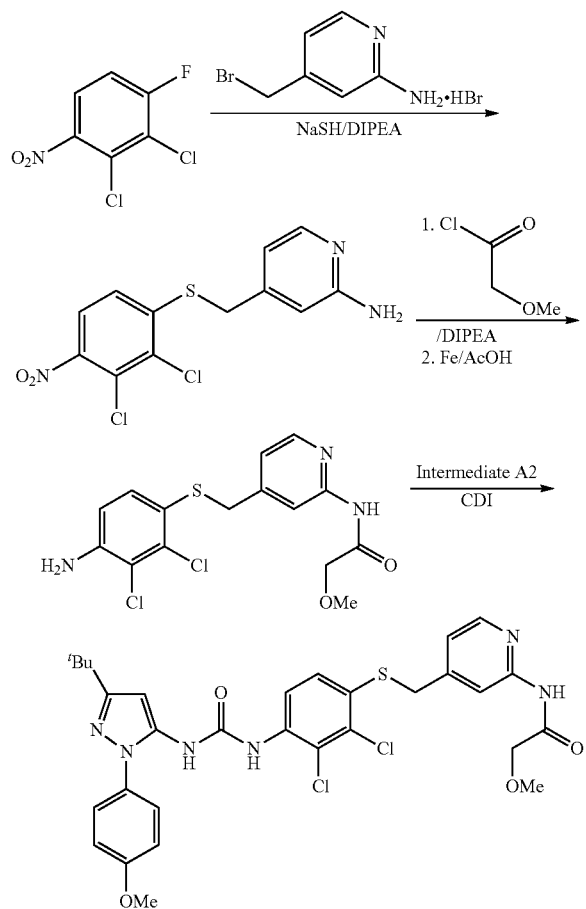

Example 26

A solution of sodium hydrogensulfide (720 mg, 8.70 mmol) in DMF (10.0 mL) was simultaneously sonicated and purged with $N_2$ for 30 min and then treated, dropwise over 30 min, with a similarly purged solution of 4-(bromomethyl)pyridin-2-amine hydrobromide (2.13 g, 7.94 mmol) in DMF (10.0 mL). After 30 min the reaction mixture was cooled to 0° C. and a nitrogen purged solution of DIPEA (2.8 mL, 16 mmol) and 2,3-dichloro-1-fluoro-4-nitrobenzene (2.00 g, 9.53 mmol) in DMF (10.0 mL) was added and the mixture warmed to RT for 1 hr. The reaction mixture was treated with AcOH (5.0 mL), maintained at RT for a further 72 hr and then partitioned between water (150 mL) and EtOAc (150 mL). The aq layer was separated and extracted with EtOAc (150 mL) and was then neutralised with saturated aq. $NaHCO_3$ (100 mL) and extracted a second time with EtOAc (100 mL). The combined organic extracts were washed sequentially with saturated aq. $NaHCO_3$ (150 mL), water (2×100 mL) and brine (2×100 mL) and then dried and evaporated in vacuo. The residue was recrystallized from MeOH (30 mL) and the product was collected by filtration, washed with MeOH (2×10 mL) and ether (2×50 mL) and dried in vacuo to afford 4-((2,3-dichloro-4-nitrophenylthio)methyl)pyridin-2-amine as a yellow solid (360 mg 12%); $R^t$ 4.78 min (Method 1 basic); m/z 330/332 $(M+H)^+$ $(ES^+)$.

To a suspension of the thioether obtained above (350 mg, 1.06 mmol) in DCM (10 mL) and THF (5.0 mL) containing DIPEA (370 μL, 2.1 mmol) at 0° C. under $N_2$ was added 2-methoxyacetyl chloride (126 μL, 1.38 mmol) dropwise over 10 mins. Upon completion of the addition the reaction mixture was warmed to RT during which time a deep red solution was obtained. After 1 hr the mixture was treated with $NH_3$ (1% solution in MeOH, 30 mL) and after 30 min was evaporated in vacuo. The residue was taken up into EtOAc (50 mL) and was washed with water (2×30 mL), saturated aq. $NaHCO_3$ (30 mL) and brine (30 mL) and then dried and evaporated in vacuo to furnish N-(4-((2,3-dichloro-4-nitrophenylthio)methyl)pyridin-2-yl)-2-methoxyacetamide as a yellow oil (401 mg, 89%); $R^t$ 4.92 min (Method 1 basic); m/z 402/404 $(M+H)^+$ $(ES^+)$.

A suspension of the nitroarene obtained above (400 mg, 0.99 mmol) and iron powder (389 mg, 6.96 mmol) in AcOH (5.0 mL) was heated at 50° C. for 1 hr and was then cooled to RT, diluted with EtOAc (100 mL) and poured carefully onto solid $K_2CO_3$. The resulting mixture was diluted with water (50 mL) and the aq layer was separated and extracted with EtOAc (2×50 mL). The combined organic extracts were washed with saturated aq. $NaHCO_3$ (75 mL), water (75 mL) and brine (75 mL) and then dried and evaporated in vacuo to afford N-(4-((4-amino-2,3-dichlorophenylthio)methyl)pyridin-2-yl)-2-methoxyacetamide as a pale yellow solid (338 mg, 90% pure, 82%); $R^t$ 4.45 min (Method 1 basic, ~90% pure); m/z 372/374 $(M+H)^+$ $(ES^+)$. This material was used directly in the subsequent step without further purification.

To a solution of CDI (500 mg, 3.00 mmol) in DCM (6.0 mL) was added Intermediate A2 (756 mg, 3.08 mmol) and the resulting solution maintained at RT for 4 hr. An aliquot of this solution (3.2 mL, 1.6 mmol) was added to a solution of the anilino thioether obtained above (300 mg, 0.725 mmol) in DCM (5.0 mL) and the reaction mixture was maintained at RT for 17 hr. The mixture was washed with water (5.0 mL) and the DCM layer was separated and evaporated in vacuo. The residue was purified by flash column chromatography ($SiO_2$, 40 g, EtOAc in isohexane, 20-80%, gradient elution) to yield the title compound, Example 26, as a pale yellow solid (360 mg, 73.3% yield); $R^t$ 5.47 min (Method 1 basic); m/z 643/645 $(M+H)^+$ $(ES^+)$; $^1$H NMR (400 MHz, DMSO-$d_6$) δ: 1.26 (9H, s), 3.35 (3H, s), 3.81 (3H, s), 4.04 (2H, s), 4.33 (2H, s), 6.34 (1H, s), 7.08 (2H, m), 7.12 (1H, dd), 7.35 (1H, d), 7.40 (2H, m), 7.99 (1H, d), 8.11 (1H, br s), 8.23 (1H, dd), 8.74 (1H, s), 9.12 (1H, s), 9.98 (1H, s).

Further compound examples listed below (Table 1) have been prepared from appropriate starting materials by adaptation of the methods described above. Unless otherwise indicated all NMR spectroscopic data reported in the table was acquired at 400 MHz using DMSO-$d_6$ as the solvent

TABLE 2

Additional Compound Examples of the Invention

| Ex. No. | Structure | Name and Analytical Data |
|---|---|---|
| 27 | 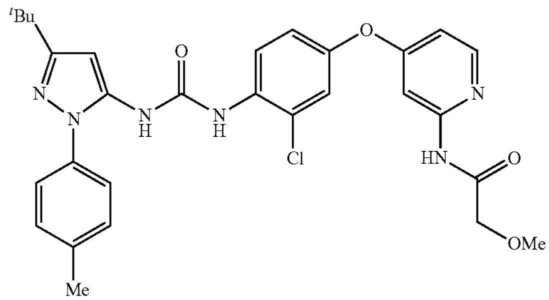 [SMILES: COCC(=O)Nc1cc(Oc2ccc(NC(=O)Nc3cc(C(C)(C)C)nn3-c3ccc(C)cc3)c(Cl)c2)ccn1] | N-(4-(4-(3-(3-tert-butyl-1-p-tolyl-1H-pyrazol-5-yl)ureido)-3-chlorophenoxy)pyridin-2-yl)-2-methoxyacetamide. $R^t$ 2.67 min; m/z 563 $(M + H)^+$ $(ES^+)$, Method 2; $^1$H NMR δ: 1.27 (9H, s), 2.38 (3H, s), 3.33 (3H, s), 4.02 (2H, s), 6.38 (1H, s), 6.72 (1H, dd), 7.17 (1H, dd), 7.33-7.43 (5H, overlapping m), 7.64 (1H, br d), 8.15 (1H, d), 8.21 (1H, d), 8.71 (1H, br s), 9.12 (1H, br s), 10.1 (1H, br s). |
| 28 | 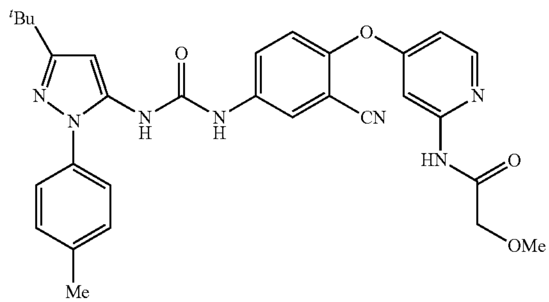 [SMILES: COCC(=O)Nc1cc(Oc2ccc(NC(=O)Nc3cc(C(C)(C)C)nn3-c3ccc(C)cc3)cc2C#N)ccn1] | N-(4-(4-(3-(3-tert-butyl-1-p-tolyl-1H-pyrazol-5-yl)ureido)-2-cyanophenoxy)pyridin-2-yl)-2-methoxyacetamide. $R^t$ 2.56 min; m/z 554 $(M + H)^+$ $(ES^+)$, Method 2; $^1$H NMR δ: 1.28 (9H, s), 2.37 (3H, s), 3.33 (3H, s), 4.03 (2H, s), 6.37 (1H, s), 6.79 (1H, dd), 7.32-7.42 (5H, overlapping m), 7.65 (1H, d), 7.72 (1H, d), 8.04 (1H, d), 8.26 (1H, d), 8.55 (1H, br s), 9.43 (1H, br s), 10.19 (1H, s). |
| 29 | 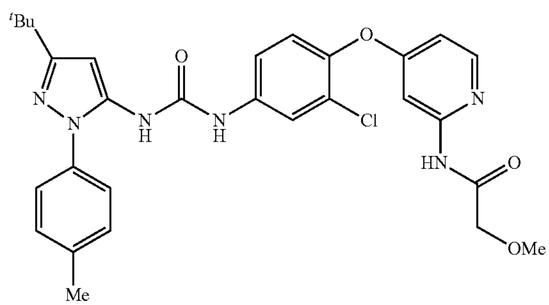 [SMILES: COCC(=O)Nc1cc(Oc2ccc(NC(=O)Nc3cc(C(C)(C)C)nn3-c3ccc(C)cc3)cc2Cl)ccn1] | N-(4-(4-(3-(3-tert-butyl-1-p-tolyl-1H-pyrazol-5-yl)ureido)-2-chlorophenoxy)pyridin-2-yl)-2-methoxyacetamide. $R^t$ 2.65 min; m/z 563/565 $(M + H)^+$ $(ES^+)$, Method 2; $^1$H NMR δ: 1.28 (9H, s), 2.37 (3H, s), 3.33 (3H, s), 4.02 (2H, s), 6.37 (1H, s), 6.65 (1H, dd), 7.27-7.35 (4H, overlapping m), 7.41 (2H, m), 7.56 (1H, d), 7.86 (1H, d), 8.19 (1H, d), 8.46 (1H, s), 9.31 (1H, s), 10.05 (1H, s). |
| 30 | 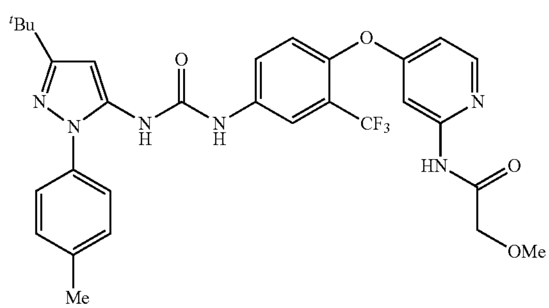 | N-(4-(4-(3-(3-tert-butyl-1-p-tolyl-1H-pyrazol-5-yl)ureido)-2-trifluoromethylphenoxy)pyridin-2-yl)-2-methoxyacetamide. $R^t$ 5.27 min; m/z 597 $(M + H)^+$ $(ES^+)$, Method 1, Basic; $^1$H NMR δ: 1.28 (9H, s), 2.37 (3H, s), 3.32 (3H, s) 4.02 (2H, s), 6.38 (1H, s), 6.72 (1H, dd), 7.31-7.35 (3H, overlapping m), 7.41 (2H, m), 7.63 (2H, overlapping m), 8.06 (1H, d), 8.21 (1H, d), 8.49 (1H, br s), 9.47 (1H, br s), 10.13 (1H, br s). |
| 31 | 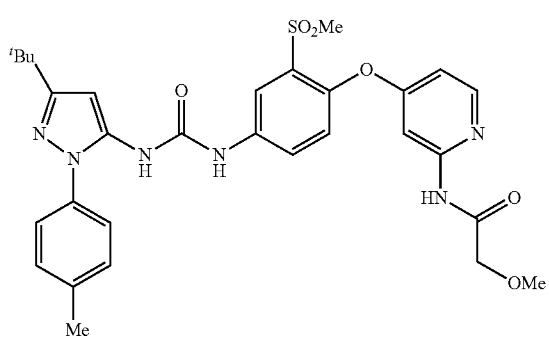 [SMILES: COCC(=O)Nc1cc(Oc2ccc(NC(=O)Nc3cc(C(C)(C)C)nn3-c3ccc(C)cc3)cc2S(C)(=O)=O)ccn1] | N-(4-(4-(3-(3-tert-butyl-1-p-tolyl-1H-pyrazol-5-yl)ureido)-2-methylsulfonylphenoxy)pyridin-2-yl)-2-methoxyacetamide. $R^t$ 4.64 min; m/z 601 $(M + H)^+$ $(ES^+)$, Method 1, Basic; $^1$H NMR δ: 1.28 (9H, s), 2.37 (3H, s), 2.29 (3H, s), 3.35 (4H, br s), 4.03 (2H, s), 6.39 (1H, s), 6.74 (1H, dd), 7.34 (3H, overlapping m), 7.41 (2H, m), 7.69 (1H, d), 7.72 (1H, dd), 8.45 (1H, s), 9.56 (1H, s), 10.15 (1H, s). |

TABLE 2-continued

Additional Compound Examples of the Invention

| Ex. No. | Structure | Name and Analytical Data |
|---|---|---|
| 32 | 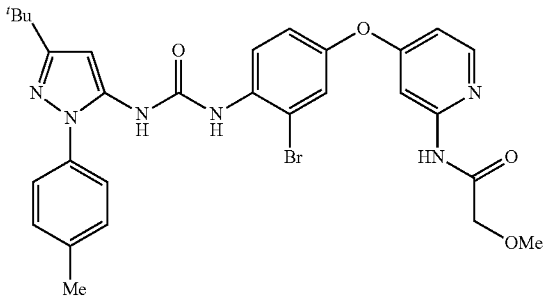 | N-(4-(3-bromo-4-(3-(3-tert-butyl-1-p-tolyl-1H-pyrazol-5-yl)ureido)phenoxy)pyridin-2-yl)-2-methoxyacetamide. $R^r$ 5.28 min; m/z 607/609 (M + H)$^+$ (ES$^+$), Method 1 (Basic); $^1$H NMR δ: 1.27 (9H, s), 2.38 (3H, s), 3.33 (3H, s), 4.02 (2H, s), 6.37 (1H, s), 6.72 (1H, dd), 7.21 (1H, dd), 7.35 (2H, m), 7.41 (2H, m), 7.54 (1H, d), 7.65 (1H, d), 8.03 (1H, d), 8.21 (1H, d), 8.54 (1H, s), 9.15 (1H, s), 10.11 (1H, s). |
| 33 | 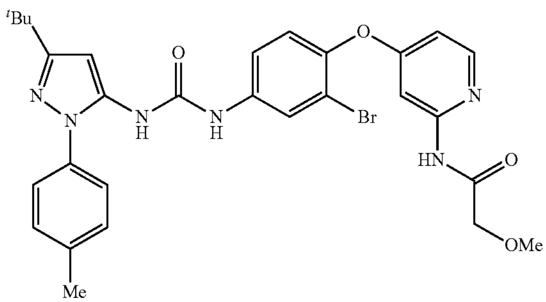 | N-(4-(2-bromo-4-(3-(3-tert-butyl-1-p-tolyl-1H-pyrazol-5-yl)ureido)phenoxy) pyridin-2-yl)-2-methoxyacetamide. $R^r$ 5.25 min; m/z 607/609 (M + H)$^+$ (ES$^+$); Method 1 (Basic); $^1$H NMR δ: 1.28 (9H, s), 2.37 (3H, s), 3.32 (3H, s), 4.02 (2H, s), 6.37 (1H, s), 6.64 (1H, dd), 7.27 (1H, d), 7.33-735 (3H, overlapping m), 7.40 (2H, m), 7.56 (1H, d), 8.02 (1H, d), 8.19 (1H, d), 8.45 (1H, s), 9.32 (1H, s), 10.10 (1H, s). |
| 34 | 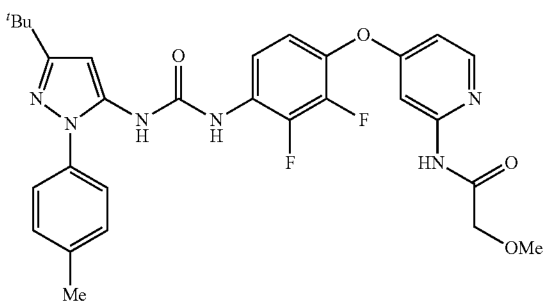 | N-(4-(4-(3-(3-tert-butyl-1-p-tolyl-1H-pyrazol-5-yl)ureido)-2,3-difluorophenoxy)pyridin-2-yl)-2-methoxyacetamide. $R^r$ 5.30 min; m/z 565 (M + H)$^+$ (ES$^+$), Method 1 (basic); $^1$H NMR δ: 1.28 (9H, s), 2.39 (3H, s), 3.34 (3H, s), 4.03 (2H, s), 6.39 (1H, s), 6.78 (1H, dd), 7.20 (1H, ddd), 7.34-7.41 (4H, overlapping m), 7.67 (1H, d), 8.01 (1H, ddd), 7.23 (1H, d), 8.67 (1H, s), 9.21 (1H, br s), 10.16 (1H, s). |
| 35 | 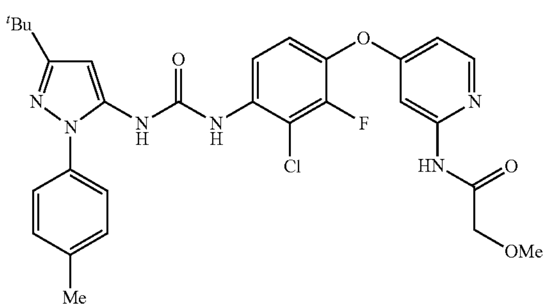 [SMILES: COCC(=O)Nc1cc(Oc2ccc(NC(=O)Nc3cc(C(C)(C)C)nn3-c3ccc(C)cc3)c(Cl)c2F)ccn1] | N-(4-(4-(3-(3-tert-butyl-1-p-tolyl-1H-pyrazol-5-yl)ureido)-3-chloro-2-fluorophenoxy)pyridin-2-yl)-2-methoxyacetamide. $R^r$ 5.34 min; m/z 581 (M + H)$^+$ (ES$^+$), Method 1 (Basic); $^1$H NMR δ: 1.27 (9H, s), 2.38 (3H, s), 3.33 (3H, s), 4.03 (2H, s), 6.38 (1H, s), 6.77 (1H, dd), 7.34-7.42 (5H, overlapping m), 7.65 (1H, br s), 8.05 (1H, dd), 8.23 (1H, d), 8.87 (1H, br s), 9.21 (1H, br s), 10.16 (1H, br s). |
| 36 | 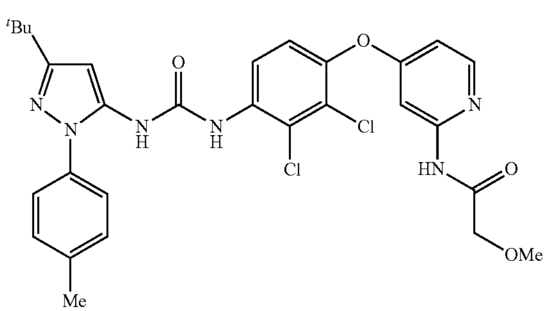 [SMILES: COCC(=O)Nc1cc(Oc2ccc(NC(=O)Nc3cc(C(C)(C)C)nn3-c3ccc(C)cc3)c(Cl)c2Cl)ccn1] | N-(4-(4-(3-(3-tert-butyl-1-p-tolyl-1H-pyrazol-5-yl)ureido)-2,3-dichlorophenoxy)pyridin-2-yl)-2-methoxyacetamide. $R^r$ 2.81 min; m/z 597/599 (M + H)$^+$ (ES$^+$), Method 2; $^1$H NMR δ: 1.27 (9H, s), 2.38 (3H, s), 3.33 (3H, s), 4.02 (2H, s), 6.39 (1H, s), 6.70 (1H, dd), 7.34-7.42 (5H, overlapping m), 7.60 (1H, d), 8.18 (1H, d) 8.22 (1H, d), 8.58 (1H, br s), 9.20 (1H, br s), 10.11 (1H, br s). |

TABLE 2-continued

Additional Compound Examples of the Invention

| Ex. No. | Structure | Name and Analytical Data |
|---|---|---|
| 37 | 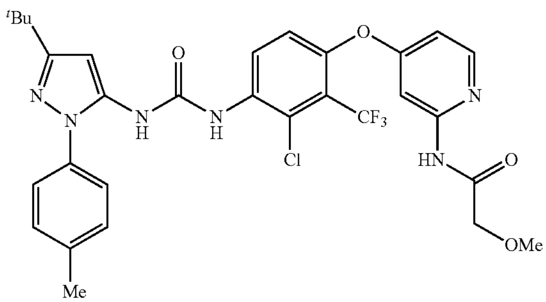 | N-(4-(4-(3-(3-tert-butyl-1-p-tolyl-1H-pyrazol-5-yl)ureido)-3-chloro-2-trifluoromethylphenoxy)pyridin-2-yl)-2-methoxyacetamide. $R^t$ 5.47 min; m/z 631 (M + H)$^+$ (ES$^+$), Method 1 (basic); $^1$H NMR δ: 1.27 (9H, s), 2.38 (3H, s), 3.33 (3H, s), 4.03 (2H, s), 6.39 (1H, s), 6.73 (1H, dd), 7.34-7.42 (5H, overlapping m), 7.62 (1H, d), 8.23 (1H, d), 8.42 (1H, d), 8.96 (1H, br s), 9.24 (1H, br s), 10.15 (1H, br s). |
| 38 | 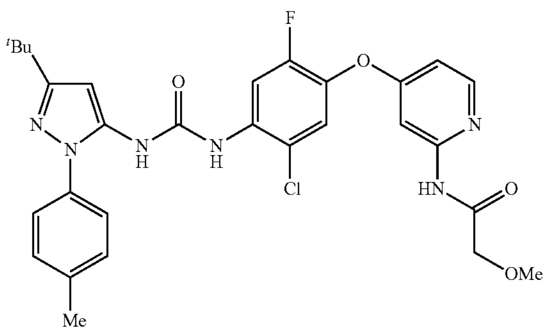 | N-(4-(4-(3-(3-tert-butyl-1-p-tolyl-1H-pyrazol-5-yl)ureido)-5-chloro-2-fluorophenoxy)pyridin-2-yl)-2-methoxyacetamide. $R^t$ 2.78 min; m/z 581 (M + H)$^+$ (ES$^+$), Method 2; $^1$H NMR δ: 1.27 (9H, s), 2.38 (3H, s), 3.33 (3H, s) 4.03 (2H, s), 6.40 (1H, s), 6.76 (1H, dd), 7.35 (2H, m), 7.41 (2H, m), 7.65 (1H, d), 7.69 (1H, d), 7.22 (1H, d), 8.26 (1H, d), 8.84 (1H, br s), 9.29 (1H, br s), 10.15 (1H, br s). |
| 39 | 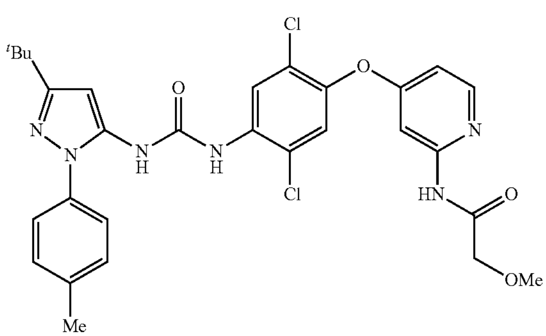 [SMILES: COCC(=O)Nc1cc(Oc2cc(Cl)c(NC(=O)Nc3cc(C(C)(C)C)nn3-c3ccc(C)cc3)cc2F)ccn1] | N-(4-(4-(3-(3-tert-butyl-1-p-tolyl-1H-pyrazol-5-yl)ureido)-2,5-dichlorophenoxy)pyridin-2-yl)-2-methoxyacetamide. $R^t$ 2.90 min; m/z 597/599 (M + H)$^+$ (ES$^+$), Method 2; $^1$H NMR δ: 1.28 (9H, s), 2.38 (3H, s), 4.03 (2H, s), 3.33 (3H, s), 6.40 (1H, s), 6.70 (1H, dd), 7.34-7.42 (4H, overlapping m), 7.60 (1H, d), 7.68 (1H, s), 8.22 (1H, d), 8.43 (1H, s), 8.87 (1H, br s), 9.26 (1H, br s), 10.11 (1H, br s). |
| 40 | 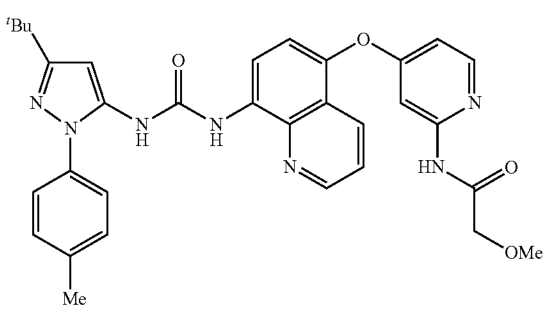 [SMILES: COCC(=O)Nc1cc(Oc2ccc(NC(=O)Nc3cc(C(C)(C)C)nn3-c3ccc(C)cc3)c3ncccc23)ccn1] | N-(4-(8-(3-(3-tert-butyl-1-p-tolyl-1H-pyrazol-5-yl)ureido)quinolin-5-yloxy)pyridin-2-yl)-2-methoxyacetamide. $R^t$ 2.74 min; m/z 580 (M + H)$^+$ (ES$^+$), Method 2; $^1$H NMR δ: 1.30 (9H, s), 2.38 (3H, s), 3.30 (3H, s), 3.98 (2H, s), 6.42 (1H, s), 6.73 (1H, dd), 7.34 (2H, d), 7.42-7.44 (3H, overlapping m), 7.63-7.66 (2H, overlapping m), 8.19 (1H, d), 8.26 (1H, dd), 8.58 (1H, d), 8.95 (1H, dd), 9.57 (1H, br s), 10.01 (1H, br s), 10.04 (1H, br s). |

TABLE 2-continued

Additional Compound Examples of the Invention

| Ex. No. | Structure | Name and Analytical Data |
|---|---|---|
| 41 | 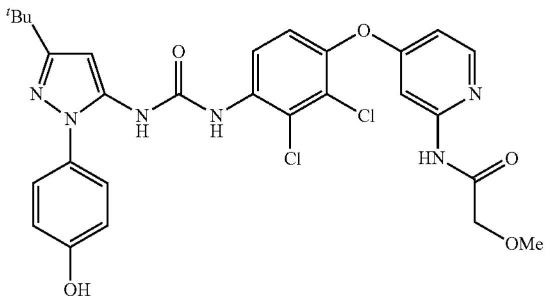 [SMILES: COCC(=O)Nc1cc(Oc2ccc(NC(=O)Nc3cc(C(C)(C)C)nn3-c3ccc(O)cc3)c(Cl)c2Cl)ccn1] | N-(4-(4-(3-(3-tert-butyl-1-(4-hydroxyphenyl)-1H-pyrazol-5-yl)ureido)-2,3-dichloro phenoxy)pyridin-2-yl)-2-methoxyacetamide. R$^t$ 4.80 min; m/z 599/601 (M + H)$^+$ (ES$^+$), Method 1 (basic); $^1$H NMR δ: 1.26 (9H, s), 3.33 (3H, s), 4.03 (2H, s), 6.36 (1H, s), 6.71 (1H, dd), 6.91 (2H, m), 7.29 (2H, m), 7.39 (1H, d), 7.61 (1H, br d), 8.19 (1H, d), 8.22 (1H, d), 8.89 (1H, br s), 9.12 (1H, br s.), 9.80 (1H, br s), 10.14 (1H, br s). |
| 42 | 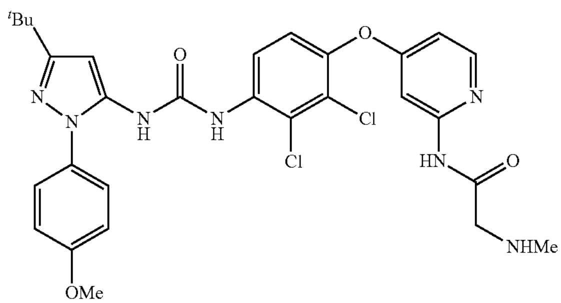 [SMILES: CNCC(=O)Nc1cc(Oc2ccc(NC(=O)Nc3cc(C(C)(C)C)nn3-c3ccc(OC)cc3)c(Cl)c2Cl)ccn1] | N-(4-(4-(3-(3-tert-butyl-1-(4-methoxyphenyl)-1H-pyrazol-5-yl)ureido)-2,3-dichlorophenoxy)pyridin-2-yl)-2-(methylamino)acetamide. R$^t$ 1.68 min; m/z 612 (M + H)$^+$ (ES$^+$), Method 2; $^1$H NMR δ: 1.27 (9H, s), 2.30 (3H, s), 3.29 (2H, s), 3.82 (3H, s), 6.37 (1H, s), 6.72 (1H, dd), 7.10 (2H, m), 7.39 (1H, d), 7.43 (2H, m), 7.62 (1H, s), 8.18 (1H, d), 8.21 (1H, d), 8.87 (1H, s), 9.18 (1H, s), 10.21 (1H, br s). |
| 43 | 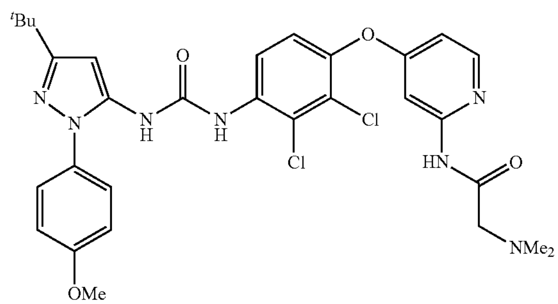 [SMILES: COc1ccc(-n2nc(C(C)(C)C)cc2NC(=O)Nc2ccc(Oc3ccnc(NC(=O)CN(C)C)c3)c(Cl)c2Cl)cc1] | N-(4-(4-(3-(3-tert-butyl-1-(4-methoxyphenyl)-1H-pyrazol-5-yl)ureido)-2,3-dichlorophenoxy)pyridin-2-yl)-2-(dimethylamino)acetamide. R$^t$ 1.73 min; m/z 626 (M + H)$^+$ (ES$^+$), Method 2; $^1$H NMR δ: 1.27 (9H, s), 2.26 (6H, s), 3.08 (2H, s), 3.82 (3H, s), 6.37 (1H, s), 6.70 (1H, dd), 7.10 (2H, m), 7.39 (1H, d), 7.43 (2H, m), 7.62 (1H, d), 8.17-8.21 (2H, overlapping m), 8.86 (1H, s), 9.17 (1H, s), 9.97 (1H, s). |
| 44 | 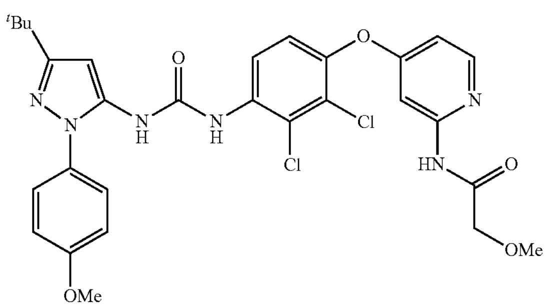 [SMILES: COCC(=O)Nc1cc(Oc2ccc(NC(=O)Nc3cc(C(C)(C)C)nn3-c3ccc(OC)cc3)c(Cl)c2Cl)ccn1] | N-(4-(4-(3-(3-tert-butyl-1-(4-methoxyphenyl)-1H-pyrazol-5-yl)ureido)-2,3-dichlorophenoxy)pyridin-2-yl)-2-methoxyacetamide. R$^t$ 5.37 min; m/z 613/615 (M + H)$^+$ (ES$^+$), Method 1 (basic); $^1$H NMR δ: 1.27 (9H, s), 3.32 (3H, s), 3.82 (3H, s), 4.02 (2H, s), 6.37 (1H, s), 6.71 (1H, dd), 7.10 (2H, m), 7.40 (1H, d), 7.43 (2H, d), 7.60 (1H, br d), 8.19 (1H, d), 8.22 (1H, d), 8.86 (1H, br s), 9.17 (1H, br s), 10.15 (1H, br s). |
| 45 | 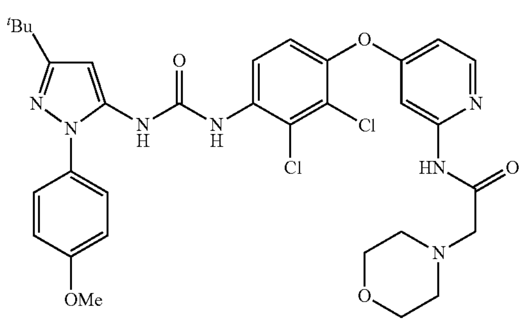 [SMILES: COc1ccc(-n2nc(C(C)(C)C)cc2NC(=O)Nc2ccc(Oc3ccnc(NC(=O)CN4CCOCC4)c3)c(Cl)c2Cl)cc1] | N-(4-(4-(3-(3-tert-butyl-1-(4-methoxyphenyl)-1H-pyrazol-5-yl)ureido)-2,3-dichlorophenoxy)pyridin-2-yl)-2-morpholinoacetamide. R$^t$ 2.03 min; m/z 668 (M + H)$^+$ (ES$^+$), Method 2; $^1$H NMR δ: 1.27 (9H, s), 2.48 (4H, m), 3.15 (2H, s), 3.60 (4H, m), 3.82 (3H, s), 6.38 (1H, s), 6.70 (1H, dd), 7.10 (2H, m), 7.39 (1H, d), 7.44 (2H, m), 7.62 (1H, d), 8.19 (1H, d), 8.21 (1H, d), 8.86 (1H, s), 9.16 (1H, s), 10.07 (1H, s). |

TABLE 2-continued

Additional Compound Examples of the Invention

| Ex. No. | Structure | Name and Analytical Data |
|---|---|---|
| 46 | 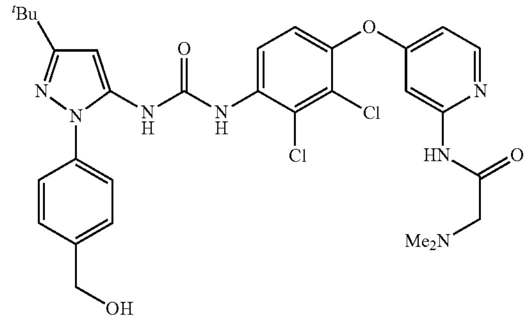 [SMILES: CN(C)CC(=O)Nc1cc(Oc2ccc(NC(=O)Nc3cc(C(C)(C)C)nn3-c3ccc(CO)cc3)c(Cl)c2Cl)ccn1] | N-(4-(4-(3-(3-tert-butyl-1-(4-hydroxymethyl phenyl)-1H-pyrazol-5-yl)ureido)-2,3-dichloro phenoxy)pyridin-2-yl)-2-(dimethylamino) acetamide. R$^t$ 1.55 min; m/z 626/628 (M + H)$^+$ (ES$^+$), Method 2; $^1$H NMR δ: 1.28 (9H, s), 2.27 (6H, s), 3.08 (2H, s), 4.57 (2H, s), 5.31 (1H, br s), 6.40 (1H, s), 6.69 (1H, dd), 7.38 (1H, d), 7.48 (4H, s), 7.62 (1H, d), 8.18 (1H, d), 8.21 (1H, d), 8.87 (1H, br s), 9.24 (1H, br s), 9.95 (1H, br s). |
| 47 | 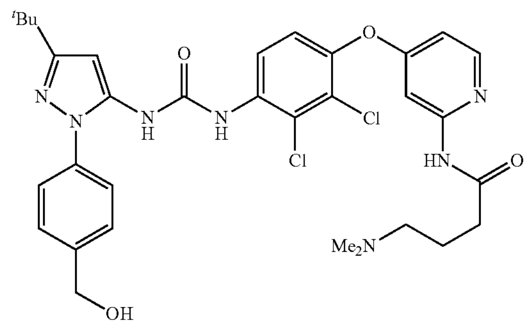 [SMILES: CN(C)CCCC(=O)Nc1cc(Oc2ccc(NC(=O)Nc3cc(C(C)(C)C)nn3-c3ccc(CO)cc3)c(Cl)c2Cl)ccn1] | N-(4-(4-(3-(3-tert-butyl-1-(4-hydroxymethyl phenyl)-1H-pyrazol-5-yl)ureido)-2,3-dichloro phenoxy)pyridin-2-yl)-4-(dimethylamino) butanamide. R$^t$ 1.64 min; m/z 654 (M + H)$^+$ (ES$^+$), Method 2; $^1$H NMR δ: 1.30 (9H, s), 1.69 (2H, tt), 2.13 (6H, s), 2.23 (2H, t), 2.38 (2H, t), 4.58 (2H, s), 5.08 (1H, br s), 6.37 (1H, s), 6.63 (1H, dd), 7.32 (1H, d), 7.46-7.51 (4H, overlapping m), 7.64 (1H, d), 8.13 (1H, d), 8.19 (1H, d), 8.69 (1H, br s), 9.05 (1H, br s), 10.34 (1H, br s) |
| 48 | 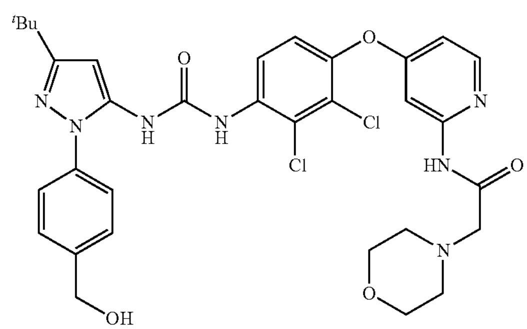 [SMILES: CC(C)(C)c1cc(NC(=O)Nc2ccc(Oc3ccnc(NC(=O)CN4CCOCC4)c3)c(Cl)c2Cl)n(-c2ccc(CO)cc2)n1] | N-(4-(4-(3-(3-tert-butyl-1-(4-hydroxymethyl phenyl)-1H-pyrazol-5-yl)ureido)-2,3-dichloro phenoxy)pyridin-2-yl)-2-morpholino acetamide. R$^t$ 1.80 min; m/z 668 (M + H)$^+$ (ES$^+$), Method 2; $^1$H NMR δ: 1.28 (9H, s), 2.48 (4H, m), 3.15 (2H, s), 3.60 (4H, m), 4.58 (2H, d), 5.33 (1H, t), 6.40 (1H, s), 6.70 (1H, dd), 7.39 (1H, d), 7.48 (4H, s), 7.62 (1H, d), 8.19 (1H, d), 8.22 (1H, d), 8.88 (1H, s), 9.25 (1H, s), 10.07 (1H. s). |
| 49 | 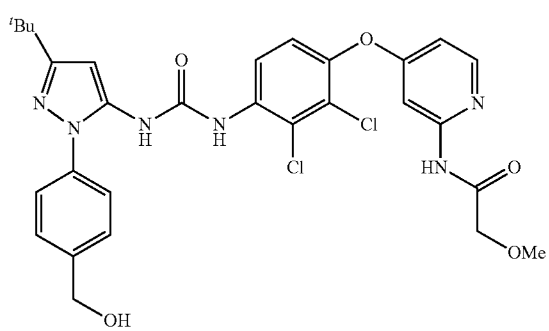 [SMILES: COCC(=O)Nc1cc(Oc2ccc(NC(=O)Nc3cc(C(C)(C)C)nn3-c3ccc(CO)cc3)c(Cl)c2Cl)ccn1] | N-(4-(4-(3-(3-tert-butyl-1-(4-hydroxymethyl phenyl)-1H-pyrazol-5-yl)ureido)-2,3-dichloro phenoxy)pyridin-2-yl)-2-methoxyacetamide. R$^t$ 2.33 min; m/z 611/613 (M + H)$^+$ (ES$^+$), Method 2; $^1$H NMR δ: 1.28 (9H, s), 3.32 (3H, s), 4.02 (2H, s), 4.58 (2H, d), 5.31 (1H, t), 6.40 (1H, s), 6.70 (1H, dd), 7.39 (1H, d), 7.48 (4H, s), 7.60 (1H, dd), 8.18 (1H, d), 8.21 (1H, d), 8.87 (1H, s), 9.23 (1H, s), 10.10 (1H, s). |

TABLE 2-continued

Additional Compound Examples of the Invention

| Ex. No. | Structure | Name and Analytical Data |
|---|---|---|
| 50 | 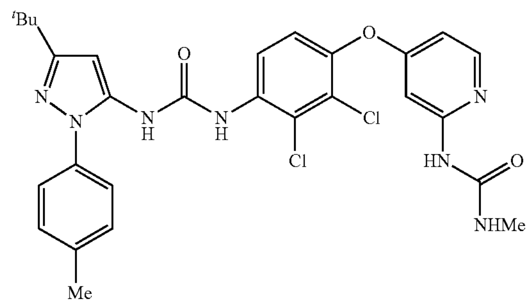 | 1-(3-tert-butyl-1-p-tolyl-1H-pyrazol-5-yl)-3-(2,3-dichloro-4-(2-(3-methylureido)pyridin-4-yloxy)phenyl)urea. $R^t$ 5.53 min; m/z 582/584 $(M + H)^+$ $(ES^+)$, Method 1 (basic); $^1$H NMR δ: 1.28 (9H, s), 2.38 (3H, s), 2.68 (3H, d), 6.39 (1H, s), 5.56 (1H, dd), 6.85 (1H, br d), 7.35-7.42 (5H, overlapping m), 7.85 (1H, br s), 8.06 (1H, d) 8.17 (1H, d), 8.87 (1H, br s), 9.16 (1H, br s), 9.21 (1H, br s). |
| 51 | 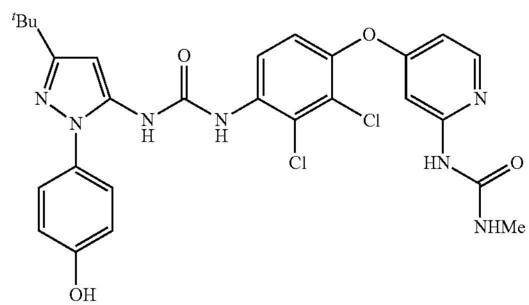 [SMILES: CNC(=O)Nc1cc(Oc2ccc(NC(=O)Nc3cc(C(C)(C)C)nn3-c3ccc(O)cc3)c(Cl)c2Cl)ccn1] | 1-(3-tert-butyl-1-(4-hydroxyphenyl)-1H-pyrazol-5-yl)-3-(2,3-dichloro-4-(2-(3-methyl ureido)pyridin-4-yloxy)phenyl)urea. $R^t$ 4.87 min; m/z 584/586 $(M + H)^+$ $(ES^+)$, Method 1 basic; $^1$H NMR δ: 1.26 (9H, s), 2.68 (3H, d), 6.35 (1H, s), 6.55 (1H, dd), 6.85 (1H, d), 6.89-6.92 (2H, overlapping m), 7.27-7.29 (2H, overlapping m), 7.36 (1H, d), 7.86 (1H, br s), 8.08 (1H, d), 8.16 (1H d), 8.88 (1H, br s), 9.10 (1H, br s), 9.16 (1H, br s), 9.80 (1H, br s). |
| 52 | 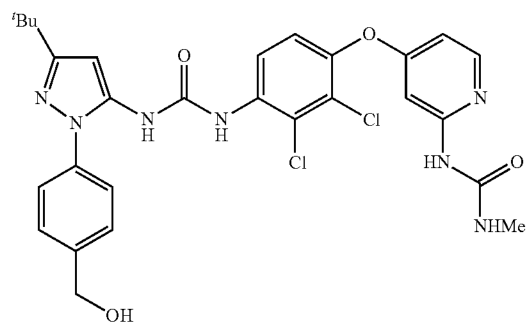 [SMILES: CNC(=O)Nc1cc(Oc2ccc(NC(=O)Nc3cc(C(C)(C)C)nn3-c3ccc(CO)cc3)c(Cl)c2Cl)ccn1] | 1-(3-tert-butyl-1-(4-hydroxymethylphenyl)-1H-pyrazol-5-yl)-3-(2,3-dichloro-4-(2-(3-methyl ureido)pyridin-4-yloxy)phenyl)urea. $R^t$ 2.07 IR min; m/z 598 $(M + H)^+$ $(ES^+)$, Method 2; $^1$H NMR δ: 1.28 (1H, s), 2.67 (3H, d), 4.57 (2H, d), 5.31 (1H, t), 6.39(1H, s), 6.54 (m, 1H), 6.85 (1H, s), 7.36 (1H, d), 7.47 (4H, s), 7.85 (1H, br s), 8.08 (1H, d), 8.18 (1H, d), 8.87 (1H, s), 9.15 (1H, s), 9.23 (1H, s). |
| 53 | 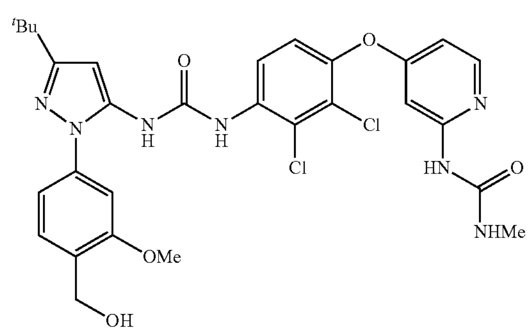 [SMILES: CNC(=O)Nc1cc(Oc2ccc(NC(=O)Nc3cc(C(C)(C)C)nn3-c3ccc(CO)c(OC)c3)c(Cl)c2Cl)ccn1] | 1-(3-tert-butyl-1-(4-hydroxymethyl-3-methoxy phenyl)-1H-pyrazol-5-yl)-3-(2,3-dichloro-4-(2-(3-methylureido)pyridin-4-yloxy)phenyl)urea. $R^t$ 1.97 min; m/z 628/630 $(M + H)^+$ $(ES^+)$, Method 1 (basic); $^1$H NMR δ: 1.28 (9H, s), 2.68 (3H, d), 3.83 (3H, s), 4.54 (2H, s), 6.41 (1H, s), 6.57 (1H, d), 6.84 (1H, d), 7.07-7.12 (2H, overlapping m), 7.37 (1H, d), 7.51 (1H, d), 7.83 (1H, br s), 8.09 (1H, d), 8.17 (1H, d), 8.92 (1H, s), 9.21 (1H, br s), 9.24 (1H, s). |

TABLE 2-continued

Additional Compound Examples of the Invention

| Ex. No. | Structure | Name and Analytical Data |
|---|---|---|
| 54 | 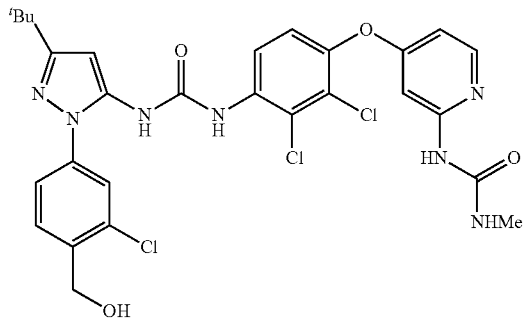 [SMILES: CNC(=O)Nc1cc(Oc2ccc(NC(=O)Nc3cc(C(C)(C)C)nn3-c3ccc(CO)c(Cl)c3)c(Cl)c2Cl)ccn1] | 1-(3-tert-butyl-1-(3-chloro-4-hydroxymethyl phenyl)-1H-pyrazol-5-yl)-3-(2,3-dichloro-4-(2-(3-methylureido)pyridin-4-yloxy) phenyl)urea. R$^t$ 2.27 min; m/z 632/634 (M + H)$^+$ (ES$^+$), Method 2; $^1$H NMR δ: 1.28 (9H, s), 2.69 (3H, d), 6.61 (2H, s), 6.40 (1H, s), 6.76 (2H, br s), 7.43 (1H, d), 7.55 (1H, dd), 7.60 (1H, d), 7.62-7.70 (2H, overlapping m), 8.12-8.16 (2H, overlapping m), 8.93 (1H, s), 9.35 (1H, s), 9.85 (1H, br s). |
| 55 | 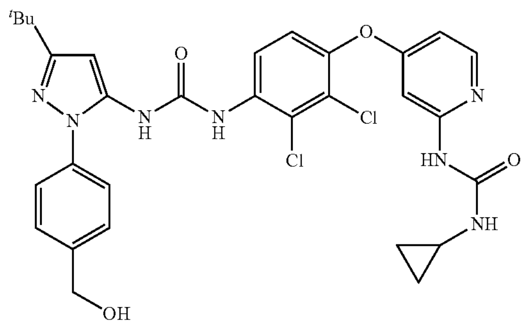 [SMILES: CC(C)(C)c1cc(NC(=O)Nc2ccc(Oc3ccnc(NC(=O)NC4CC4)c3)c(Cl)c2Cl)n(-c2ccc(CO)cc2)n1] | 1-(4-(4-(3-(3-tert-butyl-1-(4-hydroxymethyl phenyl)-1H-pyrazol-5-yl)ureido)-2,3-dichloro phenoxy)pyridin-2-yl)-3-cyclopropylurea. R$^t$ 2.20 min; m/z 624 (M + H)$^+$ (ES$^+$), Method 2; $^1$H NMR δ: 0.40 (2H, m), 0.63 (2H, m), 1.28 (9H, s), 2.51 (1H, m), 4.57 (2H, s), 5.33 (1H, s), 6.40 (1H, s), 6.56 (1H, dd), 6.94 (1H, s), 6.36 (1H, d), 7.48 (4H, s), 7.88 (1H, s), 8.07 (1H, s), 8.18 (1H, d), 8.87 (1H, br s), 9.02 (1H, br s), 9.24 (1H, br s). |
| 56 | 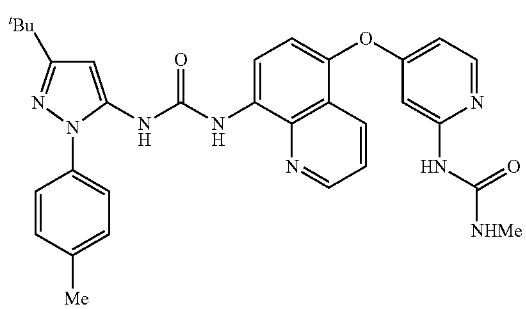 | 1-(3-tert-butyl-1-p-tolyl-1H-pyrazol-5-yl)-3-(5-(2-(3-methylureido)pyridin-4-yloxy)quinolin-8-yl)urea. R$^t$ 5.47 min; m/z 565 (M + H)$^+$ (ES$^+$), Method 1 (Basic); $^1$H NMR δ: 1.30 (9H, s), 2.38 (3H, s), 2.66 (3H, d), 6.42 (1H, s), 6.60 (1H, dd), 6.85 (1H, d), 7.34 (2H, m), 7.39-7.44 (3H, overlapping m), 7.65 (1H, dd), 7.89 (1H, br s), 8.06 (1H, d), 8.23 (1H, dd), 8.57 (1H, d), 8.95 (1H, dd), 9.07 (1H, s), 9.56 (1H, s), (10.0 (1H, s). |
| 57 | 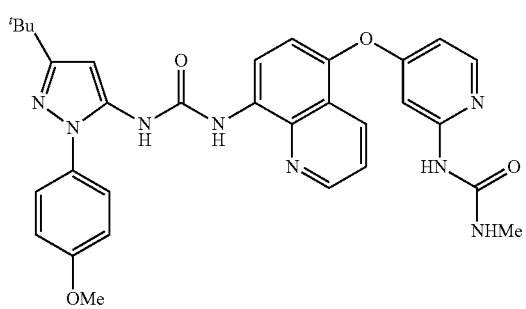 [SMILES: CNC(=O)Nc1cc(Oc2ccc(NC(=O)Nc3cc(C(C)(C)C)nn3-c3ccc(OC)cc3)c3ncccc23)ccn1] | 1-(3-tert-butyl-1-(4-methoxyphenyl)-1H-pyrazol-5-yl)-3-(5-(2-(3-methylureido) pyridin-4-yloxy)quinolin-8-yl)urea. R$^t$ 5.35 min; m/z 581 (M + H)$^+$ (ES$^+$), Method 1 (Basic); $^1$H NMR δ: 1.29 (9H, s), 2.65 (3H, d), 3.82 (3H, s), 6.41 (1H, s), 6.60 (1H, dd), 6.85 (1H, d), 7.09 (2H, m), 7.39-7.46 (3H, overlapping m), 7.65 (1H, dd), 7.88 (1H, br s), 8.07 (1H, d), 8.23 (1H, dd), 8.58 (1H, d), 8.95 (1H, dd), 9.07 (1H, s), 9.51 (1H, s), 9.99 (1H, s). |

TABLE 2-continued

Additional Compound Examples of the Invention

| Ex. No. | Structure | Name and Analytical Data |
|---|---|---|
| 58 | 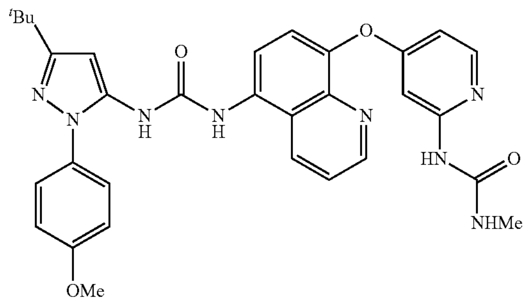 [SMILES: CNC(=O)Nc1cc(Oc2ccc(NC(=O)Nc3cc(C(C)(C)C)nn3-c3ccc(OC)cc3)c3cccnc23)ccn1] | 1-(3-tert-butyl-1-(4-methoxyphenyl)-1H-pyrazol-5-yl)-3-(8-(2-(3-methylureido)pyridin-4-yloxy)quinolin-5-yl)urea. $R^t$ 4.74 min; m/z 581 (M + H)$^+$ (ES$^+$), Method 1 (Basic); $^1$H NMR δ: 1.27 (9H, s), 2.65 (3H, d), 3.83 (3H, s), 6.39 (1H, s), 6.45 (1H, dd), 6.71 (1H, s), 7.10 (2H, m), 7.48 (2H, m), 7.58-7.64 (2H, overlapping m), 7.98-8.05 (3H, overlapping m), 8.43 (1H, dd), 8.72 (1H, d), 8.84 (1H, dd), 9.03 (1H, s), 9.25 (1H, s). |
| 59 | 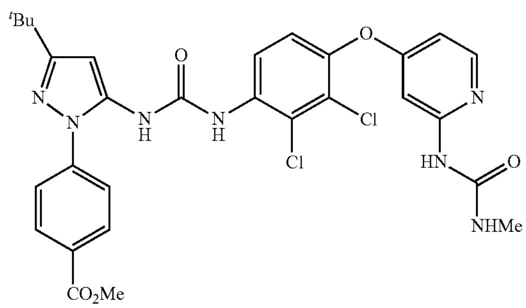 [SMILES: CNC(=O)Nc1cc(Oc2ccc(NC(=O)Nc3cc(C(C)(C)C)nn3-c3ccc(C(=O)OC)cc3)c(Cl)c2Cl)ccn1] | methyl 4-(3-tert-butyl-5-(3-(2,3-dichloro-4-(2-(3-methylureido) pyridin-4-yloxy)phenyl)ureido)-1H-pyrazol-1-yl)benzoate. $R^t$ 5.49 min; m/z 626/628 (M + H)$^+$ (ES$^+$), Method 1 (Basic); $^1$H NMR δ: 1.29 (9H, s), 2.68 (3H, d), 3.88 (3H, s), 6.45 (1H, 5), 6.56 (1H, dd), 6.85 (1H, d), 7.36 (1H, d), 7.75 (2H, m), 7.82 (1H, br s), 8.07-8.14 (4H, overlapping m), 8.84 (1H, 5), 9.18 (1H, br s), 9.36 (1H, s). |
| 60 | 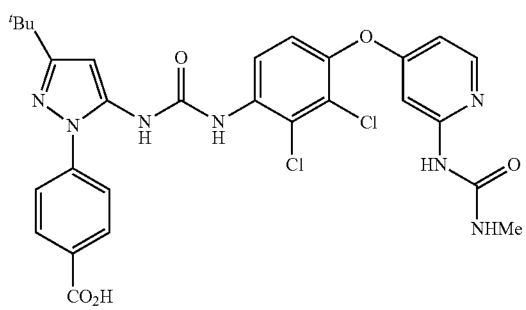 [SMILES: CNC(=O)Nc1cc(Oc2ccc(NC(=O)Nc3cc(C(C)(C)C)nn3-c3ccc(C(=O)O)cc3)c(Cl)c2Cl)ccn1] | 4-(3-tert-butyl-5-(3-(2,3-dichloro-4-(2-(3-methylureido)pyridin-4-yloxy)phenyl)ureido)-1H-pyrazol-1-yl)benzoic acid. $R^t$ 3.95 min; m/z 612/614 (M + H)$^+$ (ES$^+$), Method 1 (Basic); $^1$H NMR δ: 1.29 (9H, 5), 2.68 (3H, d), 6.43 (1H, 5), 6.55 (1H, dd), 6.84 (1H, d), 7.36 (1H, d), 7.62 (2H, m), 7.89 (1H, br s), 8.01 (2H, m), 8.07 (1H, d), 8.16 (1H, d), 9.16 (1H, s), 9.3 (1H, br 5), 9.7 (1H, br s). |
| 61 | 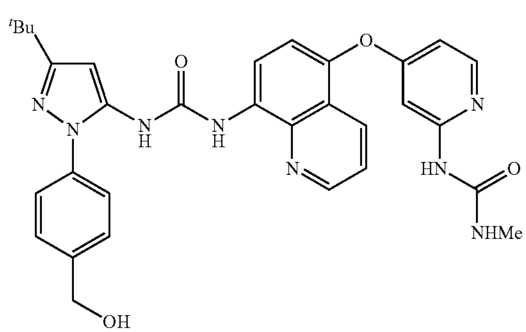 [SMILES: CNC(=O)Nc1cc(Oc2ccc(NC(=O)Nc3cc(C(C)(C)C)nn3-c3ccc(CO)cc3)c3ncccc23)ccn1] | 1-(4-(8-(3-(3-tert-butyl-1-(4-hydroxymethyl phenyl)-1H-pyrazol-5-yl)ureido)quinolin-5-yloxy)pyridin-2-yl)-3-methylurea. $R^t$ 5.10 min; m/z 581 (M + H)$^+$ (ES$^+$), Method 1 (Basic); $^1$H NMR δ: 1.30 (9H, s), 2.65 (3H, d), 4.57 (2H, d), 5.32 (1H, t), 6.43 (1H, s), 6.60 (1H, dd), 6.84 (1H, d), 7.41 (1H, d), 7.45-7.51 (4H, overlapping m), 7.65 (1H, dd), 7.90 (1H, br s), 8.07 (1H, d), 8.23 (1H, dd), 8.57 (1H, d), 8.95 (1H, dd), 9.08 (1H, s), 9.60 (1H, s), 10.02 (1H, s). |

TABLE 2-continued

Additional Compound Examples of the Invention

| Ex. No. | Structure | Name and Analytical Data |
|---|---|---|
| 62 | 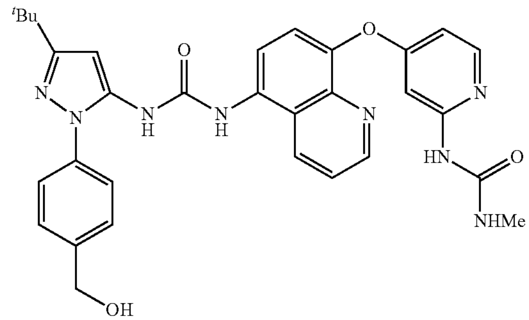 [SMILES: CNC(=O)Nc1cc(Oc2ccc(NC(=O)Nc3cc(C(C)(C)C)nn3-c3ccc(CO)cc3)c3cccnc23)ccn1] | 1-(4-(5-(3-3-tert-butyl-1-(4-hydroxymethyl phenyl)-1H-pyrazol-5-yl)ureido)quinolin-8-yloxy)pyridin-2-yl)-3-methylurea. R$^t$ 4.59 min; m/z 581 (M + H)$^+$ (ES$^+$), Method 1 (Basic); $^1$H NMR δ: 1.29 (9H, s), 2.66 (3H, d), 4.59 (2H, d), 5.34 (1H, t), 6.42 (1H, s), 6.45 (1H, dd), 6.71 (1H, d), 7.49-7.55 (4H, overlapping m), 7.59 (1H, d), 7.64 (1H, dd), 7.98-8.05 (3H, overlapping m), 8.44 (1H, dd), 8.79 (1H, s), 8.85 (1H, dd), 9.03 (1H, s), 9.26 (1H, s). |
| 63 | 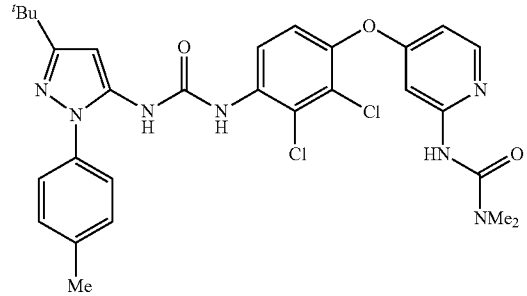 | 3-(4-(4-(3-(3-tert-butyl)-1-p-tolyl-1H-pyrazol-5-yl)ureido)-2,3-dichlorophenoxy)pyridin-2-yl)-1,1-dimethylurea. R$^t$ 5.24 min; m/z 596/598 (M + H)$^+$ (ES$^+$), Method 1 (basic); $^1$H NMR δ: 1.27 (9H, s), 2.37 (3H, s), 2.88 (6H, s), 6.38 (1H, s), 6.57 (1H, dd), 7.33-7.42 (6H, overlapping m), 8.12 (1H, d), 8.15 (1H, d), 8.84 (1H, br s), 8.93 (1H, br s), 9.19 (1H, br s). |
| 64 | 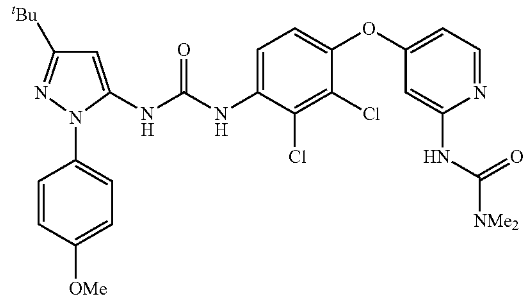 [SMILES: COc1ccc(-n2nc(C(C)(C)C)cc2NC(=O)Nc2ccc(Oc3ccnc(NC(=O)N(C)C)c3)c(Cl)c2Cl)cc1] | 3-(4-(4-(3-(3-tert-butyl-1-(4-methoxyphenyl)-1H-pyrazol-5-yl)ureido)-2,3-dichlorophenoxy)pyridin-2-yl)-1,1-dimethylurea. R$^t$ 5.34 min; m/z 612/614 (M + H)$^+$ (ES$^+$), Method 1 (basic); $^1$H NMR δ: 1.27 (9H, s), 2.89 (6H, s), 3.82 (3H, s), 6.37 (1H, s), 6.58 (1H, dd), 7.10 (2H, m), 7.34 (1H, s), 7.36 (1H, d), 2.43 (2H, m), 8.12 (1H, d), 8.16 (1H, d), 8.84 (1H, br s), 8.94 (1H, br s), 9.16 (1H, br s) |
| 65 | 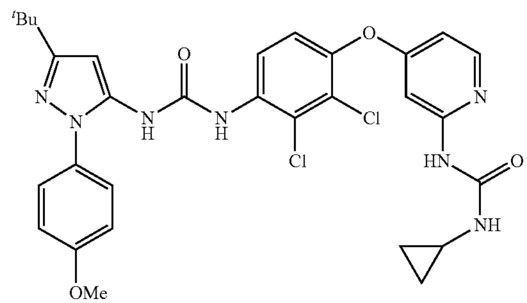 [SMILES: COc1ccc(-n2nc(C(C)(C)C)cc2NC(=O)Nc2ccc(Oc3ccnc(NC(=O)NC4CC4)c3)c(Cl)c2Cl)cc1] | 1-(4-(4-(3-(3-tert-butyl-1-(4-methoxyphenyl)-1H-pyrazol-5-yl)ureido)-2,3-dichlorophenoxy)pyridin-2-yl)-3-cyclopropylurea. R$^t$ 5.64 min; m/z 624/626 (M + H)$^+$ (ES$^+$), Method 1 (Basic); $^1$H NMR δ: 0.40 (2H, m), 0.63 (2H, m), 1.27 (9H, s), 2.55 (1H, m), 3.82 (3H, s), 6.37 (1H, s), 6.55 (1H, dd), 6.95 (1H, s), 7.09 (2H, m), 7.36 (1H, d), 7.43 (2H, m), 7.87 (1H, br s), 8.07 (1H, d), 8.17 (1H, d), 8.85 (1H, s), 9.01 (1H, s), 9.16 (1H, s). |
| 66 | 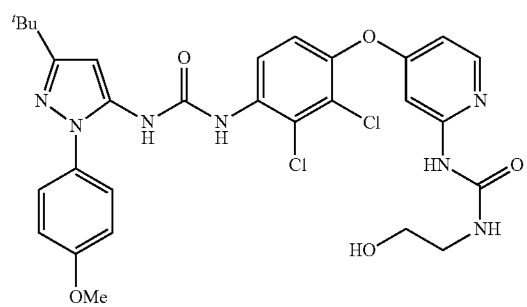 [SMILES: COc1ccc(-n2nc(C(C)(C)C)cc2NC(=O)Nc2ccc(Oc3ccnc(NC(=O)NCCO)c3)c(Cl)c2Cl)cc1] | 1-(4-(4-(3-(3-tert-butyl-1-(4-methoxyphenyl)-1H-pyrazol-5-yl)ureido)-2,3-dichlorophenoxy)pyridin-2-yl)-3-(2-hydroxyethyl)urea. R$^t$ 5.18 min; m/z 628/630 (M + H)$^+$ (ES$^+$), Method 1 (Basic); $^1$H NMR δ: 1.27 (9H, s), 3.18 (2H, dt), 3.43 (2H, dt), 3.82 (3H, s), 4.73 (1H, t), 6.37 (1H, s), 6.54 (1H, dd), 6.92 (1H, d), 7.10 (2H, m), 7.36 (1H, d), 7.43 (2H, m), 7.98 (1H, br s), 8.08 (1H, d), 8.16 (1H, d), 8.85 (1H, br s), 9.14 (1H, s), 9.15 (1H, br s). |

TABLE 2-continued

Additional Compound Examples of the Invention

| Ex. No. | Structure | Name and Analytical Data |
|---|---|---|
| 67 | 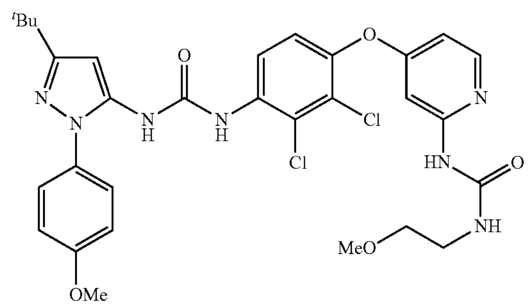 [SMILES: COCCNC(=O)Nc1cc(Oc2ccc(NC(=O)Nc3cc(C(C)(C)C)nn3-c3ccc(OC)cc3)c(Cl)c2Cl)ccn1] | 1-(4-(4-(3-(3-tert-butyl-1-(4-methoxyphenyl)-1H-pyrazol-5-yl)ureido)-2,3-dichlorophenoxy)pyridin-2-yl)-3-(2-methoxyethyl)urea. $R^t$ 5.17 min; m/z 626/628 (M + H)$^+$ (ES$^+$), Method 1 (Basic); $^1$H NMR δ: 1.27 (9H, s), 3.24-3.30 (5H, overlapping m), 3.37 (2H, t), 3.82 (3H, s), 6.37 (1H, s), 6.55 (1H, dd), 6.92 (1H, d), 7.10 (2H, m), 7.36 (1H, d), 7.42 (2H, m), 7.97 (1H, br s), 8.08 (1H, d), 8.17 (1H, d), 8.85 (1H, s), 9.15 (1H, s), 9.16 (1H, s). |
| 68 | 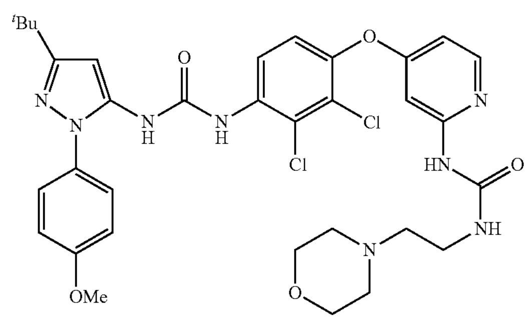 [SMILES: COc1ccc(-n2nc(C(C)(C)C)cc2NC(=O)Nc2ccc(Oc3ccnc(NC(=O)NCCN4CCOCC4)c3)c(Cl)c2Cl)cc1] | 1-(4-(4-(3-(3-tert-butyl-1-(4-methoxyphenyl)-1H-pyrazol-5-yl)ureido)-2,3-dichlorophenoxy)pyridin-2-yl)-3-(2-morpholinoethyl)urea. $R^t$ 5.43 min; m/z 697/699 (M + H)$^+$ (ES$^+$), Method 1 (Basic); $^1$H NMR δ: 1.27 (9H, s), 2.34-2.38 (6H, overlapping m), 3.23 (2H, td), 3.58 (4H, t), 3.82 (3H, s), 6.37 (1H, s), 6.55 (1H, dd), 6.86 (1H, br s), 7.90 (2H, m), 7.36 (1H, d), 7.43 (2H, m), 8.09 (1H, d), 8.06-8.12 (2H, overlapping m), 8.86 (1H, br s), 9.16 (1H, br s), 9.20 (1H, br s). |
| 69 | 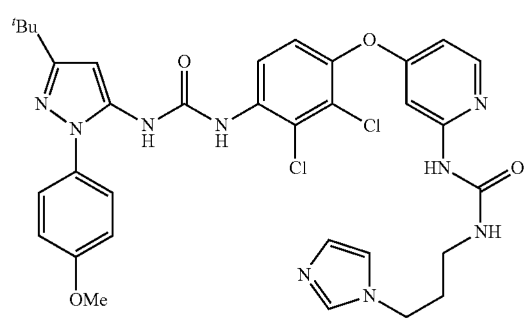 [SMILES: COc1ccc(-n2nc(C(C)(C)C)cc2NC(=O)Nc2ccc(Oc3ccnc(NC(=O)NCCCn4ccnc4)c3)c(Cl)c2Cl)cc1] | 1-(3-(1H-imidazol-1-yl)propyl)-3-(4-(4-(3-(3-tert-butyl-1-(4-methoxyphenyl)-1H-pyrazol-5-yl)ureido)-2,3-dichlorophenoxy)pyridin-2-yl)urea. $R^t$ 5.80 min; m/z 692/694 (M + H)$^+$ (ES$^+$), Method 1 (Basic); $^1$H NMR δ: 1.27 (9H, s), 1.88 (2H, overlapping tt), 3.09 (2H, overlapping dq), 3.82 (3H, s), 3.98 (2H, t), 6.37 (1H, s), 6.55 (1H, dd), 6.88 (2H, s), 7.10 (2H, m), 7.18 (1H s), 7.36 (1H, d), 7.43 (2H, m), 7.63 (1H, s), 8.03 (1H, br s), 8.10 (1H, d), 8.17 (1H, d), 8.85 (1H, s), 9.14 (1H, s), 9.15 (1H, s) |
| 70 | 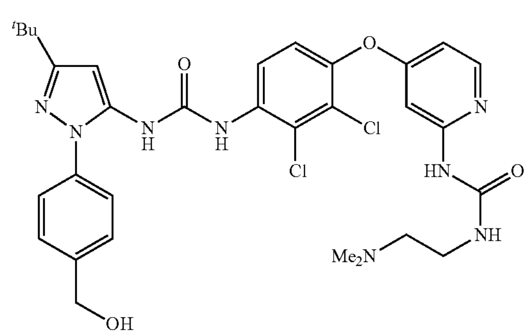 [SMILES: CN(C)CCNC(=O)Nc1cc(Oc2ccc(NC(=O)Nc3cc(C(C)(C)C)nn3-c3ccc(CO)cc3)c(Cl)c2Cl)ccn1] | 1-(3-tert-butyl-1-(4-hydroxymethylphenyl)-1H-pyrazol-5-yl)-3-(2,3-dichloro-4-(2-(3-(2-(dimethylamino)ethyl)ureido)pyridin-4-yloxy)phenyl)urea. $R^t$ 5.40 min; m/z 655 (M + H)$^+$ (ES$^+$), Method 1 (Basic); $^1$H NMR δ: 1.28 (9H, s), 2.18 (6H, s), 2.34 (2H, t), 3.21 (2H, td), 4.58 (2H, d), 5.31 (1H, t), 6.39 (1H, s), 6.54 (1H, dd), 6.94 (1H, d), 7.36 (1H, d), 7.45-7.52 (4H, overlapping m), 7.85 (1H, br s), 8.07 (1H, d), 8.16 (1H, d), 8.86 (1H, br s), 9.15 (1H, br s), 9.22 (1H, br s). |

TABLE 2-continued

Additional Compound Examples of the Invention

| Ex. No. | Structure | Name and Analytical Data |
|---|---|---|
| 71 | 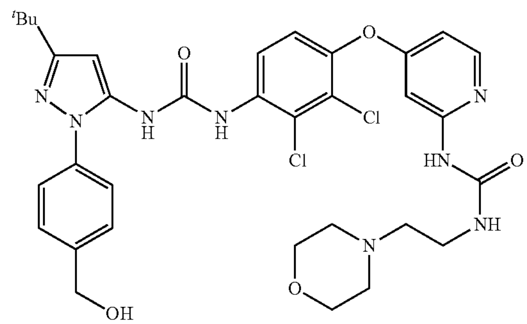 [SMILES: CC(C)(C)c1cc(NC(=O)Nc2ccc(Oc3ccnc(NC(=O)NCCN4CCOCC4)c3)c(Cl)c2Cl)n(-c2ccc(CO)cc2)n1] | 1-(4-(4-(3-(3-tert-butyl-1-(4-hydroxymethyl phenyl)-1H-pyrazol-5-yl)ureido)-2,3-dichloro phenoxy)pyridin-2-yl)-3-(2-morpholinoethyl) urea. $R^r$ 1.55 min; m/z 697/699 $(M + H)^+$ $(ES^+)$, Method 2; $^1$H NMR δ: 1.28 (9H, s), 2.36-2.41 (6H, overlapping m ), 3.24 (2H, dt), 3.58 (4H, t), 4.58 (2H, d), 5.32 (1H, t), 6.39 (1H, s), 6.54 (1H, dd), 6.86 (1H, br s), 7.36 (1H, d), 7.48 (4H, s), 8.06-8.12 (2H, overlapping m), 8.17 (1H, d), 8.87 (1H, s), 9.20 (1H, br s), 9.23 (1H, s). |
| 72 | 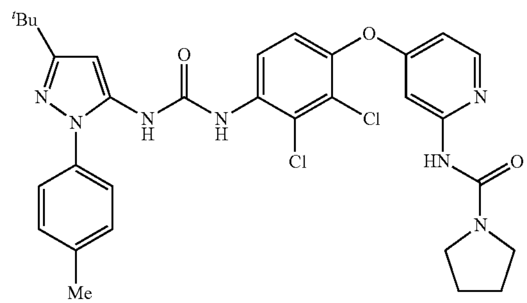 [SMILES: Cc1ccc(-n2nc(C(C)(C)C)cc2NC(=O)Nc2ccc(Oc3ccnc(NC(=O)N4CCCC4)c3)c(Cl)c2Cl)cc1] | N-(4-(4-(3-(3-tert-butyl-1-p-tolyl-1H-pyrazol-5-yl)ureido)-2,3-dichlorophenoxy)pyridin-2-yl) pyrrolidine-1-carboxamide. $R^r$ 5.60 min; m/z 622/624 $(M + H)^+$ $(ES^+)$, Method 1 (basic); $^1$H NMR δ: 1.27 (9H, s), 1.81 (4H, m), 2.38 (3H, s), 3.34 (4H, m), 6.39 (1H, s), 6.59 (1H, dd), 7.35-7.43 (6H, overlapping m), 8.12 (1H, d), 8.17 (1H, d), 8.76 (1H, br s), 8.87 (1H, br s), 9.22 (1H, br s). |
| 73 | 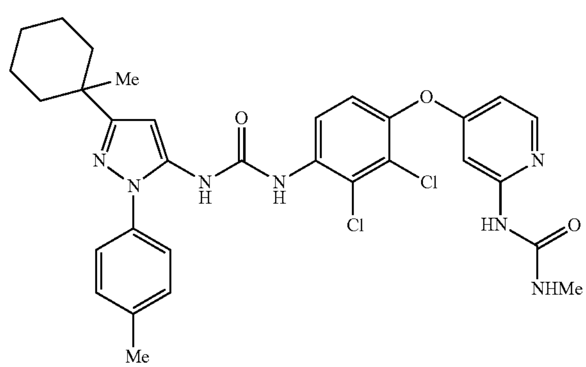 [SMILES: CNC(=O)Nc1cc(Oc2ccc(NC(=O)Nc3cc(C4(C)CCCCC4)nn3-c3ccc(C)cc3)c(Cl)c2Cl)ccn1] | 1-(3-(1-methylcyclohexyl)-1-p-tolyl-1H-pyrazol-5-yl)-3-(2,3-dichloro-4-(2-(3-methyl ureido)pyridin-4-yloxy)phenyl)urea. $R^r$ 5.77 min; m/z 622/624 $(M + H)^+$ $(ES^+)$, Method 1 basic; $^1$H NMR δ:1.17 (3H, s), 1.30-1.55 (8H, overlaping m), 1.93-2.05 (2H, overlapping m), 2.38 (3H, s), 2.68 (3H, d), 6.36 (1H, s), 6.61 (1H, br. s), 6.82 (1H, br. s), 7.34-7.43 (5H, overlapping m), 7.78 (1H, br. s), 8.10 (1H, d), 8.18 (1H, d), 8.88 (1H, s), 9.24 (1H, s), 9.35 (1H, b. s). |
| 74 | 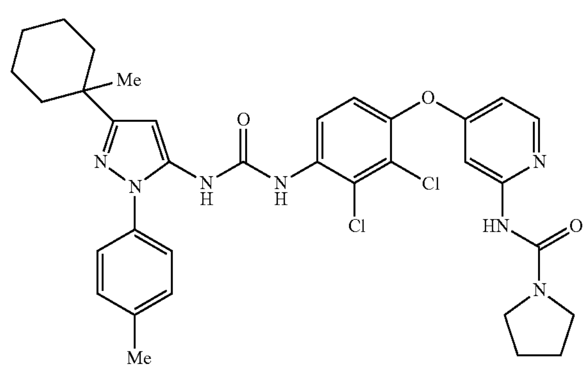 [SMILES: Cc1ccc(-n2nc(C3(C)CCCCC3)cc2NC(=O)Nc2ccc(Oc3ccnc(NC(=O)N4CCCC4)c3)c(Cl)c2Cl)cc1] | N-(4-(2,3-dichloro-4-(3-(3-(1-methyl cyclohexyl)-1-p-tolyl-1H-pyrazol-5-yl) ureido)phenoxy)pyridin-2-yl)pyrrolidine-1-carboxamide. $R^r$ 5.84 min; m/z 662/664; $(M + H)^+$ $(ES^+)$, Method 1, basic; $^1$H NMR δ: 1.18 (3H, s), 1.32-1.55 (8H, overlapping m), 1.85 (4H, br. s), 1.94-2.02 (2H, overlapping m), 2.38 (3H, s), 3.45 (4H, br. s), 6.36 (1H, s), 6.98 (1H, br. s), 7.11 (1H, br. s), 7.35 (2H, d), 7.44 (2H, d), 7.47 (1H, d), 8.22-8.25 (2H, overlapping m), 8.96 (1H, s), 9.31 (1H, s), 9.74 (1H, br. s). |

TABLE 2-continued

Additional Compound Examples of the Invention

| Ex. No. | Structure | Name and Analytical Data |
|---|---|---|
| 75 | 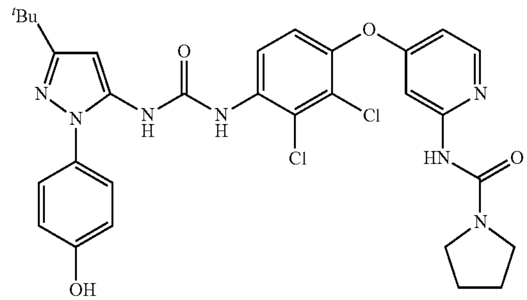 [SMILES: CC(C)(C)c1cc(NC(=O)Nc2ccc(Oc3ccnc(NC(=O)N4CCCC4)c3)c(Cl)c2Cl)n(-c2ccc(O)cc2)n1] | N-(4-(4-(3-(3-tert-butyl-1-(4-hydroxyphenyl)-1H-pyrazol-5-yl)ureido)-2,3-dichlorophenoxy) pyridin-2-yl)pyrrolidine-1-carboxamide. $R^t$ 4.93 min; m/z 624/626 (M + H)$^+$ (ES$^+$), Method 1 (basic); $^1$H NMR δ: 1.26 (9H, s), 1.80 (4H, m), 3.34 (4H, m), 6.35 (1H, s), 6.58 (1H, dd), 6.90 (2H, m), 7.29 (2H, m), 7.36 (1H, d), 7.43 (1H, d), 8.12 (1H, d), 8.17 (1H, d), 8.75 (1H, s), 8.88 (1H, s), 9.11 (1H, s), 9.80 (1H, s). |
| 76 | 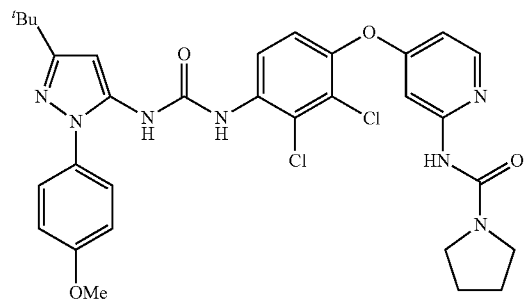 [SMILES: COc1ccc(-n2nc(C(C)(C)C)cc2NC(=O)Nc2ccc(Oc3ccnc(NC(=O)N4CCCC4)c3)c(Cl)c2Cl)cc1] | N-(4-(4-(3-(3-(tert-butyl)-1-(4-methoxyphenyl)-1H-pyrazol-5-yl)ureido)-2,3-dichlorophenoxy) pyridin-2-yl)pyrrolidine-1-carboxamide. $R^t$ 5.50 min; m/z 638/640 (M + H)$^+$ (ES$^+$), Method 1 (basic); $^1$H NMR δ: 1.27 (9H, s), 1.80 (4H, m), 3.34 (4H, m), 3.82 (3H, s), 6.37 (1H, s), 6.59 (1H, dd), 7.10 (2H, m), 7.36 (1H, d), 7.41-7.45 (3H, overlapping m), 8.12 (1H, d), 8.16 (1H, d), 8.75 (1H, s), 8.85 (1H, s), 9.16 (1H, s). |
| 77 | 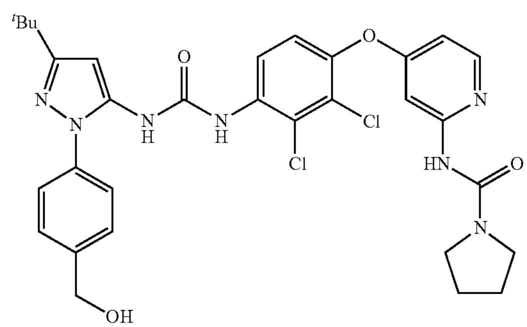 [SMILES: CC(C)(C)c1cc(NC(=O)Nc2ccc(Oc3ccnc(NC(=O)N4CCCC4)c3)c(Cl)c2Cl)n(-c2ccc(CO)cc2)n1] | N-(4-(4-(3-(3-tert-butyl-1-(4-hydroxymethyl phenyl)-1H-pyrazol-5-yl)ureido)-2,3-dichloro phenoxy)pyridin-2-yl)pyrrolidine-1-carboxamide. $R^t$ 1.92 min; m/z 638 (M + H)$^+$ (ES$^+$), Method 2; $^1$H NMR δ: 1.27 (9H, s), 1.48 (4H, m), 3.33 (4H, m), 4.57 (2H, s), 5.34 (1H, br s), 6.39 (1H, s), 6.60 (1H, br s), 7.36 (1H, d), 7.40 (1H, m), 7.48 (4H, s), 8.12 (1H, d), 8.16 (1H, d), 8.79 (1H, br s) 8.87 (1H, s), 9.24 (1H, s). |
| 78 | 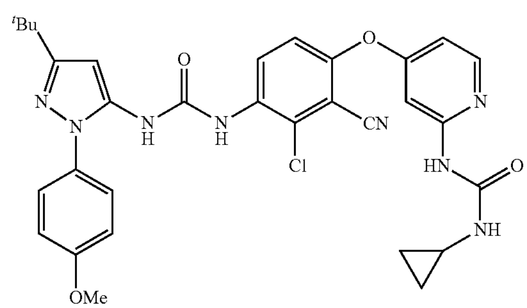 [SMILES: COc1ccc(-n2nc(C(C)(C)C)cc2NC(=O)Nc2ccc(Oc3ccnc(NC(=O)NC4CC4)c3)c(C#N)c2Cl)cc1] | 1-(3-tert-butyl-1-(4-methoxyphenyl)-1H-pyrazol-5-yl)-3-(2-chloro-3-cyano-4-(2-(3-cyclopropylureido)pyridin-4-yloxy)phenyl) urea. $R^t$ 5.28 min; m/z 615 (M + H)$^+$ (ES$^+$), Method 1 (Basic); $^1$H NMR δ: 0.41 (2H, m), 0.64 (2H, m), 1.26 (9H, s), 2.55 (1H, m), 3.82 (3H, s), 6.37 (1H, s), 6.69 (1H, dd), 7.08-7.13 (3H, overlapping m), 7.38-7.44 (3H, overlapping m), 7.79 (1H, br s), 8.15 (1H, d), 8.44 (1H, d), 8.97 (1H, s), 9.09 (1H, br s), 9.15 (1H, br s). |
| 79 | 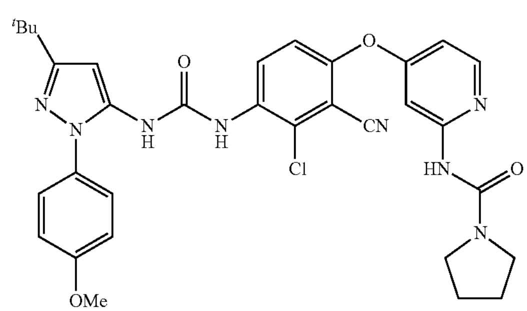 | N-(4-(4-(3-(3-tert-butyl-1-(4-methoxyphenyl)-1H-pyrazol-5-yl)ureido)-3-chloro-2-cyano phenoxy)pyridin-2-yl)pyrrolidine-1-carboxamide. $R^t$ 2.25 min; m/z 629 (M + H)$^+$ (ES$^+$), Method 2; $^1$H NMR δ: 1.26 (9H, s), 1.81 (4H, m), 3.35 (4H, m), 3.82 (3H, s), 6.37 (1H, s), 6.73 (1H, dd), 7.10 (2H, m), 7.38 (1H, d), 7.43 (2H, m), 7.56 (1H, d), 8.20 (1H, d), 8.43 (1H, d), 8.89 (1H, br s), 8.96 (1H, s), 9.15 (1H, s). |

TABLE 2-continued

Additional Compound Examples of the Invention

| Ex. No. | Structure | Name and Analytical Data |
|---|---|---|
| 80 | 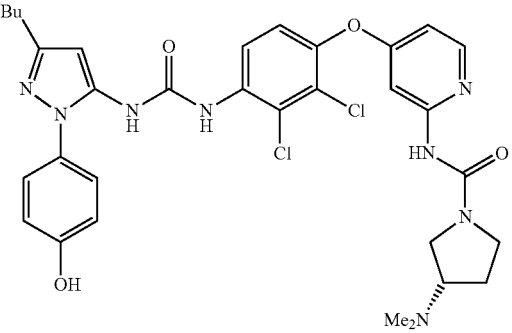 | (S)-N-(4-(4-(3-(3-tert-butyl-1-(4-hydroxy phenyl)-1H-pyrazol-5-yl)ureido)-2,3-dichloro phenoxy)pyridin-2-yl)-3-(dimethylamino) pyrrolidine-1-carboxamide. $R^t$ 4.92 min; m/z 667 (M + H)$^+$ (ES$^+$), Method 1 (Basic); $^1$H NMR δ: 1.26 (9H, s), 1.65 (1H, m), 2.01 (1H, m), 2.14 (6H, s), 2.61 (1H, m), 3.07 (1H, m), 3.28 (1H, m), 3.53 (1H,m), 3.62 (1H,m), 6.35 (1H, s), 6.58 (1H, dd), 6.89 (2H, m), 7.28 (2H, m), 7.35 (1H, d), 7.4 (1H, d), 8.11 (1H, d), 8.16 (1H, d), 8.79 (1H, s), 8.87 (1H, s), 9.11 (1H, s), 9.79 (1H, s). |
| 81 | 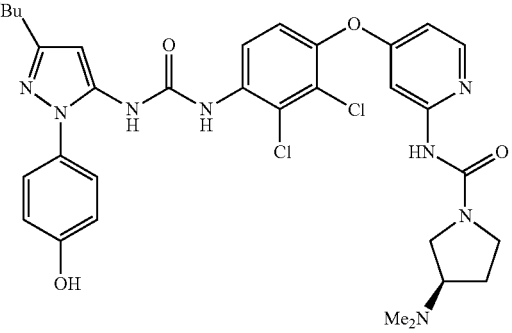 | (R)-N-(4-(4-(3-(3-tert-butyl-1-(4-methoxy phenyl)-1H-pyrazol-5-yl)ureido)-2,3-dichloro phenoxy)pyridin-2-yl)-3-(dimethylamino) pyrrolidine-1-carboxamide. $R^t$ 5.24 min; m/z 681/683 (M + H)$^+$ (ES$^+$), Method 1 (basic); $^1$H NMR δ: 1.27 (9H, s), 1.65 (1H, m), 2.00 (1H, m), 2.14 (6H, s), 2.61 (1H, m), 3.08 (1H, m), 3.28 (1H, m), 3.52 (1H, m), 3.62 (1H, m), 3.82 (3H, s), 6.37 (1H, s), 6.59 (1H, dd), 7.10 (2H, m), 7.35 (1H, d), 7.24-7.44 (3H, overlapping m), 8.12 (1H, d), 8.17 (1H, d), 8.76 (1H, br s), 8.14 (1H, br s), 9.16 (1H, br s). |
| 82 | 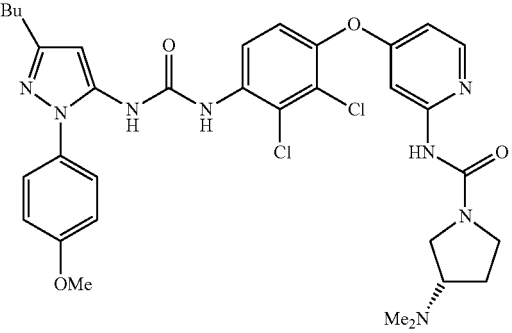 | (S)-N-(4-(4-(3-(3-tert-butyl-1-(4-methoxy phenyl)-1H-pyrazol-5-yl)ureido)-2,3-dichloro phenoxy)pyridin-2-yl)-3-(dimethylamino) pyrrolidine-1-carboxamide. $R^t$ 1.30 min; m/z 681/683 (M + H)$^+$ (ES$^+$), Method 2; $^1$H NMR δ: 1.28 (9H, s), 1.68 (1H, m), 2.05 (1H, m), 2.20 (6H, s), 2.68 (1H, m), 3.13 (1H, m), 3.32 (1H, m), 3.55 (1H, m), 3.65 (1H, m), 3.83 (3H, m), 6.38 (1H, s), 6.60 (1H, dd), 7.10 (2H, m), 7.35 (1H, d), 7.42-7.46 (3H, overlapping m), 8.13 (1H, d), 8.17 (1H, d), 8.82 (1H, s), 8.86 (1H, s), 9.18 (1H, s). |
| 83 | 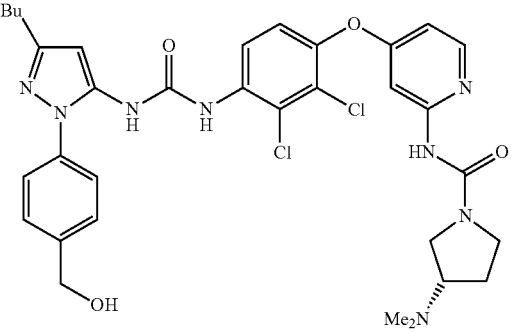 | (S)-N-(4-(4-(3-(3-tert-butyl-1-(4-hydroxy methylphenyl)-1H-pyrazol-5-yl)ureido)-2,3-dichlorophenoxy)pyridin-2-yl)-3-(dimethyl amino)pyrrolidine-1-carboxamide. $R^t$ 1.40 min; m/z 681/683 (M + H)$^+$ (ES$^+$), Method 2; $^1$H NMR δ: 1.28 (9H, s), 1.67 (1H, m), 2.03 (1H, m), 2.17 (6H, s), 2.66 (1H, m), 3.10 (1H, m), 3.32 (1H, m), 3.54 (1H, m), 3.64 (1H, m), 4.58 (2H, d), 5.33 (1H, d), 6.40 (1H, s), 6.60 (1H, dd), 7.36 (1H, d), 7.42 (1H, d), 7.50 (4H, s), 8.13 (1H, d), 8.17 (1H, d), 8.81 (1H, s), 8.88 (1H, s), 9.25 (1H, s). |

TABLE 2-continued

Additional Compound Examples of the Invention

| Ex. No. | Structure | Name and Analytical Data |
|---|---|---|
| 84 | 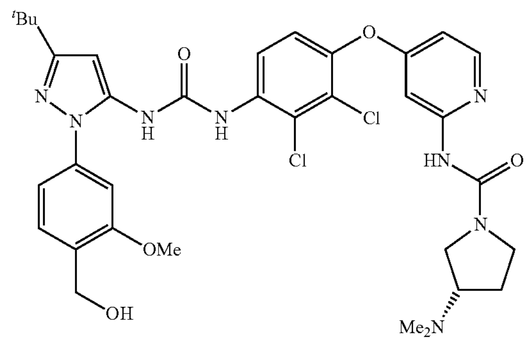 | (S)-N-(4-(4-(3-(3-tert-butyl-1-(4-hydroxy methyl-3-methoxyphenyl)-1H-pyrazol-5-yl)ureido)-2,3-dichlorophenoxy)pyridin-2-yl)-3-(dimethylamino)pyrrolidine-1-carboxamide. $R^t$ 1.38 min; m/z 711 (M + H)$^+$ (ES$^+$), Method 2; $^1$H NMR δ: 1.29 (9H, s), 1.65 (1H, m), 2.05 (1H, m), 2.15 (6H, s), 2.63 (1H, m), 3.07 (1H, m), 3.29 (1H, m), 3.55 (1H, m), 3.63 (1H, m), 3.83 (3H, s), 4.55 (2H, d), 5.16 (1H, t), 6.42 (1H, s), 6.59 (1H, dd), 7.08-7.12 (2H, overlapping m), 7.35 (1H, d), 7.43 (1H, d), 7.52 (1H, d), 8.13 (1H, d), 8.18 (1H, d), 8.80 (1H, s), 8.92 (1H, s), 9.24 (1H, s). |
| 85 | 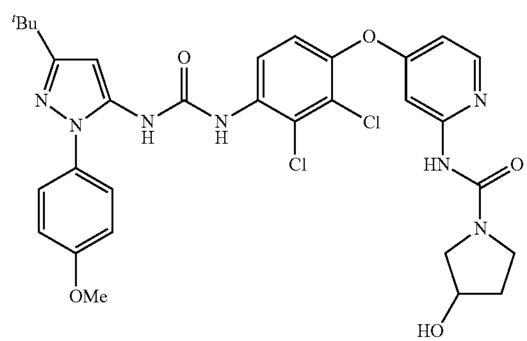 [SMILES: COc1ccc(-n2nc(C(C)(C)C)cc2NC(=O)Nc2ccc(Oc3ccnc(NC(=O)N4CCC(O)C4)c3)c(Cl)c2Cl)cc1] | N-(4-(4-(3-(3-tert-butyl-1-(4-methoxyphenyl)-1H-pyrazol-5-yl)ureido)-2,3-dichlorophenoxy)pyridin-2-yl)-3-hydroxypyrrolidine-1-carboxamide. $R^t$ 5.20 min; m/z 654/656 (M + H)$^+$ (ES$^+$), Method 1 (basic); $^1$H NMR δ: 1.27 (9H, s), 1.77 (1H, m), 1.86 (1H, m), 3.26 (1H, m), 3.43 (3H, overlapping m), 3.83 (3H, s), 4.25 (1H, br s), 4.93 (1H, br s), 6.37 (1H, s), 6.58 (1H, dd), 7.10 (2H, m), 7.36 (1H, d), 7.24-7.44 (3H, overlapping m), 8.12 (1H, d), 8.16 (1H, d), 8.79 (1H, br s), 8.85 (1H, br s), 9.16 (1H, br s). |
| 86 | 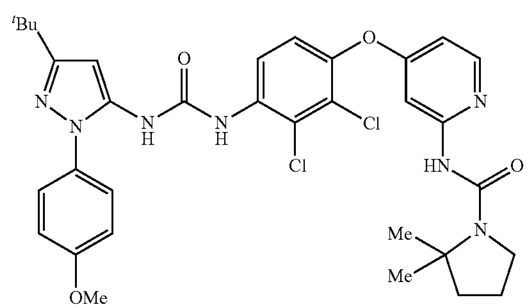 [SMILES: COc1ccc(-n2nc(C(C)(C)C)cc2NC(=O)Nc2ccc(Oc3ccnc(NC(=O)N4CCCC4(C)C)c3)c(Cl)c2Cl)cc1] | N-(4-(4-(3-(3-tert-butyl-1-(4-methoxyphenyl)-1H-pyrazol-5-yl)ureido)-2,3-dichloro phenoxy)pyridin-2-yl)-2,2-dimethylpyrrolidine-1-carboxamide. $R^t$ 5.72 min; m/z 666/668 (M + H)$^+$ (ES$^+$), Method 1 (Basic); $^1$H NMR δ: 1.27 (9H, s), 1.35 (6H, s), 1.71-1.81 (4H, overlapping m), 3.52 (2H, t), 3.82 (3H, s), 6.37 (1H, s), 6.48 (1H, dd), 7.10 (2H, m), 7.35 (1H, d), 7.43 (2H, m), 7.46 (1H, d), 8.10 (1H, d), 8.16 (1H, d), 8.38 (1H, br s), 8.84 (1H, s), 9.15 (1H, s). |
| 87 | 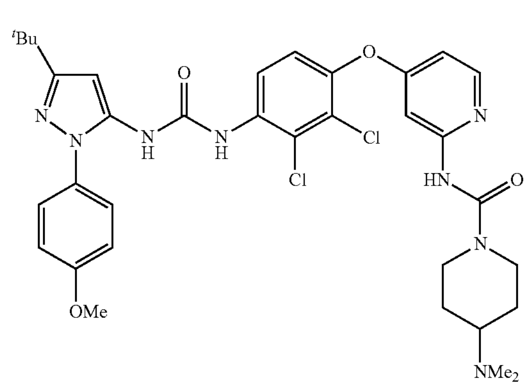 [SMILES: COc1ccc(-n2nc(C(C)(C)C)cc2NC(=O)Nc2ccc(Oc3ccnc(NC(=O)N4CCC(N(C)C)CC4)c3)c(Cl)c2Cl)cc1] | N-(4-(4-(3-(3-tert-butyl-1-(4-methoxyphenyl)-1H-pyrazol-5-yl)ureido)-2,3-dichlorophenoxy)pyridin-2-yl)-4-(dimethylamino)piperidine-1-carboxamide. $R^t$ min; m/z 695/697 (M + H)$^+$ (ES$^+$), Method 1 (Basic); $^1$H NMR δ: 1.22 (2H, m) 1.27 (9H, s), 1.71 (2H, m), 2.15 (6H, s), 2.23 (1H, m), 2.74 (2H, m), 3.82 (3H, s), 4.09 (2H, m), 6.37 (1H, s), 6.56 (1H, dd), 7.10 (2H, m), 7.34 (1H, d), 7.35 (1H, d), 7.43 (2H, m), 8.12 (1H, d), 8.16 (1H, d), 8.85 (1H, s), 9.16 (1H, s), 9.23 (1H, s). |

TABLE 2-continued

Additional Compound Examples of the Invention

| Ex. No. | Structure | Name and Analytical Data |
|---|---|---|
| 88 | | N-(4-(6-(3-(3-tert-butyl-1-p-tolyl-1H-pyrazol-5-yl)ureido)-2,3-difluorophenoxy)pyridin-2-yl)-2-methoxyacetamide. R$^t$ 5.25 min; m/z 565 (M + H)$^+$ (ES$^+$), Method 1 basic; $^1$H NMR δ: 1.25 (9H, s), 2.33 (3H, s), 3.33 (3H, s), 4.04 (2H, s), 6.31 (1H, s), 6.72 (1H, dd), 7.24-7.34 (4H, overlapping m), 7.43 (1H, dd), 7.78 (1H, d), 8.00 (1H, ddd), 8.25 (1H, d), 8.75 (1H, s), 8.80 (1H, d), 10.26 (1H, s). |

Pyrimidine Examples

| Ex. No. | Structure | Name and Analytical Data |
|---|---|---|
| 89 | 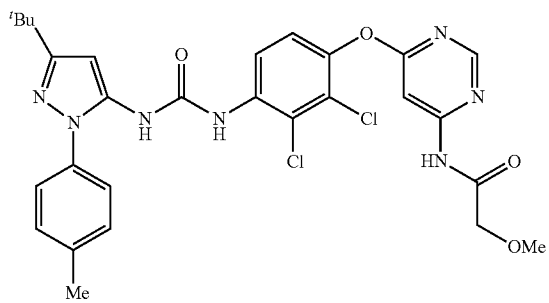 [SMILES: COCC(=O)Nc1cc(Oc2ccc(NC(=O)Nc3cc(C(C)(C)C)nn3-c3ccc(C)cc3)c(Cl)c2Cl)ncn1] | N-(6-(4-(3-(3-tert-butyl-1-p-tolyl-1H-pyrazol-5-yl)ureido)-2,3-dichlorophenoxy)pyrimidin-4-yl)-2-methoxyacetamide. R$^t$ 5.32 min; m/z 598/600 (M + H)$^+$ (ES$^+$), Method 1 (Basic); $^1$H NMR δ: 1.27 (9H, s), 2.38 (3H, s), 3.35 (3H, s), 4.12 (2H, s), 6.39 (1H, s), 7.33-7.45 (5H, overlapping m), 7.66 (1H, d), 8.10 (1H, d), 8.50 (1H, d), 8.84 (1H, br s), 9.17 (1H, br s).10.80 (1H, br s). |
| 90 | 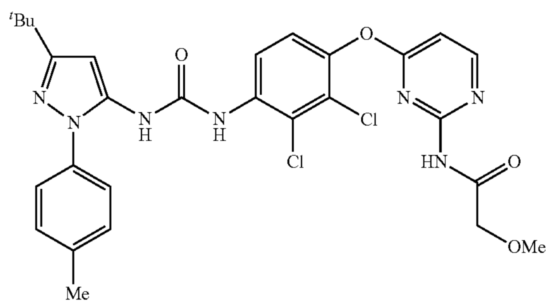 | N-(4-(4-(3-(3-tert-butyl-1-p-tolyl-1H-pyrazol-5-yl)ureido)-2,3-dichlorophenoxy)pyrimidin-2-yl)-2-methoxyacetamide. R$^t$ 5.25 min; m/z 598/600 (M + H)$^+$ (ES$^+$), Method 1 (Basic); $^1$H NMR δ: 1.27 (9H, s), 2.38 (3H, s), 3.15 (3H, s), 3.90 (2H, s), 6.38 (1H, s), 6.89 (1H, d), 7.33-7.44 (5H, overlapping m), 8.15 (1H, d), 8.55 (1H, d), 8.84 (1H, br s), 9.17 (1H, br s), 10.42 (1H, br s). |
| 91 | 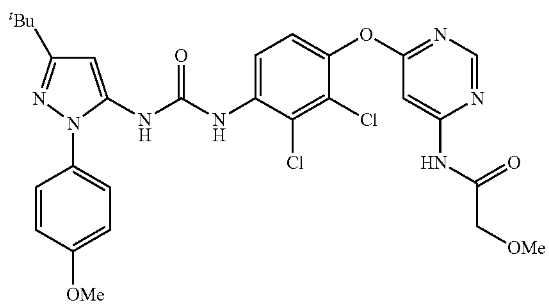 [SMILES: COCC(=O)Nc1cc(Oc2ccc(NC(=O)Nc3cc(C(C)(C)C)nn3-c3ccc(OC)cc3)c(Cl)c2Cl)ncn1] | N-(6-(4-(3-(3-tert-butyl-1-(4-methoxyphenyl)-1H-pyrazol-5-yl)ureido)-2,3-dichlorophenoxy)pyrimidin-4-yl)-2-methoxyacetamide. R$^t$ 5.22 min; m/z 614/616 (M + H)$^+$ (ES$^+$), Method 1 (Basic); $^1$H NMR δ: 1.27 (9H, s), 3.35 (3H, s), 3.82 (3H, s), 4.12 (2H, s), 6.37 (1H, s), 7.10 (2H, m), 7.39 (1H, d), 7.43 (2H, m), 7.66 (1H, d), 8.10 (1H, d), 8.50 (1H, d), 8.83 (1H, br s), 9.12 (1H, br s), 10.79 (1H, br s). |

TABLE 2-continued

Additional Compound Examples of the Invention

| Ex. No. | Structure | Name and Analytical Data |
|---|---|---|
| 92 | 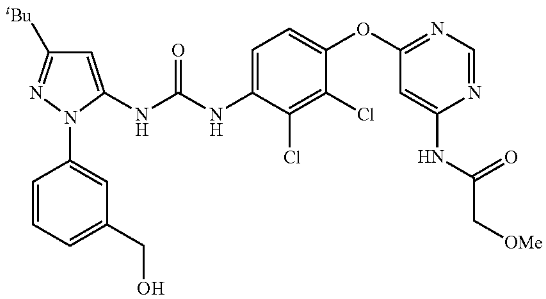 [SMILES: COCC(=O)Nc1cc(Oc2ccc(NC(=O)Nc3cc(C(C)(C)C)nn3-c3cccc(CO)c3)c(Cl)c2Cl)ncn1] | N-(6-(4-(3-(3-tert-butyl-1-(3-hydroxymethyl phenyl)-1H-pyrazol-5-yl)ureido)-2,3-dichloro phenoxy)pyrimidin-4-yl)-2-methoxyacetamide. R<sup>t</sup> 2.32 min; m/z 614/616 (M + H)<sup>+</sup> (ES<sup>+</sup>), Method 2; $^1$H NMR δ: 1.28 (9H, s), 3.35 (3H, s), 4.12 (2H, s), 4.59 (2H, d), 5.34 (1H, t), 6.39 (1H, s), 7.34-7.41 (3H, overlapping m), 7.47-7.52 (2H, overlapping m), 7.66 (1H, d), 7.89 (1H, d), 8.50 (1H, d), 8.82 (1H, s), 9.20 (1H, s), 10.77 (1H, s). |
| 93 | 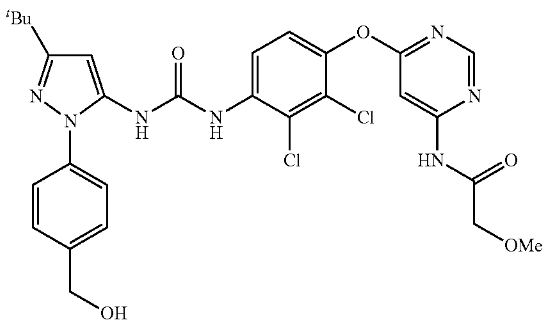 [SMILES: COCC(=O)Nc1cc(Oc2ccc(NC(=O)Nc3cc(C(C)(C)C)nn3-c3ccc(CO)cc3)c(Cl)c2Cl)ncn1] | N-(6-(4-(3-(3-tert-butyl-1-(4-hydroxymethyl phenyl)-1H-pyrazol-5-yl)ureido)-2,3-dichloro phenoxy)pyrimidin-4-yl)-2-methoxyacetamide. R<sup>t</sup> 5.07 min; m/z 614/616 (M + H)<sup>+</sup> (ES<sup>+</sup>), Method 1 (Basic); $^1$H NMR δ: 1.28 (9H, s), 3.35 (3H, s), 4.12 (2H, s), 4.57 (2H, d), 5.33 (1H, t), 6.39 (1H, s), 7.39 (1H, d), 7.48 (4H, br s), 7.66 (1H, d), 8.10 (1H, d), 8.50 (1H, d), 8.85 (1H, s), 9.21 (1H, s), 10.80 (1H, s). |
| 94 | 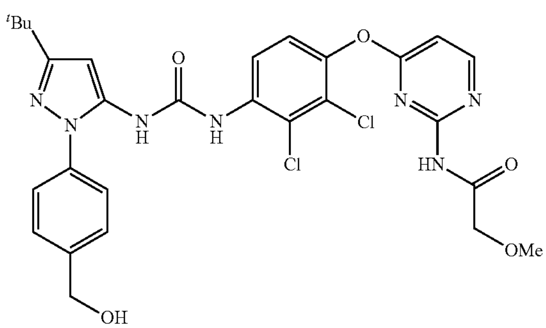 | N-(4-(4-(3-(3-tert-butyl-1-(4-hydroxymethyl phenyl)-1H-pyrazol-5-yl)ureido)-2,3-dichloro phenoxy)pyrimidin-2-yl)-2-methoxyacetamide. R<sup>t</sup> 4.97 min; m/z 614/616 (M + H)<sup>+</sup> (ES<sup>+</sup>), Method 1 (Basic); $^1$H NMR δ: 1.28 (9H, s), 3.16 (3H, s), 3.90 (2H, s), 4.57 (2H, d), 6.39 (1H, s), 6.89 (1H, d), 7.42 (1H, d), 7.47 (4H, s), 8.15 (1H, d), 8.55 (1H, d), 8.86 (1H, s), 9.12 (1H, s), 10.43 (1H, s). |
| 95 | 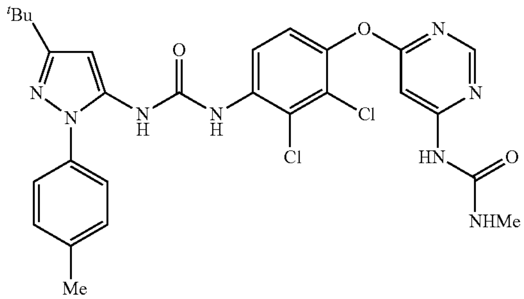 [SMILES: CNC(=O)Nc1cc(Oc2ccc(NC(=O)Nc3cc(C(C)(C)C)nn3-c3ccc(C)cc3)c(Cl)c2Cl)ncn1] | 1-(3-tert-butyl-1-p-tolyl-1H-pyrazol-5-yl)-3-(2,3-dichloro-4-(6-(3-methylureido)pyrimidin-4-yloxy)phenyl)urea. R<sup>t</sup> 5.20 min; m/z 583/585 (M + H)<sup>+</sup> (ES<sup>+</sup>), Method 1 (Basic); $^1$H NMR δ: 1.27 (9H, s), 2.37 (3H, s), 2.69 (3H, d), 6.38 (1H, s), 7.17-7.23 (2H, overlapping m), 7.33-7.38 (3H, overlapping m), 7.41 (2H, m), 8.09 (1H, d), 8.36 (1H, d), 8.84 (1H, br s), 9.18 (1H, br s), 9.71 (1H, s). |

TABLE 2-continued

Additional Compound Examples of the Invention

| Ex. No. | Structure | Name and Analytical Data |
|---|---|---|
| 96 | 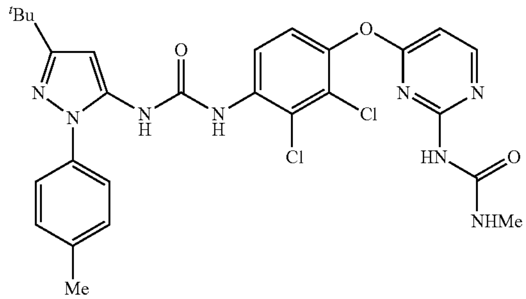 [SMILES: CNC(=O)Nc1nccc(Oc2ccc(NC(=O)Nc3cc(C(C)(C)C)nn3-c3ccc(C)cc3)c(Cl)c2Cl)n1] | 1-(3-tert-butyl-1-p-tolyl-1H-pyrazol-5-yl)-3-(2,3-dichloro-4-(2-(3-methylureido)pyrimidin-4-yloxy)phenyl)urea. $R^t$ 5.42 min; m/z 583/585 (M + H)$^+$ (ES$^+$), Method 1 (Basic); $^1$H NMR δ: 1.27 (9H, s), 2.38 (3H, s), 2.48 (3H, d), 6.38 (1H, s), 6.78 (1H, d), 7.34 (2H, m), 7.41 (2H, m), 7.46 (1H, d), 8.09-8.17 (2H, overlapping m), 8.48 (1H, d), 8.89 (1H, s), 9.16 (1H, s), 9.79 (1H, s). |
| 97 | 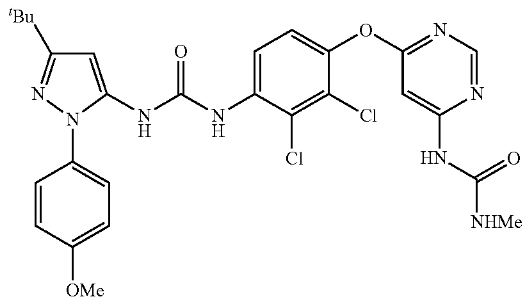 [SMILES: CNC(=O)Nc1cc(Oc2ccc(NC(=O)Nc3cc(C(C)(C)C)nn3-c3ccc(OC)cc3)c(Cl)c2Cl)ncn1] | 1-(3-tert-butyl-1-(4-methoxyphenyl)-1H-pyrazol-5-yl)-3-(2,3-dichloro-4-(6-(3-methyl ureido)pyrimidin-4-yloxy)phenyl) urea. $R^t$ 5.09 min; m/z 599/601 (M + H)$^+$ (ES$^+$), Method 1 (Basic); $^1$H NMR δ: 1.27 (9H, s), 2.70 (3H, d), 3.82 (3H, s), 6.37 (1H, s), 7.10 (2H, m), 7.16-7.23 (2H, overlapping m), 7.36 (1H, d), 7.43 (2H, m), 8.09 (1H, d), 8.36 (1H, d), 8.82 (1H, br s), 9.12 (1H, br s), 9.71 (1H, br s). |
| 98 | 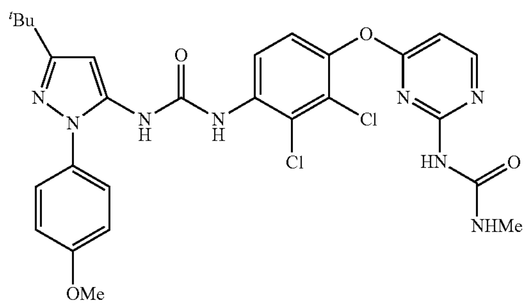 [SMILES: CNC(=O)Nc1nccc(Oc2ccc(NC(=O)Nc3cc(C(C)(C)C)nn3-c3ccc(OC)cc3)c(Cl)c2Cl)n1] | 1-(3-tert-butyl-1-(4-methoxyphenyl)-1H-pyrazol-5-yl)-3-(2,3-dichloro-4-(2-(3-methyl ureido)pyrimidin-4-yloxy)phenyl) urea. $R^t$ 2.47 min; m/z 599/601 (M + H)$^+$ (ES$^+$), Method 2; $^1$H NMR δ: 1.27 (9H, s), 2.48 (3H, d), 3.82 (3H, s), 6.37 (1H, s), 6.78 (1H, d), 7.09 (2H, m), 7.43 (2H, m), 7.46 (1H, d), 8.09-8.14 (2H, overlapping m), 8.48 (1H, d), 8.88 (1H, s), 9.12 (1H, s), 9.79 (1H, s). |
| 99 | 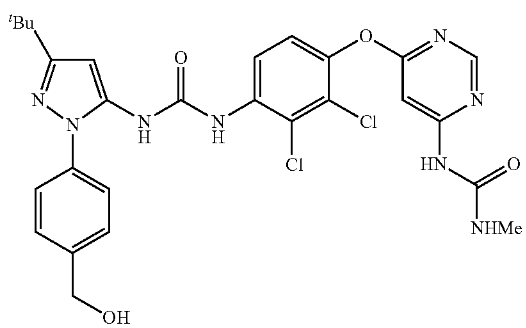 | 1-(3-tert-butyl-1-(4-hydroxymethylphenyl)-1H-pyrazol-5-yl)-3-(2,3-dichloro-4-(6-(3-methyl ureido)pyrimidin-4-yloxy)phenyl)urea. $R^t$ 4.89 min; m/z 599/601 (M + H)$^+$ (ES$^+$), Method 1 (Basic); $^1$H NMR δ: 1.28 (9H, s), 2.69 (3H, d), 4.57 (2H, d), 5.33 (1H, t), 6.39 (1H, s), 7.16-7.23 (2H, overlapping m), 7.36 (1H, d), 7.48 (4H br s), 8.08 (1H, d), 8.36 (1H, d), 8.84 (1H, s), 9.20 (1H, s), 9.70 (1H, s). |
| 100 | 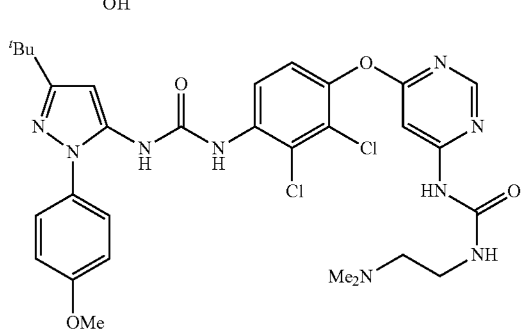 | 1-(3-tert-butyl)-1-(4-methoxyphenyl)-1H-pyrazol-5-yl)-3-(2,3-dichloro-4-(6-(3-(2-(dimethylamino)ethyl)ureido)pyrimidin-4-yloxy)phenyl)urea. $R^t$ 5.27 min; m/z 656/658 (M + H)$^+$ (ES$^+$), Method 1 (Basic); $^1$H NMR δ: 1.27 (9H, s), 2.16 (6H, s), 2.33 (2H, t), 3.21 (2H, td), 3.82 (3H, s), 6.37 (1H, s), 7.10 (2H, m), 7.22-7.31 (2H, overlapping m), 7.35 (1H, d), 7.43 (2H, m), 8.09 (1H, m), 8.35 (1H, d), 8.83 (1H, br s), 9.12 (1H, br s), 9.68 (1H, br s). |

TABLE 2-continued

Additional Compound Examples of the Invention

| Ex. No. | Structure | Name and Analytical Data |
|---|---|---|
| 101 | 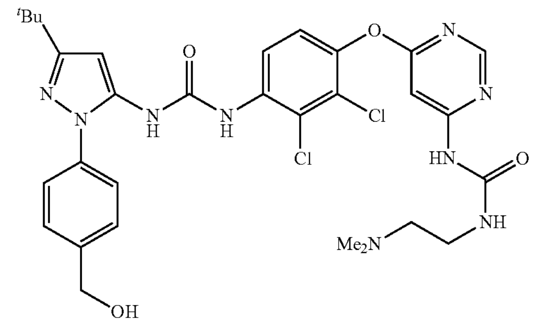 [SMILES: CN(C)CCNC(=O)Nc1cc(Oc2ccc(NC(=O)Nc3cc(C(C)(C)C)nn3-c3ccc(CO)cc3)c(Cl)c2Cl)ncn1] | 1-(3-tert-butyl-1-(4-hydroxymethylphenyl)-1H-pyrazol-5-yl)-3-(2,3-dichloro-4-(6-(3-(2-(dimethylamino)ethyl)ureido)pyrimidin-4-yloxy)phenyl)urea. $R^t$ 5.15 min; m/z 656/658 (M + H)$^+$ (ES$^+$), Method 1 (Basic); $^1$H NMR δ: 1.28 (9H, s), 2.17 (6H, s), 2.33 (2H, t), 3.22 (2H, dt), 4.77 (2H, d), 5.33 (1H, t), 6.39 (1H, s), 7.23-7.30 (2H, m), 7.36 (1H, d), 7.48 (4H, br s), 8.09 (1H, d), 8.34 (1H, d), 8.84 (1H, br s), 9.19 (1H, br s), 9.68 (1H, br s). |

Methoxy Ether Linked Example

| Ex. No. | Structure | Name and Analytical Data |
|---|---|---|
| 102 | | 1-(4-((4-(3-(3-tert-butyl-1-p-tolyl-1H-pyrazol-5-yl)ureido)-2,3-dichlorophenoxy)methyl)pyridin-2-yl)-3-methylurea. $R^t$ 5.39 min; m/z 596/598 (M + H)$^+$ (ES$^+$), Method 1 (Basic); $^1$H NMR δ: 1.26 (9H, s), 2.37 (3H, s), 2.73 (3H, d), 5.23 (2H, s), 6.34 (1H, s), 6.96 (1H, dd), 7.17 (1H, d), 7.32-7.40 (5H, overlapping m), 7.84 (1H, d), 8.10 (1H, br s), 8.18 (1H, d), 8.61 (1H, s), 8.96 (1H, s), 9.35 (1H, s). |

Biological Testing: Experimental Methods and Results
Enzyme Inhibition Assay

The enzyme inhibitory activities of compounds disclosed herein were determined by fluorescence resonance energy transfer (FRET) using synthetic peptides labelled with both donor and acceptor fluorophores (Z-LYTE, Invitrogen Ltd., Paisley, UK). Recombinant, phosphorylated p38 MAPKγ (MAPK12: Invitrogen) was diluted in HEPES buffer, mixed with the test compound at the desired final concentrations and incubated for 2 hr at RT. The FRET peptide (2 μM) and ATP (100 μM) were added to the enzyme/compound mixture and incubated for 1 hr. Development reagent (protease) was added for 1 hr prior to detection in a fluorescence microplate reader (Varioskan® Flash, ThermoFisher Scientific). The site-specific protease cleaves non-phosphorylated peptide only and eliminates the FRET signal. Phosphorylation levels of each reaction were calculated using the ratio of coumarin emission (donor) over fluorescein emission (acceptor) for which high ratios indicate high phosphorylation and low ratios indicate low phosphorylation levels. The percentage inhibition of each reaction was calculated relative to non-inhibited control and the 50% inhibitory concentration (IC$_{50}$ value) then calculated from the concentration-response curve.

For the p38 MAPKα isoform (MAPK14: Invitrogen), enzyme activity was evaluated indirectly by determining the level of activation/phosphorylation of the down-stream molecule, MAPKAP-K2. The p38 MAPKα protein was mixed with the test compound for 2 hr at RT. The p38α inactive target MAPKAP-K2 (Invitrogen) and FRET peptide (2 μM), which is a phosphorylation target for MAPKAP-K2, and ATP (10 μM) were then added to the enzymes/compound mixture and the resulting mixture incubated for 1 hr. Development reagent was then added and the mixture incubated for 1 hr before detection by fluorescence completed the assay protocol.

Cellular Potency Assays:
LPS-Induced TNFα/IL-8 Release in d-U937Cells

U937 cells, a human monocytic cell line, were differentiated to macrophage-type cells by incubation with phorbol myristate acetate (PMA; 100 ng/ml) for 48 to 72 hr. Cells were pre-incubated with final concentrations of test compound for 2 hr and were then stimulated with 0.1 μg/mL of LPS (from E. Coli: O111:B4, Sigma) for 4 hr. The supernatant was collected for determination of TNFα and IL-8 concentrations by sandwich ELISA (Duo-set, R&D systems). The inhibition of TNFα production was calculated as a percentage of that achieved by 10 μg/mL of BIRB796 at each concentration of test compound by comparison against vehicle control. The relative 50% effective concentration (REC$_{50}$) was determined from the resultant concentration-response curve. The inhibition of IL-8 production was calculated at each concentration of test compound by comparison with vehicle control. The 50% inhibitory concentration (IC$_{50}$) was determined from the resultant concentration-response curve.

LPS-Induced TNFα Release in THP-1 Cells

THP-1 cells, a human monocytic cell line, were stimulated with 3 μg/mL of LPS (from E. Coli; 0111:B4, Sigma) for 4 hr and the supernatant collected for determination of the TNFα concentration by sandwich ELISA (Duo-set, R&D systems). The inhibition of TNFα production was calculated at each concentration by comparison with vehicle control. The 50% inhibitory concentration ($IC_{50}$) was determined from the resultant concentration-response curve.

Poly I:C-Induced ICAM-1 Induction in BEAS2B Cells

Poly I:C (1 μg/mL) (Invivogene Ltd., San Diego, Calif.) was transfected into BEAS2B cells (human bronchial epithelial cells, ATCC) with Oligofectamine (Invitrogen, Carlsbad, Calif.). Cells were pre-incubated with final concentrations of test compounds for 2 hr and the level of ICAM1 expression on the cell surface was determined by cell-based ELISA. At a time point 18 hr after poly I:C transfection, cells were fixed with 4% formaldehyde in PBS and then endogenous peroxidase was quenched by the addition of 0.1% sodium azide and 1% hydrogen peroxide. Cells were washed with wash-buffer (0.1% Tween in PBS: PBS-Tween). and after blocking the wells with 5% milk in PBS-Tween for 1 hr, the cells were incubated with anti-human ICAM-1 antibody (Cell Signaling Technology, Danvers, Mass.) in 1% BSA PBS overnight at 4° C. The cells were washed with PBS-Tween and incubated with the secondary antibody (HRP-conjugated anti-rabbit IgG, Dako Ltd., Glostrup, Denmark). The ICAM-1 signal was detected by adding substrate and reading the absorbance at 450 nm against a reference wavelength of 655 nm using a spectrophotometer. The cells were then washed with PBS-Tween and total cell numbers in each well were determined by reading absorbance at 595 nm after Crystal Violet staining and elution by 1% SDS solution. The measured OD 450-655 readings were corrected for cell number by dividing with the OD595 reading in each well. The inhibition of ICAM-1 expression was calculated at each concentration of test compound by comparison with vehicle control. The 50% inhibitory concentration ($IC_{50}$) was determined from the resultant concentration-response curve.

Cell Viability Assay:

MTT Assay

Differentiated U937 cells were pre-incubated with each test compound under two protocols: the first for 4 hr in 5% FCS and the second in 10% FCS for 24 h. The supernatant was replaced with 200 μL of new media and 10 μL of MTT stock solution (5 mg/mL) was added to each well. After incubation for 1 hr the media were removed, 200 μL of DMSO was added to each well and the plates were shaken lightly for 1 hr prior to reading the absorbance at 550 nm. The percentage loss of cell viability was calculated for each well relative to vehicle (0.5% DMSO) treatment. Consequently an apparent increase in cell viability for drug treatment relative to vehicle is tabulated as a negative percentage.

The in vitro profiles of the compound examples disclosed herein, as determined using the protocols described above, are presented below (Table 3).

TABLE 3

In Vitro Profiles of Compound Examples

| | Enzyme Inhibition | | Cellular Profiles | | | | MTT Assay (Viability) | |
|---|---|---|---|---|---|---|---|---|
| | | | LPS/TNFα | | LPS/IL-8 | PolyIC/ICAM1 | | |
| Test Cmpd | $IC_{50}$ | | $IC_{50}$ | $REC_{50}$ | $IC_{50}$ | | 4 h | 24 h |
| Ex. No | p38α | p38γ | THP-1 | d-U937 | d-U937 | BEAS2B | d-U937 | |
| 1 | 105.4 | 40.5 | 0.9 | 2.3 | 9.6 | 8.8 | 1.7 | 76.1 |
| 2 | 37.7 | 366.0 | 5.3 | 29.4 | 174.5 | 427.2 | −3.1 | 32.7 |
| 3 | 5.1 | 175.1 | 1.0 | 1.1 | 41.2 | 24.4 | 3.4 | 22.9 |
| 4 | 4.5 | 237.9 | 0.2 | 0.1 | 0.1 | 1.1 | −24.1 | 64.5 |
| 5 | 18.7 | 1358 | 1.4 | 0.4 | 50.6 | 21.9 | −3.5 | 18.7 |
| 6 | 6.7 | 57.9 | 1.6 | 0.1 | 3.9 | 7.2 | −21.3 | −14.6 |
| 7 | 1.3 | 36.6 | 111.3 | 112.1 | 124.2 | 149.5 | −2.0 | 64.5 |
| 8 | 7.6 | 17.2 | 0.5 | 0.9 | 4.7 | 2.4 | −7.0 | 85.6 |
| 9 | 19.1 | 67.2 | 1.0 | 0.2 | 0.8 | 0.3 | −26.8 | 65.3 |
| 10 | 36.7 | 184.0 | 0.4 | 0.8 | 1.2 | 1.7 | −18.7 | 17.0 |
| 11 | 15.9 | 38.7 | 0.7 | 0.8 | 4.5 | 1.8 | −1.3 | 42.0 |
| 12 | 24.7 | 57.2 | 1.6 | 1.7 | 0.2 | 2.7 | 5.0 | 24.1 |
| 13 | 11.2 | 21.7 | 1.7 | 2.1 | 1.3 | 2.1 | −6.4 | 63.9 |
| 14 | 17.0 | 33.1 | 6.1 | 40.8 | 70.2 | 32.2 | −7.9 | 49.6 |
| 15 | 15.7 | 106.7 | 19.9 | 83.8 | 162.5 | 31.2 | −12.2 | 12.4 |
| 16 | 36.7 | 1445 | >1686 | 876.3 | 4956 | >1686 | −8.1 | −21.3 |
| 17 | 54.2 | >16420 | >1642 | 16233 | 17051 | >1642 | −11.5 | 4.0 |
| 18 | 29.4 | >16340 | 4.7 | 6.7 | 48.4 | 342.6 | 39.5 | −4.6 |
| 19 | 18.5 | 4371.5 | 12.3 | 25.6 | 837.1 | 23.7 | −13.5 | 6.9 |
| 20 | 30.7 | >15337 | 45.2 | 69.5 | 1060 | 16.5 | −19.1 | 9.6 |
| 21 | 81.5 | >17301 | 1768 | 163.8 | 12874 | >1730 | 14.5 | −12.0 |
| 22 | 7.6 | 20.6 | 1.1 | 1.5 | 33.8 | 4.9 | −20.9 | 85.2 |
| 23 | 15.7 | 47.9 | 2.2 | 0.3 | 11.9 | 2.0 | −37.1 | −24.5 |
| 24 | 5.7 | 46.3 | 1.7 | 1.7 | 1.1 | 10.5 | −17.7 | 39.5 |
| 25 | 10.7 | 139.2 | 1.7 | 1.2 | 2.5 | 10.8 | −3.5 | 58.6 |
| 26 | 29.0 | 2860 | 97.2 | 170.9 | 266.4 | >155.5 | 10.5 | −4.3 |
| 27 | 18.8 | 110.8 | 0.6 | 0.5 | 3.3 | 6.3 | 7.2 | 54.9 |
| 28 | 48.3 | 30.1 | 3.2 | 2.7 | 7.0 | 11.6 | −3.8 | 71.0 |
| 29 | 46.1 | 46.1 | 2.2 | 0.8 | 17.9 | 77.0 | −0.7 | 30.8 |
| 30 | 163.7 | 152.5 | 1.3 | 2.5 | 6.5 | 6.9 | 3.3 | 61.6 |
| 31 | 153.5 | 289.6 | 143.4 | 175.7 | 263.7 | 108.1 | 1.1 | 49.3 |
| 32 | 42.9 | 148.5 | 1.3 | 0.6 | 29.1 | 6.5 | 17.2 | 65.3 |
| 33 | 25.3 | 59.7 | 1.5 | 6.4 | 4.8 | 3.0 | −12.6 | 68.9 |
| 34 | 134.5 | 24.0 | 0.4 | 0.3 | 2.2 | 2.5 | 2.4 | 82.1 |
| 35 | 24.7 | 134.5 | 0.6 | 0.5 | 2.8 | 1.5 | −0.2 | 73.1 |
| 36 | 18.4 | 379.7 | 2.2 | 0.7 | 3.4 | 1.9 | −11.2 | 68.8 |

TABLE 3-continued

In Vitro Profiles of Compound Examples

| Test Cmpd | Enzyme Inhibition $IC_{50}$ | | Cellular Profiles | | | | MTT Assay (Viability) | |
|---|---|---|---|---|---|---|---|---|
| | | | LPS/TNFα | | LPS/IL-8 | PolyIC/ICAM1 | 4 h | 24 h |
| | | | $IC_{50}$ | $REC_{50}$ | $IC_{50}$ | | | |
| Ex. No | p38α | p38γ | THP-1 | d-U937 | d-U937 | BEAS2B | d-U937 | |
| 37 | 102.3 | 159.0 | 1.8 | 1.9 | 6.9 | 4.0 | −0.4 | 24.7 |
| 38 | 63.0 | 35.9 | 3.7 | 54.1 | 160.4 | 24.8 | 0.6 | 64.1 |
| 39 | 11.5 | 3470 | 9.6 | 27.0 | 108.2 | 109.0 | 6.5 | −3.0 |
| 40 | 0.3 | 189.4 | 0.7 | 1.6 | 2.0 | 16.6 | −10.7 | 28.4 |
| 41 | 54.9 | 46.5 | 0.3 | 0.2 | 1.6 | 1.4 | −24.0 | 76.5 |
| 42 | 14.6 | 28.0 | 0.7 | 1.3 | 1.1 | 3.1 | −4.4 | 67.9 |
| 43 | 27.5 | 78.1 | 0.4 | 0.9 | 1.3 | 2.3 | −18.7 | 79.1 |
| 44 | 7.9 | 48.4 | 1.8 | 2.2 | 20.7 | 0.9 | −25.9 | 87.1 |
| 45 | 27.4 | 84.7 | 0.8 | 0.7 | 1.0 | 9.0 | −4.8 | 56.2 |
| 46 | 20.9 | 38.7 | 0.3 | 0.9 | 1.1 | 2.4 | −12.6 | 82.7 |
| 47 | 2.2 | 5.9 | 0.5 | 1.6 | 8.2 | 6.4 | −42.5 | 85.0 |
| 48 | 6.3 | 22.4 | 0.4 | 1.1 | 5.1 | 2.2 | 12.5 | 84.1 |
| 49 | 16.5 | 36.0 | 1.2 | 0.7 | 2.2 | 1.5 | −4.8 | 92.2 |
| 50 | 41.2 | 59.2 | 1.3 | 0.2 | 0.6 | 1.1 | −5.4 | 35.9 |
| 51 | 34.2 | 174.3 | 0.7 | 1.2 | 6.8 | 0.7 | −17.3 | 57.3 |
| 52 | 16.8 | 32.1 | 1.0 | 0.5 | 1.9 | 2.4 | −43.8 | 8.1 |
| 53 | 46.9 | 35.8 | 1.8 | 1.3 | 7.7 | 2.2 | −1.1 | 87.8 |
| 54 | 87.7 | 52.8 | 2.2 | 0.3 | 3.2 | 2.5 | −34.9 | 71.2 |
| 55 | 50.1 | 200.1 | 4.8 | 1.0 | 3.1 | 1.7 | −15.0 | 49.2 |
| 56 | 52.4 | 193.9 | 8.6 | 0.9 | 4.6 | 12.3 | −25.5 | −28.0 |
| 57 | 47.3 | 166.6 | 14.9 | 2.3 | 3.0 | 141.8 | −23.6 | −56.2 |
| 58 | 34.1 | 175.7 | 2.2 | 2.1 | 3.3 | 13.2 | −12.4 | −29.0 |
| 59 | 125.1 | 198.2 | 2.0 | 1.6 | 1.9 | 0.9 | −24.8 | 0.0 |
| 60 | 10.3 | 12.9 | 22.7 | 9.2 | 23.5 | >163.3 | −15.4 | −52.4 |
| 61 | 32.7 | 94.0 | 2.5 | 181.5 | 234.7 | 11.4 | −31.9 | −12.9 |
| 62 | 37.2 | 135.3 | 7.1 | 17.6 | 25.8 | 70.8 | −13.4 | −22.9 |
| 63 | 28.9 | 140.0 | 0.5 | 0.3 | 11.4 | 3.0 | −29.7 | 51.6 |
| 64 | 13.3 | 58.0 | 0.4 | 0.3 | 15.1 | 1.5 | −37.2 | 37.2 |
| 65 | 37.7 | 121.7 | 2.7 | 2.0 | 3.8 | 17.5 | −4.7 | 20.2 |
| 66 | 21.6 | 45.0 | 1.1 | 0.3 | 4.9 | 5.5 | 15.0 | 90.3 |
| 67 | 27.9 | 67.8 | 1.2 | 1.7 | 5.8 | 2.0 | −11.4 | 40.9 |
| 68 | 18.2 | 137.3 | 1.4 | 0.2 | 10.3 | 3.3 | 11.3 | 73.3 |
| 69 | 15.2 | 68.3 | 1.4 | 0.6 | 4.2 | 22.2 | 8.8 | 75.5 |
| 70 | 3.5 | 30.1 | 2.4 | 1.5 | 5.7 | 10.1 | 6.1 | 94.1 |
| 71 | 19.4 | 60.4 | 0.7 | 1.1 | 1.4 | 1.9 | −20.5 | 84.3 |
| 72 | 41.3 | 315.3 | 0.6 | 1.9 | 0.2 | 7.5 | −13.7 | 26.9 |
| 73 | 150.9 | 242.6 | 12.8 | 1.7 | 1.9 | 1303 | −27.3 | 12.3 |
| 74 | 327.7 | 743.6 | 11.5 | 0.5 | 2.7 | 4.6 | 1.2 | 5.5 |
| 75 | 147.2 | 181.3 | 0.4 | 1.3 | 1.7 | 0.3 | −33.7 | 6.6 |
| 76 | 21.0 | 134.5 | 0.6 | 0.9 | 0.8 | 0.3 | −25.5 | 27.2 |
| 77 | 18.4 | 24.3 | 0.4 | 0.2 | 0.4 | 2.5 | −8.8 | 53.3 |
| 78 | 84.6 | 96.2 | 1.4 | 1.6 | 2.2 | 2.2 | 1.0 | 20.9 |
| 79 | 32.3 | 36.6 | 0.5 | 0.4 | 6.6 | 1.3 | −13.9 | 23.2 |
| 80 | 12.3 | 59.3 | 0.6 | 0.8 | 3.6 | 2.3 | −3.0 | 15.7 |
| 81 | 7.7 | 58.5 | 1.1 | 0.8 | 4.9 | 14.0 | −8.7 | 33.3 |
| 82 | 14.1 | 33.6 | 0.3 | 1.8 | 4.6 | 2.1 | −13.2 | 20.5 |
| 83 | 6.7 | 19.8 | 0.7 | 1.7 | 34.0 | 2.4 | −9.9 | 34.3 |
| 84 | 13.8 | 27.0 | 1.2 | 1.4 | 9.6 | 2.6 | 3.2 | 56.7 |
| 85 | 12.8 | 27.2 | 0.3 | 1.1 | 5.4 | 0.6 | −25.1 | 58.6 |
| 86 | 137.6 | 436.1 | 0.8 | 2.7 | 2.6 | 8.0 | −5.1 | 26.7 |
| 87 | 14.5 | 16.9 | 1.0 | 1.7 | 2.1 | 1.0 | 7.1 | 39.3 |
| 88 | 2086 | >17731 | 988.8 | 27.0 | >1773 | 1691 | 12.3 | 10.0 |
| 89 | 58.8 | 175.3 | 1.7 | 0.3 | 13.4 | 1.8 | −49.9 | −7.5 |
| 90 | 45.4 | 126.5 | 1.3 | 1.3 | 2.3 | 6.8 | −26.8 | −0.5 |
| 91 | 58.3 | 162.3 | 1.6 | 1.2 | 5.9 | 2.9 | −47.2 | 6.9 |
| 92 | 25.8 | 164.8 | 14.2 | 0.9 | 9.9 | 1.9 | −14.4 | 81.0 |
| 93 | 8.9 | 159.7 | 0.8 | 1.3 | 19.2 | 0.5 | −1.4 | 91.5 |
| 94 | 17.0 | 123.0 | 1.0 | 0.6 | 21.6 | 8.9 | 2.3 | 76.6 |
| 95 | 29.9 | 171.8 | 1.6 | 0.2 | 0.2 | 1.1 | −38.0 | 22.5 |
| 96 | 21.2 | 152.2 | 2.6 | 0.2 | 1.9 | 30.0 | −16.1 | −13.4 |
| 97 | 33.2 | 203.1 | 1.4 | 0.1 | 0.1 | 1.2 | −27.2 | 32.9 |
| 98 | 32.5 | 101.3 | 1.4 | 1.9 | 2.7 | 4.1 | −25.9 | −29.3 |
| 99 | 23.9 | 145.3 | 1.1 | 1.0 | 6.9 | 3.2 | 3.7 | 92.4 |
| 100 | 5.3 | 59.4 | 0.7 | 0.3 | 12.9 | 2.0 | −43.0 | 17.2 |
| 101 | 5.6 | 57.7 | 10.4 | 1.1 | 3.1 | 5.2 | 2.8 | 73.9 |
| 102 | 44.1 | 140.4 | 3.5 | 4.7 | 4.8 | 25.4 | −14.1 | 8.8 |

LPS-Induced Neutrophil Accumulation in Mice

Non-fasted Balb/c mice were dosed by the intra tracheal route with either vehicle, or the test substance at the indicated times (within the range 2-8 hr) before stimulation of the inflammatory response by application of an LPS challenge. At T=0, mice were placed into an exposure chamber and exposed to LPS. After a further 8 hr the animals were anesthetized, their tracheas cannulated and BALF extracted by infusing and then withdrawing from their lungs 1.0 mL of PBS via the tracheal catheter. Total and differential white cell counts in the BALF samples were measured using a Neubaur haemocytometer. Cytospin smears of the BALF samples were prepared by centrifugation at 200 rpm for 5 min at RT and stained using a DiffQuik stain system (Dade Behring). Cells were counted using oil immersion microscopy.

Treatment of mice with compound Example 9 was found to produce a dose-dependent inhibition of neutrophil accumulation into the BALF when administered 2 hr prior to LPS challenge. Moreover, the effects of treatment were sustained and still detectable when the compound was dosed 8 hr prior to the endotoxin challenge (Table 4).

TABLE 4

The effects of treatment with Compound Example 9 on LPS-induced airway neutrophilia in mice.

| Treatment with Compound | Neutrophil numbers in BAL $\times 10^5$/mL (% inhibition) | |
|---|---|---|
| Example 9 (mg/mL) | 2 hr pre-dose | 8 h pre-dose |
| Vehicle | 16.88 ± 2.40 (0) | — |
| 0.05 | 14.98 ± 2.25 (11) | — |
| 0.2 | 8.75 ± 1.38 (48) | 13.44 ± 2.03 (20) |
| 1.0 | 5.80 ± 1.18 (66) | — |

Similarly, treatment of mice with compounds Examples 24, 75, 76, 80 and 91 also showed inhibitory effects versus neutrophil influx into the BALF when dosed 8 hr before the inflammatory stimulus. The effects of treatment with compound Example 91 (Table 5) and compound Example 75 (Table 6) were particularly marked.

TABLE 5

The effects of treatment with Compound Examples 24, 80 and 91 on LPS-induced airway neutrophilia in mice.

| Treatment with Compound Example (0.2 mg/mL) | Neutrophil numbers in BAL $\times 10^5$/mL 8 h pre-dose | % inhibition of Influx |
|---|---|---|
| Vehicle | 17.29 ± 2.65 | — |
| 24 | 15.71 ± 2.48 | 9 |
| 80 | 15.22 ± 2.34 | 12 |
| 91 | 11.67 ± 2.07 | 33 |

TABLE 6

The effects of treatment with Compound Examples 75 and 76 on LPS-induced airway neutrophilia in mice.

| Treatment with Compound Example (0.2 mg/mL) | Neutrophil numbers in BAL $\times 10^5$/mL 8 h pre-dose | % inhibition of Influx |
|---|---|---|
| Vehicle | 14.03 ± 2.33 | 0 |
| 75 | 10.87 ± 2.13 | 23 |
| 76 | 12.94 ± 2.41 | 8 |

Cigarette Smoke Model

A/J mice (males, 5 weeks old) were exposed to cigarette smoke (4% cigarette smoke, diluted with air) for 30 min/day for 11 days using a Tobacco Smoke Inhalation Experiment System for small animals (Model SIS-CS; Sibata Scientific Technology, Tokyo, Japan). Test substances were administered intra-nasally (35 μL of solution in 50% DMSO/PBS) twice daily for 3 days after the final cigarette smoke exposure. At 12 hr after the last dosing, each of the animals was anesthetized, the trachea cannulated and bronchoalveolar lavage fluid (BALF) was collected. The numbers of alveolar macrophages and neutrophils were determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil).

The data for cell numbers are shown as the mean±SEM. The cigarette smoke model used for this study is reported to be a corticosteroid refractory system, (Medicherla S. et al., *J. Pharmacol. Exp. Ther.*, 2008, 324(3):921-9) and it was confirmed that fluticasone propionate did not inhibit either neutrophil or macrophage accumulation into airways at 1.75 μg/mouse (35 μL, bid, i.n.), the same dose that produced >80% inhibition of LPS-induced neutrophil accumulation.

Treatment of mice with either compound Example 9 or compound Example 76 was found to produce a dose-dependent inhibition of both macrophage and neutrophil accumulation into the BALF of animals previously exposed to cigarette smoke (Tables 7 and 8 respectively).

TABLE 7

The effects of treatment with Compound Example 9 on macrophage and neutrophil accumulation into BALF of mice exposed to cigarette smoke.

| Treatment: Compound | N | Cell numbers in BAL $\times 10^4$/mL (% Inhibition) | |
|---|---|---|---|
| Example 9 (μg/mL) | Values | Macrophage | Neutrophil |
| Air + vehicle | 11 | 3.9 ± 0.27 | 1.8 ± 0.18 |
| Cigarette smoke + Vehicle | 10 | 19.0 ± 2.2 | 18.1 ± 2.0 |
| Cigarette smoke + 9 (0.064) | 5 | 16.2 ± 1.7 (19) | 17.7 ± 2.5 (3) |
| Cigarette smoke + 9 (0.32) | 5 | 16.5 ± 2.4 (17) | 15.5 ± 0.47(16) |
| Cigarette smoke + 9 (1.6) | 5 | 16.2 ± 1.3 (19) | 14.7 ± 1.6 (21) |
| Cigarette smoke + 9 (8.0) | 10 | 13.1 ± 1.2 (39) | 13.4 ± 1.4 (29) |
| Cigarette smoke + 9 (40) | 6 | 9.9 ± 1.6 (61) | 11.2 ± 2.1 (42) |
| Cigarette smoke + 9 (200) | 6 | 6.1 ± 0.93 (85) | 6.3 ± 0.79 (72) |

TABLE 8

The effects of treatment with Compound Example 76 on macrophage and neutrophil accumulation into BALF of mice exposed to cigarette smoke.

| Treatment: Compound | N | Cell numbers in BAL $\times 10^4$/mL (% Inhibition) | |
|---|---|---|---|
| Example 76 (μg/mL) | Values | Macrophages | Neutrophils |
| Air + vehicle | 6 | 3.3 ± 0.43 | 1.7 ± 0.14 |
| Cigarette smoke + Vehicle | 6 | 15.4 ± 1.3 | 18.4 ± 2.3 |
| Cigarette smoke + 76 (8.0) | 6 | 8.5 ± 0.35 (57) | 9.6 ± 0.48 (52) |
| Cigarette smoke + 76 (40) | 6 | 5.3 ± 0.36 (84) | 7.4 ± 0.76 (66) |
| Cigarette smoke + 76 (200) | 6 | 3.6 ± 0.39 (97) | 4.0 ± 0.49 (86) |

The results of treatment with compound Example 9, in mice exposed to cigarette smoke, on the accumulation of neutrophil and activated alveolar macrophages is represented graphically in the appended figures (FIG. 1 and FIG. 2 respectively).

The invention claimed is:
1. A compound of formula (I):

(I)

wherein,
$R^1$ is H,
phenyl, or
a saturated or unsaturated branched or unbranched $C_{1-10}$ alkylene acyclic or alicyclic chain wherein one or more carbons in the chain are optionally replaced by a heteroatom(s) independently selected from O, N and $S(O)_n$ and the chain is optionally substituted by:
one oxo group and/or
one or more halogen atoms;
$R^{2a}$ is H, halo, saturated or unsaturated branched or unbranched $C_{1-8}$ alkylene chain, wherein one or more carbons are optionally replaced by a heteroatom(s) independently selected from —O—, —N— or $S(O)_m$ and the chain is optionally substituted by one or more halogen atoms;
$R^{2b}$ is H, halo, $C_{1-6}$ alkoxy or $C_{1-6}$ alkyl optionally substituted by OH;
$R^3$ is halo, haloalkyl, $S(O)_p C_{1-6}$ alkyl or cyano;
$R^4$ is H, halo, haloalkyl, or cyano; or
$R^3$ and $R^4$ taken together with the carbons atoms to which they are attached form:
a 5 to 6 membered saturated or partially unsaturated carbocyclic ring, or
a 5 to 6 membered saturated or partially unsaturated or unsaturated heterocyclic ring containing 1 or more heteroatoms independently selected from N, O or S;
L is saturated or unsaturated branched or unbranched $C_{1-6}$ alkylene chain, wherein one or more carbons are optionally replaced by a heteroatom selected from —O— or S, and the chain is optionally substituted by one or two oxo groups;
X is pyridine or pyrimidine optionally substituted by $C_{1-3}$ alkyl, or $C_{1-3}$ haloalkyl;
$R^5$ H or $C_{1-4}$ alkyl;
$R^6$ is selected from:
a) a saturated or unsaturated, branched or unbranched $C_{1-10}$ alkyl chain, wherein optionally at least one carbon is replaced by a heteroatom independently selected from O, N, $S(O)_p$, wherein said chain is optionally, substituted by one or more groups independently selected from oxo, halogen, a $C_{6-10}$ aryl group, a 5 or 6 membered heteroaryl group, a 5 or 6 membered heterocyclyl group or a $C_{3-8}$ cycloalkyl group,
each aryl, heteroaryl, heterocyclyl or cycloalkyl group bearing 0 to 3 substituents selected from halogen, hydroxyl, $C_{1-6}$ alkyl, $C_{1-6}$ alkoxy, $C_{1-6}$ haloalkyl, amino, $C_{1-4}$ mono or $C_{2-8}$ di-alkyl amino, $C_{1-4}$ mono or $C_{2-8}$ di-acyl amino, $S(O)_q C_{1-6}$ alkyl, $C_{0-6}$ alkylC(O)$C_{1-6}$ alkyl or $C_{0-6}$ alkylC(O)N$C_{0-6}$ alkyl $C_{0-6}$ alkyl, $C_{0-6}$ alkylC(O)$C_{0-6}$ heteroalkyl,
with the proviso that the atom linked directly to the carbonyl in —NR$^5$C(O)— is not an oxygen or a sulfur atom; and
b) a $C_{0-8}$ alkyl-heterocycle wherein the heterocyclyl group has 5 or 6 members and comprises at least one heteroatom selected from O, N, and S, and said heterocycle is optionally substituted by one, two or three groups independently selected from halogen, hydroxyl, $C_{1-6}$ alkyl, $C_{1-6}$ alkoxy, $C_{1-6}$ haloalkyl, amino, $C_{1-4}$ mono and $C_{2-8}$ di-alkyl amino, $C_{1-4}$ mono or $C_{2-8}$ di-acyl amino, $S(O)_q C_{1-6}$ alkyl, $C_{0-6}$ alkylC(O)$C_{1-6}$ alkyl, $C_{0-6}$ alkylC(O)N$C_{0-6}$ alkyl $C_{0-6}$ alkyl or $C_{0-6}$ alkylC(O)$C_{0-6}$ heteroalkyl;
n is 0, 1 or 2;
m is 0, 1 or 2;
p is 0, 1 or 2;
q is 0, 1 or 2; or
a pharmaceutically acceptable salt thereof, including all stereoisomers, tautomers and isotopic derivatives thereof.

2. A compound of formula (I) according to claim 1, wherein $R^1$ is —$C_{1-6}$ alkyl optionally substituted by OH, $C_{3-10}$ cycloalkyl, $C_{3-10}$ heterocycloalkyl, $C_{1-6}$ haloalkyl or $C_{1-6}$ alkylOC(O)CH$_3$.

3. A compound of formula (I) according to claim 1, wherein $R^1$ is selected from methyl, ethyl, propyl, iso-propyl, butyl, tert-butyl, —C(CH$_3$)$_2$CH$_2$OH, cyclopropyl, 1-methylcyclopropyl, cyclopentyl, cyclohexyl, 1-methylcyclohexyl or adamantyl.

4. A compound of formula (I) according to claim 1, wherein $R^1$ is tetrahydropyranyl or 4-methyltetrahydro-2H-pyran-4-yl.

5. A compound of formula (I) according to claim 1, wherein $R^1$ is —CF$_3$, —CF$_2$CF$_3$ or —CCl$_3$.

6. A compound of formula (I) according to claim 1, wherein $R^1$ is phenyl.

7. A compound of formula (I) according to claim 1, wherein $R^{2a}$ is in the 2, 3, or 4 position.

8. A compound of formula (I) according to claim 1, wherein $R^{2a}$ is methyl, ethyl, n-propyl, iso-propyl, n-butyl or tert-butyl.

9. A compound of formula (I) according to claim 1, wherein $R^{2a}$ is —OH.

10. A compound of formula (I) according to claim 1, wherein $R^{2a}$ is halo.

11. A compound of formula (I) according to claim 1, wherein $R^{2a}$ is selected from —$C_{1-6}$ alkyl substituted by a hydroxyl group, —$C_{1-6}$ alkoxy, —S$C_{1-6}$ alkyl or —SO$_2$$C_{1-6}$ alkyl.

12. A compound of formula (I) according to claim 1, wherein $R^{2a}$ is —OCF$_3$.

13. A compound of formula (I) according to claim 1, wherein $R^{2a}$ is —NR'R'' wherein R' is H, —$C_{1-3}$ alkyl or —SO$_2$$C_{1-3}$alkyl, and R'' is H or —$C_{1-3}$ alkyl.

14. A compound of formula (I) according to claim 13, wherein $R^{2a}$ is —NHSO$_2$CH$_3$.

15. A compound of formula (I) according to claim 1, wherein $R^{2b}$ is selected from H or halo.

16. A compound of formula (I) according to claim 15, wherein $R^{2a}$ is chloro and $R^{2b}$ is chloro.

17. A compound of formula (I) according to claim 1, wherein $R^{2a}$ is chloro and $R^{2b}$ is —OCH$_3$.

18. A compound of formula (I) according to claim 1, wherein $R^{2a}$ is —OCH$_3$ and $R^{2b}$ is —OCH$_3$.

19. A compound of formula (I) according to claim 1, wherein $R^{2a}$ is chloro and $R^{2b}$ is —OH.

20. A compound of formula (I) according to claim 1, wherein $R^3$ is fluoro, chloro, —SO$_2$CH$_3$, or —CF$_3$.

21. A compound of formula (I) according to claim 1, wherein $R^4$ is H, chloro or cyano.

22. A compound of formula (I) according to claim 1, wherein $R^3$ and $R^4$ respectively represent chloro and cyano or chloro and chloro.

23. A compound of formula (I) according to claim 1, wherein $R^3$ and $R^4$ together with the phenyl to which they are attached represents 1H-indazolyl or 5,6,7,8-tetrahydronaphthalenyl.

24. A compound of formula (I) according to claim 1, wherein L represents O, CH$_2$, C=O or S(O)$_t$ where $t$ is 0, 1 or 2.

25. A compound of formula (I) according to claim 24 wherein L is O.

26. A compound of formula (I) according to claim 1, wherein L represents —OCH$_2$— or —OCH$_2$CH$_2$—.

27. A compound of formula (I) according to claim 1, wherein X is pyridine.

28. A compound of formula (I) according to claim 1, wherein $R^5$ is H.

29. A compound of formula (I) according to claim 1, wherein $R^6$ is
  a saturated or unsaturated, branched or unbranched $C_{1-10}$ alkyl chain, wherein at least one carbon is replaced by a heteroatom independently selected from O, N, S(O)$_p$, wherein said chain is optionally, substituted by one or more groups independently selected from oxo, halogen, a $C_{6-10}$ aryl group, a 5 or 6 membered heteroaryl group, a 5 or 6 membered heterocyclyl group or a $C_{3-8}$ cycloalkyl group,
    each aryl, heteroaryl, heterocyclyl or cycloalkyl group bearing 0 to 3 substituents selected from halogen, hydroxyl, $C_{1-6}$ alkyl, $C_{1-6}$ alkoxy, $C_{1-6}$ haloalkyl, amino, $C_{1-4}$ mono or $C_{2-8}$ di-alkyl amino, $C_{1-4}$ mono or $C_{2-8}$ di-acyl amino, S(O)$_q$$C_{1-6}$ alkyl, $C_{0-6}$ alkylC(O)$C_{1-6}$ alkyl or $C_{0-6}$ alkylC(O)N$C_{0-6}$ alkyl $C_{0-6}$ alkyl, $C_{0-6}$ alkylC(O)$C_{1-6}$ heteroalkyl,
with the proviso that the atom linked directly to the carbonyl in —NR$^5$C(O)— is not an oxygen or a sulfur atom.

30. A compound of formula (I) according to claim 1, wherein the compound is:
  N-(4-(4-(3-(3-tert-Butyl-1-p-tolyl-1H-pyrazol-5-yl)ureido)-3-fluorophenoxy)pyridin-2-yl)-2-methoxyacetamide;
  N-(4-(4-(3-(3-tert-Butyl-1-p-tolyl-1H-pyrazol-5-yl)ureido)-3-(methylsulfonyl)phenoxy)pyridin-2-yl)-2-methoxyacetamide;
  N-(4-(4-(3-(3-tert-Butyl-1-p-tolyl-1H-pyrazol-5-yl)ureido)-3-(trifluoromethyl)phenoxy)pyridin-2-yl)-2-methoxyacetamide;
  N-(4-(4-(3-(3-tert-Butyl-1-p-tolyl-1H-pyrazol-5-yl)ureido)-3-chloro-2-cyanophenoxy)pyridin-2-yl)-2-methoxyacetamide;
  N-(4-(4-(3-(3-tert-Butyl-1-p-tolyl-1H-pyrazol-5-yl)ureido)-5,6,7,8-tetrahydronaphthalen-1-yloxy)pyridin-2-yl)-2-methoxyacetamide;
  N-(4-(5-(3-(3-tert-Butyl-1-p-tolyl-1H-pyrazol-5-yl)ureido)quinolin-8-yloxy)pyridin-2-yl)-2-methoxyacetamide;
  N-(4-(7-(3-(3-tert-Butyl-1-p-tolyl-1H-pyrazol-5-yl)ureido)-1H-indazol-4-yloxy)pyridin-2-yl)-2-methoxyacetamide;
  N-(4-(4-(3-(3-tert-Butyl-1-(4-(hydroxymethyl)phenyl)-1H-pyrazol-5-yl)ureido)-2,3-dichlorophenoxy)pyridin-2-yl)-2-(methylamino)acetamide;
  N-Methyl-N'-4-(4-(3-(3-tert-butyl-1-p-anisyl-1H-pyrazol-5-yl)ureido)-2,3-dichlorophen-1-yloxy)pyridin-2-ylurea;
  N-(4-(4-(3-(3-tert-Butyl-1-(4-(methylthio)phenyl)-1H-pyrazol-5-yl)ureido)-2,3-dichlorophenoxy)pyridin-2-yl)pyrrolidine-1-carboxamide;
  (R)-N-(4-(4-(3-(3-tert-Butyl-1-(4-hydroxyphenyl)-1H-pyrazol-5-yl)ureido)-2,3-dichlorophenoxy)pyridin-2-yl)-3-(dimethylamino)pyrrolidine-1-carboxamide;
  1-(4-(4-(3-(3-tert-Butyl-1-(4-methoxyphenyl)-1H-pyrazol-5-yl)ureido)-2,3-dichlorophenoxy)pyridin-2-yl)-3-ethylurea;
  1-(3-tert-Butyl-1-(4-methoxyphenyl)-1H-pyrazol-5-yl)-3-(2,3-dichloro-4-((2-(3-(2-(dimethylamino)ethyl)ureido)pyridin-4-yl)oxy)phenyl)urea;
  N-(4-((4-(3-(3-tert-Butyl-1-p-tolyl-1H-pyrazol-5-yl)ureido)-2,3-dichlorophenoxy)methyl)pyridin-2-yl)-2-methoxyacetamide;
  N-(4-((4-(3-(3-tert-Butyl-1-(4-methoxyphenyl)-1H-pyrazol-5-yl)ureido)-2,3-dichlorophenoxy)methyl)pyridin-2-yl)-2-methoxyacetamide;
  N-(4-((5-(3-(3-tert-Butyl-1-p-tolyl-1H-pyrazol-5-yl)ureido)quinolin-8-yloxy)methyl) pyridin-2-yl)-2-methoxyacetamide;
  N-(4-((5-(3-(3-tert-Butyl-1-(4-methoxyphenyl)-1H-pyrazol-5-yl)ureido)quinolin-8-yloxy)methyl)pyridin-2-yl)-2-methoxyacetamide;
  1-(3-tert-Butyl-1-(4-methoxyphenyl)-1H-pyrazol-5-yl)-3-(2,3-dichloro-4-((2-(3-methylureido)pyridin-4-yl)methoxy)phenyl)urea;
  N-(4-((4-(3-(3-tert-Butyl-1-(p-tolyl)-1H-pyrazol-5-yl)ureido)-2,3-dichlorophenoxy)methyl)pyridin-2-yl)pyrrolidine-1-carboxamide;
  N-(4-((4-(3-(3-tert-Butyl-1-(4-methoxyphenyl)-1H-pyrazol-5-yl)ureido)-2,3-dichlorophenoxy)methyl)pyridin-2-yl)pyrrolidine-1-carboxamide;
  1-(3-tert-Butyl-1-p-tolyl-1H-pyrazol-5-yl)-3-(8-((2-(3-methylureido)pyridin-4-yl)methoxy)quinolin-5-yl)urea;
  N-(6-(4-(3-(3-tert-Butyl-1-(4-hydroxymethyl)phenyl)-1H-pyrazol-5-yl)ureido)-2,3-dichlorophenoxy)pyrimidin-4-yl)-4-(dimethylamino)butanamide;
  N-(4-(4-(3-(3-tert-Butyl-1-(4-methoxyphenyl)-1H-pyrazol-5-yl)ureido)-2,3-dichlorophenoxy)pyrimidin-2-yl)-2-methoxyacetamide;
  1-(3-tert-Butyl-1-p-tolyl-1H-pyrazol-5-yl)-3-(2,3-dichloro-4-(6-(3-(2-(dimethylamino)ethyl)ureido)pyrimidin-4-yloxy)phenyl)urea;
  1-(4-(4-(3-(3-tert-Butyl-1-(4-(hydroxymethyl)phenyl)-1H-pyrazol-5-yl)ureido)-2,3-dichlorophenoxy)pyrimidin-2-yl)-3-methylurea;
  N-(4-((4-(3-(3-tert-Butyl-1-(4-methoxyphenyl)-1H-pyrazol-5-yl)ureido)-2,3-dichlorophenylthio)methyl)pyridin-2-yl)-2-methoxyacetamide;
  N-(4-(4-(3-(3-tert-Butyl-1-p-tolyl-1H-pyrazol-5-yl)ureido)-3-chlorophenoxy)pyridin-2-yl)-2-methoxyacetamide;
  N-(4-(4-(3-(3-tert-Butyl-1-p-tolyl-1H-pyrazol-5-yl)ureido)-2-cyanophenoxy)pyridin-2-yl)-2-methoxyacetamide;

N-(4-(4-(3-(3-tert-Butyl-1-p-tolyl-1H-pyrazol-5-yl)ureido)-2-chlorophenoxy)pyridin-2-yl)-2-methoxyacetamide;
N-(4-(4-(3-(3-tert-Butyl-1-p-tolyl-1H-pyrazol-5-yl)ureido)-2-trifluoromethylphenoxy)pyridin-2-yl)-2-methoxyacetamide;
N-(4-(4-(3-(3-tert-Butyl-1-p-tolyl-1H-pyrazol-5-yl)ureido)-2-methylsulfonylphenoxy)pyridin-2-yl)-2-methoxyacetamide;
N-(4-(3-Bromo-4-(3-(3-tert-butyl-1-p-tolyl-1H-pyrazol-5-yl)ureido)phenoxy)pyridin-2-yl)-2-methoxyacetamide;
N-(4-(2-Bromo-4-(3-(3-tert-butyl-1-p-tolyl-1H-pyrazol-5-yl)ureido)phenoxy)pyridin-2-yl)-2-methoxyacetamide;
N-(4-(4-(3-(3-tert-Butyl-1-p-tolyl-1H-pyrazol-5-yl)ureido)-2,3-difluorophenoxy)pyridin-2-yl)-2-methoxyacetamide;
N-(4-(4-(3-(3-tert-Butyl-1-p-tolyl-1H-pyrazol-5-yl)ureido)-3-chloro-2-fluorophenoxy)pyridin-2-yl)-2-methoxyacetamide;
N-(4-(4-(3-(3-tert-Butyl-1-p-tolyl-1H-pyrazol-5-yl)ureido)-2,3-dichlorophenoxy)pyridin-2-yl)-2-methoxyacetamide;
N-(4-(4-(3-(3-tert-Butyl-1-p-tolyl-1H-pyrazol-5-yl)ureido)-3-chloro-2-trifluoromethylphenoxy)pyridin-2-yl)-2-methoxyacetamide;
N-(4-(4-(3-(3-tert-Butyl-1-p-tolyl-1H-pyrazol-5-yl)ureido)-5-chloro-2-fluorophenoxy)pyridin-2-yl)-2-methoxyacetamide;
N-(4-(4-(3-(3-tert-Butyl-1-p-tolyl-1H-pyrazol-5-yl)ureido)-2,5-dichlorophenoxy)pyridin-2-yl)-2-methoxyacetamide;
N-(4-(8-(3-(3-tert-Butyl-1-p-tolyl-1H-pyrazol-5-yl)ureido)quinolin-5-yloxy)pyridin-2-yl)-2-methoxyacetamide;
N-(4-(4-(3-(3-tert-Butyl-1-(4-hydroxyphenyl)-1H-pyrazol-5-yl)ureido)-2,3-dichlorophenoxy)pyridin-2-yl)-2-methoxyacetamide;
N-(4-(4-(3-(3-tert-Butyl-1-(4-methoxyphenyl)-1H-pyrazol-5-yl)ureido)-2,3-dichlorophenoxy)pyridin-2-yl)-2-(methylamino)acetamide;
N-(4-(4-(3-(3-tert-Butyl-1-(4-methoxyphenyl)-1H-pyrazol-5-yl)ureido)-2,3-dichlorophenoxy)pyridin-2-yl)-2-(dimethylamino)acetamide;
N-(4-(4-(3-(3-tert-Butyl-1-(4-methoxyphenyl)-1H-pyrazol-5-yl)ureido)-2,3-dichlorophenoxy)pyridin-2-yl)-2-methoxyacetamide;
N-(4-(4-(3-(3-tert-Butyl-1-(4-methoxyphenyl)-1H-pyrazol-5-yl)ureido)-2,3-dichlorophenoxy)pyridin-2-yl)-2-morpholinoacetamide;
N-(4-(4-(3-(3-tert-Butyl-1-(4-hydroxymethylphenyl)-1H-pyrazol-5-yl)ureido)-2,3-dichlorophenoxy)pyridin-2-yl)-2-(dimethylamino)acetamide;
N-(4-(4-(3-(3-tert-Butyl-1-(4-hydroxymethylphenyl)-1H-pyrazol-5-yl)ureido)-2,3-dichlorophenoxy)pyridin-2-yl)-4-(dimethylamino)butanamide;
N-(4-(4-(3-(3-tert-Butyl-1-(4-hydroxymethylphenyl)-1H-pyrazol-5-yl)ureido)-2,3-dichlorophenoxy)pyridin-2-yl)-2-morpholinoacetamide;
N-(4-(4-(3-(3-tert-Butyl-1-(4-hydroxymethylphenyl)-1H-pyrazol-5-yl)ureido)-2,3-dichlorophenoxy)pyridin-2-yl)-2-methoxyacetamide;
1-(3-tert-Butyl-1-p-tolyl-1H-pyrazol-5-yl)-3-(2,3-dichloro-4-(2-(3-methylureido)pyridin-4-yloxy)phenyl)urea;
1-(3-tert-Butyl-1-(4-hydroxyphenyl)-1H-pyrazol-5-yl)-3-(2,3-dichloro-4-(2-(3-methylureido)pyridin-4-yloxy)phenyl)urea;
1-(3-tert-Butyl-1-(4-hydroxymethylphenyl)-1H-pyrazol-5-yl)-3-(2,3-dichloro-4-(2-(3-methylureido)pyridin-4-yloxy)phenyl)urea;
1-(3-tert-Butyl-1-(4-hydroxymethyl-3-methoxyphenyl)-1H-pyrazol-5-yl)-3-(2,3-dichloro-4-(2-(3-methylureido)pyridin-4-yloxy)phenyl)urea;
1-(3-tert-Butyl-1-(3-chloro-4-hydroxymethylphenyl)-1H-pyrazol-5-yl)-3-(2,3-dichloro-4-(2-(3-methylureido)pyridin-4-yloxy)phenyl)urea;
1-(4-(4-(3-(3-tert-Butyl-1-(4-hydroxymethylphenyl)-1H-pyrazol-5-yl)ureido)-2,3-dichlorophenoxy)pyridin-2-yl)-3-cyclopropylurea;
1-(3-tert-Butyl-1-p-tolyl-1H-pyrazol-5-yl)-3-(5-(2-(3-methylureido)pyridin-4-yloxy)quinolin-8-yl)urea;
1-(3-tert-Butyl-1-(4-methoxyphenyl)-1H-pyrazol-5-yl)-3-(5-(2-(3-methylureido)pyridin-4-yloxy)quinolin-8-yl)urea;
1-(3-tert-Butyl-1-(4-methoxyphenyl)-1H-pyrazol-5-yl)-3-(8-(2-(3-methylureido)pyridin-4-yloxy)quinolin-5-yl)urea;
Methyl 4-(3-tert-butyl-5-(3-(2,3-dichloro-4-(2-(3-methylureido)pyridin-4-yloxy)phenyl)ureido)-1H-pyrazol-1-yl)benzoate;
4-(3-tert-Butyl-5-(3-(2,3-dichloro-4-(2-(3-methylureido)pyridin-4-yloxy)phenyl)ureido)-1H-pyrazol-1-yl)benzoic acid;
1-(4-(8-(3-(3-tert-Butyl-1-(4-hydroxymethylphenyl)-1H-pyrazol-5-yl)ureido)quinolin-5-yloxy)pyridin-2-yl)-3-methylurea;
1-(4-(5-(3-(3-tert-Butyl-1-(4-hydroxymethylphenyl)-1H-pyrazol-5-yl)ureido)quinolin-8-yloxy)pyridin-2-yl)-3-methylurea;
3-(4-(4-(3-(3-tert-Butyl)-1-p-tolyl-1H-pyrazol-5-yl)ureido)-2,3-dichlorophenoxy)pyridin-2-yl)-1,1-dimethylurea;
3-(4-(4-(3-(3-tert-Butyl-1-(4-methoxyphenyl)-1H-pyrazol-5-yl)ureido)-2,3-dichlorophenoxy)pyridin-2-yl)-1,1-dimethylurea;
1-(4-(4-(3-(3-tert-Butyl-1-(4-methoxyphenyl)-1H-pyrazol-5-yl)ureido)-2,3-dichlorophenoxy)pyridin-2-yl)-3-cyclopropylurea;
1-(4-(4-(3-(3-tert-Butyl-1-(4-methoxyphenyl)-1H-pyrazol-5-yl)ureido)-2,3-dichlorophenoxy)pyridin-2-yl)-3-(2-hydroxyethyl)urea;
1-(4-(4-(3-(3-tert-Butyl-1-(4-methoxyphenyl)-1H-pyrazol-5-yl)ureido)-2,3-dichlorophenoxy)pyridin-2-yl)-3-(2-methoxyethyl)urea;
1-(4-(4-(3-(3-tert-Butyl-1-(4-methoxyphenyl)-1H-pyrazol-5-yl)ureido)-2,3-dichlorophenoxy)pyridin-2-yl)-3-(2-morpholinoethyl)urea;
1-(3-(1H-Imidazol-1-yl)propyl)-3-(4-(4-(3-(3-tert-butyl-1-(4-methoxyphenyl)-1H-pyrazol-5-yl)ureido)-2,3-dichlorophenoxy)pyridin-2-yl)urea;
1-(3-tert-Butyl-1-(4-hydroxymethylphenyl)-1H-pyrazol-5-yl)-3-(2,3-dichloro-4-(2-(3-(2-(dimethylamino)ethyl)ureido)pyridin-4-yloxy)phenyl)urea;
1-(4-(4-(3-(3-tert-Butyl-1-(4-hydroxymethylphenyl)-1H-pyrazol-5-yl)ureido)-2,3-dichlorophenoxy)pyridin-2-yl)-3-(2-morpholinoethyl)urea;
N-(4-(4-(3-(3-tert-Butyl-1-p-tolyl-1H-pyrazol-5-yl)ureido)-2,3-dichlorophenoxy)pyridin-2-yl)pyrrolidine-1-carboxamide;

1-(3-(1-Methylcyclohexyl)-1-p-tolyl-1H-pyrazol-5-yl)-3-(2,3-dichloro-4-(2-(3-methylureido)pyridin-4-yloxy)phenyl)urea;

N-(4-(2,3-Dichloro-4-(3-(3-(1-methylcyclohexyl)-1-p-tolyl-1H-pyrazol-5-yl)ureido)phenoxy)pyridin-2-yl)pyrrolidine-1-carboxamide;

N-(4-(4-(3-(3-tert-Butyl-1-(4-hydroxyphenyl)-1H-pyrazol-5-yl)ureido)-2,3-dichlorophenoxy)pyridin-2-yl)pyrrolidine-1-carboxamide;

N-(4-(4-(3-(3-(tert-Butyl)-1-(4-methoxyphenyl)-1H-pyrazol-5-yl)ureido)-2,3-dichlorophenoxy)pyridin-2-yl)pyrrolidine-1-carboxamide;

N-(4-(4-(3-(3-tert-Butyl-1-(4-hydroxymethylphenyl)-1H-pyrazol-5-yl)ureido)-2,3-dichlorophenoxy)pyridin-2-yl)pyrrolidine-1-carboxamide;

1-(3-tert-Butyl-1-(4-methoxyphenyl)-1H-pyrazol-5-yl)-3-(2-chloro-3-cyano-4-(2-(3-cyclopropylureido)pyridin-4-yloxy)phenyl)urea;

N-(4-(4-(3-(3-tert-Butyl-1-(4-methoxyphenyl)-1H-pyrazol-5-yl)ureido)-3-chloro-2-cyanophenoxy)pyridin-2-yl)pyrrolidine-1-carboxamide;

(S)-N-(4-(4-(3-(3-tert-Butyl-1-(4-hydroxyphenyl)-1H-pyrazol-5-yl)ureido)-2,3-dichlorophenoxy)pyridin-2-yl)-3-(dimethylamino)pyrrolidine-1-carboxamide;

(R)-N-(4-(4-(3-(3-tert-Butyl-1-(4-methoxyphenyl)-1H-pyrazol-5-yl)ureido)-2,3-dichlorophenoxy)pyridin-2-yl)-3-(dimethylamino)pyrrolidine-1-carboxamide;

(S)-N-(4-(4-(3-(3-tert-Butyl-1-(4-methoxyphenyl)-1H-pyrazol-5-yl)ureido)-2,3-dichlorophenoxy)pyridin-2-yl)-3-(dimethylamino)pyrrolidine-1-carboxamide;

(S)-N-(4-(4-(3-(3-tert-Butyl-1-(4-hydroxymethylphenyl)-1H-pyrazol-5-yl)ureido)-2,3-dichlorophenoxy)pyridin-2-yl)-3-(dimethylamino)pyrrolidine-1-carboxamide;

(S)-N-(4-(4-(3-(3-tert-Butyl-1-(4-hydroxymethyl-3-methoxyphenyl)-1H-pyrazol-5-yl)ureido)-2,3-dichlorophenoxy)pyridin-2-yl)-3-(dimethylamino)pyrrolidine-1-carboxamide;

N-(4-(4-(3-(3-tert-Butyl-1-(4-methoxyphenyl)-1H-pyrazol-5-yl)ureido)-2,3-dichlorophenoxy)pyridin-2-yl)-3-hydroxypyrrolidine-1-carboxamide;

N-(4-(4-(3-(3-tert-Butyl-1-(4-methoxyphenyl)-1H-pyrazol-5-yl)ureido)-2,3-dichlorophenoxy)pyridin-2-yl)-2,2-dimethylpyrrolidine-1-carboxamide;

N-(4-(4-(3-(3-tert-Butyl-1-(4-methoxyphenyl)-1H-pyrazol-5-yl)ureido)-2,3-dichlorophenoxy)pyridin-2-yl)-4-(dimethylamino)piperidine-1-carboxamide;

N-(4-(6-(3-(3-tert-Butyl-1-p-tolyl-1H-pyrazol-5-yl)ureido)-2,3-difluorophenoxy)pyridin-2-yl)-2-methoxyacetamide;

N-(6-(4-(3-(3-tert-Butyl-1-p-tolyl-1H-pyrazol-5-yl)ureido)-2,3-dichlorophenoxy)pyrimidin-4-yl)-2-methoxyacetamide;

N-(4-(4-(3-(3-tert-Butyl-1-p-tolyl-1H-pyrazol-5-yl)ureido)-2,3-dichlorophenoxy)pyrimidin-2-yl)-2-methoxyacetamide;

N-(6-(4-(3-(3-tert-Butyl-1-(4-methoxyphenyl)-1H-pyrazol-5-yl)ureido)-2,3-dichlorophenoxy)pyrimidin-4-yl)-2-methoxyacetamide;

N-(6-(4-(3-(3-tert-Butyl-1-(3-hydroxymethylphenyl)-1H-pyrazol-5-yl)ureido)-2,3-dichlorophenoxy)pyrimidin-4-yl)-2-methoxyacetamide;

N-(6-(4-(3-(3-tert-Butyl-1-(4-hydroxymethylphenyl)-1H-pyrazol-5-yl)ureido)-2,3-dichlorophenoxy)pyrimidin-4-yl)-2-methoxyacetamide;

N-(4-(4-(3-(3-tert-Butyl-1-(4-hydroxymethylphenyl)-1H-pyrazol-5-yl)ureido)-2,3-dichlorophenoxy)pyrimidin-2-yl)-2-methoxyacetamide;

1-(3-tert-Butyl-1-p-tolyl-1H-pyrazol-5-yl)-3-(2,3-dichloro-4-(6-(3-methylureido)pyrimidin-4-yloxy)phenyl)urea;

1-(3-tert-Butyl-1-p-tolyl-1H-pyrazol-5-yl)-3-(2,3-dichloro-4-(2-(3-methylureido)pyrimidin-4-yloxy)phenyl)urea;

1-(3-tert-Butyl-1-(4-methoxyphenyl)-1H-pyrazol-5-yl)-3-(2,3-dichloro-4-(6-(3-methylureido)pyrimidin-4-yloxy)phenyl)urea;

1-(3-tert-Butyl-1-(4-methoxyphenyl)-1H-pyrazol-5-yl)-3-(2,3-dichloro-4-(2-(3-methylureido)pyrimidin-4-yloxy)phenyl)urea;

1-(3-tert-Butyl-1-(4-hydroxymethylphenyl)-1H-pyrazol-5-yl)-3-(2,3-dichloro-4-(6-(3-methylureido)pyrimidin-4-yloxy)phenyl)urea;

1-(3-tert-Butyl)-1-(4-methoxyphenyl)-1H-pyrazol-5-yl)-3-(2,3-dichloro-4-(6-(3-(2(dimethylamino)ethyl)ureido)pyrimidin-4-yloxy)phenyl)urea;

1-(3-tert-Butyl-1-(4-hydroxymethylphenyl)-1H-pyrazol-5-yl)-3-(2,3-dichloro-4-(6-(3-(2-(dimethylamino)ethyl)ureido)pyrimidin-4-yloxy)phenyl)urea;

1-(4-((4-(3-(3-tert-Butyl-1-p-tolyl-1H-pyrazol-5-yl)ureido)-2,3-dichlorophenoxy)methyl)pyridin-2-yl)-3-methylurea;

1-(3-(1-methylcyclohexyl)-1-p-tolyl-1H-pyrazol-5-yl)-3-(2,3-dichloro-4-(2-(3-methylureido)pyridin-4-yloxy)phenyl)urea;

or a pharmaceutically acceptable salt thereof, including all stereoisomers, tautomers and isotopic derivatives thereof.

31. A pharmaceutical composition comprising a compound according to claim 1, in combination with one or more pharmaceutically acceptable diluents or carriers.

* * * * *